United States Patent
Nielsen et al.

(10) Patent No.: US 9,586,961 B2
(45) Date of Patent: Mar. 7, 2017

(54) HOMOPIPERAZINE DERIVATIVES AS PROTEIN TYROSINE KINASE INHIBITORS AND PHARMACEUTICAL USE THEREOF

(75) Inventors: Simon Felbæk Nielsen, Herlev (DK); Daniel R. Greve, Stenløse (DK); Gunnar Grue-Sørensen, Roskilde (DK); Carsten Ryttersgaard, Roskilde (DK); Søren Christian Schou, Roskilde (DK); Anette Graven Sams, Værløse (DK)

(73) Assignee: LEO PHARMA A/S, Ballerup (DK)

( * ) Notice: Subject to any disclaimer, the term of this patent is extended or adjusted under 35 U.S.C. 154(b) by 566 days.

(21) Appl. No.: 13/809,059

(22) PCT Filed: Jul. 8, 2011

(86) PCT No.: PCT/DK2011/000080
§ 371 (c)(1),
(2), (4) Date: Mar. 14, 2013

(87) PCT Pub. No.: WO2012/003829
PCT Pub. Date: Jan. 12, 2012

(65) Prior Publication Data
US 2013/0172325 A1 Jul. 4, 2013

Related U.S. Application Data

(60) Provisional application No. 61/363,095, filed on Jul. 9, 2010.

(51) Int. Cl.
| | | |
|---|---|---|
| A01N 43/62 | (2006.01) | |
| A61K 31/55 | (2006.01) | |
| C07D 223/14 | (2006.01) | |
| C07D 487/00 | (2006.01) | |
| C07D 491/00 | (2006.01) | |
| C07D 513/00 | (2006.01) | |
| C07D 487/04 | (2006.01) | |
| A61K 31/5513 | (2006.01) | |
| A61K 45/00 | (2006.01) | |

(52) U.S. Cl.
CPC ........ *C07D 487/04* (2013.01); *A61K 31/5513* (2013.01); *A61K 45/00* (2013.01)

(58) Field of Classification Search
CPC ... A61K 31/5513; A61K 45/00; C07D 487/04
USPC .......................................... 514/218; 540/543
See application file for complete search history.

(56) References Cited

FOREIGN PATENT DOCUMENTS

| | | |
|---|---|---|
| WO | WO 99/65909 A1 | 12/1999 |
| WO | WO 2005/117909 A2 | 12/2005 |
| WO | WO 2008/008518 A1 | 1/2008 |
| WO | WO 2008/119792 A1 | 10/2008 |
| WO | WO 2009/017838 A2 | 2/2009 |
| WO | WO 2009/098236 A1 | 8/2009 |
| WO | WO 2009/131687 A2 | 10/2009 |

OTHER PUBLICATIONS

International Preliminary Report on Patentability for PCT/DK2011/000080 mailed on Jul. 23, 2012.
International Search Report for PCT/DK2011/000080 mailed on Sep. 16, 2011.
Written Opinion of the International Searching Authority for PCT/DK2011/000080 mailed on Sep. 16, 2011.
Partial English translation of Japanese Office Action, dated May 14, 2015, for Japanese Application No. 2013-517018.

*Primary Examiner* — Uma Ramachandran
(74) *Attorney, Agent, or Firm* — Birch, Stewart, Kolasch & Birch, LLP

(57) ABSTRACT

The invention relates to compounds of general formula (I) wherein $R_1$, $R_2$, $R_3$, $R_4$, m and n are defined as defined herein, and pharmaceutically acceptable salts, hydrates, or solvates thereof, for use—alone or in combination with one or more other pharmaceutically active compounds—in therapy, as JAK kinase and protein tyrosine kinase inhibitors for preventing, treating or ameliorating diseases and complications thereof, including, for example, psoriasis, atopic dermatitis, rosacea, lupus, multiple sclerosis, rheumatoid arthritis, Type I diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immuno-suppression would be desirable for example in organ transplantation.

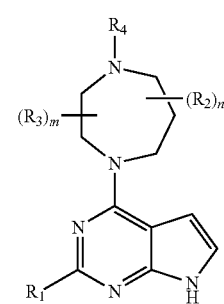

I

9 Claims, No Drawings

HOMOPIPERAZINE DERIVATIVES AS PROTEIN TYROSINE KINASE INHIBITORS AND PHARMACEUTICAL USE THEREOF

CROSS REFERENCE TO RELATED APPLICATIONS

This non-provisional application is a National Stage entry under U.S.C. §371 of International Application No. PCT/DK2011/000080 filed on Jul. 8, 2011, which claims the benefit of U.S. Provisional Application No. 61/363,095 filed on Jul. 9, 2010. The entire contents of all of the above applications are hereby incorporated by reference.

FIELD OF THE INVENTION

This invention relates to compounds which are inhibitors of protein tyrosine kinases, such as the Janus kinases, and to said compounds for use in therapy, to pharmaceutical compositions comprising said compounds, to methods of treating diseases comprising administering to a patient in need thereof an effective amount of said compound, and to the use of said compounds in the manufacture of medicaments.

BACKGROUND OF THE INVENTION

This invention relates to novel compounds which are inhibitors of protein tyrosine kinases such as the Janus kinases, also referred to as JAK1, JAK2, JAK3 and TYK2. Said compounds are useful in the treatment of diseases related to activity of Janus kinases, including, for example, psoriasis, atopic dermatitis, rosacea, lupus, multiple sclerosis, rheumatoid arthritis, Type I diabetes and complications from diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immunosuppression would be desirable for example in organ transplantation.

Protein tyrosine kinases are a family of enzymes catalysing the transfer of the terminal phosphate of adenosine triphosphate to tyrosine residues in protein substrates. Phosphorylation of tyrosine residues on protein substrates leads to transduction of intracellular signals which regulate a wide variety of intracellular processes such as growth, differentiation and activation of cells of the immune system. As activation of T-cells and B-cells as well as other cells of the immune system such as monocytes and macrophages is implicated in a number of inflammatory conditions and other disorders of the immune system (e.g. autoimmune diseases), modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 have essential roles in cytokine-dependent regulation of proliferation and function of cells involved in immune response. They are critical in signal transduction in response to their activation via tyrosine phosphorylation by stimulation of interleukin receptors.

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

JAK2 is implicated in signalling by several single chain receptors (including Epo-R, GHR, PRL-R), the IL-3 receptor family, the gp130 receptor family and Class II receptor cytokine family. Thus, JAK2 plays a critical role in transducing signals for Epo, IL-3, GM-CSF, IL-5 and IFNγ. JAK2 knockout mice exhibit an embryonic lethal phenotype.

JAK3 is involved in signal transduction by receptors that employ the common gamma chain of the type I cytokine receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signalling through the JAK3 pathway. Animal studies have suggested that JAK3 not only plays a critical role in B and T lymphocyte maturation, but that JAK3 is constitutively required to maintain T cell function. Modulation of immune activity through this novel mechan ism can prove useful in the treatment of T cell proliferative disorders such as immune system diseases, in particular autoimmune diseases.

TYK2 is implicated in type I interferons, IL-6, IL-10, IL-12 and IL-23 signalling. A human patient with a TYK2 deficiency has been described and this patient had a primary immunodeficiency disorder characterized as a hyper-IgE-like syndrome with many opportun istic infections by virus, bacteria and fungi. Because IL-23 has been found to play an important role in many chronic inflammatory conditions, a TYK2 inhibitor could conceivably be very effective in treating diseased influenced by IL-23. Inhibitors of the Janus kinases are accordingly expected to show utility in the treatment of inflammatory and non-infectious autoimmune diseases wherein these kinases are involved.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells.

SUMMARY OF THE INVENTION

The present inventors have surprisingly found that a novel class of compounds exhibit a high inhibitory activity on one or more of the Janus kinase receptors JAK1, JAK2, JAK3 and TYK2.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells and as such show utility in the treatment of inflammatory and non-infectious autoimmune diseases wherein these kinases are involved.

Compounds of the present invention may have improved pharmakokinetic properties such as improved solubility and absorption, reduced adverse side effects and decreased metabolic stability in comparison to known structurally related compounds. A particular advantage of some of the compounds of the present invention is that they show high systemic clearance.

Accordingly, the invention relates to compounds of general formula I:

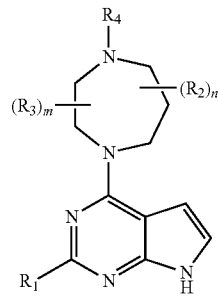

wherein
m is 0, 1 or 2;
n is 2 or 4;
$R_1$ is selected from the group consisting of hydrogen, halogen, cyano, —NH$_2$, —SO$_2$NH$_2$, —SONH$_2$, and —CONH$_2$;
or $R_1$ is selected from the group consisting of alkyl-, heteroalkyl-, cycloalkyl-, heterocyclyl-, $R_{1a}$O—, $R_{1a}$S—, $(R_{1a})_2$N—, $R_{1b}$—C(=O)N($R_{1c}$)—, $R_{1b}$O—C(=O)N($R_{1c}$)—, $(R_{1b})_2$N—C(=O)N($R_{1c}$)—, $R_{1b}$—S(=O)$_2$N($R_{1c}$)— and $(R_{1b})_2$N—S(=O)$_2$N($R_{1c}$)— either of which may be optionally substituted with one or more $R_{1d}$;
$R_{1a}$ is hydrogen;
or $R_{1a}$ independently at each occurrence is selected from the group consisting of alkyl-, heteroalkyl-, cycloalkyl-, heterocyclyl- either of which may be optionally substituted with one or more $R_{1e}$;
or in the case where two $R_{1a}$s are attached to the same N, they may together with the N atom to which they are attached form a heterocycle which may be optionally substituted with one or more $R_{1e}$;
$R_{1b}$ and $R_{1c}$ independently at each occurrence are selected from the group consisting of hydrogen, alkyl-, heteroalkyl-, cycloalkyl-, heterocyclyl- either of which may be optionally substituted with one or more $R_{1e}$;
or in the case where two $R_{1b}$s are attached to the same N, they may together with the N atom to which they are attached form a heterocycle which may be optionally substituted with one or more $R_{1e}$;
$R_{1d}$ and $R_{1e}$ independently at each occurrence are selected from the group consisting of halogen, cyano, hydroxy, oxo, —NH$_2$, —SO$_2$NH$_2$, —CONH$_2$, alkyl-, heteroalkyl-, cycloalkyl-, heterocyclyl-, $R_{1f}$O—, $R_{1f}$S—, $(R_{1f})_2$N—, $R_{1f}$O—C(=O)—, $(R_{1f})_2$N—C(=O)—, $R_{1f}$—C(=O)N($R_{1f}$)—, $R_{1f}$O—C(=O)N($R_{1f}$)—, $(R_{1f})_2$N—C(=O)N($R_{1f}$)—, $R_{1f}$—C(=O)O—, $(R_{1f})_2$N—C(=O)O—, $(R_{1f})_2$N—S(=O)$_2$—, $R_{1f}$—S(=O)$_2$N($R_{1f}$)—
$R_{1f}$ independently at each occurrence is selected from the group consisting of hydrogen, alkyl-, heteroalkyl-, cycloalkyl-, heterocyclyl-or
in the case where two $R_{1f}$s are attached to the same N, they may together with the N atom to which they are attached form a heterocycle
$R_2$ is independently at each occurrence a covalent bond or alkyl- or heteroalkyl- group, where any two $R_2$s are attached to the same C ring atom, and together with this C ring atom said two $R_2$s form a carbocycle or heterocycle, hence always forming a spirocyclic homopiperazine.

$R_3$ independently at each occurrence is selected from the group consisting of halogen, cyano, hydroxy, oxo, alkyl-, heteroalkyl-, cycloalkyl-, heterocyclyl-, $R_{3a}$O—, $R_{3a}$S—, $(R_{3a})_2$N—, $R_{3a}$—C(=O)—, $R_{3a}$O—C(=O)—, $(R_{3a})_2$N—C(=O)—, $R_{3a}$—C(=O)N($R_{3b}$)—, $R_{3a}$O—C(=O)N($R_{3b}$)—, $R_{3a}$—C(=O)O—, $(R_{3a})_2$N—C(=O)O—, $R_{3a}$—S(=O)$_2$—, $(R_{3a})_2$N—S(=O)$_2$—, $R_{3a}$—S(=O)$_2$N($R_{3b}$)—
$R_{3a}$ and $R_{3b}$ independently at each occurrence are selected from the group consisting of hydrogen, alkyl-, heteroalkyl-, cycloalkyl-, heterocyclyl-or
in the case where two $R_{1a}$s are attached to the same N, they may together with the N atom to which they are attached form a heterocycle
$R_4$ is selected from the group consisting of hydrogen or

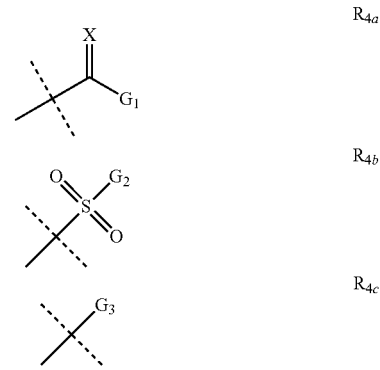

wherein
X is O or S;
$G_1$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, $R_{G1a}$O-L-, $R_{G1a}$S-L-, $(R_{G1a})_2$N-L-, $R_{G1a}$—C(=O)-L-, $R_{G1a}$O—C(=O)-L-, $(R_{G1a})_2$N—C(=O)-L-, $R_{G1a}$—C(=O)N($R_{G1b}$)-L-, $R_{G1a}$O—C(=O)N($R_{G1b}$)-L-, $(R_{G1a})_2$N—C(=O)$_2$N($R_{G1b}$)-L-, $R_{G1a}$—C(=O)O-L-, $(R_{G1a})_2$N—C(=O)O-L-, $R_{G1a}$—S(=O)$_2$-L-, $(R_{G1a})_2$N—S(=O)$_2$-L-, $R_{G1a}$—S(=O)$_2$N($R_{G1b}$)-L-, $(R_{G1a})_2$N—S(=O)$_2$N($R_{G1b}$)—, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more $R_{G1c}$;
$R_{G1a}$ and $R_{G1b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more $R_{G1c}$;
or in the case where two $R_{G1a}$s are attached to the same N, they may together with the N atom to which they are attached form a heterocycle which may be optionally substituted with one or more $R_{G1c}$; $R_{G1c}$ is selected from the group consisting of halogen, cyano, hydroxy, trifluoromethyl, oxo, —NH$_2$, —SO$_2$NH$_2$, —SONH$_2$, —CONH$_2$ or $R_{G1c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{G1d}$O-L-, $R_{G1d}$S-L-, $(R_{G1d})_2$N-L-, $R_{G1d}$—C(=O)-L-, $R_{G1d}$O—C(=O)-L-, $(R_{G1c})_2$N—C(=O)-L-, $R_{G1d}$—C (=O)N(R$_{G1e}$)-L-, R$_{G1d}$O—C(=O)N(R$_{G1e}$)-L-, (R$_{G1d}$)$_2$N—C(=O)N(R$_{G1e}$)-L-, R$_{G1d}$—C(=O)O-L-, (R$_{G1d}$)$_2$N—C(=O)O-L-, R$_{G1d}$—S(=O)$_2$-L-, (R$_{G1d}$)$_2$N—S(=O)$_2$-L-, R$_{G1d}$—S(=O)$_2$N(R$_{G1e}$)-L-, (R$_{G1d}$)$_2$N—S(=O)$_2$N(R$_{G1e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ R$_{G1d}$ and R$_{G1e}$ independently at each occurrence are selected from the group consisting of hydrogen or of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, heteroarylalkyl- and alkoxyalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ or in the case where two R$_{G1d}$s are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ G$_2$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, R$_{G2a}$O-L-, R$_{G2a}$S-L-, (R$_{G2a}$)$_2$N-L-, R$_{G2a}$—C(=O)-L-, R$_{G2a}$O—C(=O)-L-, (R$_{G2a}$)$_2$N—C(=O)-L-, R$_{G2a}$—C(=O)N(R$_{G2b}$)-L-, R$_{G2a}$O—C(=O)N(R$_{G2b}$)-L-, (R$_{G2a}$)$_2$N—C(=O)N(R$_{G2b}$)-L-, R$_{G2a}$—C(=O)O-L-, (R$_{G2a}$)$_2$N—C(=O)O-L-, R$_{G2a}$—S(=O)$_2$-L-, (R$_{G2a}$)$_2$N—S(=O)$_2$-L-, R$_{G2a}$—S(=O)$_2$N(R$_{G2b}$)-L-, (R$_{G2a}$)$_2$N—S(=O)$_2$N(R$_{G2b}$)-L-, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more R$_{G2c}$;

R$_{G2a}$ and R$_{G2b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more R$_{G2c}$;

or in the case where two R$_{G2a}$s are attached to the same N, they may together with the N atom to which they are attached form a heterocycle which may be optionally substituted with one or more R$_{G2c}$;

R$_{G2c}$ is selected from the group consisting of halogen, cyano, hydroxy, trifluoromethyl, oxo, —NH$_2$, —SO$_2$NH$_2$, —SONH$_2$, —CONH$_2$ or R$_{G2c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, R$_{G2d}$O-L-, R$_{G2d}$S-L-, (R$_{G2d}$)$_2$N-L-, R$_{G2d}$—C(=O)-L-, R$_{G2d}$—C(=O)-L-, (R$_{G2d}$)O$_2$N—C(=O)-L-, R$_{G2d}$—C(=O)N(R$_{G2e}$)-L-, R$_{G2d}$O—C(=O)N(R$_{G2e}$)-L-, (R$_{G2d}$)$_2$N—C(=O)N(R$_{G2e}$)-L-, R$_{G2d}$—C(=O)O-L-, (R$_{G2d}$)$_2$N—C(=O)O-L-, R$_{G2d}$—S(=O)$_2$-L-, (R$_{G2d}$)$_2$N—S(=O)$_2$-L-, R$_{G2d}$—S(=O)$_2$N(R$_{G2e}$)-L-, (R$_{G2d}$)$_2$N—S(=O)$_2$N(R$_{G2e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ R$_{G2d}$ and R$_{G2e}$ independently at each occurrence are selected from the group consisting of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ G$_3$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more R$_{G3c}$;

R$_{G3a}$ and R$_{G3b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more R$_{G3c}$;

or in the case where two R$_{G3a}$s are attached to the same N, they may together with the N atom to which they are attached form a heterocycle which may be optionally substituted with one or more R$_{G3c}$;

R$_{G3c}$ is selected from the group consisting of halogen, cyano, hydroxy, trifluoromethyl, oxo, —NH$_2$, —SO$_2$NH$_2$, —SONH$_2$, —CONH$_2$ or R$_{G3c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, R$_{G3d}$O-L-, R$_{G3d}$S-L-, (R$_{G3d}$)$_2$N-L-, R$_{G3d}$—C(=O)-L-, R$_{G3d}$O—C(=O)-L-, (R$_{G3d}$)$_2$N—C(=O)-L-, R$_{G3d}$—C(=O)N(R$_{G3e}$)-L-, R$_{G3d}$O—C(=O)N(R$_{G3e}$)-L-, (R$_{G3d}$)$_2$N—C(=O)N(R$_{G3e}$)-L-, R$_{G3d}$—C(=O)O-L-, (R$_{G3d}$)$_2$N—C(=O)O-L-, R$_{G3d}$—S(=O)$_2$-L-, (R$_{G3d}$)$_2$N—S(=O)$_2$-L-, R$_{G3d}$—S(=O)$_2$N(R$_{G3e}$)-L-, (R$_{G3d}$)$_2$N—S(=O)$_2$N(R$_{G3e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ R$_{G3d}$ and R$_{G3e}$ independently at each occurrence are selected from the group consisting of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ or in the case where two R$_{G3d}$s are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ L is a covalent bond or L is independently at each occurrence selected from the group consisting of alkyl-, heteroalkyl-, cycloalkyl-, heterocyclyl-, alkylcycloalkyl-, cycloalkylalkyl-, aryl and heteroaryl;

and pharmaceutically acceptable salts, prodrugs, hydrates, or solvates thereof;

In another aspect, the invention relates to pharmaceutical compositions comprising a compound of formula I or a pharmaceutically acceptable salt, hydrate, or solvate thereof together with a pharmaceutically acceptable vehicle or excipient.

In another aspect, the invention relates to pharmaceutical compositions comprising a compound of formula I or a pharmaceutically acceptable salt, hydrate, or solvate thereof further comprising another therapeutically active compound.

In one aspect, the invention relates to the compounds of general formula I for use—alone or in combination with one or more other pharmaceutically active compounds—in therapy.

In another aspect, the invention relates to the compounds of general formula I for use —alone or in combination with one or more other pharmaceutically active compounds—for treating diseases associated with the immune system, such as autoimmune diseases.

In another aspect, the invention relates to the compounds of general formula I for use —alone or in combination with one or more other pharmaceutically active compounds—in the prophylaxis, treatment or amelioration of skin diseases, such as psoriasis, rosacea, lupus, and other autoimmune diseases such as multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases.

In another aspect, the invention relates to a use of a compound of general formula I—alone or in combination with one or more other pharmaceutically active compounds—for the manufacture of a medicament for the prophylaxis, treatment and/or amelioration of diseases of the immune system, such as autoimmune diseases.

In another aspect, the invention relates to compounds according to formula I for use as an anti-inflammatory agent capable of modulating the activity of a protein tyrosin kinase of the Janus kinase family.

In another aspect, the invention relates to compounds according to formula I for use as an anti-inflammatory agent capable of modulating the activity of JAK1, JAK2, JAK3 or TYK2 protein tyrosine kinases.

In another aspect, the invention relates to compounds according to formula I for use in the treatment, amelioration or prophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-vs-host disease, or chronic inflammatory diseases such as osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

In another aspect, the invention relates to method of preventing, treating or ameliorating diseases of the immune system, such as autoimmune diseases, the method comprising administering an effective amount of a compound according to formula I to a patient in need thereof.

DETAILED DESCRIPTION OF THE INVENTION

Definitions

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12 or 1-10 e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

In the present context, the term "alkyl" is intended to indicate the radical obtained when one hydrogen atom is removed from a hydrocarbon. Said alkyl may be branched or straight-chained and comprises 1-20, preferably 1-10, such as 2-6, such as 3-4 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl, isopentyl, hexyl and isohexyl.

The term "alkylene" is intended to indicate a divalent saturated aliphatic hydrocarbyl group preferably having from 1 to 6 and more preferably 1 to 3 carbon atoms that are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—), and the like.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl and cyclooctyl.

The term "cycloalkylene" is intended to indicate a divalent cycloalkyl group as defined herein.

The term "alkenyl" is intended to indicate a hydrocarbon radical comprising 2-20 carbon atoms, preferably 2-10, in particular 2-6 carbon atoms, such as 2-4 carbon atoms, and having at least 1 and preferably from 1 to 2 sites of double bond unsaturation, e.g. ethenyl, allyl, propenyl, butenyl, pentenyl, nonenyl, or hexenyl. Included within this term are the cis and trans isomers or mixtures of these isomers.

The term "alkenylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of double bond unsaturation. This term is exemplified by groups such as ethenylene (—CH=CH—), propenylene (—CH=CHCH$_2$—), 1-butenylene (—CH=CHCH$_2$CH$_2$—) or 2-butenylene (—CH$_2$CH=CHCH$_2$—), and the like.

The term "cycloalkenyl" is intended to indicate mono-, di- tri- or tetraunsaturated non-aromatic cyclic hydrocarbon radicals, including polycyclic radicals, comprising 4-20 carbon atoms, typically comprising 4-10 carbon atoms, such as 4-8 carbon atoms, such as 4-6 carbon atoms, e.g., cyclobutenyl, cyclopentenyl or cyclohexenyl.

The term "cycloalkenylene" is intended to indicate a divalent cycloalkenyl group as defined herein.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "alkynylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of triple bond unsaturation. This term is exemplified by groups such as ethynylene (—CC—), propynylene (—CCCH$_2$—), 1-butynylene (—CCCH$_2$CH$_2$—) or 2-butynylene (—CH$_2$CCCH$_2$—), and the like.

The term "cycloalkynyl" is intended to indicate mono-, di-, tri- or tetra-unsaturated non-aromatic cyclic hydrocarbon radicals, including polycyclic radicals, comprising 4-20 carbon atoms, typically comprising 4-10 carbon atoms, such as 4-8 carbon atoms, such as 4-6 carbon atoms, and at least 1 and preferably from 1 to 2 sites of triple bond unsaturation, e.g., cyclobutynyl, cyclopentynyl or cyclohexynyl.

The term "cycloalkynylene" is intended to indicate a divalent cycloalkynyl group as defined herein.

The term "heterocyclic" and "heterocyclyl" is intended to indicate a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulphur and oxygen, wherein, in fused ring systems, one or more of the rings can be cycloalkyl, aryl, or heteroaryl, provided that the point of attachment is through the non-aromatic ring. In one embodiment, the nitrogen and/or sulphur atom(s) of the heterocyclic group are optionally oxidized to provide for the N-oxide, —S(O)—, or —SO$_2$-moieties. Examples include tetrahydrofuranyl, pyrrolidinyl, dioxolanyl, morpholinyl, piperidinyl, thiazolidinyl, imidazolidinyl, oxazolidinyl, 4,5-dihydroisoxazolyl, tetrahydropyranyl.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. tetrahydropyranol.

The term "heterocyclylalkyl" is intended to indicate a heterocyclyl group as defined herein connected via an alkyl group as defined herein, such as thiazolidinylmethyl, imidazolidinylmethyl, oxazolidinylmethyl, pyrrolidinylmethyl.

The term "aryl" is intended to indicate a radical of aromatic carbocyclic rings comprising 6-20 carbon atoms, such as 6-14 carbon atoms, preferably 6-12, such as 6-10 carbon atoms, in particular 5- or 6-membered rings, optionally fused carbocyclic rings with at least one aromatic ring, such as phenyl, naphthyl, biphenyl, anthracenyl, indenyl or indanyl.

The terms "arylalkyl" and "arylcycloalkyl" are intended to indicate an aryl group as defined herein connected via an alkyl or a cycloalkyl group as defined herein, respectively, such as benzyl, phenylethyl.

The term "heteroaryl" is intended to include radicals of heterocyclic aromatic rings, optionally fused with carbocyclic rings or heterocyclic rings, comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms or 1-2 heteroatoms selected from O, S and N, or optionally fused bicyclic rings with 1-4 heteroatoms, and wherein at least one ring is aromatic. Examples of heteroaryl include, but are not limited to, pyridyl, quinolyl, isoquinolyl, indolyl, tetrazolyl, furyl, thiazolyl, imidazolyl, imidazo[1,2-a]pyrimidinyl, pyrazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, imidazo[2,1-b]thiazolyl, benzimidazolyl, benzothiophenyl, benzofuranyl, 5,6-dihydro-4H-cyclopenta[b]thiophenyl, pyrrolyl, oxadiazolyl, 1,2,5-oxadiazolyl, 1,3,4-oxadiazolyl, thiadiazolyl, pyridazinyl or 1,2,5-thiadiazolyl The term "aryloxy" is intended to indicate groups —O-aryl, wherein aryl is as defined herein, including, by way of example, phenoxy, napthoxy, and the like.

The term "alkyloxy" is intended to indicate the groups —O-alkyl, —O-alkenyl-, and —O-alkynyl-, wherein alkyl, alkenyl and alkynyl are as defined herein.

The term "halogen" is intended to indicate a substituent from the 7$^{th}$ main group of the periodic table, preferably fluoro, chloro, bromo and iodo.

The term "amino" refers to the group —NH$_2$.

The term "aminoalkyl" is intended to indicate a radical of the formula -alkyl-NH$_2$, wherein alkyl represents alkylene, cycloalkylene as indicated above, e.g. aminoalkylene, aminocycloethylene etc.

The term "arylamino" is intended to indicate a radical of the formula —NR$_2$, wherein R is aryl as indicated above e.g. phenylamino.

The term "arylaminoalkyl" is intended to indicate an arylamino group as defined herein connected via an alkyl group as defined herein.

The term "alkylthio" is intended to indicate a radical of the formula —S—R, wherein R is alkyl as indicated above.

The term "oxo" is intended to indicate a substituent of the formula =O, wherein oxygen is connected via a double bond to for example a carbon atom.

The term "heteroalkyl" is intended to indicate an alkyl radical as indicated above, comprising 1-3 heteroatoms, preferably 1-2 heteroatoms, selected from O, N, or S, The term "cycloalkylalkyl" is intended to indicate a radical of the formula (cycloalkyl)-(alkyl)- wherein cycloalkyl and alkyl are as defined herein, such as cyclopentylmethyl.

The term "arylalkyloxy" is intended to indicate a radical of the formula (aryl)-(alkyl)-O— wherein aryl and alkyl are as defined herein.

The term "aryloxyalkyl" is intended to indicate a radical of the formula (aryl)-O-(alkyl)- wherein aryl and alkyl are as defined herein, such as phenyloxymethyl.

The term "aryloxyalkyloxy" is intended to indicate a radical of the formula (aryl)-0-(alkyl)-O— wherein aryl and alkyl are as defined herein.

The term "heteroaryloxy" is intended to indicate a radical of the formula (heteroaryl)-O— wherein heteroaryl is as defined herein.

The term "heteroarylalkyl" is intended to indicate a radical of the formula (heteroaryl)-(alkyl)- wherein heteroaryl and alkyl are as defined herein, such as thienylmethyl, thienylethyl, isoxazolylmethyl, thiazolylmethyl, imidazolylmethyl, pyridylmethyl, tetrazolylmethyl, oxadiazolylmethyl, pyrazolylmethyl.

The term "heteroarylalkyloxy" is intended to indicate a radical of the formula (heteroaryl)-(alkyl)-O— wherein heteroaryl and alkyl are as defined herein.

The term "heteroaryloxyalkyl" is intended to indicate a radical of the formula (heteroaryl)-O-(alkyl)- wherein heteroaryl and alkyl are as defined herein.

The term "heteroaryloxyalkyloxy" is intended to indicate a radical of the formula (heteroaryl)-O-(alkyl)-O— wherein heteroaryl and alkyl are as defined herein.

Unless indicated otherwise, the nomenclature of substituents that are not explicitly defined herein are arrived at by naming the terminal portion of the functionality followed by the adjacent functionality towards the point of attachment. For example, the group "arylalkyloxycarbonyl" refers to the group (aryl)-(alkyl)-O—C(O)—.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Unless indicated otherwise, the nomenclature of substituents that are not explicitly defined herein are arrived at by naming the terminal portion of the functionality followed by the adjacent functionality towards the point of attachment. For example, the group "arylalkyloxycarbonyl" refers to the group (aryl)-(alkyl)-O—C(O)—.

The term "JAK1" is used to indicate a protein tyrosine kinase of the JAK (Janus protein tyrosine kinase) family highly expressed in immune cells where it is essential for signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

The term "JAK2" is used to indicate a protein tyrosine kinase of the JAK (Janus protein tyrosine kinase) family highly expressed in immune cells where it is essential for signalling downstream of many cytokines and growth factors including the proinflammatory cytokines Epo, IFN-γ, IL-3, IL-5, and GM-CSF.

The term "JAK3" is used to indicate a protein tyrosine kinase of the JAK (Janus protein tyrosine kinase) family highly expressed in immune cells where it is essential for signalling downstream of many cytokines and growth factors including the proinflammatory cytokines IL-2, IL-4, IL-7, IL-9, IL-15 and IL-21.

The term "TYK2" is used to indicate a protein tyrosine kinase of the JAK (Janus protein tyrosine kinase) family, and TYK2 is implicated in type I interferons, IL-6, IL-10, IL-12 and IL-23 signaling.

Embodiments of Compounds of Formula I

An embodiment of the invention is the compound of general formula I,
wherein
m is 0, 1 or 2;
n is 2 or 4;
$R_1$ is selected from the group consisting of hydrogen, halogen, cyano, —$NH_2$, —$SO_2NH_2$, —$SONH_2$, and —$CONH_2$;

or $R_1$ is selected from the group consisting of alkyl-, heteroalkyl-, cycloalkyl-, heterocyclyl-, $R_{1a}O$—, $R_{1a}S$—, $(R_{1a})_2N$—, $R_{1b}$—C(=O)N($R_{1c}$)—, $R_{1b}O$—C(=O)N($R_{1c}$)—, $(R_{1b})_2N$—C(=O)N($R_{1c}$)—, $R_{1b}$—S(=O)$_2$N($R_{1c}$)— and $(R_{1b})_2N$—S(=O)$_2$N($R_{1c}$)— either of which may be optionally substituted with one or more $R_{1d}$;

$R_{1a}$ is hydrogen;

or $R_{1a}$ independently at each occurrence is selected from the group consisting of alkyl-, heteroalkyl-, cycloalkyl-, heterocyclyl- either of which may be optionally substituted with one or more $R_{1e}$;

or in the case where two $R_{1a}$s are attached to the same N, they may together with the N atom to which they are attached form a heterocycle which may be optionally substituted with one or more $R_{1e}$;

$R_{1b}$ and $R_{1c}$ independently at each occurrence are selected from the group consisting of hydrogen, alkyl-, heteroalkyl-, cycloalkyl-, heterocyclyl- either of which may be optionally substituted with one or more $R_{1e}$;

or in the case where two $R_{1b}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of halogen, cyano, hydroxy, oxo, —$NH_2$, —$SO_2NH_2$, —$CONH_2$, alkyl-, heteroalkyl-, cycloalkyl-, heterocyclyl-, $R_{1f}O$—, $R_{1f}S$—, $(R_{1f})_2N$—, $R_{1f}O$—C(=O)—, $(R_{1f})_2N$—C(=O)—, $R_{1f}$—C(=O)N($R_{1f}$)—, $R_{1f}O$—C(=O)N($R_{1f}$)—, $(R_{1f})_2N$—C(=O)N($R_{1f}$)—, $R_{1f}$—C(=O)O—, $(R_{1f})_2N$—C(=O)O—, $(R_{1f})_2N$—S(=O)$_2$—, $R_{1f}$—S(=O)$_2$N($R_{1f}$)—

$R_{1f}$ independently at each occurrence is selected from the group consisting of hydrogen, alkyl-, heteroalkyl-, cycloalkyl-, heterocyclyl-or in the case where two $R_{1f}$s are attached to the same N, they may together with the N atom to which they are attached form a heterocycle $R_2$ is independently at each occurrence a covalent bond or alkyl- or heteroalkyl- group, where any two $R_2$s are attached to the same C ring atom, and together with this C ring atom said two $R_2$s form a carbocycle or heterocycle, hence always forming a spirocyclic homopiperazine.

$R_3$ independently at each occurrence is selected from the group consisting of halogen, cyano, hydroxy, oxo, alkyl-, heteroalkyl-, cycloalkyl-, heterocyclyl-, $R_{3a}O$—, $R_{3a}S$—, $(R_{3a})_2N$—, $R_{3a}$—C(=O)—, $R_{3a}O$—C(=O)—, $(R_{3a})_2N$—C(=O)—, $R_{3a}$—C(=O)N($R_{3b}$)—, $R_{3a}O$—C(=O)N($R_{3b}$)—, $R_{3a}$—C(=O)O—, $(R_{3a})_2N$—C(=O)O—, $R_{3a}$—S(=O)$_2$—, $(R_{3a})_2N$—S(=O)$_2$—, $R_{3a}$—S(=O)$_2$N($R_{3b}$)—

$R_{3a}$ and $R_{3b}$ independently at each occurrence are selected from the group consisting of hydrogen, alkyl-, heteroalkyl-, cycloalkyl-, heterocyclyl-or in the case where two $R_{3a}$s are attached to the same N, they may together with the N atom to which they are attached form a heterocycle $R_4$ is selected from the group consisting of

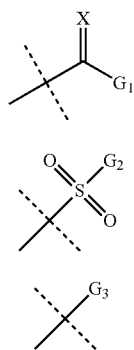

$R_{4a}$ $R_{4b}$ $R_{4c}$ wherein

X is O or S;

$G_1$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, $R_{G1a}$O-L-, $(R_{G1a})_2$N-L-, $R_{G1a}$—C(=O)-L-, $R_{G1a}$O—C(=O)-L-, $(R_{G1a})_2$N—C(=O)-L-, $R_{G1a}$—C(=O)N($R_{G1b}$)-L-, $R_{G1a}$O—C(=O)N($R_{G1b}$)-L-, $(R_{G1a})_2$N—C(=O)N($R_{G1b}$)-L-, $R_{G1a}$—C(=O)O-L, $(R_{G1a})_2$N—C(=O)O-L-, $R_{G1a}$—S(=O)_2-L-, $(R_{G1a})_2$N—S(=O)_2-L-, $R_{G1a}$—S(=O)_2N($R_{G1b}$)-L-, $(R_{G1a})_2$N—S(=O)_2N($R_{G1b}$)—, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more $R_{G1c}$;

$R_{G1a}$ and $R_{G1b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more $R_{G1c}$;

or in the case where two $R_{G1a}$s are attached to the same N, they may together with the N atom to which they are attached form a heterocycle which may be optionally substituted with one or more $R_{G1c}$;

$R_{G1c}$ is selected from the group consisting of halogen, cyano, hydroxy, trifluoromethyl, oxo, —NH_2, —SO_2NH_2, —SONH_2, —CONH_2 or $R_{G1c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{G1d}$O-L-, $R_{G1d}$S-L-, $(R_{G1d})_2$N-L-, $R_{G1d}$—C(=O)-L-, $R_{G1d}$O—C(=O)-L-, $(R_{G1d})_2$N—C(=O)-L-, $R_{G1d}$—C(=O)N($R_{G1e}$)-L-, $R_{G1d}$O—C(=O)N($R_{G1e}$)-L-, $(R_{G1d})_2$N—C(=O)N($R_{G1e}$)-L-, $R_{G1d}$—C(=O)O-L-, $(R_{G1d})_2$N—C(=O)O-L, $R_{G1d}$—S(=O)_2-L-, $(R_{G1d})_2$N—S(=O)_2-L-, $R_{G1d}$—S(=O)_2N($R_{G1e}$)-L-, $(R_{G1d})_2$N—S(=O)_2N($R_{G1e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-either of which may be optionally substituted with one or more substituents selected from the group consisting of halogen, cyano, hydroxy, trifluoromethyl, oxo, —NH_2, —SO_2NH_2, —SONH_2, —CONH_2

$R_{G1d}$ and $R_{G1e}$ independently at each occurrence are selected from the group consisting of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl-either of which may be optionally substituted with one or more substituents selected from the group consisting of halogen, cyano, hydroxy, trifluoromethyl, oxo, —NH_2, —SO_2NH_2, —SONH_2, —CONH_2 or in the case where two $R_{G1d}$s are attached to the same N, they may together with the N atom to which they are attached form a heterocycle which may be optionally substituted with one or more substituents selected from the group consisting of halogen, cyano, hydroxy, trifluoromethyl, oxo, —NH_2, —SO_2NH_2, —SONH_2, —CONH_2

$G_2$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, $R_{G2a}$O-L-, $R_{G2a}$S-L-, $(R_{G2a})_2$N-L-, $R_{G2a}$—C(=O)-L-, $R_{G2a}$O—C(=O)-L-, $(R_{G2a})_2$N—C(=O)-L-, $R_{G2a}$—C(=O)N($R_{G2a}R_{G2a}$O—C(=O)N($R_{G2b}$)-L-, $(R_{G2a})_2$N—C(=O)N($R_{G2b}$)-L-, $R_{G2a}$—C(=O)O-L-, $(R_{G2a})_2$N—C(=O)O-L-, $R_{G2a}$—S(=O)_2-L-, $(R_{G2a})_2$N—S(=O)_2-L-, $R_{G2a}$—S(=O)_2N($R_{G2b}$)-L-, $(R_{G2a})_2$N—S(=O)_2N($R_{G2b}$)-L-, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more $R_{G2c}$;

$R_{G2a}$ and $R_{G2b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more $R_{G2c}$;

or in the case where two $R_{G2a}$s are attached to the same N, they may together with the N atom to which they are attached form a heterocycle which may be optionally substituted with one or more $R_{G2c}$;

$R_{G2c}$ is selected from the group consisting of halogen, cyano, hydroxy, trifluoromethyl, oxo, —NH_2, —SO_2NH_2, —SONH_2, —CONH_2 or $R_{G2c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, $R_{G2d}$O-L-, $R_{G2d}$S-L-, $(R_{G2d})_2$N-L-, $R_{G2d}$—C(=O)-L-, $R_{G2d}$O—C(=O)-L-, $(R_{G2d})_2$N—C(=O)-L-, $R_{G2d}$—C(=O)N($R_{G2e}$)-L-, $R_{G2d}$O—C(=O)N($R_{G2e}$)-L-, $(R_{G2d})_2$N—C(=O)N($R_{G2e}$)-L-, $R_{G2d}$—C(=O)O-L-, $(R_{G2d})_2$N—C(=O)O-L-, $R_{G2d}$—S(=O)_2-L-, $(R_{G2d})_2$N—S(=O)_2-L-, $R_{G2d}$—S(=O)_2N($R_{G2e}$)-L-, $(R_{G2d})_2$N—S(=O)_2N($R_{G2e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl-either of which may be optionally substituted with one or more substituents selected from the group consisting of halogen, cyano, hydroxy, trifluoromethyl, oxo, —NH_2, —SO_2NH_2, —SONH_2, —CONH_2

$R_{G2d}$ and $R_{G2e}$ independently at each occurrence are selected from the group consisting of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ G$_3$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl-, aryl-, aryloxy-, arylalkyl-, arylalkyloxy-, aryloxyalkyl-, aryloxyalkyloxy-, heteroaryl-, heteroaryloxy-, heteroarylalkyl-, heteroarylalkyloxy-, heteroaryloxyalkyl-, heteroaryloxyalkyloxy- either of which may be optionally substituted with one or more R$_{G3c}$;

R$_{G3a}$ and R$_{G3b}$ independently at each occurrence are selected from the group consisting of hydrogen, alkyl-, heteroalkyl-, alkenyl-, alkynyl-, cycloalkyl-, heterocyclyl-, aryl- and heteroaryl- either of which may be optionally substituted with one or more R$_{G3c}$;

or in the case where two R$_{G3a}$s are attached to the same N, they may together with the N atom to which they are attached form a heterocycle which may be optionally substituted with one or more R$_{G3c}$;

R$_{G3c}$ is selected from the group consisting of halogen, cyano, hydroxy, trifluoromethyl, oxo, —NH$_2$, —SO$_2$NH$_2$, —SONH$_2$, —CONH$_2$ or R$_{G3c}$ is selected from the group consisting of alkyl-, heteroalkyl-, cycloalkyl-, alkenyl-, alkynyl-, alkenylalkyl-, alkynylalkyl-, cycloalkenyl-, cycloalkylalkyl-, cycloalkylalkenyl-, cycloalkylalkynyl-, cycloalkenylalkyl-, cycloalkenylalkenyl-, cycloalkenylalkynyl-, heterocyclyl-, heterocyclylalkyl-, heterocyclylalkenyl-, heterocyclylalkynyl-, R$_{G3d}$O-L-, R$_{G3d}$S-L-, (R$_{G3d}$)$_2$N-L-, R$_{G3d}$—C(=O)-L-, R$_{G3d}$O—C(=O)-L-, (R$_{G3d}$)$_2$N—C(=O)-L-, R$_{G3d}$—C(=O)N(R$_{G3e}$)-L-, R$_{G3d}$O—C(=O)N(R$_{G3e}$)-L-, (R$_{G3d}$)$_2$N—C(=O)N(R$_{G3d}$)-L-, R$_{G3d}$—C(=O)O-L-, (R$_{G3c}$)$_2$N—C(=O)O-L-, R$_{G3d}$—S(=O)$_2$-L-, (R$_{G3d}$)$_2$N—S(=O)$_2$-L-, R$_{G3d}$—S(=O)$_2$N(R$_{G3e}$)-L-, (R$_{G3d}$)$_2$N—S(=O)$_2$N(R$_{G3e}$)-L-, aryl-, arylalkyl-, arylcycloalkyl-, aryloxy-, aryloxyalkyl-, aryloxycycloalkyl-, heteroaryl-, heteroarylalkyl-, heteroarylcycloalkyl, heteroaryloxy-, heteroaryloxyalkyl-, and heteroaryloxycycloalkyl- either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ R$_{G3d}$ and R$_{G3e}$ independently at each occurrence are selected from the group consisting of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl-either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ or in the case where two R$_{G3d}$s are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ L is a covalent bond or L is independently at each occurrence selected from the group consisting of alkyl-, heteroalkyl-, cycloalkyl-, heterocyclyl-, alkylcycloalkyl-, cycloalkylalkyl-, aryl and heteroaryl;

and pharmaceutically acceptable salts, prodrugs, hydrates, or solvates thereof;

In an embodiment of the invention m is 0 or 1.

In an embodiment of the invention m is 0.

In another embodiment of the invention n is 2.

In another embodiment R$_1$ is selected from hydrogen, (R$_{1a}$)$_2$N—, R$_{1b}$—C(=O)N(R$_{1c}$)—, R$_{1b}$O—C(=O)N(R$_{1c}$)—, (R$_{1b}$)$_2$N—C(=O)N(R$_{1c}$)—, R$_{1b}$—S(=O)$_2$N(R$_{1c}$)— and (R$_{1b}$)$_2$N—S(=O)$_2$N(R$_{1c}$)—.

In another embodiment (R$_2$)$_n$ together with the C-ring carbon forms a spirocyclopropyl.

In another embodiment (R$_2$)$_n$ is selected so as to form a compound selected from

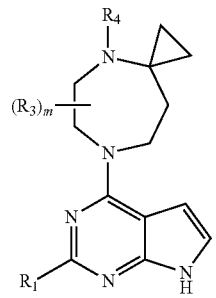
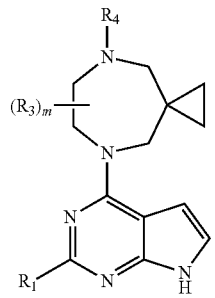

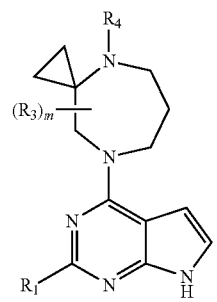
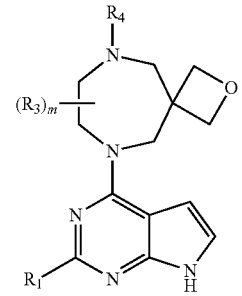

In another embodiment (R$_2$)$_n$ is selected so as to form a compound selected from

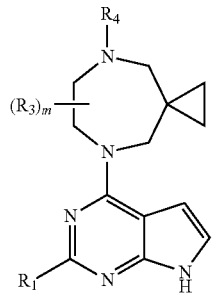
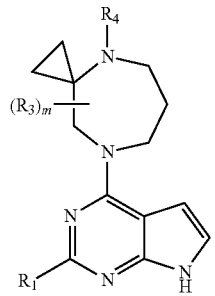

Another embodiment of the invention is a compound of general formula Ia

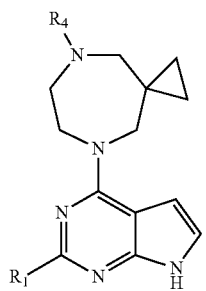

Ia wherein $R_1$ and $R_4$ are as defined above.

In another embodiment $R_3$ is independently selected from cyano, hydroxy, oxo, alkyl-, heteroalkyl-, $R_3O-$ or $R_{3a}S-$.

In another embodiment $R_1$ is hydrogen.

In another embodiment $R_4$ is selected from the group consisting of hydrogen,

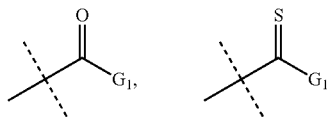

In another embodiment $R_4$ is

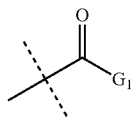

In another embodiment $G_1$ is selected from the group consisting of alkyl-, alkenyl-, cycloalkyl-, heterocyclyl-, $R_{G1a}$—C(=O)-L-, $(R_{G1a})_2$N—C(=O)-L-, aryl-, arylalkyl-, aryloxyalkyl-, heteroaryl-, heteroarylalkyl-, cycloalkylalkyl-, heterocyclylalkyl-, $(R_{G1a})_2$N-L-, either of which may be optionally substituted with one or more $R_{G1c}$.

In another embodiment $G_1$ is selected from the group consisting of methyl, ethyl, propyl, isopropyl phenyl, pyridyl, indolyl, tetrazolyl, furyl, thiazolyl, imidazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, benzothiophenyl, 5,6-dihydro-4H-cyclopenta[b]thiophenyl, pyrrolyl, oxadiazolyl, 1,2,5-oxadiazolyl, 1,3,4-oxadiazolyl, thiadiazolyl, pyridazinyl or 1,2,5-thiadiazolyl, piperidinyl, thiazolidinyl, imidazolidinyl, oxazolidinyl, 4,5-dihydroisoxazolyl, cyclopropyl, cyclobutyl, cyclopentyl, cyclohexyl, benzyl, thienylmethyl, phenylethyl, tetrahydropyranyl, thienylethyl, phenyloxymethyl thiazolidinylmethyl, imidazolidinylmethyl, oxazolidinylmethyl, pyrrolidinylmethyl, isoxazolylmethyl, thiazolylmethyl, imidazolylmethyl, cyclopentylmethyl, pyridylmethyl, tetrazolylmethyl, oxadiazolylmethyl and pyrazolylmethyl, (alkyl)$_2$-N—, phenyl-NH— either of which may be optionally substituted with one or more $R_{G1c}$.

In another embodiment each $R_{G1c}$ is independently selected from the group consisting of alkyl, heteroaryl, halogen, oxo, cyano, hydroxy, —SO$_2$NH$_2$, —NH$_2$, $R_{G1d}$O-L-, $(R_{G1d})_2$N—S(=O)$_2$-L-, $R_{G1d}$—S(=O)$_2$-L-, $(R_{G1d})_2$N—S(=O)$_2$-L-.

In another embodiment each $R_{G1c}$ is independently selected from the group consisting of cyano, methyl-O—, methyl, ethyl, propyl, isopropyl, butyl, oxo, —SO$_2$NH$_2$, —NH$_2$, methyl-NH—S(=O)$_2$—, (methyl)$_2$-N—S(=O)$_2$—, fluoro, chloro, bromo, iodo, methyl-S(=O)$_2$—, tetrazolyl, hydroxyl.

In another embodiment each $R_{G1c}$ is independently selected from the group consisting of cyano, methyl-O—, methyl, oxo, —SO$_2$NH$_2$, methyl-NH—S(=O)$_2$—, fluoro, chloro, methyl-S(=O)$_2$—.

In another embodiment each $R_{G1d}$ is independently selected from the group consisting of hydrogen, alkyl-, cyclolalkylalkyl-, heterocyclylalkyl-, wherein said alkyl-, cyclolalkylalkyl-, heterocyclylalkyl- may be optionally substituted with one or more substituents selected from the group consisting of halogen, cyano and —SO$_2$NH$_2$.

In another embodiment the compound of general formula I is selected from:

4-Oxo-4-[8-(7H-pyrrolo[2,3-d]pyrimidin-4-yl)-5,8-diazaspiro[2.6]non-5-yl]butyronitrile
(2,3-Dimethoxyphenyl)-[8-(7H-pyrrolo[2,3-d]pyrimidin-4-yl)5,8-diazaspiro[2.6]non-5-yl]methanone
3-[8-(7H-pyrrolo[2,3-d]pyrimidin-4-yl)-5,8-diazaspiro[2.6]nonane-5-carbonyl]benzonitrile
(2-Methoxypyridin-3-yl)-[8-(7H-pyrrolo[2,3-d]pyrimidin-4-yl)-5,8-diazaspiro[2.6]non-5-yl]methanone
3-Oxo-3-[8-(7H-pyrrolo[2,3-d]pyrimidin-4-yl)-5,8-diazaspiro[2.6]non-5-yl]propionitrile
1-{4-[8-(7H-pyrrolo[2,3-d]pyrimidin-4-yl)-5,8-diazaspiro[2.6]nonane-5-carbonyl]piperidin-1-yl}ethanone
2-[8-(7H-pyrrolo[2,3-d]pyrimidin-4-yl)-5,8-diazaspiro[2.6]nonane-5-carbonyl]benzonitrile
2-[8-(7H-pyrrolo[2,3-d]pyrimidin-4-yl)-5,8-diazaspiro[2.6]nonane-5-carbonyl]-1H-indole-5-carbonitrile
3-{2-Oxo-2-[8-(7H-pyrrolo[2,3-d]pyrimidin-4-yl)-5,8-diazaspiro[2.6]non-5-yl]ethyl}benzonitrile
4-{2-Oxo-2-[8-(7H-pyrrolo[2,3-d]pyrimidin-4-yl)-5,8-diazaspiro[2.6]non-5-yl]ethyl}benzonitrile
2,2-Dimethyl-3-oxo-3-[8-(7H-pyrrolo[2,3-d]pyrimidin-4-yl)-5,8-diazaspiro[2.6]non-5-yl]propionitrile
{4-[8-(7H-pyrrolo[2,3-d]pyrimidin-4-yl)-5,8-diazaspiro[2.6]nonane-5-carbonyl]phenyl}acetonitrile
4-[1,1-difluoro-2-oxo-2-[5-(7H-pyrrolo[2,3-d]pyrimidin-4-yl)-5,8-diazaspiro[2.6]nonan-8-yl]ethyl]benzonitrile
2-[3-[5-(7H-pyrrolo[2,3-d]pyrimidin-4-yl)-5,8-diazaspiro[2.6]nonane-8-carbonyl]phenoxy]acetonitrile
2-[4-[5-(7H-pyrrolo[2,3-d]pyrimidin-4-yl)-5,8-diazaspiro[2.6]nonane-8-carbonyl]phenoxy]acetonitrile
2-[4-[2-oxo-2-[5-(7H-pyrrolo[2,3-d]pyrimidin-4-yl)-5,8-diazaspiro[2.6]nonan-8-yl]ethyl]phenoxy]acetonitrile
2-[3-[2-oxo-2-[5-(7H-pyrrolo[2,3-d]pyrimidin-4-yl)-5,8-diazaspiro[2.6]nonan-8-yl]ethyl]phenoxy]acetonitrile
benzothiophen-2-yl-[5-(7H-pyrrolo[2,3-d]pyrimidin-4-yl)-5,8-diazaspiro[2.6]nonan-8-yl]methanone
5-[5-(7H-pyrrolo[2,3-d]pyrimidin-4-yl)-5,8-diazaspiro[2.6]nonane-8-carbonyl]thiophene-3-carbonitrile
4-[2-oxo-2-[5-(7H-pyrrolo[2,3-d]pyrimidin-4-yl)-5,8-diazaspiro[2.6]nonan-8-yl]ethyl]benzenesulfonamide
5,6-dihydro-4H-cyclopenta[b]thiophen-2-yl-[5-(7H-pyrrolo[2,3-d]pyrimidin-4-yl)-5,8-diazaspiro[2.6]nonan-8-yl]methanone
(4-methoxy-2-thienyl)-[5-(7H-pyrrolo[2,3-d]pyrimidin-4-yl)-5,8-diazaspiro[2.6]nonan-8-yl]methanone
N,4-dimethyl-5-[5-(7H-pyrrolo[2,3-d]pyrimidin-4-yl)-5,8-diazaspiro[2.6]nonane-8-carbonyl]thiophene-3-sulfonamide 2-methyl-5-[5-(7H-pyrrolo[2,3-d]pyrimidin-4-yl)-5,8-diazaspiro[2.6]nonane-8-carbonyl]thiophene-3-sulfonamide
4-methyl-5-[5-(7H-pyrrolo[2,3-d]pyrimidin-4-yl)-5,8-diazaspiro[2.6]nonane-8-carbonyl]thiophene-3-sulfonamide
N,2-dimethyl-5-[5-(7H-pyrrolo[2,3-d]pyrimidin-4-yl)-5,8-diazaspiro[2.6]nonane-8-carbonyl]thiophene-3-sulfonamide
5-[5-(7H-pyrrolo[2,3-d]pyrimidin-4-yl)-5,8-diazaspiro[2.6]nonane-8-carbonyl]thiophene-3-sulfonamide
N-methyl-5-[5-(7H-pyrrolo[2,3-d]pyrimidin-4-yl)-5,8-diazaspiro[2.6]nonane-8-carbonyl]thiophene-3-sulfonamide
2-methyl-4-[5-(7H-pyrrolo[2,3-d]pyrimidin-4-yl)-5,8-diazaspiro[2.6]nonane-8-carbonyl]benzenesulfonamide
1-[5-(7H-pyrrolo[2,3-d]pyrimidin-4-yl)-5,8-diazaspiro[2.6]nonan-8-yl]-2-(2-thienyl)ethanone
4-[5-(7H-pyrrolo[2,3-d]pyrimidin-4-yl)-5,8-diazaspiro[2.6]nonane-8-carbonyl]benzenesulfonamide
2-chloro-4-[5-(7H-pyrrolo[2,3-d]pyrimidin-4-yl)-5,8-diazaspiro[2.6]nonane-8-carbonyl]benzenesulfonamide
N,N-dimethyl-4-[5-(7H-pyrrolo[2,3-d]pyrimidin-4-yl)-5,8-diazaspiro[2.6]nonane-8-carbonyl]benzenesulfonamide
4-[3-oxo-3-[5-(7H-pyrrolo[2,3-d]pyrimidin-4-yl)-5,8-diazaspiro[2.6]nonan-8-yl]propyl]benzenesulfonamide
1-methyl-5-[5-(7H-pyrrolo[2,3-d]pyrimidin-4-yl)-5,8-diazaspiro[2.6]nonane-8-carbonyl]pyrrole-2-sulfonamide
1-methyl-5-[5-(7H-pyrrolo[2,3-d]pyrimidin-4-yl)-5,8-diazaspiro[2.6]nonane-8-carbonyl]pyrrole-3-sulfonamide
5-[5-(7H-pyrrolo[2,3-d]pyrimidin-4-yl)-5,8-diazaspiro[2.6]nonane-8-carbonyl]furan-2-sulfonamide
2-methyl-5-[5-(7H-pyrrolo[2,3-d]pyrimidin-4-yl)-5,8-diazaspiro[2.6]nonane-8-carbonyl]benzenesulfonamide
4-oxo-4-[5-(7H-pyrrolo[2,3-d]pyrimidin-4-yl)-5,8-diazaspiro[2.6]nonan-8-yl]butane-1-sulfonamide
1-[5-(7H-pyrrolo[2,3-d]pyrimidin-4-yl)-5,8-diazaspiro[2.6]nonane-8-carbonyl]cyclopentanecarbonitrile
4-[5-(7H-pyrrolo[2,3-d]pyrimidin-4-yl)-5,8-diazaspiro[2.6]nonane-8-carbonyl]tetrahydropyran-4-carbonitrile
2-fluoro-4-[5-(7H-pyrrolo[2,3-d]pyrimidin-4-yl)-5,8-diazaspiro[2.6]nonane-8-carbonyl]benzonitrile
(3,5-dimethoxyphenyl)-[5-(7H-pyrrolo[2,3-d]pyrimidin-4-yl)-5,8-diazaspiro[2.6]nonan-8-yl]methanone
1-[6-(7H-pyrrolo[2,3-d]pyrimidin-4-yl)-6,9-diazaspiro[2.6]nonane-9-carbonyl]cyclopropanecarbonitrile
4,4,4-trifluoro-1-[6-(7H-pyrrolo[2,3-d]pyrimidin-4-yl)-6,9-diazaspiro[2.6]nonan-9-yl]butan-1-one
benzothiophen-2-yl-[6-(7H-pyrrolo[2,3-d]pyrimidin-4-yl)-6,9-diazaspiro[2.6]nonan-9-yl]methanone
3-[2-oxo-2-[6-(7H-pyrrolo[2,3-d]pyrimidin-4-yl)-6,9-diazaspiro[2.6]nonan-9-yl]ethyl]benzonitrile
2-[2-[6-(7H-pyrrolo[2,3-d]pyrimidin-4-yl)-6,9-diazaspiro[2.6]nonane-9-carbonyl]phenyl]acetonitrile
4-oxo-4-[6-(7H-pyrrolo[2,3-d]pyrimidin-4-yl)-6,9-diazaspiro[2.6]nonan-9-yl]butanenitrile
4-[5-(7H-pyrrolo[2,3-d]pyrimidin-4-yl)-5,8-diazaspiro[2.6]nonane-8-carbonyl]-N-[2-(2-thienyl)ethyl]benzenesulfonamide
5-[5-(7H-pyrrolo[2,3-d]pyrimidin-4-yl)-5,8-diazaspiro[2.6]nonane-8-carbonyl]thiophene-2-carbonitrile
3-methoxy-4-[5-(7H-pyrrolo[2,3-d]pyrimidin-4-yl)-5,8-diazaspiro[2.6]nonane-8-carbonyl]benzenesulfonamide
2-methoxy-4-[5-(7H-pyrrolo[2,3-d]pyrimidin-4-yl)-5,8-diazaspiro[2.6]nonane-8-carbonyl]benzenesulfonamide
4-[(E)-3-oxo-3-[5-(7H-pyrrolo[2,3-d]pyrimidin-4-yl)-5,8-diazaspiro[2.6]nonan-8-yl]prop-1-enyl]benzenesulfonamide
2-(4-methylsulfonylphenyl)-1-[5-(7H-pyrrolo[2,3-d]pyrimidin-4-yl)-5,8-diazaspiro[2.6]nonan-8-yl]ethanone
4-[5-(7H-pyrrolo[2,3-d]pyrimidin-4-yl)-5,9-diazaspiro[2.6]nonane-9-carbonyl]benzonitrile
3-[(5-(7H-pyrrolo[2,3-d]pyrimidin-4-yl)-5,9-diazaspiro[2.6]nonane-9-carbonyl]benzonitrile
3-[2-oxo-2-[5-(7H-pyrrolo[2,3-d]pyrimidin-4-yl)-5,9-diazaspiro[2.6]nonan-9-yl]ethyl]benzonitrile
4-[2-oxo-2-[5-(7H-pyrrolo[2,3-d]pyrimidin-4-yl)-5,9-diazaspiro[2.6]nonan-9-yl]ethyl]benzonitrile
1-[5-(7H-pyrrolo[2,3-d]pyrimidin-4-yl)-5,9-diazaspiro[2.6]nonane-9-carbonyl]cyclopropanecarbonitrile
4-oxo-4-[5-(7H-pyrrolo[2,3-d]pyrimidin-4-yl)-5,9-diazaspiro[2.6]nonan-9-yl]butanenitrile
4-[5-(7H-pyrrolo[2,3-d]pyrimidin-4-yl)-5,8-diazaspiro[2.6]nonane-8-carbonyl]benzonitrile
4-[2-oxo-2-[5-(7H-pyrrolo[2,3-d]pyrimidin-4-yl)-5,8-diazaspiro[2.6]nonan-8-yl]ethoxy]benzenesulfonamide
2-oxo-2-[5-(7H-pyrrolo[2,3-d]pyrimidin-4-yl)-5,8-diazaspiro[2.6]nonan-8-yl]-N-(4-sulfamoylphenyl)acetamide
4-[5-[5-(7H-pyrrolo[2,3-d]pyrimidin-4-yl)-5,8-diazaspiro[2.6]nonane-8-carbonyl]-2-furyl]benzenesulfonamide
2-(4-iodophenyl)-1-[5-(7H-pyrrolo[2,3-d]pyrimidin-4-yl)-5,8-diazaspiro[2.6]nonan-8-yl]ethanone
4-(9-benzyl-5,9-diazaspiro[2.6]nonan-5-yl)-7H-pyrrolo[2,3-d]pyrimidin-2-amine
4-(5-benzyl-5,8-diazaspiro[2.6]nonan-8-yl)-7H-pyrrolo[2,3-d]pyrimidin-2-amine
N-(2-cyanoethyl)-4-[5-(7H-pyrrolo[2,3-d]pyrimidin-4-yl)-5,8-diazaspiro[2.6]nonane-8-carbonyl]benzenesulfonamide
4-[5-(7H-pyrrolo[2,3-d]pyrimidin-4-yl)-5,8-diazaspiro[2.6]nonane-8-carbonyl]-N-(tetrahydrofuran-2-ylmethyl)benzenesulfonamide
3-methyl-4-[5-(7H-pyrrolo[2,3-d]pyrimidin-4-yl)-5,8-diazaspiro[2.6]nonane-8-carbonyl]benzenesulfonamide
N-methyl-4-[5-(7H-pyrrolo[2,3-d]pyrimidin-4-yl)-5,8-diazaspiro[2.6]nonane-8-carbonyl]benzenesulfonamide
3-[5-(7H-pyrrolo[2,3-d]pyrimidin-4-yl)-5,8-diazaspiro[2.6]nonane-8-carbonyl]benzenesulfonamide
N-(2-methoxyethyl)-4-[5-(7H-pyrrolo[2,3-d]pyrimidin-4-yl)-5,8-diazaspiro[2.6]nonane-8-carbonyl]benzenesulfonamide
4-[5-(7H-pyrrolo[2,3-d]pyrimidin-4-yl)-5,8-diazaspiro[2.6]nonane-8-carbonyl]thiophene-2-sulfonamide
5-[2-oxo-2-[5-(7H-pyrrolo[2,3-d]pyrimidin-4-yl)-5,8-diazaspiro[2.6]nonan-8-yl]ethyl]thiophene-2-sulfonamide
1-[5-(7H-pyrrolo[2,3-d]pyrimidin-4-yl)-5,8-diazaspiro[2.6]nonan-8-yl]-2-[4-(2H-tetrazol-5-yl)phenyl]ethanone
(4-propyl-2-thienyl)-[5-(7H-pyrrolo[2,3-d]pyrimidin-4-yl)-5,8-diazaspiro[2.6]nonan-8-yl]methanone
3-[2-oxo-2-[5-(7H-pyrrolo[2,3-d]pyrimidin-4-yl)-5,8-diazaspiro[2.6]nonan-8-yl]ethyl]thiazolidine-2,4-dione
1-methyl-3-[2-oxo-2-[5-(7H-pyrrolo[2,3-d]pyrimidin-4-yl)-5,8-diazaspiro[2.6]nonan-8-yl]ethyl]imidazolidine-2,4-dione
3-[2-oxo-2-[5-(7H-pyrrolo[2,3-d]pyrimidin-4-yl)-5,8-diazaspiro[2.6]nonan-8-yl]ethyl]oxazolidin-2-one
1-methyl-3-[2-oxo-2-[5-(7H-pyrrolo[2,3-d]pyrimidin-4-yl)-5,8-diazaspiro[2.6]nonan-8-yl]ethyl]imidazolidin-2-one
1-methyl-3-[2-oxo-2-[5-(7H-pyrrolo[2,3-d]pyrimidin-4-yl)-5,9-diazaspiro[2.6]nonan-9-yl]ethyl]imidazolidin-2-one
1-[2-oxo-2-[5-(7H-pyrrolo[2,3-d]pyrimidin-4-yl)-5,9-diazaspiro[2.6]nonan-9-yl]ethyl]pyrrolidine-2,5-dione
3-[2-oxo-2-[5-(7H-pyrrolo[2,3-d]pyrimidin-4-yl)-5,9-diazaspiro[2.6]nonan-9-yl]ethyl]thiazolidine-2,4-dione
3-[2-oxo-2-[5-(7H-pyrrolo[2,3-d]pyrimidin-4-yl)-5,9-diazaspiro[2.6]nonan-9-yl]ethyl]oxazolidin-2-one 2-(5-methylisoxazol-3-yl)-1-[5-(7H-pyrrolo[2,3-d]pyrimidin-4-yl)-5,8-diazaspiro[2.6]nonan-8-yl]ethanone 1-[5-(7H-pyrrolo[2,3-d]pyrimidin-4-yl)-5,8-diazaspiro[2.6]nonan-8-yl]-2-thiazol-4-yl-ethanone 2-(1H-imidazol-5-yl)-1-[5-(7H-pyrrolo[2,3-d]pyrimidin-4-yl)-5,8-diazaspiro[2.6]nonan-8-yl]ethanone N-phenyl-5-(7H-pyrrolo[2,3-d]pyrimidin-4-yl)-5,9-diazaspiro[2.6]nonane-9-carboxamide N-phenyl-5-(7H-pyrrolo[2,3-d]pyrimidin-4-yl)-5,9-diazaspiro[2.6]nonane-9-carbothioamide 2-cyclopentyl-1-[5-(7H-pyrrolo[2,3-d]pyrimidin-4-yl)-5,9-diazaspiro[2.6]nonan-9-yl]ethanone cyclohexyl-[5-(7H-pyrrolo[2,3-d]pyrimidin-4-yl)-5,9-diazaspiro[2.6]nonan-9-yl]methanone 4-[9-(p-tolylsulfonyl)-5,9-diazaspiro[2.6]nonan-5-yl]-7H-pyrrolo[2,3-d]pyrimidine 2-cyclopentyl-1-[5-(7H-pyrrolo[2,3-d]pyrimidin-4-yl)-5,9-diazaspiro[2.6]nonan-9-yl]ethanethione 4-[8-(p-tolylsulfonyl)-5,8-diazaspiro[2.6]nonan-5-yl]-7H-pyrrolo[2,3-d]pyrimidine 4-(8-butylsulfonyl-5,8-diazaspiro[2.6]nonan-5-yl)-7H-pyrrolo[2,3-d]pyrimidine 4-[7-methyl-8-(p-tolylsulfonyl)-5,8-diazaspiro[2.6]nonan-5-yl]-7H-pyrrolo[2,3-d]pyrimidine 7-methyl-N-phenyl-5-(7H-pyrrolo[2,3-d]pyrimidin-4-yl)-5,8-diazaspiro[2.6]nonane-8-carboxamide 4-[2-oxo-2-[5-(7H-pyrrolo[2,3-d]pyrimidin-4-yl)-5,8-diazaspiro[2.6]nonan-8-yl]acetyl]benzonitrile 2-[5-(7H-pyrrolo[2,3-d]pyrimidin-4-yl)-5,8-diazaspiro[2.6]nonane-8-carbonyl]-1H-indole-5-sulfonamide N-[4-[5-(7H-pyrrolo[2,3-d]pyrimidin-4-yl)-5,8-diazaspiro[2.6]nonane-8-carbonyl]phenyl]methanesulfonamide N-(2-cyanoethyl)-N-methyl-5-(7H-pyrrolo[2,3-d]pyrimidin-4-yl)-5,8-diazaspiro[2.6]nonane-8-sulfonamide N,N-diethyl-5-(7H-pyrrolo[2,3-d]pyrimidin-4-yl)-5,8-diazaspiro[2.6]nonane-8-sulfonamide N-cyclohexyl-N-methyl-5-(7H-pyrrolo[2,3-d]pyrimidin-4-yl)-5,8-diazaspiro[2.6]nonane-8-sulfonamide 4-[2-oxo-2-[5-(7H-pyrrolo[2,3-d]pyrimidin-4-yl)-5,8-diazaspiro[2.6]nonan-8-yl]ethoxy]benzonitrile 4-(5-benzyl-5,8-diazaspiro[2.6]nonan-8-yl)-7H-pyrrolo[2,3-d]pyrimidine (5-methylisoxazol-4-yl)-[5-(7H-pyrrolo[2,3-d]pyrimidin-4-yl)-5,8-diazaspiro[2.6]nonan-8-yl]methanone o-tolyl-[5-(7H-pyrrolo[2,3-d]pyrimidin-4-yl)-5,8-diazaspiro[2.6]nonan-8-yl]methanone o-tolyl-[5-(7H-pyrrolo[2,3-d]pyrimidin-4-yl)-5,9-diazaspiro[2.6]nonan-9-yl]methanone (2-fluorophenyl)-[5-(7H-pyrrolo[2,3-d]pyrimidin-4-yl)-5,8-diazaspiro[2.6]nonan-8-yl]methanone (2-fluorophenyl)-[5-(7H-pyrrolo[2,3-d]pyrimidin-4-yl)-5,9-diazaspiro[2.6]nonan-9-yl]methanone (4-fluorophenyl)-[5-(7H-pyrrolo[2,3-d]pyrimidin-4-yl)-5,8-diazaspiro[2.6]nonan-8-yl]methanone (4-fluorophenyl)-[5-(7H-pyrrolo[2,3-d]pyrimidin-4-yl)-5,9-diazaspiro[2.6]nonan-9-yl]methanone 4-[3-oxo-3-[5-(7H-pyrrolo[2,3-d]pyrimidin-4-yl)-5,8-diazaspiro[2.6]nonan-8-yl]propyl]benzonitrile 3-[3-oxo-3-[5-(7H-pyrrolo[2,3-d]pyrimidin-4-yl)-5,8-diazaspiro[2.6]nonan-8-yl]propyl]benzonitrile 4-[(E)-3-oxo-3-[5-(7H-pyrrolo[2,3-d]pyrimidin-4-yl)-5,8-diazaspiro[2.6]nonan-8-yl]prop-1-enyl]benzonitrile 3-[2-oxo-2-[5-(7H-pyrrolo[2,3-d]pyrimidin-4-yl)-5,8-diazaspiro[2.6]nonan-8-yl]ethoxy]benzonitrile 5-[5-(7H-pyrrolo[2,3-d]pyrimidin-4-yl)-5,9-diazaspiro[2.6]nonane-9-carbonyl]thiophene-3-carbonitrile 5-[5-(7H-pyrrolo[2,3-d]pyrimidin-4-yl)-5,9-diazaspiro[2.6]nonane-9-carbonyl]thiophene-2-carbonitrile 1,2,5-oxadiazol-3-yl-[5-(7H-pyrrolo[2,3-d]pyrimidin-4-yl)-5,9-diazaspiro[2.6]nonan-9-yl]methanone (3-methylisoxazol-5-yl)-[5-(7H-pyrrolo[2,3-d]pyrimidin-4-yl)-5,9-diazaspiro[2.6]nonan-9-yl]methanone (3-ethyl-4,5-dihydroisoxazol-5-yl)-[5-(7H-pyrrolo[2,3-d]pyrimidin-4-yl)-5,9-diazaspiro[2.6]nonan-9-yl]methanone 1-[5-(7H-pyrrolo[2,3-d]pyrimidin-4-yl)-5,9-diazaspiro[2.6]nonan-9-yl]prop-2-en-1-one (rac)-2-(3-ethyl-2,5-dihydroisoxazol-5-yl)-1-[5-(7H-pyrrolo[2,3-d]pyrimidin-4-yl)-5,8-diazaspiro[2.5]nonan-8-yl]ethanone.

(3-propyl-4,5-dihydroisoxazol-5-yl)-[5-(7H-pyrrolo[2,3-d]pyrimidin-4-yl)-5,9-diazaspiro[2.6]nonan-9-yl]methanone 2-(4-chlorophenyl)-1-[5-(7H-pyrrolo[2,3-d]pyrimidin-4-yl)-5,8-diazaspiro[2.6]nonan-8-yl]ethanone 2-(4-chlorophenyl)-[5-(7H-pyrrolo[2,3-d]pyrimidin-4-yl)-5,9-diazaspiro[2.6]nonan-9-yl]ethanone 3-pyridyl-[5-(7H-pyrrolo[2,3-d]pyrimidin-4-yl)-5,8-diazaspiro[2.6]nonan-8-yl]methanone 3-pyridyl-[5-(7H-pyrrolo[2,3-d]pyrimidin-4-yl)-5,9-diazaspiro[2.6]nonan-9-yl]methanone 4-pyridyl-[5-(7H-pyrrolo[2,3-d]pyrimidin-4-yl)-5,8-diazaspiro[2.6]nonan-8-yl]methanone 4-pyridyl-[5-(7H-pyrrolo[2,3-d]pyrimidin-4-yl)-5,9-diazaspiro[2.6]nonan-9-yl]methanone (6-hydroxy-3-pyridyl)-[5-(7H-pyrrolo[2,3-d]pyrimidin-4-yl)-5,8-diazaspiro[2.6]nonan-8-yl]methanone (6-hydroxy-3-pyridyl)-[5-(7H-pyrrolo[2,3-d]pyrimidin-4-yl)-5,9-diazaspiro[2.6]nonan-9-yl]methanone 1H-imidazol-4-yl-[5-(7H-pyrrolo[2,3-d]pyrimidin-4-yl)-5,8-diazaspiro[2.6]nonan-8-yl]methanone 1H-imidazol-4-yl-[5-(7H-pyrrolo[2,3-d]pyrimidin-4-yl)-5,9-diazaspiro[2.6]nonan-9-yl]methanone (2-methyl-3-pyridyl)-[5-(7H-pyrrolo[2,3-d]pyrimidin-4-yl)-5,8-diazaspiro[2.6]nonan-8-yl]methanone (2-methyl-3-pyridyl)-[5-(7H-pyrrolo[2,3-d]pyrimidin-4-yl)-5,9-diazaspiro[2.6]nonan-9-yl]methanone (3-methyl-4-pyridyl)-[5-(7H-pyrrolo[2,3-d]pyrimidin-4-yl)-5,8-diazaspiro[2.6]nonan-8-yl]methanone (3-methyl-4-pyridyl)-[5-(7H-pyrrolo[2,3-d]pyrimidin-4-yl)-5,9-diazaspiro[2.6]nonan-9-yl]methanone pyridazin-4-yl-[5-(7H-pyrrolo[2,3-d]pyrimidin-4-yl)-5,8-diazaspiro[2.6]nonan-8-yl]methanone 2-(2,4-dimethylthiazol-5-yl)-1-[5-(7H-pyrrolo[2,3-d]pyrimidin-4-yl)-5,9-diazaspiro[2.6]nonan-9-yl]ethanone (5-methylisoxazol-3-yl)-[5-(7H-pyrrolo[2,3-d]pyrimidin-4-yl)-5,9-diazaspiro[2.6]nonan-9-yl]methanone

[5-(7H-pyrrolo[2,3-d]pyrimidin-4-yl)-5,9-diazaspiro[2.6]nonan-9-yl]-(thiadiazol-4-yl)methanone (2,5-dimethylpyrazol-3-yl)-[5-(7H-pyrrolo[2,3-d]pyrimidin-4-yl)-5,8-diazaspiro[2.6]nonan-8-yl]methanone (3-methylimidazol-4-yl)-[5-(7H-pyrrolo[2,3-d]pyrimidin-4-yl)-5,8-diazaspiro[2.6]nonan-8-yl]methanone (3-methylimidazol-4-yl)-[5-(7H-pyrrolo[2,3-d]pyrimidin-4-yl)-5,9-diazaspiro[2.6]nonan-9-yl]methanone (4-methylthiadiazol-5-yl)-[5-(7H-pyrrolo[2,3-d]pyrimidin-4-yl)-5,8-diazaspiro[2.6]nonan-8-yl]methanone (4-methylthiadiazol-5-yl)-[5-(7H-pyrrolo[2,3-d]pyrimidin-4-yl)-5,9-diazaspiro[2.6]nonan-9-yl]methanone (5-methyl-1H-pyrazol-3-yl)-[5-(7H-pyrrolo[2,3-d]pyrimidin-4-yl)-5,8-diazaspiro[2.6]nonan-8-yl]methanone (5-methyl-1H-pyrazol-3-yl)-[5-(7H-pyrrolo[2,3-d]pyrimidin-4-yl)-5,9-diazaspiro[2.6]nonan-9-yl]methanone (4-methyl-3-pyridyl)-[5-(7H-pyrrolo[2,3-d]pyrimidin-4-yl)-5,8-diazaspiro[2.6]nonan-8-yl]methanone
(4-methyl-3-pyridyl)-[5-(7H-pyrrolo[2,3-d]pyrimidin-4-yl)-5,9-diazaspiro[2.6]nonan-9-yl]methanone
isoxazol-3-yl-[5-(7H-pyrrolo[2,3-d]pyrimidin-4-yl)-5,8-diazaspiro[2.6]nonan-8-yl]methanone
isoxazol-3-yl-[5-(7H-pyrrolo[2,3-d]pyrimidin-4-yl)-5,9-diazaspiro[2.6]nonan-9-yl]methanone
(5-methyl-1,3,4-oxadiazol-2-yl)-[5-(7H-pyrrolo[2,3-d]pyrimidin-4-yl)-5,9-diazaspiro[2.6]nonan-9-yl]methanone
oxazol-5-yl-[5-(7H-pyrrolo[2,3-d]pyrimidin-4-yl)-5,8-diazaspiro[2.6]nonan-8-yl]methanone
oxazol-5-yl-[5-(7H-pyrrolo[2,3-d]pyrimidin-4-yl)-5,9-diazaspiro[2.6]nonan-9-yl]methanone
1H-pyrazol-4-yl-[5-(7H-pyrrolo[2,3-d]pyrimidin-4-yl)-5,8-diazaspiro[2.6]nonan-8-yl]methanone
2-(4-fluorophenyl)-1-[5-(7H-pyrrolo[2,3-d]pyrimidin-4-yl)-5,8-diazaspiro[2.6]nonan-8-yl]ethanone
2-(4-fluorophenyl)-1-[5-(7H-pyrrolo[2,3-d]pyrimidin-4-yl)-5,9-diazaspiro[2.6]nonan-9-yl]ethanone
pyrimidin-5-yl-[5-(7H-pyrrolo[2,3-d]pyrimidin-4-yl)-5,8-diazaspiro[2.6]nonan-8-yl]methanone
pyrimidin-5-yl-[5-(7H-pyrrolo[2,3-d]pyrimidin-4-yl)-5,9-diazaspiro[2.6]nonan-9-yl]methanone
2-[5-(7H-pyrrolo[2,3-d]pyrimidin-4-yl)-5,9-diazaspiro[2.6]nonane-9-carbonyl]benzonitrile
(6-hydroxy-2-pyridyl)-[5-(7H-pyrrolo[2,3-d]pyrimidin-4-yl)-5,8-diazaspiro[2.6]nonan-8-yl]methanone
(6-hydroxy-2-pyridyl)-[5-(7H-pyrrolo[2,3-d]pyrimidin-4-yl)-5,9-diazaspiro[2.6]nonan-9-yl]methanone
pyrimidin-4-yl-[5-(7H-pyrrolo[2,3-d]pyrimidin-4-yl)-5,8-diazaspiro[2.6]nonan-8-yl]methanone
pyrimidin-4-yl-[5-(7H-pyrrolo[2,3-d]pyrimidin-4-yl)-5,9-diazaspiro[2.6]nonan-9-yl]methanone
2-(2-pyridyl)-1-[5-(7H-pyrrolo[2,3-d]pyrimidin-4-yl)-5,8-diazaspiro[2.6]nonan-8-yl]ethanone
(3-methylpyrazin-2-yl)-[5-(7H-pyrrolo[2,3-d]pyrimidin-4-yl)-5,8-diazaspiro[2.6]nonan-8-yl]methanone
(6-methylpyrazin-2-yl)-[5-(7H-pyrrolo[2,3-d]pyrimidin-4-yl)-5,8-diazaspiro[2.6]nonan-8-yl]methanone
(3,5-dimethylisoxazol-4-yl)-[5-(7H-pyrrolo[2,3-d]pyrimidin-4-yl)-5,8-diazaspiro[2.6]nonan-8-yl]methanone
(2-methyl-4-pyridyl)-[5-(7H-pyrrolo[2,3-d]pyrimidin-4-yl)-5,8-diazaspiro[2.6]nonan-8-yl]methanone
(2-methyl-4-pyridyl)-[5-(7H-pyrrolo[2,3-d]pyrimidin-4-yl)-5,9-diazaspiro[2.6]nonan-9-yl]methanone
2-(2-chlorophenyl)-1-[5-(7H-pyrrolo[2,3-d]pyrimidin-4-yl)-5,8-diazaspiro[2.6]nonan-8-yl]ethanone
2-(2-chlorophenyl)-1-[5-(7H-pyrrolo[2,3-d]pyrimidin-4-yl)-5,9-diazaspiro[2.6]nonan-9-yl]ethanone
(5-methylisoxazol-3-yl)-[5-(7H-pyrrolo[2,3-d]pyrimidin-4-yl)-5,8-diazaspiro[2.6]nonan-8-yl]methanone
(4-chlorophenyl)-[5-(7H-pyrrolo[2,3-d]pyrimidin-4-yl)-5,8-diazaspiro[2.6]nonan-8-yl]methanone
isoxazol-5-yl-[5-(7H-pyrrolo[2,3-d]pyrimidin-4-yl)-5,8-diazaspiro[2.6]nonan-8-yl]methanone
(2-chlorophenyl)-[5-(7H-pyrrolo[2,3-d]pyrimidin-4-yl)-5,9-diazaspiro[2.6]nonan-9-yl]methanone
(3-chlorophenyl)-[5-(7H-pyrrolo[2,3-d]pyrimidin-4-yl)-5,9-diazaspiro[2.6]nonan-9-yl]methanone
(4-chlorophenyl)-[5-(7H-pyrrolo[2,3-d]pyrimidin-4-yl)-5,9-diazaspiro[2.6]nonan-9-yl]methanone
isoxazol-5-yl-[5-(7H-pyrrolo[2,3-d]pyrimidin-4-yl)-5,9-diazaspiro[2.6]nonan-9-yl]methanone
1H-pyrazol-3-yl-[5-(7H-pyrrolo[2,3-d]pyrimidin-4-yl)-5,8-diazaspiro[2.6]nonan-8-yl]methanone
1H-pyrazol-3-yl-[5-(7H-pyrrolo[2,3-d]pyrimidin-4-yl)-5,9-diazaspiro[2.6]nonan-9-yl]methanone
2-(3-methylisoxazol-5-yl)-1-[5-(7H-pyrrolo[2,3-d]pyrimidin-4-yl)-5,8-diazaspiro[2.6]nonan-8-yl]ethanone
(2-chlorophenyl)-[5-(7H-pyrrolo[2,3-d]pyrimidin-4-yl)-5,8-diazaspiro[2.6]nonan-8-yl]methanone
(3-chlorophenyl)-[5-(7H-pyrrolo[2,3-d]pyrimidin-4-yl)-5,8-diazaspiro[2.6]nonan-8-yl]methanone
(5-methylisoxazol-4-yl)-[5-(7H-pyrrolo[2,3-d]pyrimidin-4-yl)-5,9-diazaspiro[2.6]nonan-9-yl]methanone
2-pyridyl-[5-(7H-pyrrolo[2,3-d]pyrimidin-4-yl)-5,8-diazaspiro[2.6]nonan-8-yl]methanone
2-pyridyl-[5-(7H-pyrrolo[2,3-d]pyrimidin-4-yl)-5,9-diazaspiro[2.6]nonan-9-yl]methanone
(2-hydroxy-4-pyridyl)-[5-(7H-pyrrolo[2,3-d]pyrimidin-4-yl)-5,8-diazaspiro[2.6]nonan-8-yl]methanone
(4-methyloxazol-5-yl)-[5-(7H-pyrrolo[2,3-d]pyrimidin-4-yl)-5,8-diazaspiro[2.6]nonan-8-yl]methanone
(4-methyloxazol-5-yl)-[5-(7H-pyrrolo[2,3-d]pyrimidin-4-yl)-5,9-diazaspiro[2.6]nonan-9-yl]methanone
(2,5-dimethylpyrazol-3-yl)-[5-(7H-pyrrolo[2,3-d]pyrimidin-4-yl)-5,9-diazaspiro[2.6]nonan-9-yl]methanone
(5-methyl-1,3,4-oxadiazol-2-yl)-[5-(7H-pyrrolo[2,3-d]pyrimidin-4-yl)-5,8-diazaspiro[2.6]nonan-8-yl]methanone
[5-(7H-pyrrolo[2,3-d]pyrimidin-4-yl)-5,8-diazaspiro[2.6]nonan-8-yl]-(1H-1,2,4-triazol-3-yl)methanone
(5-methylpyrazin-2-yl)-[5-(7H-pyrrolo[2,3-d]pyrimidin-4-yl)-5,8-diazaspiro[2.6]nonan-8-yl]methanone
(5-methylpyrazin-2-yl)-[5-(7H-pyrrolo[2,3-d]pyrimidin-4-yl)-5,9-diazaspiro[2.6]nonan-9-yl]methanone
(6-methylpyrazin-2-yl)-[5-(7H-pyrrolo[2,3-d]pyrimidin-4-yl)-5,9-diazaspiro[2.6]nonan-9-yl]methanone
(3,5-dimethylisoxazol-4-yl)-[5-(7H-pyrrolo[2,3-d]pyrimidin-4-yl)-5,9-diazaspiro[2.6]nonan-9-yl]methanone
isothiazol-3-yl-[5-(7H-pyrrolo[2,3-d]pyrimidin-4-yl)-5,8-diazaspiro[2.6]nonan-8-yl]methanone
isothiazol-3-yl-[5-(7H-pyrrolo[2,3-d]pyrimidin-4-yl)-5,9-diazaspiro[2.6]nonan-9-yl]methanone
[5-(7H-pyrrolo[2,3-d]pyrimidin-4-yl)-5,8-diazaspiro[2.6]nonan-8-yl]-(1,2,5-thiadiazol-3-yl)methanone
[5-(7H-pyrrolo[2,3-d]pyrimidin-4-yl)-5,9-diazaspiro[2.6]nonan-9-yl]-(1,2,5-thiadiazol-3-yl)methanone
[5-(7H-pyrrolo[2,3-d]pyrimidin-4-yl)-5,8-diazaspiro[2.6]nonan-8-yl]-(1H-triazol-4-yl)methanone
[5-(7H-pyrrolo[2,3-d]pyrimidin-4-yl)-5,9-diazaspiro[2.6]nonan-9-yl]-(1H-triazol-4-yl)methanone
(5-methyl-1H-pyrazol-4-yl)-[5-(7H-pyrrolo[2,3-d]pyrimidin-4-yl)-5,8-diazaspiro[2.6]nonan-8-yl]methanone
(5-methyl-1H-pyrazol-4-yl)-[5-(7H-pyrrolo[2,3-d]pyrimidin-4-yl)-5,9-diazaspiro[2.6]nonan-9-yl]methanone
5-[5-(7H-pyrrolo[2,3-d]pyrimidin-4-yl)-5,8-diazaspiro[2.6]nonane-8-carbonyl]-1H-pyrrole-3-carbonitrile
5-[5-(7H-pyrrolo[2,3-d]pyrimidin-4-yl)-5,9-diazaspiro[2.6]nonane-9-carbonyl]-1H-pyrrole-3-carbonitrile
isothiazol-4-yl-[5-(7H-pyrrolo[2,3-d]pyrimidin-4-yl)-5,8-diazaspiro[2.6]nonan-8-yl]methanone
isothiazol-4-yl-[5-(7H-pyrrolo[2,3-d]pyrimidin-4-yl)-5,9-diazaspiro[2.6]nonan-9-yl]methanone
(5-hydroxy-1H-pyrazol-3-yl)-[5-(7H-pyrrolo[2,3-d]pyrimidin-4-yl)-5,9-diazaspiro[2.6]nonan-9-yl]methanone
(5-fluoro-3-pyridyl)-[5-(7H-pyrrolo[2,3-d]pyrimidin-4-yl)-5,8-diazaspiro[2.6]nonan-8-yl]methanone
(5-fluoro-3-pyridyl)-[5-(7H-pyrrolo[2,3-d]pyrimidin-4-yl)-5,9-diazaspiro[2.6]nonan-9-yl]methanone
1-[5-(7H-pyrrolo[2,3-d]pyrimidin-4-yl)-5,8-diazaspiro[2.6]nonan-8-yl]-2-(1H-tetrazol-5-yl)ethanone

[5-(7H-pyrrolo[2,3-d]pyrimidin-4-yl)-5,8-diazaspiro[2.6]
nonan-8-yl]-thiazol-4-yl-methanone
2-(3-methylisoxazol-5-yl)-1-[5-(7H-pyrrolo[2,3-d]pyrimi-
din-4-yl)-5,9-diazaspiro[2.6]nonan-9-yl]ethanone
N-(2-cyanoethyl)-N-ethyl-5-(7H-pyrrolo[2,3-d]pyrimidin-
4-yl)-5,8-diazaspiro[2.6]nonane-8-carboxamide
N-(cyanomethyl)-N-methyl-5-(7H-pyrrolo[2,3-d]pyrimi-
din-4-yl)-5,8-diazaspiro[2.6]nonane-8-carboxamide
N,N-bis(cyanomethyl)-5-(7H-pyrrolo[2,3-d]pyrimidin-4-
yl)-5,8-diazaspiro[2.6]nonane-8-carboxamide
N-(2-cyanoethyl)-N-methyl-5-(7H-pyrrolo[2,3-d]pyrimi-
din-4-yl)-5,8-diazaspiro[2.6]nonane-8-carboxamide
(2R)-1-[5-(7H-pyrrolo[2,3-d]pyrimidin-4-yl)-5,8-diazaspiro
[2.6]nonane-8-carbonyl]pyrrolidine-2-carbonitrile
(2S)-1-[5-(7H-pyrrolo[2,3-d]pyrimidin-4-yl)-5,8-diazaspiro
[2.6]nonane-8-carbonyl]pyrrolidine-2-carbonitrile
N-isopropyl-N-methyl-5-(7H-pyrrolo[2,3-d]pyrimidin-4-
yl)-5,8-diazaspiro[2.6]nonane-8-carboxamide
N,N-bis(2-cyanoethyl)-5-(7H-pyrrolo[2,3-d]pyrimidin-4-
yl)-5,8-diazaspiro[2.6]nonane-8-carboxamide
1-[5-(7H-pyrrolo[2,3-d]pyrimidin-4-yl)-5,9-diazaspiro[2.6]
nonan-9-yl]-2-(1H-tetrazol-5-yl)ethanone
[5-(7H-pyrrolo[2,3-d]pyrimidin-4-yl)-5,9-diazaspiro[2.6]
nonan-9-yl]-thiazol-4-yl-methanone
[5-(7H-pyrrolo[2,3-d]pyrimidin-4-yl)-5,9-diazaspiro[2.6]
nonan-9-yl]-(1H-1,2,4-triazol-3-yl)methanone
(5-methylisothiazol-4-yl)-[5-(7H-pyrrolo[2,3-d]pyrimidin-
4-yl)-5,8-diazaspiro[2.6]nonan-8-yl]methanone
(5-methylisothiazol-4-yl)-[5-(7H-pyrrolo[2,3-d]pyrimidin-
4-yl)-5,9-diazaspiro[2.6]nonan-9-yl]methanone
(5-chloro-1H-1,2,4-triazol-3-yl)-[5-(7H-pyrrolo[2,3-d]py-
rimidin-4-yl)-5,8-diazaspiro[2.6]nonan-8-yl]methanone
(5-chloro-1H-1,2,4-triazol-3-yl)-[5-(7H-pyrrolo[2,3-d]py-
rimidin-4-yl)-5,9-diazaspiro[2.6]nonan-9-yl]methanone
(3-methylisothiazol-5-yl)-[5-(7H-pyrrolo[2,3-d]pyrimidin-
4-yl)-5,8-diazaspiro[2.6]nonan-8-yl]methanone
(3-methylisothiazol-5-yl)-[5-(7H-pyrrolo[2,3-d]pyrimidin-
4-yl)-5,9-diazaspiro[2.6]nonan-9-yl]methanone
isothiazol-5-yl-[5-(7H-pyrrolo[2,3-d]pyrimidin-4-yl)-5,8-
diazaspiro[2.6]nonan-8-yl]methanone
isothiazol-5-yl-[5-(7H-pyrrolo[2,3-d]pyrimidin-4-yl)-5,9-
diazaspiro[2.6]nonan-9-yl]methanone
(3-methyl-1H-pyrazol-5-yl)-[5-(7H-pyrrolo[2,3-d]pyrimi-
din-4-yl)-5,8-diazaspiro[2.6]nonan-8-yl]methanone
(3-methyl-1H-pyrazol-5-yl)-[5-(7H-pyrrolo[2,3-d]pyrimi-
din-4-yl)-5,9-diazaspiro[2.6]nonan-9-yl]methanone
[5-(7H-pyrrolo[2,3-d]pyrimidin-4-yl)-5,8-diazaspiro[2.6]
nonan-8-yl]-thiazol-5-yl-methanone
[5-(7H-pyrrolo[2,3-d]pyrimidin-4-yl)-5,9-diazaspiro[2.6]
nonan-9-yl]-thiazol-5-yl-methanone
(5-methylthiazol-2-yl)-[5-(7H-pyrrolo[2,3-d]pyrimidin-4-
yl)-5,8-diazaspiro[2.6]nonan-8-yl]methanone
1H-imidazol-5-yl-[5-(7H-pyrrolo[2,3-d]pyrimidin-4-yl)-5,
8-diazaspiro[2.6]nonan-8-yl]methanone
1H-imidazol-5-yl-[5-(7H-pyrrolo[2,3-d]pyrimidin-4-yl)-5,
9-diazaspiro[2.6]nonan-9-yl]methanone
(3-methylisoxazol-4-yl)-[5-(7H-pyrrolo[2,3-d]pyrimidin-4-
yl)-5,8-diazaspiro[2.6]nonan-8-yl]methanone
(3-methylisoxazol-4-yl)-[5-(7H-pyrrolo[2,3-d]pyrimidin-4-
yl)-5,9-diazaspiro[2.6]nonan-9-yl]methanone
2-(4-methylthiazol-5-yl)-1-[5-(7H-pyrrolo[2,3-d]pyrimidin-
4-yl)-5,8-diazaspiro[2.6]nonan-8-yl]ethanone
2-(2-methylthiazol-5-yl)-1-[5-(7H-pyrrolo[2,3-d]pyrimidin-
4-yl)-5,8-diazaspiro[2.6]nonan-8-yl]ethanone
2-(5-methyl-1H-pyrazol-3-yl)-1-[5-(7H-pyrrolo[2,3-d]py-
rimidin-4-yl)-5,8-diazaspiro[2.6]nonan-8-yl]ethanone
2-(3,5-dimethylisoxazol-4-yl)-1-[5-(7H-1-pyrrolo[2,3-d]py-
rimidin-4-yl)-5,8-diazaspiro[2.6]nonan-8-yl]ethanone
2-(3-methyl-1H-1,2,4-triazol-5-yl)-1-[5-(7H-pyrrolo[2,3-d]
pyrimidin-4-yl)-5,8-diazaspiro[2.6]nonan-8-yl]ethanone
2-(4-methyl-1,2,5-oxadiazol-3-yl)-1-[5-(7H-pyrrolo[2,3-d]
pyrimidin-4-yl)-5,8-diazaspiro[2.6]nonan-8-yl]ethanone
1-[5-(7H-pyrrolo[2,3-d]pyrimidin-4-yl)-5,8-diazaspiro[2.6]
nonan-8-yl]-2-thiazol-5-yl-ethanone
2-(1-methylpyrazol-4-yl)-1-[5-(7H-pyrrolo[2,3-d]pyrimi-
din-4-yl)-5,8-diazaspiro[2.6]nonan-8-yl]ethanone
2-(2-methylthiazol-4-yl)-1-[5-(7H-pyrrolo[2,3-d]pyrimidin-
4-yl)-5,8-diazaspiro[2.6]nonan-8-yl]ethanone
[5-(7H-pyrrolo[2,3-d]pyrimidin-4-yl)-5,9-diazaspiro[2.6]
nonan-9-yl]-(1H-pyrrol-2-yl)methanone
(4-amino-1,2,5-oxadiazol-3-yl)-[5-(7H-pyrrolo[2,3-d]py-
rimidin-4-yl)-5,9-diazaspiro[2.6]nonan-9-yl]methanone
(5-methyl-4H-1,2,4-triazol-3-yl)-[5-(7H-pyrrolo[2,3-d]py-
rimidin-4-yl)-5,9-diazaspiro[2.6]nonan-9-yl]methanone
5-[5-(7H-pyrrolo[2,3-d]pyrimidin-4-yl)-5,9-diazaspiro[2.6]
nonane-9-carbonyl]furan-2-carbonitrile
2-phenyl-[5-(7H-pyrrolo[2,3-d]pyrimidin-4-yl)-5,8-diaz-
aspiro[2.6]nonan-8-yl]ethanone
(1-phenylcyclopropyl)-[5-(7H-pyrrolo[2,3-d]pyrimidin-4-
yl)-5,8-diazaspiro[2.6]nonan-8-yl]methanone
2-(4-methoxyphenyl)-1-[5-(7H-pyrrolo[2,3-d]pyrimidin-4-
yl)-5,8-diazaspiro[2.6]nonan-8-yl]ethanone
2-(m-tolyl)-1-[5-(7H-pyrrolo[2,3-d]pyrimidin-4-yl)-5,8-di-
azaspiro[2.6]nonan-8-yl]ethanone
2-(p-tolyl)-1-[5-(7H-pyrrolo[2,3-d]pyrimidin-4-yl)-5,8-di-
azaspiro[2.6]nonan-8-yl]ethanone
2-(4-bromophenyl)-1-[5-(7H-pyrrolo[2,3-d]pyrimidin-4-
yl)-5,8-diazaspiro[2.6]nonan-8-yl]ethanone
2-(2-naphthyl)-1-[5-(7H-pyrrolo[2,3-d]pyrimidin-4-yl)-5,8-
diazaspiro[2.6]nonan-8-yl]ethanone
2-[4-[2-oxo-2-[5-(7H-pyrrolo[2,3-d]pyrimidin-4-yl)-5,8-di-
azaspiro[2.6]nonan-8-yl]ethyl]phenyl]acetonitrile
2-(4-tert-butylphenyl)-1-[5-(7H-pyrrolo[2,3-d]pyrimidin-4-
yl)-5,8-diazaspiro[2.6]nonan-8-yl]ethanone
2-(4-dimethylaminophenyl)-1-[5-(7H-pyrrolo[2,3-d]py-
rimidin-4-yl)-5,8-diazaspiro[2.6]nonan-8-yl]ethanone
2-(4-chlorophenyl)-2-methyl-1-[5-(7H-pyrrolo[2,3-d]py-
rimidin-4-yl)-5,8-diazaspiro[2.6]nonan-8-yl]propan-1-
one
2-(2,4-dichlorophenyl)-1-[5-(7H-pyrrolo[2,3-d]pyrimidin-
4-yl)-5,8-diazaspiro[2.6]nonan-8-yl]ethanone
2-[2-oxo-2-[5-(7H-pyrrolo[2,3-d]pyrimidin-4-yl)-5,8-diaz-
aspiro[2.6]nonan-8-yl]ethyl]benzonitrile
2-fluoro-5-[2-oxo-2-[5-(7H-pyrrolo[2,3-d]pyrimidin-4-yl)-
5,8-diazaspiro[2.6]nonan-8-yl]ethyl]benzonitrile
1-[5-(7H-pyrrolo[2,3-d]pyrimidin-4-yl)-5,8-diazaspiro[2.6]
nonan-8-yl]-2-[4-(trifluoromethoxy)phenyl]ethanone
2-phenyl-1-[5-(7H-pyrrolo[2,3-d]pyrimidin-4-yl)-5,8-diaz-
aspiro[2.6]nonan-8-yl]propan-1-one
N-[4-[2-oxo-2-[5-(7H-pyrrolo[2,3-d]pyrimidin-4-yl)-5,8-
diazaspiro[2.6]nonan-8-yl]ethyl]phenyl]acetamide
(4-methyl-1H-pyrrol-2-yl)-[5-(7H-pyrrolo[2,3-d]pyrimidin-
4-yl)-5,9-diazaspiro[2.6]nonan-9-yl]methanone
2-methyl-5-[5-(7H-pyrrolo[2,3-d]pyrimidin-4-yl)-5,9-diaz-
aspiro[2.6]nonane-9-carbonyl]-1H-pyrrole-3-carbonitrile
4-(5-butyl-5,8-diazaspiro[2.6]nonan-8-yl)-7H-pyrrolo[2,3-
d]pyrimidine
4-(9-benzyl-5,9-diazaspiro[2.6]nonan-5-yl)-7H-pyrrolo[2,
3-d]pyrimidine
4-(9-butyl-5,9-diazaspiro[2.6]nonan-5-yl)-7H-pyrrolo[2,3-
d]pyrimidine
N-[4-(5-benzyl-5,8-diazaspiro[2.6]nonan-8-yl)-7H-pyrrolo
[2,3-d]pyrimidin-2-yl]pentanamide N-[4-(9-benzyl-5,9-diazaspiro[2.6]nonan-5-yl)-7H-pyrrolo[2,3-d]pyrimidin-2-yl]pentanamide

[7-methyl-5-(7H-pyrrolo[2,3-d]pyrimidin-4-yl)-5,8-diazaspiro[2.6]nonan-8-yl]-phenyl-methanone 2-cyclopentyl-1-[7-methyl-5-(7H-pyrrolo[2,3-d]pyrimidin-4-yl)-5,8-diazaspiro[2.6]nonan-8-yl]ethanone 4-[2-[7-methyl-5-(7H-pyrrolo[2,3-d]pyrimidin-4-yl)-5,8-diazaspiro[2.6]nonan-8-yl]-2-oxo-ethyl]benzonitrile N-[4-[9-(2-phenylacetyl)-5,9-diazaspiro[2.6]nonan-5-yl]-7H-pyrrolo[2,3-d]pyrimidin-2-yl]pentanamide N-[4-[9-(5-cyanothiophene-2-carbonyl)-5,9-diazaspiro[2.6]nonan-5-yl]-7H-pyrrolo[2,3-d]pyrimidin-2-yl]pentanamide N-[4-[8-(5-cyanothiophene-2-carbonyl)-5,8-diazaspiro[2.6]nonan-5-yl]-7H-pyrrolo[2,3-d]pyrimidin-2-yl]pentanamide 5-(7H-pyrrolo[2,3-d]pyrimidin-4-yl)-5,8-diazaspiro[2.6]nonane 4-(6,9-diazaspiro[2.6]nonan-6-yl)-7H-pyrrolo[2,3-d]pyrimidine 4-(5,9-diazaspiro[2.6]nonan-5-yl)-7H-pyrrolo[2,3-d]pyrimidine 4-(6-methyl-5,8-diazaspiro[2.6]nonan-8-yl)-7H-pyrrolo[2,3-d]pyrimidine N-[4-(5,9-diazaspiro[2.6]nonan-5-yl)-7H-pyrrolo[2,3-d]pyrimidin-2-yl]pentanamide N-[4-(5,8-diazaspiro[2.6]nonan-8-yl)-7H-pyrrolo[2,3-d]pyrimidin-2-yl]pentanamide 1-[5-(7H-pyrrolo[2,3-d]pyrimidin-4-yl)-5,8-diazaspiro[2.6]nonan-8-yl]-2-[4-(trifluoromethyl)phenyl]ethanone.

In an embodiment of the invention $G_1$ is selected from the group consisting of alkyl, aryl and arylalkyl.

In an embodiment of the invention $R_{G1c}$ is independently selected from the group consisting of cyano, halogen and —$SO_2NH_2$.

In an embodiment of the invention $R_4$ is

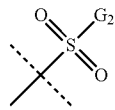

In an embodiment of the invention $R_4$ is

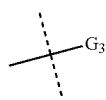

In an embodiment of the invention m is 0 or 1;

n is 2;

$R_1$ is selected from hydrogen, $(R_{1a})_2N$—, $R_{1b}$—C(=O)N($R_{1c}$)—, $R_{1b}$O—C(=O)N($R_{1c}$)—, $(R_{1b})_2N$—C(=O)N($R_{1c}$)—, $R_{1b}$—S(=O)$_2$N($R_{1c}$)— and $(R_{1b})_2N$—S(=O)$_2$N($R_{1c}$)—;

$R_3$ is independently selected from cyano, hydroxy, oxo, alkyl-, heteroalkyl-, $R_{3a}$O— or $R_{3a}$S—;

$G_1$ is selected from the group consisting of alkyl-, alkenyl-, cycloalkyl-, heterocyclyl-, $R_{G1a}$—C(=O)-L-, $(R_{G1a})_2N$—C(=O)-L-, aryl-, arylalkyl-, aryloxyalkyl-, heteroaryl-, heteroarylalkyl-, cycloalkylalkyl-, heterocyclylalkyl-, $(R_{G1a})_2N$-L-, either of which may be optionally substituted with one or more $R_{G1c}$;

$R_{G1c}$ is independently selected from the group consisting of alkyl, heteroaryl, halogen, oxo, cyano, hydroxy, —$SO_2NH_2$, —$NH_2$, $R_{G1d}$O-L-, $(R_{G1d})_2N$—S(=O)$_2$-L-, $R_{G1d}$—S(=O)$_2$-L-, $(R_{G1d})_2N$—S(=O)$_2$-L-;

$R_{G1d}$ is independently selected from the group consisting of hydrogen, alkyl-, cyclolalkylalkyl-, heterocyclylalkyl-, wherein said alkyl-, cyclolalkylalkyl-, heterocyclylalkyl- may be optionally substituted with one or more substituents selected from the group consisting of halogen, cyano and —$SO_2NH_2$.

In an embodiment of the invention $(R_2)_n$ is selected so as to form a compound selected from

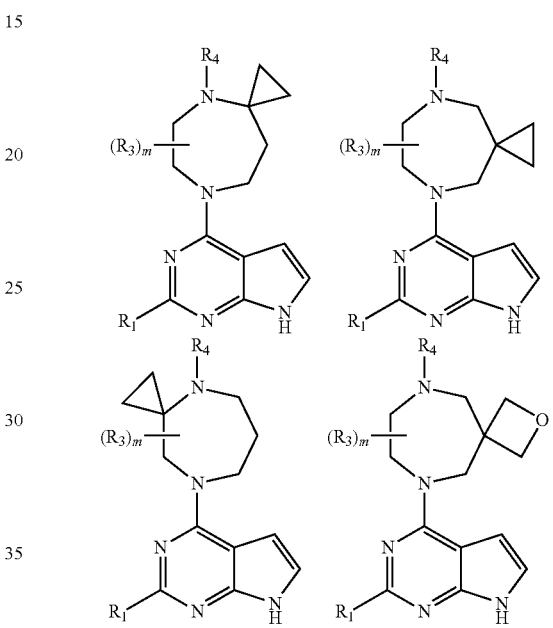

wherein $R_4$ is selected from the group consisting of hydrogen,

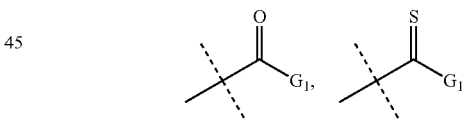

m is 0 or 1;

$R_1$ is selected from hydrogen, $(R_{1a})_2N$—, $R_{1b}$—C(=O)N($R_{1c}$)—, $R_{1b}$O—C(=O)N($R_{1c}$)—, $(R_{1b})_2N$—C(=O)N($R_{1c}$)—, $R_{1b}$—S(=O)$_2$N($R_{1c}$)— and $(R_{1b})_2N$—S(=O)$_2$N($R_{1c}$)—;

$R_3$ is independently selected from cyano, hydroxy, oxo, alkyl-, heteroalkyl-, $R_{3a}$O— or $R_{3a}$S—;

$G_1$ is selected from the group consisting of alkyl-, alkenyl-, cycloalkyl-, heterocyclyl-, $R_{G1a}$—C(=O)-L-, $(R_{G1a})_2N$—C(=O)-L-, aryl-, arylalkyl-, aryloxyalkyl-, heteroaryl-, heteroarylalkyl-, cycloalkylalkyl-, heterocyclylalkyl-, $(R_{G1a})_2N$-L-, either of which may be optionally substituted with one or more $R_{G1c}$.

In an embodiment of the invention $(R_2)_n$ is selected so as to form a compound selected from

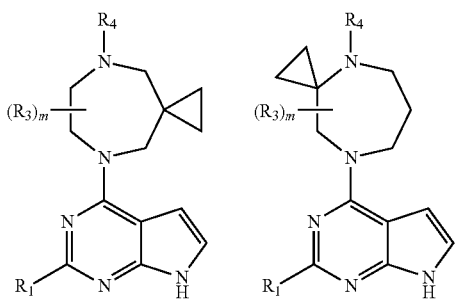

wherein m is 0;
R₄ is selected from the group consisting of hydrogen,

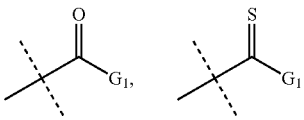

R₁ is hydrogen;
G₁ is selected from the group consisting of alkyl-, cycloalkyl-, heterocyclyl-, aryl-, arylalkyl-, aryloxyalkyl-, heteroaryl-, heteroarylalkyl-, cycloalkylalkyl-, heterocyclylalkyl-, $(R_{G1a})_2$N-L-.

In one or more embodiments of the present invention, the compounds of general formula I have a molecular weight below 800 Dalton, such as below 750 Dalton, e.g. below 700 Dalton, or below 650, 600, 550, or 500 Dalton.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. The invention also relates to all possible tautomers of the compounds of formula I.

In an embodiment of the invention the compounds of formula I according to the invention may be used in therapy.

In an embodiment of the invention the compounds of formula I according to the invention may be useful in therapy, such as for the use in the treatment of dermal diseases or conditions or acute or chronic cutaneous wound disorders.

In an embodiment of the invention the dermal disease or condition is selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

In an embodiment of the invention the compounds of formula I according to the invention may be used in the prophylaxis, treatment and/or amelioration of diseases of the immune system, in particular autoimmune diseases.

In an embodiment of the invention the compounds of formula I according to the invention may be used in the prophylaxis, treatment and/or amelioration of diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases In an embodiment of the invention the compounds of formula I according to the invention may be used as an anti-inflammatory agent capable of modulating the activity of a protein tyrosin kinase of the JAK family of protein tyrosine kinases.

In an embodiment of the invention the compounds of formula I according to the invention may be used as an anti-inflammatory agent capable of modulating the activity of JAK1, JAK2, JAK3 or TYK2 protein tyrosine kinases.

In an embodiment of the invention the compounds of formula I according to the invention may be used in the treatment, amelioration or prophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-versus-host disease, or chronic inflammatory diseases such as osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of auto-immune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition or pharmaceutical formulation. The invention therefore relates to a pharmaceutical composition comprising a compound of formula I, optionally together with one or more other therapeutically active compounds, such as differentiating agents such as vitamin D derivatives and all-trans retinoid acid; corticosteroids, such as dexamethasone and prednisone, chemotherapeutic agents, anticancer agents, cytotoxic agents, together with a pharmaceutically acceptable excipient or vehicle. The excipient must be "acceptable" in the sense of being compatible with the other ingredients of the composition and not deleterious to the recipient thereof.

If the treatment involves administration of another therapeutically active compound it is recommended to consult *Goodman & Gilman's The Pharmacological Basis of Therapeutics*, 9th Ed., J. G. Hardman and L. E. Limbird (Eds.), McGraw-Hill 1995, for useful dosages of said compounds.

Conveniently, the active ingredient comprises from 0.1-99.9% by weight of the composition.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. In the form of a dosage unit, the compound may be administered one or more times a day at appropriate intervals, always depending, however, on the condition of the patient, and in accordance with the prescription made by the medical practitioner. It is also envisaged that in certain treatment regimes, administration with longer intervals e.g. every other day, every week, or even with longer intervals may be beneficial.

Conveniently, dosage unit of a formulation contains between 0.01 mg and 1000 mg, preferably between 1 mg and 500 mg, such as between 5 mg and 100 mg of a compound of formula I.

The formulations include e.g. those in a form suitable for ophthalmic (including sustained or time-released), oral (including sustained or timed release), rectal, parenteral (including subcutaneous, intraperitoneal, intramuscular, intraarticular and intravenous), transdermal, topical, nasal or buccal administration.

The formulations may conveniently be presented in dosage unit form and may be pre-pared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Tehcnology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops, intravitreal injection and time-released drug systems.

For topical administration, the compound of formula I may typically be present in an amount of from 0.01 to 20% by weight of the composition, such as 0.1% to about 10%, but may also be present in an amount of up to about 50% of the composition.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution.

The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for nasal or buccal administration include powder, self-propelling and spray formulations, such as aerosols and atomisers. Such formulations are disclosed in greater detail in e.g. *Modern Pharmaceutics*, 2$^{nd}$ ed., G. S. Banker and C. T. Rhodes (Eds.), page 427-432, Marcel Dekker, New York; *Modern Pharmaceutics*, 3$^{th}$ ed., G. S. Banker and C. T. Rhodes (Eds.), page 618-619 and 718-721, Marcel Dekker, New York and *Encyclopedia of Pharmaceutical Technology* vol. 10, J Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

EXAMPLES

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz or 600 MHz. Chemical shift values (δ, in ppm) are quoted in the specified solvent relative to internal tetramethylsilane (δ=0.00) or chloroform (δ=7.25) standards. DMSO-d$_6$ is simply referred to as DMSO in the lists containing the NMR data. The value of a multiplet, either defined (doublet (d), triplet (t), quartet (q)) or not (m) at the approximate midpoint is given unless a range is quoted. (br) indicates a broad peak, while (s) indicates a singlet. The organic solvents used were usually anhydrous. Chromatography was performed on Merck silica gel 60 (0.040-0-063 mm). The solvent ratios indicated refer to v:v unless otherwise noted.

The following abbreviations have been used throughout:
BOC tert-butoxycarbonyl
Bz benzyl
CBT 1,1'-carbonylbisbenzotriazole
CDI N,N-carbonyldiimidazole
COMU (1-Cyano-2-ethoxy-2-oxoethylidenaminooxy)-dimethylamino-morpholino-carbenium hexafluorophosphate
DCC dicyclohexylcarbodiimide
DCM dichloromethane
DIPEA N,N-Diisopropylethylamine
DMF N,N'-Dimethylformamide
DMSO dimethyl sulfoxide
EDC 1-ethyl-3-(3-dimethylaminopropyl)carbodiimide
EtOAc ethylacetate
EtOH ethanole
HATU O-(7-azabenzotriazol-1-yl)-1,1,3,3-tetramethyluronium hexafluorophosphate
L litre
LG leaving group
m milli
Me methyl
NMR nuclear magnetic resonance
Ms mesylate
PG protecting group
PyBroP bromotri(pyrrolidino)phosphoniumhexafluorophosphate
RT ambient/room temperature
SEM 2-(trimethylsilyl)ethoxymethyl
TIPS triisopropylsilyl
TFA trifluoroacetic acid
THF tetrahydrofuran
Ts tosylate
v volume Preparative HPLC/MS:

Preparative HPLC/MS was performed on a DionexAPS-system with two Shimadzu PP150 prep. pumps and a Thermo MSQ Plus mass spectrometer. Column: Waters XTerra C-18, 150 mm×19 mm, 5 μm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

Analytical UPLC-MS Method 1:

Analytical UPLC/MS was performed on a system consisting of a Waters Acquity UPLC with a PDA detector, Waters LCT Premier XE mass spectrometer. Column: Waters, HSS T3 1.8 μm, 2.1×50 mm; solventsystem: A=10 mM ammonium acetate+0.1% HCOOH and B: CH$_3$CN+0.1% HCOOH; flow rate=0.7 mL/min; method (4.8 min): Linear gradient method going from 1% B to 95% B in 2.6 minutes and staying at 95 B for 1.2 minute. Detection was based on UV and positive/negative electrospray ionization mode.

Analytical UPLC-MS Method 2:

Analytical UPLC/MS was performed on a system consisting of a Waters Acquity UPLC with a PDA detector, Waters LCT Premier XE mass spectrometer. Column: Waters, HSS T3 1.8 μm, 2.1×50 mm; column kept at 60° C.; solvent system: A=10 mM ammonium acetate+0.1% HCOOH and B: CH$_3$CN+0.1% HCOOH; flow rate=1.2 mL/min; method (1.4 min): Linear gradient method going from 5% B to 95% B in 0.91 minutes and staying at 95% B for 0.29 minute. Detection was based on UV and positive/negative electrospray ionization mode.

General Procedure of Preparation:

The compounds of the invention can for example be prepared by one or more of the general methods outlined in schemes below:

Scheme 1:
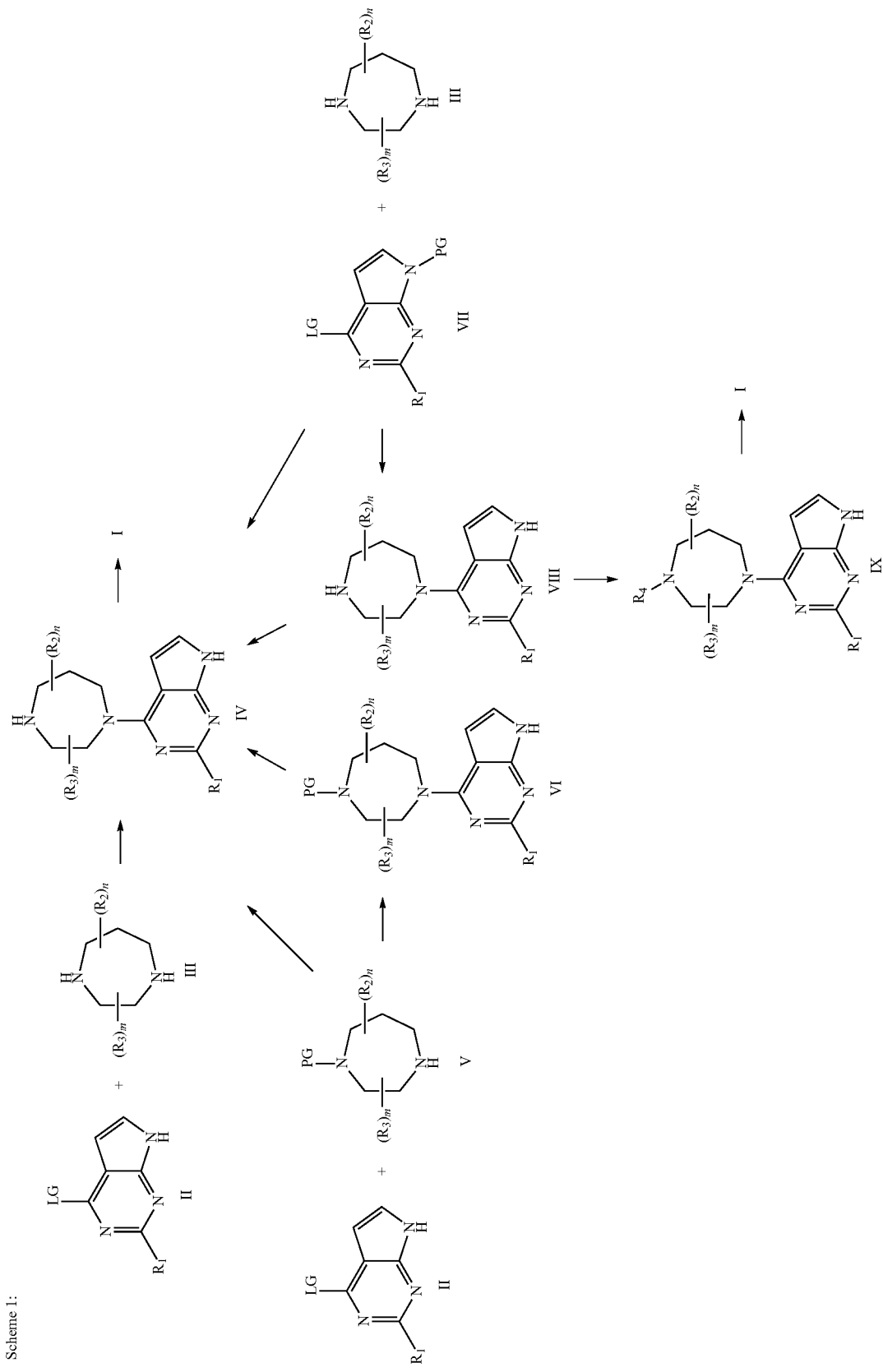

Scheme 2:

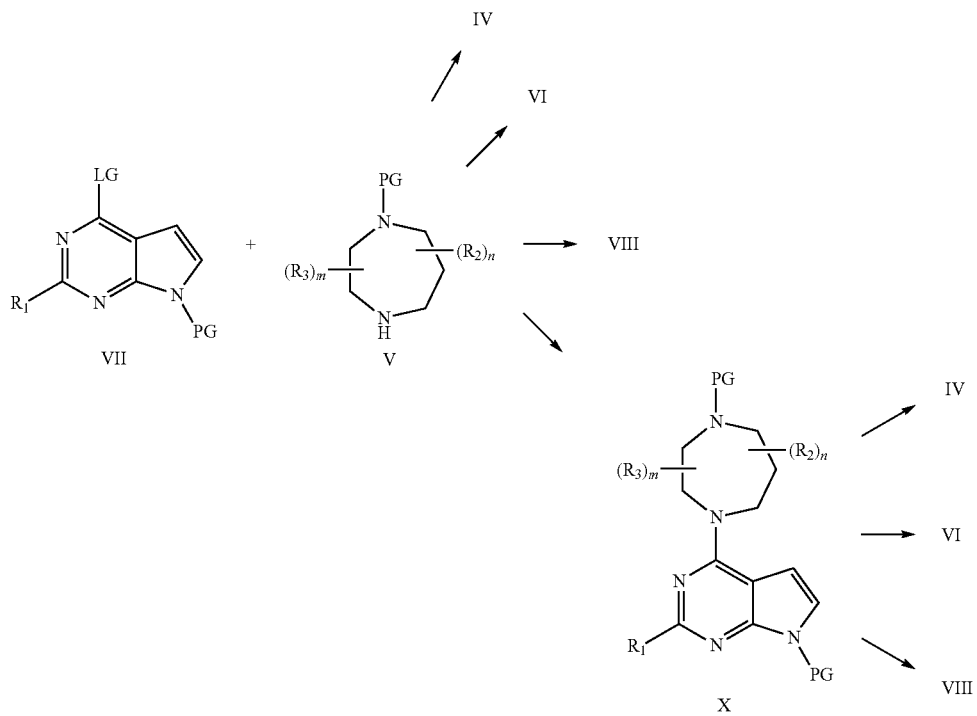

Scheme 3:

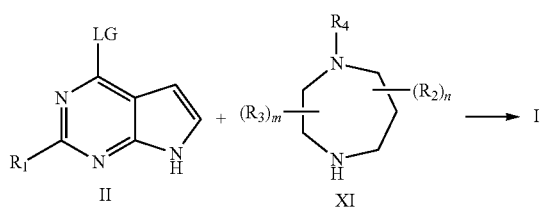

Scheme 4:

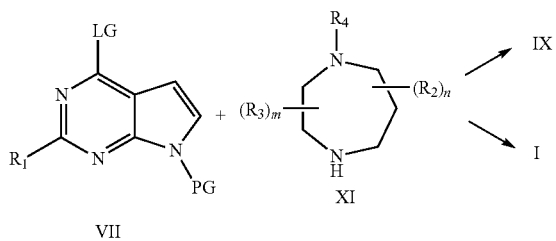

wherein $R_1$, $R_2$, $R_3$, $R_4$, m and n are defined as described herein, while PGa suitable protecting group (see e.g. "Protective Groups in Organic Synthesis", $3^{rd}$ ed., Greene T. W. and Wuts P. G. M., John Wiley & Sons Inc.), such as, but not restricted to BOC, SEM, TIPS and Ts. LG represents a suitable leaving group, such as, but not restricted to: fluorine, chlorine, bromide, iodide, methoxy, —OMs or —OTs.

The reactions between II and III to form IV can be performed in the presence or absence of an acid (such as HCl or TFA) or a base (such as $Et_3N$ or $K_2CO_3$), in a suitable solvent (such as water, DMF or EtOH) at a suitable temperature such as from room temperature to 200° C. by conventional heating or microwave induced heating.

In similar manners, the reaction between II and V to form VI and/or IV, and between VII and III to form VIII and/or IV, and between VII and V to form X and/or IV and/or VI and/or VIII, and between II and XI to form I and between VII and XI to form IX and/or I, can be performed.

Alternatively, the reaction between II and III to form IV can be performed in the presence of a transition metal based catalysis with a suitable ligand and a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

In similar manners, the reaction between II and V to form VI and/or IV, and between VII and III to form VIII and/or IV, and between VII and V to form X and/or IV and/or VI and/or VIII, and between II and XI to form I and between VII and XI to form IX and/or I, can be performed.

Any protecting group represented by PGin the above schemes can in general be introduced and removed by standard procedures known to a chemist skilled in the art of organic synthesis (see e.g *Protective Groups in Organic Synthesis*", $3^{rd}$ ed., Greene T. W. and Wuts P. G. M., John Wiley & Sons Inc.).

Compounds of the general formula II, III, V, VII and XI are either commercially available or are prepared from commercially available molecules by synthetic transformations according to standard procedures known to a chemist skilled in the art of organic synthesis.

Compounds of the general formula V can for example be prepared by derivatisation of commercially available derivatives of general formula III, or by cyclisation of appropriately substituted C2 and C3 fragments, as exemplified in the section describing the synthesis of intermediates.

Compounds of the general formula III can for example be prepared from compounds of general formula V by appropriate removal of the protecting group.

Compounds of the general formula VII can for example be prepared from compounds of general formula II by appropriate introduction of the protecting group.

Introduction of $R_4$ in compounds of general formula IV to form compounds of general formula I, can for example be achieved by reacting compounds of general formula IV with appropriate and suitable derivatives of $R_4$, such as, but not restricted to, carboxylic acid halide or ester derivatives of $R_4$, isocyanate derivatives of $R_4$, isothiocyanate derivatives of $R_4$, sulfonylhalide or ester derivatives of $R_4$, halide derivatives of $R_4$, carboxylic acid derivatives of Rounder suitable coupling conditions, and amine derivatives of $R_4$ with a suitable carbonylating agent.

Typical conditions for such reactions are described in further detail in the following.

In similar manners, the $R_4$ group can be introduced in compounds of general formula VIII to form compounds of general formula IX, followed by removal of the PG to form compounds of general formula I.

In similar manners, the $R_4$ group can be introduced in compounds of general formula III to form compounds of general formula XI.

In similar manners, the $R_4$ group can be introduced in compounds of general formula V to form compounds of general formula XI after removal of the PG.

Compounds of the general formula I where $R_4=R_{4a}$ (X=O) can for example be prepared by reacting compounds of the general formula IV with appropriate carboxylic acid halide derivatives of $R_{4a}$ in the presence or absence of a base such as $Et_3N$ in a suitable solvent such as DCM, THF or DMF at an appropriate temperature such as from 0° C. to 200° C. Furthermore, compounds of the general formula I where $R_4=R_4$, (X=O) can for example be prepared by reacting compounds of the general formula IV with appropriate carboxylic acid derivatives of $R_{4a}$ in the presence of a suitable amide coupling reagent (see e.g. E. Valeur, M. Bradley Chem. Soc. Rev. 2009, 38, 606-631) such as DCC, HATU, COMU, EDC, CDI or PyBroP, in the presence or absence of a base such as $Et_3N$ or DIPEA, and in a suitable solvent such as DCM, DMSO or DMF at a suitable temperature such as from 0° C. to 200° C.

Compounds of the general formula I where $R_4=R_{4a}$ (X=S) can for example be prepared by reacting compounds of the general formula I where $R_4=R_{4a}$ (X=O) with Lawessons reagent.

Compounds of the general formula I where $R_4=R_{4a}$ can for example be prepared by reacting compounds of the general formula IV with appropriate isocyanato (X=O) or isothiocyanato (X=S) derivatives of $R_{4a}$ in a suitable solvent such as DCM, THF or DMF at an appropriate temperature such as from 0° C. to 150° C.

Furthermore, compounds of the general formula I where $R_4=R_{4a}$ can for example be prepared by reacting compounds of the general formula IV with appropriate amino derivatives of $R_{4ab}$ in the presence of a suitable carbonylating reagent such as appropriate carbonates, CDI or CBT (see e.g. J. Org. Chem. 1997, 62, 4155-4158) in a suitable solvent such as DCM, THF or DMF at an appropriate temperature such as from 0° C. to 150° C.

Compounds of the general formula I where $R_4=R_{4a}$ and X=O can for example be prepared by reacting compounds of the general formula IV with appropriate chloroformate or dicarbonate derivatives of $R_{4a}$ in a suitable solvent such as DCM, THF or DMF at an appropriate temperature such as from 0° C. to 150° C.

Compounds of the general formula I where $R_4=R_{4b}$ can for example be prepared by reacting compounds of the general formula IV with appropriate sulfonic acid halide or ester derivatives of $R_{4b}$ in the presence or absence of a base such as $Et_3N$ in a suitable solvent such as DCM, THF or DMF at an appropriate temperature such as from 0° C. to 150° C.

Compounds of the general formula I where $R_4=R_{4c}$ can for example be prepared by reacting compounds of the general formula IV with appropriate $R_{ac}$ derivatives, such as halides and mesylates under suitable alkylating conditions in the presence or absence of a base such as NaH or $Et_3N$ in a suitable solvent such as DCM, THF or DMF at an appropriate temperature such as from 0° C. to 150° C.

INTERMEDIATES

Intermediate 1

1,1-Bis(mesyloxymethyl)cyclopropane

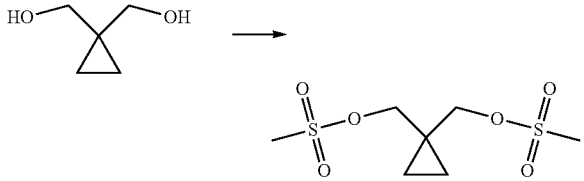

To a stirred solution of commercially available 1,1-bis (hydroxymethyl)cyclopropane (300 g, 2941.1 mmol) in dichloromethane (2.5 L) at 0° C., were added triethylamine (1187.8 g, 11760 mmol) and methanesulfonyl chloride (1005.9 g, 8823 mmol) in dichloromethane and the resultant reaction mixture was warmed to RT over 3 h. After completion of reaction (by TLC), the reaction mixture was diluted with dichloromethane and washed with water (3×). The combined dichloromethane layer was washed with brine and dried over anhydrous sodium sulphate and concentrated under reduced pressure to afford the title compound as a pale brown solid (500 g, 70%)

$^1$H NMR (300 MHz, DMSO) δ=4.11 (s, 4H), 3.15 (s, 6H), 0.72 (br, 4H).

Intermediate 2

(General Formula V, PG=Bz)

5-Benzyl-5,8-diazaspiro[2.6]nonane

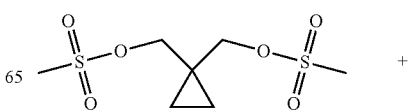 +

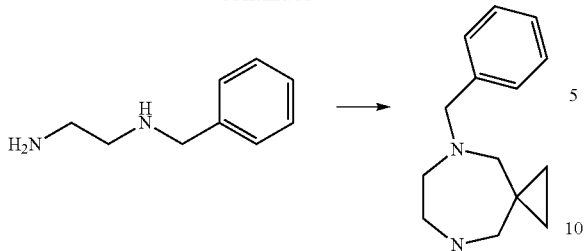

1,1-Bis(mesyloxymethyl)cyclopropane (intermediate 1) (50 g, 193.5 mmol) and commercially available N-benzylethane-1,2-diamine (29.07 g, 193.5 mmol) was dissolved in acetonitrile (5.0 L). To this solution was added potassium carbonate (80 g, 580.5 mmol) and the resultant reaction mixture was heated to reflux for 16 h. The reaction mixture was filtered and the obtained filtrate was concentrated under reduce pressure. Purification by column chromatography (0-10% methanol in dichloromethane) gave the title compound as a pale brown liquid (9.4 g, 22%)

$^1$H NMR (300 MHz, DMSO) δ=7.32 (m, 5H), 3.62 (s, 2H), 3.20 (br 2H), 3.05 (br, 2H), 2.82 (br, 2H), 2.37 (br, 2H), 0.68 (br, 2H), 0.42 (br, 2H).

Intermediate 3

(General Formula VI, PG=Bz)/Example 107

5-Benzyl-8-(7H-pyrrolo[2,3-d]pyrimidin-4-yl)-5,8-diazaspiro[2.6]nonane

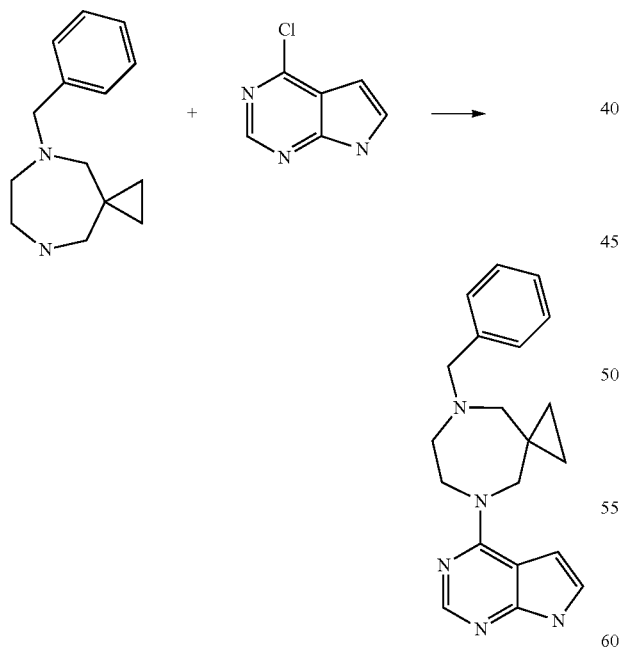

To 5-benzyl-5,8-diazaspiro[2.6]nonane(intermediate 2) (50 g, 231.5 mmol) and commercially available 4-chloro-7H-pyrrolo[2,3-d]pyrimidine (35.4 g, 231.5 mmol) in water (1.0 L), was added potassium carbonate (95.6 g, 693 mmol) and the resultant reaction mixture was heated to 100° C. for 16 h. The reaction mixture was filtered and the obtained solid was dried under vacuum. Purification by column chromatography (0-5% methanol in dichloromethane) afforded the title compound as a white solid (50 g, 65%)

$^1$H NMR (300 MHz, CDC$_{l3}$) δ=11.58 (br, 1H), 8.05 (s, 1H), 7.30 (m, 5H), 7.10 (m, 1H), 6.42 (m, 1H), 4.05 (m, 2H), 3.78 (m, 2H), 3.55 (m, 2H), 2.80 (br, 2H), 2.37 (br, 2H), 0.65 (br, 2H), 0.48 (br, 2H).

Intermediate 4

(General Formula IV)

5-(7H-pyrrolo[2,3-d]pyrimidin-4-yl)-5,8-diazaspiro[2.6]nonane

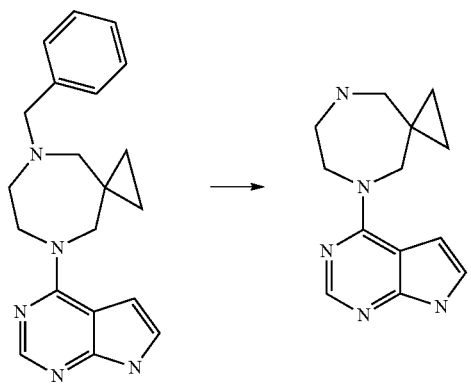 [SMILES: c1ccc(CN2CCN(c3ncnc4[nH]ccc34)CC3(CC3)C2)cc1 ; c1nc(N2CCNCC3(CC3)C2)c2cc[nH]c2n1]

To a stirred solution of 5-benzyl-8-(7H-pyrrolo[2,3-d]pyrimidin-4-yl)-5,8-diazaspiro[2.6]nonane (intermediate 3) (20 g, 60.06 mmol) in dichloroethane (500 mL), was added chloroethylchloroformate (69 g, 485.9 mmol) and the resultant reaction mixture was heated to 80° C. for 24 h. The reaction mixture was concentrated and the obtained residue was diluted with methanol (500 mL) and heated to 60° C. for 12 h. The reaction mixture was basified with triethylamine and concentrated under reduced pressure. Purification by column chromatography (0-15% methanol in dichloromethane) afforded the title compound as a pale brown ish solid (10 g, 70%)

$^1$H NMR (300 MHz, CDCl$_3$) δ=11.64 (br, 1H), 8.10 (s, 1H), 7.16 (m, 1H), 6.52 (m, 1H), 4.12 (m, 2H), 3.80 (br, 2H), 3.18 (m, 2H), 2.84 (br, 2H), 0.70 (br, 4H).

Intermediate 5 tert-butyl 5-oxo-1,4-diazepane-1-carboxylate

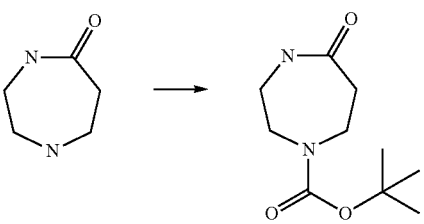

To a stirred solution of commercially available 1,4-diazepan-5-one (3.3 g, 28.94 mmol) in THF cooled to 10° C., was added di-tert-butyl dicarbonate (9.5 g, 43.42 mmol) and the resultant reaction mixture was stirred at RT for 2 h. The reaction mixture was concentrated under reduced pressure and the resulting residue was washed with n-pentane (50 mL) to afford the title compound as a solid (5.5 g, 89%).

¹H NMR (300 MHz, DMSO) δ=7.62 (s, 1H), 3.45-3.40 (m, 4H), 3.12-3.08 (m, 2H), 2.43-2.39 (m, 2H).

Intermediate 6 tert-butyl 4-benzyl-5-oxo-1,4-diazepane-1-carboxylate

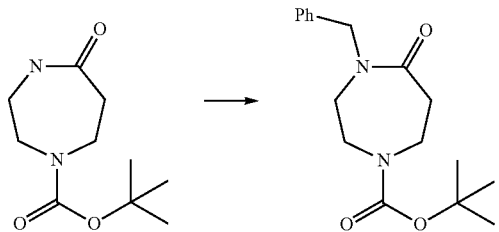 [SMILES: CC(C)(C)OC(=O)N1CCNC(=O)CC1 ; CC(C)(C)OC(=O)N1CCC(=O)N(Cc2ccccc2)CC1]

To a suspension of sodium hydride (874 mg, 36.44 mmol) in THF (20 mL) cooled to 0° C. was added tert-butyl 5-oxo-1,4-diazepane-1-carboxylate (Intermediate 5) (5.2 g, 24.29 mmol) and benzyl bromide (6.23 g, 36.44 mmol). The reaction mixture was warmed to RT, and stirred for 3 h. The reaction mixture was diluted with water (100 mL) and extracted with ethyl acetate (3×50 mL). The combined ethyl acetate layer was washed with water (50 mL) and dried over anhydrous sodium sulphate and concentrated under reduced pressure. Purification by n-pentane washings (3×10 mL) afforded the title compound as a solid (6.2 g, 84%).

¹H NMR (300 MHz, CDCl₃) δ=7.33-7.24 (m, 5H), 4.61 (s, 2H), 3.62-3.58 (m, 2H), 3.39-3.36 (m, 4H), 2.74-2.71 (m, 2H), 1.44 (s, 9H).

Intermediate 7 tert-butyl 9-benzyl-6,9-diazaspiro[2.6]nonane-6-carboxylate

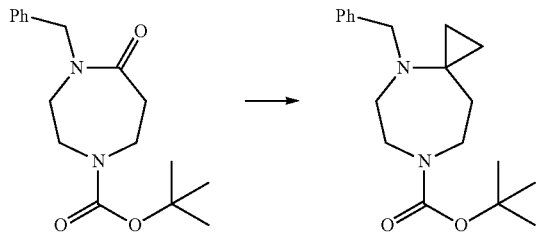 [SMILES: CC(C)(C)OC(=O)N1CCC(=O)N(Cc2ccccc2)CC1 ; CC(C)(C)OC(=O)N1CCN(Cc2ccccc2)C2(CC1)CC2]

To a stirred solution of tert-butyl 4-benzyl-5-oxo-1,4-diazepane-1-carboxylate (Intermediate 6) (3 g, 9.866 mmol) in THF (100 mL) cooled to −78° C., was added titanium(IV) isopropoxide (5.6 g, 19.73 mmol) and the mixture was stirred for 15 min, followed by heating to reflux for 1 h. The reaction mixture was cooled to 5° C. and ethyl magnesium chloride (25 mL) and titanium(IV) isopropoxide (5.6 g, 19.73 mmol) was added. The reaction mixture was warmed to RT and stirred for 4 h. Saturated ammonium chloride solution (100 mL) was added to the reaction mixture and extracted with ethyl acetate (3×100 mL). The combined ethyl acetate layer was washed with water and dried over anhydrous sodium sulphate and concentrated under reduced pressure. Purification by column chromatography (silica gel, 0-10% ethyl acetate in pet. ether) afforded the title compound as a liquid (2 g, 64%).

¹H NMR (300 MHz, CDCl₃) δ=7.31-7.20 (m, 5H), 3.86-3.84 (m, 2H), 3.52-3.43 (m, 4H), 2.83-2.77 (m, 2H), 1.79-1.71 (m, 2H), 1.50 (s, 9H), 0.72-0.69 (m, 2H), 0.52-0.46 (m, 2H).

Intermediate 8

9-benzyl-6,9-diazaspiro[2.6]nonane as hydrochloride salt

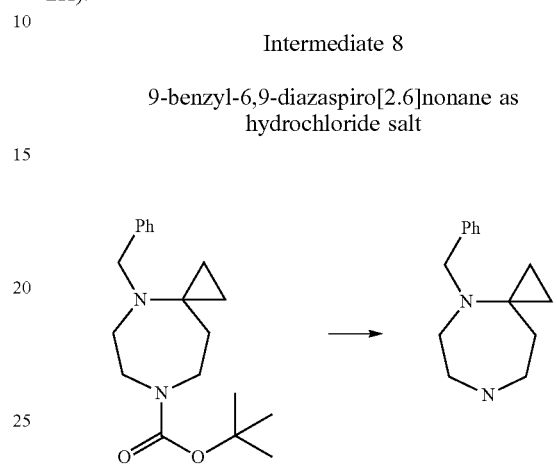

To a stirring solution of tert-butyl 9-benzyl-6,9-diazaspiro[2.6]nonane-6-carboxylate (Intermediate 7) (2 g) in dioxane (10 mL), was added 4N hydrochloric acid solution (40 mL) and the resulting reaction mixture was stirred at RT for 4 h. The reaction mixture was concentrated under reduced pressure. The obtained solid was purified by washings with n-pentane to afford the compound as the hydrochloride salt (1.5 g).

¹H NMR (300 MHz, CD₃OD) δ=7.65-7.63 (m, 2H), 7.51-7.49 (m, 3H), 4.67 (s, 2H), 3.77-3.66 (m, 4H), 3.39-3.35 (m, 2H), 1.42-1.40 (m, 2H), 1.13-1.12 (m, 2H).

Intermediate 9

4-(9-benzyl-6,9-diazaspiro[2.6]nonan-6-yl)-7H-pyrrolo[2,3-d]pyrimidine

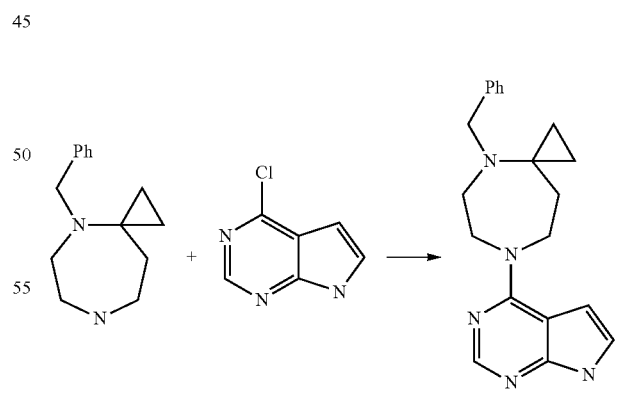

To a stirring solution of 9-benzyl-6,9-diazaspiro[2.6]nonanehydrochloride Intermediate 8 (900 mg, 5.88 mmol) in water (25 mL) were added 4-chloro-7H-pyrrolo[2,3-d]pyrimidine (1.48 g, 5.88 mmol) and potassium carbonate (2.43 g, 17.64 mmol). The reaction mixture was heated to 100° C. for 16 h. The reaction mixture was cooled to RT and the insoluble inorganics were filtered off and the filtrate was concentrated under reduced pressure. The obtained solid was purified by washings with diethyl ether to afford the title compound as an off white solid (1.6 g, 82%).

¹H NMR (300 MHz, DMSO) δ=11.61 (br, 1H), 8.13 (s, 1H), 7.28-7.11 (m, 6H), 6.48 (s, 1H), 3.99-3.95 (m, 4H), 3.71 (s, 2H), 2.89-2.85 (m, 2H), 1.92 (m, 2H), 0.58 (m, 2H), 0.44 (m, 2H).

Intermediate 10

4-(6,9-diazaspiro[2.6]nonan-6-yl)-7H-pyrrolo[2,3-d]pyrimidine

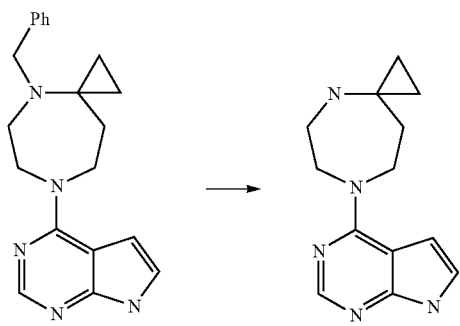 [SMILES: c1ccc(CN2CCN(c3ncnc4[nH]ccc34)CCC23CC3)cc1 ; c1nc(N2CCNC3(CC2)CC3)c2cc[nH]c2n1]

To a stirred solution of 4-(9-benzyl-6,9-diazaspiro[2.6]nonan-6-yl)-7H-pyrrolo[2,3-d]pyrimidine (Intermediate 9) (800 mg) in methanol (150 mL) and acetic acid (7.5 mL) was added 10% palladium on carbon (200 mg) and the resulting reaction mixture was stirred under a hydrogen atmosphere for 4 h at RT. The reaction mixture was filtered through celite and the filtrate was concentrated under reduced pressure. Purification by column chromatography (silica gel, 0-5% methanol in dichloromethane) afforded the title compound as a solid (330 mg, 59%).

¹H NMR (300 MHz, DMSO) δ=11.61 (br, 1H), 8.13 (s, 1H), 7.28-7.11 (m, 6H), 6.48 (s, 1H), 3.99-3.95 (m, 4H), 2.89-2.85 (m, 2H), 1.92 (m, 2H), 0.58 (m, 2H), 0.44 (m, 2H).

Intermediate 11 tert-butyl 3-oxo-1,4-diazepane-1-carboxylate

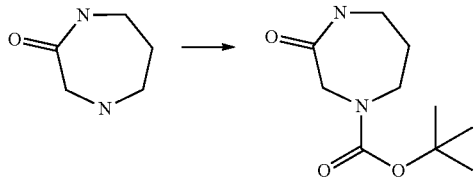

To a stirred solution of commercially available 1,4-diazepan-2-one (5 g, 43.85 mmol) in THF (100 mL) was added di-tert-butyl dicarbonate (14.34 g, 65.78 mmol) and the resulting reaction mixture was stirred at RT for 5 h. The reaction mixture was concentrated under reduced pressure and the obtained residue was triturated with pentane to afford the title compound as a solid (6.3 g, 67%).

¹H NMR (300 MHz, DMSO) δ=7.46 (m, 1H), 3.88 (s, 2H), 3.47-3.44 (m, 2H), 3.14-3.09 (m, 2H), 1.66 (m, 2H), 1.37 (s, 9H).

Intermediate 12 tert-butyl 4-benzyl-3-oxo-1,4-diazepane-1-carboxylate

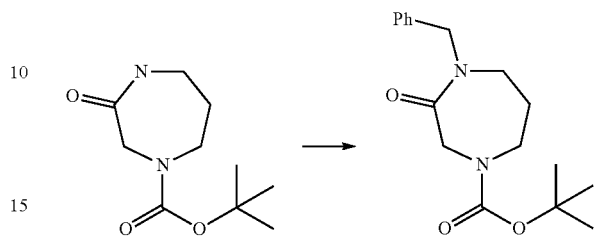

To a suspension of sodium hydride (1.06 g, 44.15 mmol) in THF at 0° C. was added tert-butyl 3-oxo-1,4-diazepane-1-carboxylate (Intermediate 11) (6.3 g, 29.47 mmol) in THF and stirred for 10 min followed by addition of benzyl bromide (7.55 g, 44.15 mmol). The resultant reaction mixture was warmed to RT and stirred for 5 h. The reaction mixture was diluted with ice water and extracted with ethyl acetate (3×10 mL). The combined ethyl acetate layer was washed with brine and dried over anhydrous sodium sulphate and concentrated under reduced pressure. Purification by n-pentane washings afforded the title compound as a solid (4.4 g, 49%).

¹H NMR (300 MHz, DMSO) δ=7.32-7.24 (m, 5H), 4.48 (s, 2H), 4.08 (s, 2H), 3.41-3.37 (m, 4H), 1.58 (brs, 2H), 1.39 (s, 9H).

Intermediate 13 tert-butyl 9-benzyl-5,9-diazaspiro[2.6]nonane-5-carboxylate

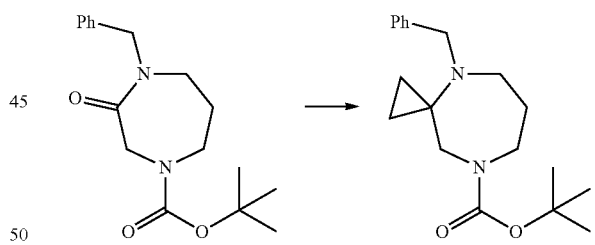

To a solution of ethyl magnesium bromide (36.2 mL, 36.18 mmol) in THF cooled to −78° C. was added tert-butyl 4-benzyl-3-oxo-1,4-diazepane-1-carboxylate (4.4 g, 14.47 mmol) (Intermediate 12) in THF and titanium(IV) isopropoxide (4.3 mL, 14.47 mmol). The reaction mixture was heated to reflux for 1 h. The reaction mixture was cooled to −78° C. and another lot of ethyl magnesium bromide (76.2 mL, 36.18 mmol) and titanium(IV) isopropoxide (4.3 mL, 14.47 mmol) was added. The resultant reaction mixture was warmed to RT for 5 h. The reaction mixture was quenched with saturated ammonium chloride solution and filtered and the filtrate was extracted with ethyl acetate (3×20 mL). The combined ethyl acetate layer was washed with brine and dried over anhydrous sodium sulphate and concentrated under reduced pressure. Purification by column chromatography (silica gel, 0-10% ethyl acetate in pet ether) afforded the title compound as a solid (1.7 g, 37%).

¹H NMR (300 MHz, DMSO) δ=7.30-7.19 (m, 5H), 3.78 (s, 2H), 3.44-3.40 (m, 4H), 2.64-2.61 (m, 2H), 1.75-1.69 (m, 2H), 1.43 (s, 9H), 0.65-0.59 (m, 4H).

Intermediate 14

9-benzyl-5,9-diazaspiro[2.6]nonane as hydrochloride salt

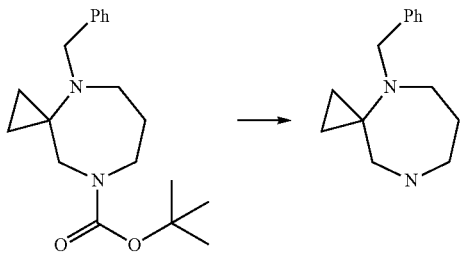 [SMILES: CC(C)(C)OC(=O)N1CCCN(Cc2ccccc2)C2(CC2)C1 ; c1ccc(CN2CCCNCC23CC3)cc1]

To a stirred solution of tert-butyl 9-benzyl-5,9-diazaspiro[2.6]nonane-5-carboxylate (1.7 g) (Intermediate 13) in dioxane (20 mL), was added 4N hydrochloric acid in dioxane (150 mL) and the resultant reaction mixture was stirred at RT for 16 h. The reaction mixture was concentrated under reduce pressure. Purification was done by washings with n-pentane to afford the title compound as a solid (1.3 g, 96%).

¹H NMR (300 MHz, D₂O) δ=7.61-7.53 (m, 5H), 4.68 (s, 2H), 3.77 (m, 2H), 3.58-3.51 (m, 4H), 2.46-2.41 (m, 2H), 1.58-1.51 (m, 2H), 1.46-1.41 (m, 2H).

Intermediate 15

4-(9-benzyl-5,9-diazaspiro[2.6]nonan-5-yl)-7H-pyrrolo[2,3-d]pyrimidine

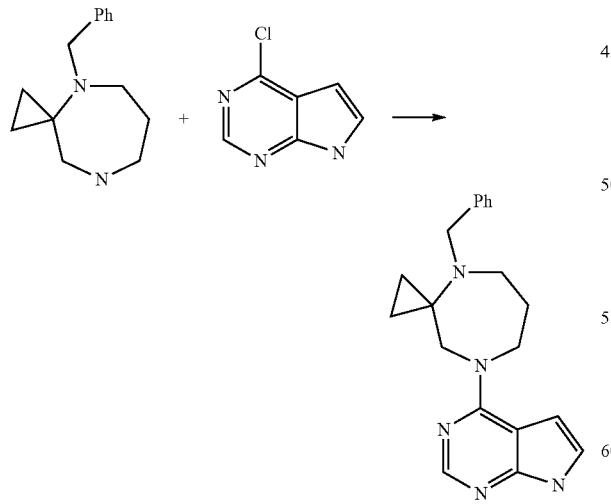

A mixture of 9-benzyl-5,9-diazaspiro[2.6]nonanehydrochloride (717 mg, 4.689 mmol) (Intermediate 14), 4-chloro-7H-pyrrolo[2,3-d]pyrimidine (1.3 g, 5.15 mmol) and potassium carbonate (1.94 g, 14.06 mmol) in water (100 mL) was heated to reflux for 16 h. The reaction mixture was cooled to RT and the obtained solid was separated by filtration. The solid was dried under vacuum and washed with ether to afford the title compound as an off white solid (1.3 g, 86%).

¹H NMR (300 MHz, DMSO) δ=11.62 (br, 1H), 8.11 (s, 1H), 7.28-7.13 (m, 6H), 6.54 (d, J=2 Hz; 1H), 4.03 (s, 2H), 3.96 (s, 2H), 3.78 (s, 2H), 2.70-2.69 (m, 2H), 1.94 (m, 2H), 0.75-0.61 (m, 4H).

Intermediate 16

4-(5,9-diazaspiro[2.6]nonan-5-yl)-7H-pyrrolo[2,3-d]pyrimidine

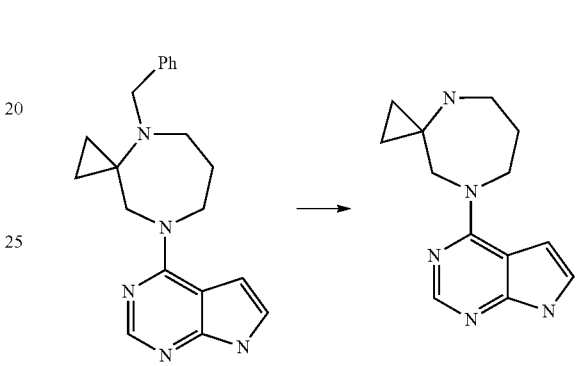

To a stirred solution of 4-(9-benzyl-5,9-diazaspiro[2.6]nonan-5-yl)-7H-pyrrolo[2,3-d]pyrimidine (1.3 g, 3.903 mmol) (Intermediate 15) in methanol (100 mL) was added 10% palladium carbon (650 mg) and ammonium formate (2.45 g, 39.039 mmol). The reaction mixture was heated to reflux for 90 min. The reaction mixture was filtered through celite and the filtrate was concentrated under reduced pressure. The obtained residue was basified with sodium hydroxide solution and extracted with ethyl acetate (3 x). The combined ethyl acetate layer was washed with brine and dried over anhydrous sodium sulphate and concentrated under reduced pressure. Purification by column chromatography (silica gel, 0-5% methanol in dichloromethane) afforded the title compound as a solid (430 mg, 45%).

¹H NMR (300 MHz, DMSO) δ=11.55 (br, 1H), 8.05 (s, 1H), 7.10 (s, 1H), 6.49 (d, J=1.2 Hz; 1H), 4.02-3.99 (m, 2H), 3.84 (s, 2H), 2.72-2.67 (m, 2H), 2.32 (m, 1H), 1.86-1.87 (m, 1H), 0.64-0.58 (m, 4H).

Intermediate 17

N1,N2-dibenzylpropane-1,2-diamine

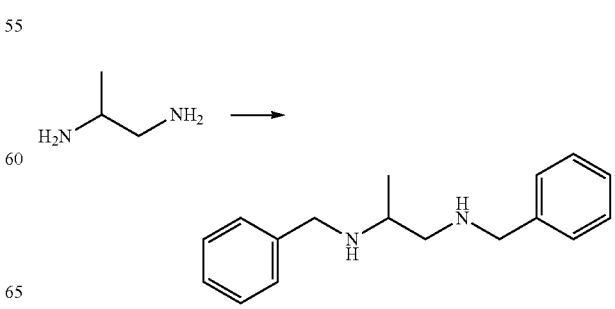

To a stirred solution of propane-1,2-diamine (30 g, 1.0 eq) in methanol (300 mL, 10 vol), benzaldehyde (85.94 g, 2.0 eq) was added at 0° C. for 30 min. After addition the reaction mixture was stirred at RT for 2 h and then treated with sodium borohydride (29.9 g, 2.0 eq) in portions at 0° C. After addition was complete the reaction mixture was stirred at RT for 16 h. The reaction mixture was concentrated under reduced pressure and the residue was diluted with cold water and dichloromethane and filtered.

The layers were separated from the filtrate and the aqueous layer was extracted with dichloromethane. The combined dichloromethane layer was washed with brine, dried over Na$_2$SO$_4$ and concentrated. The obtained residue was purified by silica gel column chromatography using 30-50% ethyl acetate in petroleum ether as eluent to remove the impurities and then with 10% methanol in dichloromethane to afford the title compound (52 g, 50%).

$^1$H NMR (300 MHz, DMSO) δ=7.33-7.28 (m, 8H), 7.24-7.21 (m, 2H), 3.89 (s, 2H), 3.73 (s, 2H), 2.80-2.77 (m, 1H), 2.67-2.64 (m, 1H), 2.63-2.49 (m, 1H), 1.07 (d, 3H).

Intermediate 18

5,8-dibenzyl-7-methyl-5,8-diazaspiro[2.6]nonane

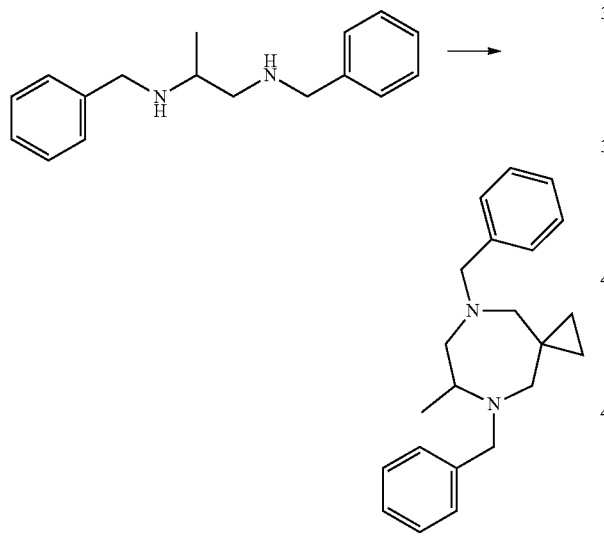

To a stirred solution of Intermediate 17 (52 g, 1.0 eq) and triethylamine (62.03 g, 3.0 eq) in acetonitrile (1.04 L, 20 vol), Intermediate 1 (55.46 g, 1.05 eq) was added in portions at RT. After complete addition the reaction mixture was stirred at reflux for 20 h. The reaction mixture was concentrated under reduced pressure and the residue was diluted with cold water (200 mL) and dichloromethane (300 mL), acidified with 2N HCl and filtered. The layers were separated from the filtrate and the aqueous layer was extracted with dichloromethane (2×150 mL). The aqueous layer basified with 20% NaOH (pH: 12) and extracted with dichloromethane (3×200 mL). The combined organic layer was washed with brine, dried over Na$_2$SO$_4$ and concentrated. The residue was purified by silica gel column chromatography using 15-25% ethyl acetate in petroleum ether as eluent to afford the title compound (21.64 g, 33%).

$^1$H NMR (300 MHz, CDCl$_3$) δ=7.37-7.27 (m, 8H), 7.24-7.19 (m, 2H), 3.93-3.89 (m, 2H), 3.79-3.65 (m, 2H), 3.17-3.12 (m, 1H), 2.81-2.38 (m, 6H), 1.06-1.05 (m, 3H), 0.21-0.11 (m, 4H).

Intermediate 19

7-methyl-5,8-diazaspiro[2.6]nonane

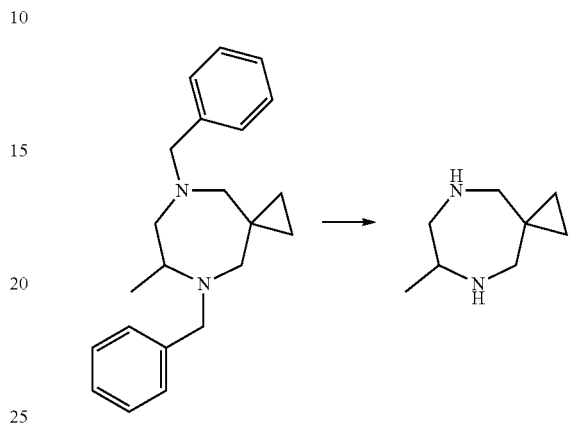

To a solution of Intermediate 18 (21 g 1.0 eq) in ethanol (190 mL), 10% Pd/C (2.1 g) was added followed by water (21 mL) and ammonium formate (4.13 g, 1.0 eq) and the reaction mixture was stirred at 50° C. for 20 h. The reaction mixture was cooled to RT, filtered through celite and the bed was washed with ethanol and concentrated. The residue was purified by silica gel column chromatography using 10-15% methanol in dichloromethane as eluent to afford a mixture of mono-debenzylated products (8.2 g, 63%) and the title compound (1.1 g).

$^1$H NMR (300 MHz, CDCl$_3$) δ=7.38-7.19 (m, 1H), 3.09-3.02 (m, 1H), 2.59-2.40 (m, 2H), 2.74-2.65 (m, 2H), 2.60-2.45 (m, 2H), 1.05 (d, 3H), 0.45-0.31 (m, 2H).

Intermediate 20

4-(6-methyl-5,8-diazaspiro[2.6]nonan-8-yl)-7H-pyrrolo[2,3-d]pyrimidine

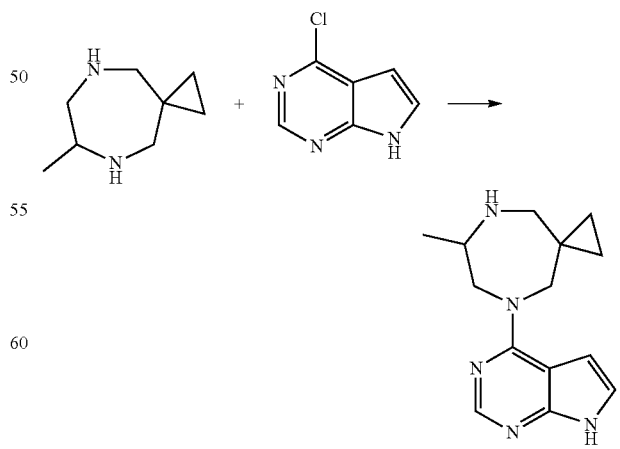

A solution of 4-chloro-7H-pyrrolo[2,3-d]pyrimidine (910 mg 1.0 eq) and Intermediate 19 (1 g 1.2 eq) in acetonitrile (20 mL) was stirred at 85° C. for 16 h. The reaction mixture was cooled to RT, the solid was filtered and washed with acetonitrile. The solid was taken into water (5 vol), stirred for 15 min and filtered. The filtrate was basified (pH-10-11) with 10% NaOH solution and stirred for 15 min. The resulted solid was collected by filtration and dried to afford the title compound (820 mg, 54.6%) as an off white solid.

$^1$H NMR (300 MHz, DMSO) δ 11.06 (br, 1H), 8.08 (s, 1H), 7.12 (d, 1H), 6.43 (d, 1H), 4.36-4.29 (m, 2H), 3.27-3.23 (m, 2H), 3.03-2.97 (m, 1H), 2.75 (d, 1H), 2.38 (d, 1H), 1.17 (br, 1H), 1.11 (d, 3H), 0.67-0.57 (m, 2H), 0.52-0.47 (m, 1H), 0.41-0.37 (m, 1H).

Intermediate 21/Example 67

4-(9-benzyl-5,9-diazaspiro[2.6]nonan-5-yl)-7H-pyrrolo[2,3-d]pyrimidin-2-amine

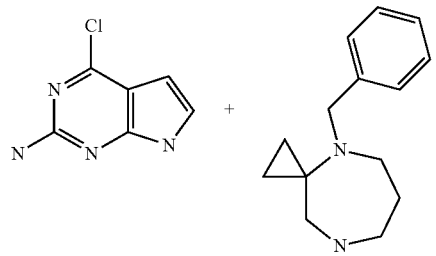

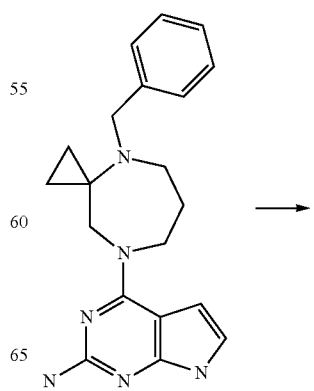

4-Chloro-7H-pyrrolo[2,3-d]pyrimidin-2-amine (1 g, 5.93 mmol), 9-benzyl-5,9-diazaspiro[2.6]nonane hydrochloride (Intermediate 14) (1.57 g, 6.23 mmol) and K$_2$CO$_3$ (2.46 g, 17.8 mmol) were taken up in dry DMF (20 mL) and stirred at 130° C. for 5 h. Reaction mixture cooled to rt, added H$_2$O (200 mL) and extracted with EtOAc (3×100 mL). The combined organic phases were dried (Na$_2$SO$_4$), filtered and concentrated on Celite. Purified by flash chromatography using ethyl acetate as eluent afforded the title compound as off-white powder (1.41 g, 68%).

$^1$H NMR (300 MHz, DMSO) δ 10.75 (s, 1H), 7.45-6.93 (m, 5H), 6.71 (dd, J=3.5, 2.2 Hz, 1H), 6.30 (dd, J=3.5, 1.7 Hz, 1H), 5.39 (s, 2H), 4.04-3.91 (m, 2H), 3.88 (s, 2H), 3.79 (s, 2H), 2.68 (t, J=5.6 Hz, 2H), 1.91 (s, 2H), 0.83-0.56 (m, 4H).

Intermediate 22, Example 68

4-(5-benzyl-5,8-diazaspiro[2.6]nonan-8-yl)-7H-pyrrolo[2,3-d]pyrimidin-2-amine

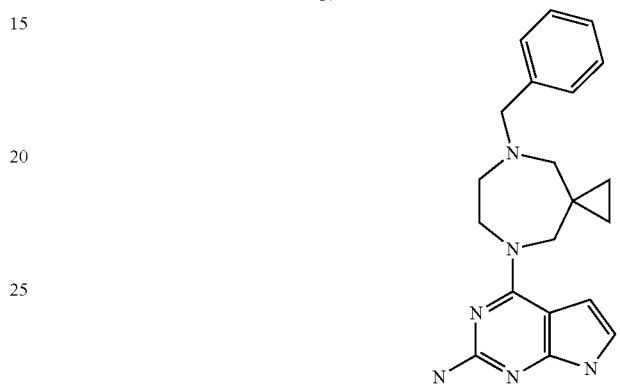

4-Chloro-7H-pyrrolo[2,3-d]pyrimidin-2-amine (1 g, 5.93 mmol), 5-Benzyl-5,8-diazaspiro[2.6]nonane (1.28 g, 6.23 mmol) (Intermediate 2) and K$_2$CO$_3$ (2.46 g, 17.8 mmol) were taken up in dry DMF (20 mL) and stirred at 130° C. for 5 h. Reaction mixture cooled to rt, added H$_2$O (200 mL) and extracted with EtOAc (3×100 mL). The combined organic phases were dried (Na$_2$SO$_4$), filtered and concentrated on Celite. Purified by flash chromatography using EtOAc as eluent afforded the title compound as off-white powder (0.29 g, 14%).

$^1$H NMR (300 MHz, DMSO) δ 10.73 (s, 1H), 7.54-7.08 (m, 5H), 6.67 (dd, J=3.4, 2.2 Hz, 1H), 6.22 (dd, J=3.4, 1.7 Hz, 1H), 5.36 (s, 2H), 4.10-3.94 (m, 2H), 3.69 (s, 2H), 3.55 (s, 2H), 2.83-2.69 (m, 2H), 2.38 (s, 2H), 0.79-0.40 (m, 4H).

Intermediate 23 (Example 283)

N-[4-(9-benzyl-5,9-diazaspiro[2.6]nonan-5-yl)-7H-pyrrolo[2,3-d]pyrimidin-2-yl]pentanamide

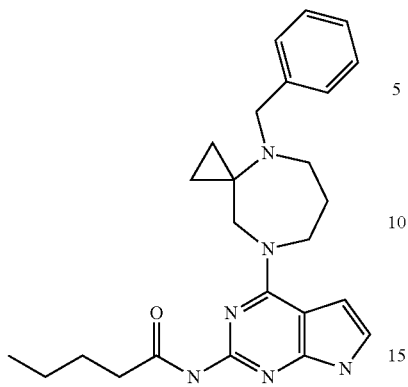

Prepared analogously to Intermediate 25 using the relevant starting materials.

¹H NMR (300 MHz, DMSO) δ 11.42 (1H), 9.53 (1H), 7.25 (br, 5H), 7.00 (m, 1H), 6.50 (m, 1H), 4.00 (br, 2H), 3.80 (2H), 3.57 (2H), 2.69 (m, 2H), 2.57 (m, 2H), 1.93 (br, 2H), 1.55 (m, 2H), 1.32 (m, 2H), 0.89 (t, 3H), 0.78 (br, 2H), 0.65 (br, 2H).

Intermediate 24

N-[4-(5,9-diazaspiro[2.6]nonan-5-yl)-7H-pyrrolo[2,3-d]pyrimidin-2-yl]pentanamide

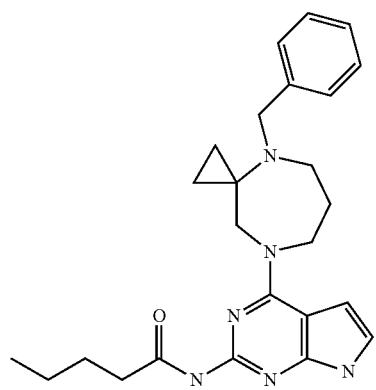

Prepared analogously to Intermediate 26 using the relevant starting materials.

¹H NMR (300 MHz, DMSO) δ11.37 (1H), 9.46 (1H), 6.98 (1H), 6.43 (1H), 4.00 (2H), 3.84 (2H), 2.74 (2H), 2.45 (br, 2H), 1.87 (2H), 1.54 (m, 2H), 1.33 (m, 2H), 0.89 (m, 3H), 0.64 (br, 4H).

Intermediate 25 (Example 282)

N-[4-(5-benzyl-5,8-diazaspiro[2.6]nonan-8-yl)-7H-pyrrolo[2,3-d]pyrimidin-2-yl]pentanamide

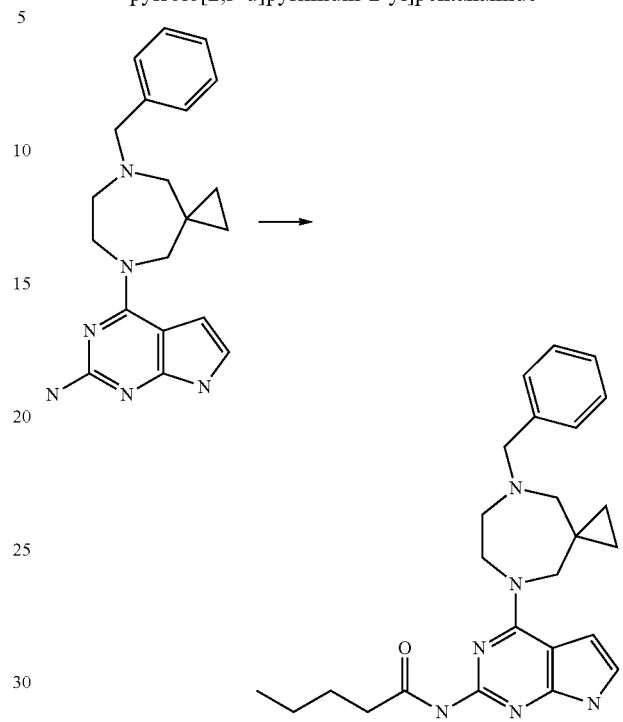

To a solution of Intermediate 22 (0.34 mmol) in pyridine (5 mL) is added pentanoyl chloride (0.76 mmol). The reaction mixture is stirred for 16 hours and then concentrated in vacuum. The crude is dissolved in methanol and NH₄OH (150 μL, 24% aqueous solution) is added. The mixture is stirred for 1 hour. The title compound was obtained by standard preparative HPLC purification of the reaction mixture.

¹H NMR (300 MHz, DMSO) δ 11.42 (1H), 9.48 (1H), 7.30 (br, 5H), 6.98 (m, 1H), 6.42 (m, 1H), 4.08 (br, 2H), 3.78 (2H), 3.57 (2H), 2.79 (br, 2H), 2.52 (br, 2H), 2.41 (2H), 1.52 (m, 2H), 1.30 (m, 2H), 0.87 (t, 3H), 0.68 (br, 2H), 0.51 (br, 2H).

Intermediate 26

N-[4-(5,8-diazaspiro[2.6]nonan-8-yl)-7H-pyrrolo[2,3-d]pyrimidin-2-yl]pentanamide

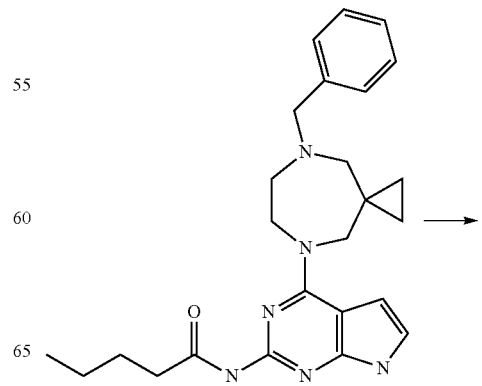

-continued

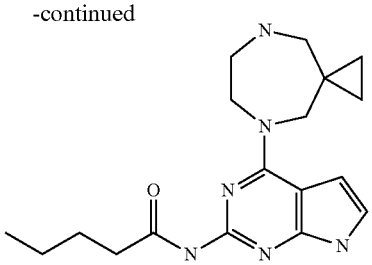

¹H NMR (300 MHz, DMSO) δ 11.40 (1H), 9.48 (1H), 6.97 (1H), 6.42 (1H), 3.98 (2H), 3.78 (2H), 2.99 (2H), 2.54 (br, 4H), 1.54 (m, 2H), 1.33 (m, 2H), 0.89 (m, 3H), 0.55 (br, 4H)

EXAMPLES

From the ¹H NMR spectra, compounds of general formula I are often observed as a mixture of two rotamers. Based on the ¹H NMR integrated peak values, one rotamer typically constitutes ~20-40% of the rotameric mixture, while a second rotamer typically constitutes ~60-80% of the rotameric mixture, depending on the nature of R₄ in the general formula I.

Example 1

4-Oxo-4-[8-(7H-pyrrolo[2,3-d]pyrimidin-4-yl)-5,8-diazaspiro[2.6]non-5-yl]butyronitrile

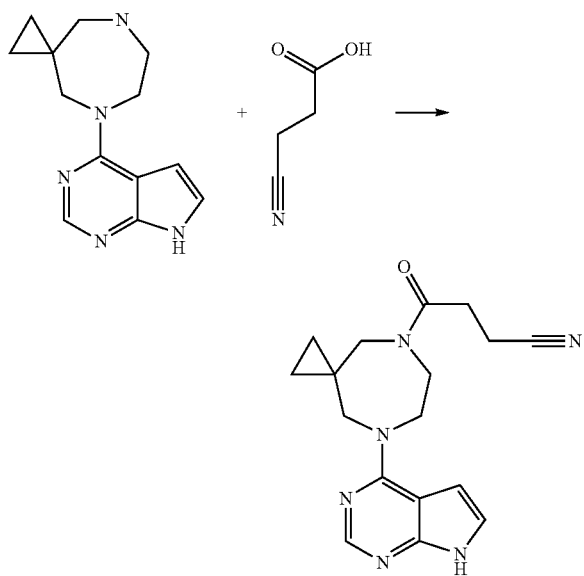

To a suspension of 5-(7H-pyrrolo[2,3-d]pyrimidin-4-yl)-5,8-diazaspiro[2.6]nonane (intermediate 4) (12.2 mg, 0.05 mmol), 3-cyanopropionic acid (5.0 mg, 0.05 mmol) and HATU (23.0 mg, 0.06 mmol) was added dry DMSO (0.3 mL) followed by DIPEA (0.3 mL). The reaction mixture was heated in a sealed tube in a microwave reactor to 120° C. for 2 minutes. The title compound was obtained by standard preparative HPLC purification of the reaction mixture.

¹H NMR (300 MHz, CDCl₃) δ=11.61 (br, 1H), 8.07 (br, 1H), 7.17 (m, 1H), 6.55 (m, 1H), 4.13 (m, 1H), 4.02 (br, 1H), 3.89 (br, 1H), 3.85 (br, 2H), 3.80 (br, 1H), 2.70 (m, 2H), 2.55-2.60, (br, 4H), 0.75 (m, 1H), 0.62 (m, 1H), 0.55 (m, 2H).

The following examples were prepared analogously using the relevant starting materials in each case:
Examples: 2-66, 69-89, 92-93, 100-102, 287-289

Example 271

1-[5-(7H-pyrrolo[2,3-d]pyrimidin-4-yl)-5,8-diazaspiro[2.6]nonan-8-yl]-2-[4-(trifluoromethyl)phenyl]ethanone 100 uL of a stock solution of 2-[4-(trifluoromethyl)phenyl]acetic acid (0.35 M in DMSO) was combined with 100 uL of a stock solution of 4-(5,8-diazaspiro[2.6]nonan-5-yl)-7H-pyrrolo[2,3-d]pyrimidine (Intermediate 4) (0.35 M in DMSO) and 100 uL of a stock solution of O-(7-azabenzotriazol-1-yl)-N,N,N',N'-tetramethyluroniumhexafluorophosphate (HATU) (0.35 M in DMSO). The reaction mixture was added 40 uLN,N-diisopropylethylamine (DIPEA) (neat) and the reaction stirred at room temperature overnight. The title compound was obtained after standard preparative HPLC purification of the reaction mixture.

¹H NMR (600 MHz, DMSO) δ: 11.68 (1H), 8.09 (1H), 7.63-7.60 (1H), 7.56-7.58 (1H), 7.43-7.39 (1H), 7.38-7.34 (1H), 7.16 (1H), 6.53 (1H), 4.10-4.03 (3.91-3.80 (6H), 2H), 3.51-3.45 (2H), 2.49 (2H), 0.76-0.53 (4H).

Analytical UPLC-MS method 1: retention time (min.)= 2.12; Observed mass (m/z)=430.183;

The following examples were prepared analogously using the relevant starting materials in each case:
Examples 106, 108-217, 226-278 and 284-286.

Example 2

(2,3-Dimethoxyphenyl)-[8-(7H-pyrrolo[2,3-d]pyrimidin-4-yl)5,8-diaza spiro[2.6]non-5-yl]methanone¹H NMR (300 MHz, DMSO) δ=11.65-11.68 (s, 0.4H), 11.62-11.65 (s, 0.6H), 8.09 (s, 0.4H), 8.07 (s, 0.6H), 7.17 (m, 0.4H), 7.11 (m, 0.6H), 7.05-7.08 (br, 1.4H), 7.03 (m, 0.6H), 6.72 (m, 0.4H), 6.57 (m, 0.4H), 6.50 (m, 0.6H), 6.43 (br, 0.6H), 4.07-4.20 (br, 1.6H), 3.95-4.03 (br, 1.4H), 3.80-3.88 (br, 3.4H), 3.60-3.72 (br, 4.6H), 3.48-3.57 (br, 2.6H), 2.97-3.01 (br, 0.4H), 0.77 (br, 2H), 0.68 (br, 1H), 0.60 (br, 1H)

Example 3

3-[8-(7H-pyrrolo[2,3-d]pyrimidin-4-yl)-5,8-diazaspiro[2.6]nonane-5-carbonyl]benzonitrile ¹H NMR (300 MHz, DMSO) δ=11.68 (s, 1H), 8.10 (br, 1H), 7.90 (br, 1.4H), 7.70 (br, 1H), 7.63 (m, 0.4H), 7.58 (m, 0.6H), 7.48 (m, 0.6H), 7.12 (br, 1H), 6.51 (br. 1H), 4.18 (br, 1H), 4.05 (br, 2H), 3.90 (br, 2H), 3.61 (br, 2H), 3.24 (br, 1H), 0.72 (br, 4H).

Example 4

(2-Methoxypyridin-3-yl)-[8-(7H-pyrrolo[2,3-d]pyrimidin-4-yl)-5,8-diazaspiro[2.6]non-5-yl]methanone ¹H NMR (300 MHz, DMSO) δ=11.67 (br, 0.4H), 11.63 (br, 0.6H), 8.21 (m, 1H), 8.10 (s, 0.4H), 8.06 (s, 0.6H), 7.63 (m, 0.4H), 7.34 (m, 0.6H), 7.18 (m, 0.4H), 7.10 (m, 0.6H), 7.03 (m, 0.4H), 6.96 (m, 0.6H), 6.57 (br, 0.4H), 6.43 (br, 0.6H), 3.87-4.20 (br, 4H), 3.83 (s, 1.2H), 3.71 (s, 1.8H), 3.47-3.68 (br, 4H), 0.65 (br, 4H).

Example 5

3-oxo-3-[8-(7H-pyrrolo[2,3-d]pyrimidin-4-yl)-5,8-diazaspiro[2.6]non-5-yl]propionitrile $^1$H NMR (300 MHz, DMSO) δ=11.67 (br, 1H), 8.11 (s, 0.6H), 8.08 (s, 0.4H), 7.17 (m, 1H), 6.60 (m, 1H), 4.12 (m, 1.2H), 4.07 (m, 1.2H), 4.04 (m, 0.8H), 3.98 (m, 0.8H), 3.90 (m, 0.8H), 3.86 (m, 2H), 3.72 (m, 1.2H), 3.44 (br, 2H), 0.73 (m, 0.8H), 0.63 (m, 1.2H), 0.56 (m, 2H).

Example 6

1-{4-[8-(7H-pyrrolo[2,3-d]pyrimidin-4-yl)-5,8-diazaspiro[2.6]nonane-5-carbonyl]piperidin-1-yl}ethanone $^1$H NMR (300 MHz, DMSO) δ=11.66 (br, 1H), 8.09 (br, 1H), 7.16 (m, 1H), 6.56 (m, 1H), 4.32 (m, 1H), 4.14 (m, 1H), 3.99 (m, 1H), 3.89 (m, 2H), 3.80 (br, 3H), 3.48 (br, 3H), 3.04 (m, 1H), 2.85 (m, 1H), 1.97 (br, 3H), 1.20-1.62 (br, 4H), 0.76 (br, 0.8H), 0.58 (m, 3.2H).

Example 7

2-[8-(7H-pyrrolo[2,3-d]pyrimidin-4-yl)-5,8-diazaspiro[2.6]nonane-5-carbonyl]benzonitrile $^1$H NMR (300 MHz, DMSO) δ=11.67 (br, 1H), 8.11 (s, 0.4H), 8.06 (s, 0.6H), 7.92 (m, 1H), 7.76 (m, 0.4H), 7.69 (m, 0.6H), 7.62 (m, 1H), 7.55 (m, 0.4H), 7.26 (m, 0.6H), 7.18 (m, 0.4H), 7.10 (m, 0.6H), 6.59 (br, 0.4H), 6.43 (br, 0.6H), 4.18 (br, 0.7H), 4.06 (br, 2H), 3.95 (br, 0.7H), 3.88 (br, 1.3H), 3.66 (br, 1.3H), 3.58 (br, 1H), 3.19 (br, 1H), 0.78 (m, 1.3H), 0.70 (m, 2H), 0.62 (m, 0.7H).

Example 8

2-[8-(7H-pyrrolo[2,3-d]pyrimidin-4-yl)-5,8-diazaspiro[2.6]nonane-5-carbonyl]-1H-indole-5-carbonitrile $^1$H NMR (300 MHz, DMSO) δ=12.14 (br, 1H), 11.62 (br, 1H), 8.18 (br, 1H), 8.09 (s, 1H), 7.52 (m, 2H), 7.16 (br, 1H), 6.93 (br, 1H), 6.57 (br, 1H), 4.22 (br, 4H), 3.92 (br, 2H), 3.75 (br, 2H), 0.72 (br, 4H).

Example 9

3-{2-oxo-2-[8-(7H-pyrrolo[2,3-d]pyrimidin-4-yl)-5,8-diazaspiro[2.6]non-5-yl]ethyl}benzonitrile $^1$H NMR (300 MHz, DMSO) δ=11.65 (s, 1H), 8.08 (br, 1H), 7.68 (br, 0.8H), 7.59 (br, 1.2H), 7.54 (br, 0.4H), 7.46 (br, 1H), 7.38 (br, 0.6H), 7.15 (m, 1H), 6.52 (m, 1H), 4.06 (br, 2H), 3.87 (br, 4H), 3.78 (br, 2H), 3.49 (br, 2H), 0.75 (m, 0.8H), 0.63 (m, 1.2H), 0.56 (m, 2H).

Example 10

4-{2-oxo-2-[8-(7H-pyrrolo[2,3-d]pyrimidin-4-yl)-5,8-diazaspiro[2.6]non-5-yl]ethyl}benzonitrile $^1$H NMR (300 MHz, DMSO) δ=11.67 (br, 1H), 8.08 (br, 1H), 7.72 (m, 0.8H), 7.64 (m, 1.2H), 7.41 (m, 0.8H), 7.32 (m, 1.2H), 7.15 (m, 1H), 6.52 (m, 1H), 4.06 (br, 2H), 3.86 (br, 6H), 3.48 (m, 2H), 0.74 (m, 0.8H), 0.63 (m, 1.2H), 0.55 (m, 2H).

Example 11

2,2-Dimethyl-3-oxo-3-[8-(7H-pyrrolo[2,3-d]pyrimidin-4-yl)-5,8-diazaspiro[2.6]non-5-yl]propionitrile $^1$H NMR (300 MHz, DMSO) δ=11.61 (br, 1H), 8.13 (br, 1H), 7.18 (br, 1H), 6.58 (br, 1H), 4.22 (br, 2H), 4.02 (br, 2H), 3.82 (br, 2H), 3.50 (br, 2H), 1.48 (br, 6H), 0.65 (br, 4H).

Example 12

{4-[8-(7H-pyrrolo[2,3-d]pyrimidin-4-yl)-5,8-diazaspiro[2.6]nonane-5-carbonyl]phenyl}acetonitrile $^1$H NMR (300 MHz, DMSO) δ=11.67 (s, 1H), 8.08 (s, 1H), 7.36 (br, 3H), 7.23 (m, 1H), 7.14 (m, 1H), 6.53 (m, 1H), 4.18 (br, 1H), 4.05 (br, 4H), 3.89 (br, 2H), 3.61 (br, 2H), 3.29 (br, 1H), 0.71 (br, 4H).

Example 13

4-[1,1-difluoro-2-oxo-2-[5-(7H-pyrrolo[2,3-d]pyrimidin-4-yl)-5,8-diazaspiro[2.6]nonan-8-yl]ethyl]benzonitrile Analytical UPLC-MS method 1: retention time (min.) =2.03; Observed mass (m/z)=423.072;

Example 14

2-[3-[5-(7H-pyrrolo[2,3-d]pyrimidin-4-yl)-5,8-diazaspiro[2.6]nonane-8-carbonyl]phenoxy]acetonitrile Analytical UPLC-MS method 1: retention time (min.)= 1.88; Observed mass (m/z)=403.189;

Example 15

2-[4-[5-(7H-pyrrolo[2,3-d]pyrimidin-4-yl)-5,8-diazaspiro[2.6]nonane-8-carbonyl]phenoxy]acetonitrile Analytical UPLC-MS method 1: retention time (min.)= 1.87; Observed mass (m/z)=403.188;

Example 16

2-[4-[2-oxo-2-[5-(7H-pyrrolo[2,3-d]pyrimidin-4-yl)-5,8-diazaspiro[2.6]nonan-8-yl]ethyl]phenoxy]acetonitrile Analytical UPLC-MS method 1: retention time (min.)= 1.87; Observed mass (m/z)=417.204;

Example 17

2-[3-[2-oxo-2-[5-(7H-pyrrolo[2,3-d]pyrimidin-4-yl)-5,8-diazaspiro[2.6]nonan-8-yl]ethyl]phenoxy]acetonitrile Analytical UPLC-MS method 1: retention time (min.)= 1.87; Observed mass (m/z)=417.21;

Example 18 benzothiophen-2-yl-[5-(7H-pyrrolo[2,3-d]pyrimidin-4-yl)-5,8-diazaspiro[2.6]nonan-8-yl]methanone Analytical UPLC-MS method 2: retention time (min.)= 0.65; Observed mass (m/z)=404.158;

Example 19

5-[5-(7H-pyrrolo[2,3-d]pyrimidin-4-yl)-5,8-diazaspiro[2.6]nonane-8-carbonyl]thiophene-3-carbonitrile Analytical UPLC-MS method 1: retention time (min.)= 1.88; Observed mass (m/z)=379.133;

Example 20

4-[2-oxo-2-[5-(7H-pyrrolo[2,3-d]pyrimidin-4-yl)-5,8-diazaspiro[2.6]nonan-8-yl]ethyl]benzenesulfonamide Analytical UPLC-MS method 1: retention time (min.)= 1.70; Observed mass (m/z)=441.17;

Example 21

5,6-dihydro-4H-cyclopenta[b]thiophen-2-yl-[5-(7H-pyrrolo[2,3-d]pyrimidin-4-yl)-5,8-diazaspiro[2.6]nonan-8-yl]methanone Analytical UPLC-MS method 1: retention time (min.)= 2.09; Observed mass (m/z)=394.169;

Example 22

(4-methoxy-2-thienyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.91; Observed mass (m/z)=384.15;

Example 23

N,4-dimethyl-5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.83; Observed mass (m/z)=461.141;

Example 24

2-methyl-5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.78; Observed mass (m/z)=447.128;

Example 25

4-methyl-5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.74; Observed mass (m/z)=447.126;

Example 26

N,2-dimethyl-5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.87; Observed mass (m/z)=461.138;

Example 27

5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.72; Observed mass (m/z)=433.108;

Example 28

N-methyl-5-[5-(7H-pyrrolo[2,3-d]pyrimidin-4-yl)-5,8-diazaspiro[2.6]nonane-8-carbonyl]thiophene-3-sulfonamide Analytical UPLC-MS method 1: retention time (min.)= 1.81; Observed mass (m/z)=447.126;

Example 29

2-methyl-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.77; Observed mass (m/z)=441.169;

Example 30

1-[5-(7H-pyrrolo[2,3-d]pyrimidin-4-yl)-5,8-diazaspiro[2.6]nonan-8-yl]-2-(2-thienyl)ethanone Analytical UPLC-MS method 1: retention time (min.)= 1.86; Observed mass (m/z)=368.155;

Example 31

4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.70; Observed mass (m/z)=427.153;

Example 32

2-chloro-4-[5-(7H-pyrrolo[2,3-d]pyrimidin-4-yl)-5, 8-diazaspiro[2.6]nonane-8-carbonyl]benzenesulfonamide Analytical UPLC-MS method 1: retention time (min.)= 1.78; Observed mass (m/z)=461.116;

Example 33

N,N-dimethyl-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.89; Observed mass (m/z)=455.187;

Example 34

4-[3-oxo-3-[5-(7H-pyrrolo[2,3-d]pyrimidin-4-yl)-5, 8-diazaspiro[2.6]nonan-8-yl]propyl]benzenesulfonamide Analytical UPLC-MS method 1: retention time (min.)= 1.75; Observed mass (m/z)=455.184;

Example 35

1-methyl-5-[5-(7H-pyrrolo[2,3-d]pyrimidin-4-yl)-5, 8-diazaspiro[2.6]nonane-8-carbonyl]pyrrole-2-sulfonamide Analytical UPLC-MS method 1: retention time (min.)= 1.67; Observed mass (m/z)=430.165;

Example 36

1-methyl-5-[5-(7H-pyrrolo[2,3-d]pyrimidin-4-yl)-5, 8-diazaspiro[2.6]nonane-8-carbonyl]pyrrole-3-sulfonamide Analytical UPLC-MS method 1: retention time (min.)= 1.66; Observed mass (m/z)=430.165;

Example 37

5-[5-(7H-pyrrolo[2,3-d]pyrimidin-4-yl)-5,8-diazaspiro[2.6]nonane-8-carbonyl]furan-2-sulfonamide Analytical UPLC-MS method 1: retention time (min.)= 1.72; Observed mass (m/z)=417.133;

Example 38

2-methyl-5-[5-(7H-pyrrolo[2,3-d]pyrimidin-4-yl)-5, 8-diazaspiro[2.6]nonane-8-carbonyl]benzenesulfonamide Analytical UPLC-MS method 1: retention time (min.)= 1.75; Observed mass (m/z)=441.173;

Example 39

4-oxo-4-[5-(7H-pyrrolo[2,3-d]pyrimidin-4-yl)-5,8-diazaspiro[2.6]nonan-8-yl]butane-1-sulfonamide Analytical UPLC-MS method 1: retention time (min.)= 1.61; Observed mass (m/z)=393.17;

Example 40

1-[5-(7H-pyrrolo[2,3-d]pyrimidin-4-yl)-5,8-diazaspiro[2.6]nonane-8-carbonyl]cyclopentanecarbonitrile Analytical UPLC-MS method 2: retention time (min.)= 0.59; Observed mass (m/z)=365.209;

Example 41

4-[5-(7H-pyrrolo[2,3-d]pyrimidin-4-yl)-5,8-diazaspiro[2.6]nonane-8-carbonyl]tetrahydropyran-4-carbonitrile Analytical UPLC-MS method 2: retention time (min.)= 0.50; Observed mass (m/z)=381.204;

Example 42

2-fluoro-4-[5-(7H-pyrrolo[2,3-d]pyrimidin-4-yl)-5,8-diazaspiro[2.6]nonane-8-carbonyl]benzonitrile Analytical UPLC-MS method 2: retention time (min.)= 0.55; Observed mass (m/z)=391.166;

Example 43

(3,5-dimethoxyphenyl)-[5-(7H-pyrrolo[2,3-d]pyrimidin-4-yl)-5,8-diazaspiro[2.6]nonan-8-yl]methanone Analytical UPLC-MS method 2: retention time (min.)= 0.56; Observed mass (m/z)=408.205;

Example 44

1-[6-(7H-pyrrolo[2,3-d]pyrimidin-4-yl)-6,9-diazaspiro[2.6]nonane-9-carbonyl]cyclopropanecarbonitrile Analytical UPLC-MS method 1: retention time (min.)= 1.74; Observed mass (m/z)=337.177;

Example 45

4,4,4-trifluoro-1-[6-(7H-pyrrolo[2,3-d]pyrimidin-4-yl)-6,9-diazaspiro[2.6]nonan-9-yl]butan-1-one Analytical UPLC-MS method 1: retention time (min.)= 1.85; Observed mass (m/z)=368.169;

Example 46 benzothiophen-2-yl-[6-(7H-pyrrolo[2,3-d]pyrimidin-4-yl)-6,9-diazaspiro[2.6]nonan-9-yl]methanone Analytical UPLC-MS method 1: retention time (min.)= 2.01; Observed mass (m/z)=404.154;

Example 47

3-[2-oxo-2-[6-(7H-pyrrolo[2,3-d]pyrimidin-4-yl)-6,9-diazaspiro[2.6]nonan-9-yl]ethyl]benzonitrile Analytical UPLC-MS method 1: retention time (min.)= 1.82; Observed mass (m/z)=387.193;

Example 48

2-[2-[6-(7H-pyrrolo[2,3-d]pyrimidin-4-yl)-6,9-diazaspiro[2.6]nonane-9-carbonyl]phenyl]acetonitrile Analytical UPLC-MS method 1: retention time (min.)= 1.79; Observed mass (m/z)=387.193;

Example 49

4-oxo-4-[6-(7H-pyrrolo[2,3-d]pyrimidin-4-yl)-6,9-diazaspiro[2.6]nonan-9-yl]butanenitrile Analytical UPLC-MS method 1: retention time (min.)= 1.62; Observed mass (m/z)=325.179;

Example 50

4-[5-(7H-pyrrolo[2,3-d]pyrimidin-4-yl)-5,8-diazaspiro[2.6]nonane-8-carbonyl]-N-[2-(2-thienyl)ethyl]benzenesulfonamide Analytical UPLC-MS method 1: retention time (min.)= 2.07; Observed mass (m/z)=537.175;

Example 51

5-[5-(7H-pyrrolo[2,3-d]pyrimidin-4-yl)-5,8-diazaspiro[2.6]nonane-8-carbonyl]thiophene-2-carbonitrile Analytical UPLC-MS method 1: retention time (min.)= 1.92; Observed mass (m/z)=379.136;

Example 52

3-methoxy-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.73; Observed mass (m/z)=457.165;

Example 53

2-methoxy-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.72; Observed mass (m/z)=457.164;

Example 54

4-[(E)-3-oxo-3-[5-(7H-pyrrolo[2,3-d]pyrimidin-4-yl)-5,8-diazaspiro[2.6]nonan-8-yl]prop-1-enyl]benzenesulfonamide Analytical UPLC-MS method 1: retention time (min.)= 1.78; Observed mass (m/z)=453.169;

Example 55

2-(4-methylsulfonylphenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.75; Observed mass (m/z)=440.176;

Example 56

4-[5-(7H-pyrrolo[2,3-d]pyrimidin-4-yl)-5,9-diazaspiro[2.6]nonane-9-carbonyl]benzonitrile Analytical UPLC-MS method 1: retention time (min.)= 1.82; Observed mass (m/z)=373.175;

Example 57

3-[5-(7H-pyrrolo[2,3-d]pyrimidin-4-yl)-5,9-diazaspiro[2.6]nonane-9-carbonyl]benzonitrile Analytical UPLC-MS method 1: retention time (min.)= 1.81; Observed mass (m/z)=373.172;

Example 58

3-[2-oxo-2-[5-(7H-pyrrolo[2,3-d]pyrimidin-4-yl)-5,9-diazaspiro[2.6]nonan-9-yl]ethyl]benzonitrile Analytical UPLC-MS method 1: retention time (min.)= 1.81; Observed mass (m/z)=387.193;

Example 59

4-[2-oxo-2-[5-(7H-pyrrolo[2,3-d]pyrimidin-4-yl)-5,9-diazaspiro[2.6]nonan-9-yl]ethyl]benzonitrile Analytical UPLC-MS method 2: retention time (min.)= 0.48; Observed mass (m/z)=387.194;

Example 60

1-[5-(7H-pyrrolo[2,3-d]pyrimidin-4-yl)-5,9-diazaspiro[2.6]nonane-9-carbonyl]cyclopropanecarbonitrile Analytical UPLC-MS method 1: retention time (min.)= 1.73; Observed mass (m/z)=337.172;

Example 61

4-oxo-4-[5-(7H-pyrrolo[2,3-d]pyrimidin-4-yl)-5,9-diazaspiro[2.6]nonan-9-yl]butanenitrile Analytical UPLC-MS method 1: retention time (min.)= 1.63; Observed mass (m/z)=325.179;

Example 62

4-[5-(7H-pyrrolo[2,3-d]pyrimidin-4-yl)-5,8-diazaspiro[2.6]nonane-8-carbonyl]benzonitrile Analytical UPLC-MS method 1: retention time (min.)= 1.87; Observed mass (m/z)=373.18;

Example 63

4-[2-oxo-2-[5-(7H-pyrrolo[2,3-d]pyrimidin-4-yl)-5,8-diazaspiro[2.6]nonan-8-yl]ethoxy]benzenesulfonamide Analytical UPLC-MS method 1: retention time (min.)= 1.73; Observed mass (m/z)=457.168;

Example 64

2-oxo-2-[5-(7H-pyrrolo[2,3-d]pyrimidin-4-yl)-5,8-diazaspiro[2.6]nonan-8-yl]-N-(4-sulfamoylphenyl)acetamide Analytical UPLC-MS method 1: retention time (min.)= 1.75; Observed mass (m/z)=470.161;

Example 65

4-[5-[5-(7H-pyrrolo[2,3-d]pyrimidin-4-yl)-5,8-diazaspiro[2.6]nonane-8-carbonyl]-2-furyl]benzenesulfonamide Analytical UPLC-MS method 1: retention time (min.)= 1.86; Observed mass (m/z)=493.165;

Example 66

2-(4-iodophenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 2.08; Observed mass (m/z)=488.099;

Example 67

4-(9-benzyl-5,9-diazaspiro[2.6]nonan-5-yl)-7H-pyrrolo[2,3-d]pyrimidin-2-amine

See Intermediate 21.

Example 68

4-(5-benzyl-5,8-diazaspiro[2.6]nonan-8-yl)-7H-pyrrolo[2,3-d]pyrimidin-2-amine

See Intermediate 22.

Example 69

N-(2-cyanoethyl)-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.81; Observed mass (m/z)=480.182;

Example 70

4-[5-(7H-pyrrolo[2,3-d]pyrimidin-4-yl-5,8-diazaspiro[2.6]nonane-8-carbonyl]-N-(tetrahydrofuran-2-ylmethyl)benzenesulfonamide Analytical UPLC-MS method 1: retention time (min.)= 1.87; Observed mass (m/z)=511.209;

Example 71

3-methyl-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.74; Observed mass (m/z)=441.166;

Example 72

N-methyl-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.79; Observed mass (m/z)=441.17;

Example 73

3-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.71; Observed mass (m/z)=427.152;

Example 74

N-(2-methoxyethyl)-4-[5-(7H-pyrrolo[2,3-d]pyrimidin-4-yl)-5,8-diazaspiro[2.6]nonane-8-carbonyl]benzenesulfonamide Analytical UPLC-MS method 1: retention time (min.)= 1.82; Observed mass (m/z)=485.195;

Example 75

4-[5-(7H-pyrrolo[2,3-d]pyrimidin-4-yl)-5,8-diazaspiro[2.6]nonane-8-carbonyl]thiophene-2-sulfonamide Analytical UPLC-MS method 1: retention time (min.)= 1.70; Observed mass (m/z)=433.112;

Example 76

5-[2-oxo-2-[5-(7H-pyrrolo[2,3-d]pyrimidin-4-yl)-5,8-diazaspiro[2.6]nonan-8-yl]ethyl]thiophene-2-sulfonamide Analytical UPLC-MS method 1: retention time (min.)= 1.71; Observed mass (m/z)=447.127;

Example 77

1-[5-(7H-pyrrolo[2,3-d]pyrimidin-4-yl)-5,8-diazaspiro[2.6]nonan-8-yl]-2-[4-(2H-tetrazol-5-yl)phenyl]ethanone Analytical UPLC-MS method 1: retention time (min.)= 1.70; Observed mass (m/z)=430.213;

Example 78

(4-propyl-2-thienyl)-[5-(7H-pyrrolo[2,3-d]pyrimidin-4-yl)-5,8-diazaspiro[2.6]nonan-8-yl]methanone Analytical UPLC-MS method 1: retention time (min.)= 2.14; Observed mass (m/z)=396.181;

Example 79

3-[2-oxo-2-[5-(7H-pyrrolo[2,3-d]pyrimidin-4-yl)-5,8-diazaspiro[2.6]nonan-8-yl]ethyl]thiazolidine-2,4-dione Analytical UPLC-MS method 1: retention time (min.)= 1.72; Observed mass (m/z)=401.124;

Example 80

1-methyl-3-[2-oxo-2-[5-(7H-pyrrolo[2,3-d]pyrimidin-4-yl)-5,8-diazaspiro[2.6]nonan-8-yl]ethyl]imidazolidine-2,4-dione Analytical UPLC-MS method 1: retention time (min.)= 1.60; Observed mass (m/z)=398.191;

Example 81

3-[2-oxo-2-[5-(7H-pyrrolo[2,3-d]pyrimidin-4-yl)-5,8-diazaspiro[2.6]nonan-8-yl]ethyl]oxazolidin-2-one Analytical UPLC-MS method 1: retention time (min.)= 1.59; Observed mass (m/z)=371.184;

Example 82

1-methyl-3-[2-oxo-2-[5-(7H-pyrrolo[2,3-d]pyrimidin-4-yl)-5,8-diazaspiro[2.6]nonan-8-yl]ethyl]imidazolidin-2-one Analytical UPLC-MS method 1: retention time (min.)= 1.62; Observed mass (m/z)=384.21;

Example 83

1-methyl-3-[2-oxo-2-[5-(7H-pyrrolo[2,3-d]pyrimidin-4-yl)-5,9-diazaspiro[2.6]nonan-9-yl]ethyl]imidazolidin-2-one Analytical UPLC-MS method 1: retention time (min.)= 1.60; Observed mass (m/z)=384.216;

Example 84

1-[2-oxo-2-[5-(7H-pyrrolo[2,3-d]pyrimidin-4-yl)-5,9-diazaspiro[2.6]nonan-9-yl]ethyl]pyrrolidine-2,5-dione Analytical UPLC-MS method 1: retention time (min.)= 1.60; Observed mass (m/z)=383.185;

Example 85

3-[2-oxo-2-[5-(7H-pyrrolo[2,3-d]pyrimidin-4-yl)-5,9-diazaspiro[2.6]nonan-9-yl]ethyl]thiazolidine-2,4-dione Analytical UPLC-MS method 1: retention time (min.)= 1.68; Observed mass (m/z)=401.136;

Example 86

3-[2-oxo-2-[5-(7H-pyrrolo[2,3-d]pyrimidin-4-yl)-5,9-diazaspiro[2.6]nonan-9-yl]ethyl]oxazolidin-2-one Analytical UPLC-MS method 1: retention time (min.)= 1.58; Observed mass (m/z)=371.188;

Example 87

2-(5-methylisoxazol-3-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.75; Observed mass (m/z)=367.19;

Example 88

1-[5-(7H-pyrrolo[2,3-d]pyrimidin-4-yl)-5,8-diazaspiro[2.6]nonan-8-yl]-2-thiazol-4-yl-ethanone Analytical UPLC-MS method 1: retention time (min.)= 1.67; Observed mass (m/z)=369.149;

Example 89

2-(1H-imidazol-5-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.49; Observed mass (m/z)=352.191;

Example 90

N-phenyl-5-(7H-pyrrolo[2,3-d]pyrimidin-4-yl)-5,9-diazaspiro[2.6]nonane-9-carboxamide $^1$H NMR (300 MHz, DMSO) δ=11.55 (1H), 8.08 (1H), 7.98 (1H), 7.42 (2H), 7.21 (2H), 7.15 (1H), 6.95 (1H), 6.57 (1H), 4.00 (br, 2H), 3.65 (br, 4H), 1.98 (br, 2H), 1.05 (br, 4H)

Example 91

N-phenyl-5-(7H-pyrrolo[2,3-d]pyrimidin-4-yl)-5,9-diazaspiro[2.6]nonane-9-carbothioamide

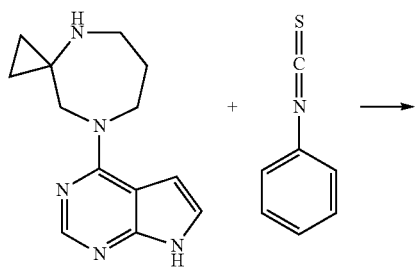

4-(5,9-diazaspiro[2.6]nonan-5-yl)-7H-pyrrolo[2,3-d]pyrimidine (intermediate 16) (0.05 mmol) was dissolved in THF (1 mL), and phenylisothiocyanate (0.06 mmol) was added. The reaction mixture was left at rt for 16 hours. The pure compounds were obtained by standard preparative HPLC purification of the reaction mixture.

$^1$H NMR (300 MHz, DMSO) δ=11.68 (1H), 9.02 (1H), 8.10 (1H), 7.30 (m, 2H), 7.18 (br, 4H), 6.58 (1H), 4.60-4.90 (br, 2H), 3.75-4.12 (br, 2H), 3.25 (m, 2H), 2.25 (br, 1H), 1.90 (br, 1H), 1.52 (br, 1H), 1.30 (m, 1H), 1.02-1.20 (br, 2H).

Examples 90 and 99 was prepared analogously using the relevant starting materials in each case.

Example 92

2-cyclopentyl-1-[5-(7H-pyrrolo[2,3-d]pyrimidin-4-yl)-5,9-diazaspiro[2.6]nonan-9-yl]ethanone $^1$H NMR (300 MHz, DMSO) δ=11.66 (1H), 8.05 (1H), 7.15 (1H), 6.52 (1H), 4.55 (m, 1H), 4.18 (m, 1H), 3.91 (br, 2H), 2.77 (m, 1H), 2.42 (m, 1H), 1.83-2.22 (br, 4H), 0.81-1.72 (br, 13H).

Example 93 cyclohexyl-[5-(7H-pyrrolo[2,3-d]pyrimidin-4-yl)-5,9-diazaspiro[2.6]nonan-9-yl]methanone $^1$H NMR (300 MHz, DMSO) δ=11.65 (1H), 8.07 (1H), 7.18 (1H), 6.55 (1H), 4.57 (m, 1H), 4.22 (m, 1H), 3.78-4.12 (br, 2H), 3.28 (br, 2H), 2.92 (br, 1H), 2.72 (br, 1H), 1.82 (br, 1H), 1.48-1.70 (br, 4H), 0.95-1.33 (br, 10H).

Example 94

4-[9-(p-tolylsulfonyl)-5,9-diazaspiro[2.6]nonan-5-yl]-7H-pyrrolo[2,3-d]pyrimidine

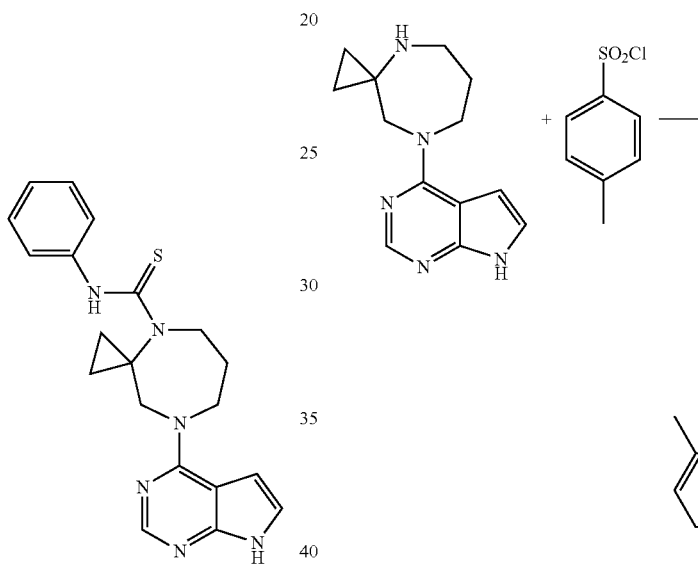

4-(5,9-diazaspiro[2.6]nonan-5-yl)-7H-pyrrolo[2,3-d]pyrimidine (intermediate 16) (0.05 mmol) was dissolved in THF (1.0 mL). Triethylamine (0.12 mmol) and p-tolylsulfonyl chloride (0.06 mmol) was added. The reaction mixture was left at rt for 16 hours. The pure compounds were obtained by standard preparative HPLC purification of the reaction mixture.

$^1$H NMR (300 MHz, DMSO) δ=11.58 (1H), 8.07 (1H), 7.48 (d, 2H), 7.15 (m, 1H), 6.98 (d, 2H), 6.38 (1H), 3.78-4.02 (br, 4H), 3.37-3.48 (br, 2H), 2.18 (br, 3H), 1.82 (m, 2H), 1.02 (br, 4H)

Examples 96-98 were prepared analogously using the relevant starting materials in each case.

Example 95

2-cyclopentyl-1-[5-(7H-pyrrolo[2,3-d]pyrimidin-4-yl)-5,9-diazaspiro[2.6]nonan-9-yl]ethanethione

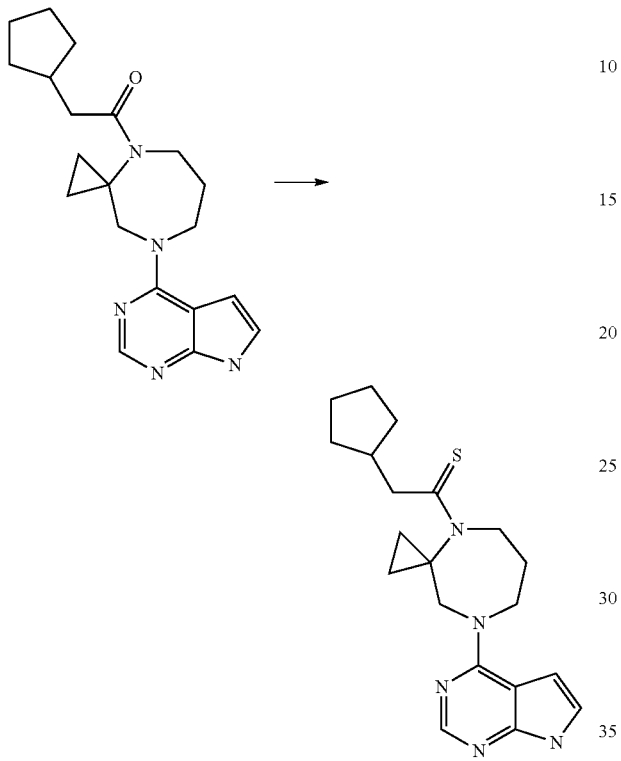

To example 92 (20 mg) in THF (5 mL) is added Lawessons reagent (30 mg) and the suspension is heated to 60° C. for 18 h. The pure compounds were obtained by standard preparative HPLC purification of the reaction mixture.

$^1$H NMR (300 MHz, DMSO) δ=11.68 (1H), 8.05 (1H), 7.17 (1H), 6.52 (1H), 5.20 (m, 1H), 4.40 (m, 1H), 4.03 (m, 1H), 3.65-3.80 (br, 2H), 3.25-3.30 (br, 2H), 2.78 (m, 2H), 2.52 (m, 1H), 2.28 (m, 1H), 0.91-1.75 (br, 12H).

Example 96

4-[8-(p-tolylsulfonyl)-5,8-diazaspiro[2.6]nonan-5-yl]-7H-pyrrolo[2,3-d]pyrimidine $^1$H NMR (300 MHz, DMSO) δ=11.61 (1H), 8.07 (1H), 7.60 (d, 2H), 7.32 (d, 2H), 7.12 (1H), 6.50 (1H), 4.12 (m, 2H), 3.81 (s, 2H), 3.42 (m, 2H), 3.08 (br, 2H), 2.37 (s, 3H), 0.62-78 (br, 4H).

Example 97

4-(8-butylsulfonyl-5,8-diazaspiro[2.6]nonan-5-yl)-7H-pyrrolo[2,3-d]pyrimidine $^1$H NMR (300 MHz, DMSO) δ=11.64 (1H), 8.10 (1H), 7.15 (1H), 6.52 (1H), 4.15 (m, 2H), 3.87 (s, 2H), 3.60 (m, 2H), 3.20 (br, 2H), 2.92 (m, 2H), 1.53 (m, 2H), 1.25 (m, 2H), 0.81 (t, 3H), 0.57-77 (br, 4H).

Example 98

4-[7-methyl-8-(p-tolylsulfonyl)-5,8-diazaspiro[2.6]nonan-5-yl]-7H-pyrrolo[2,3-d]pyrimidine $^1$H NMR (300 MHz, DMSO) δ=11.55 (1H), 7.98 (1H), 7.36 (d, 2H), 7.07 (m, 1H), 6.82 (d, 2H), 6.35 (1H), 4.20-4.35 (br, 2H), 3.98 (br, 1H), 3.80 (br, 1H), 0.40-3.60 (br, 2H), 3.18-3.25 (br, 1H), 2.21 (s, 3H), 1.10 (d, 3H), 0.75 (m, 2H), 0.48-55 (br, 2H).

Example 99

7-methyl-N-phenyl-5-(7H-pyrrolo[2,3-d]pyrimidin-4-yl)-5,8-diazaspiro[2.6]nonane-8-carboxamide $^1$H NMR (300 MHz, DMSO) δ=11.65 (1H), 8.04 (2H), 7.35 (m, 2H), 7.20 (m, 3H), 6.84 (m, 1H), 6.49 (m, 1H), 4.78 (m, 1H), 4.40 (m, 1H), 4.08 (m, 1H), 3.40-3.72 (br, 4H), 1.15 (d, 3H), 0.52-0.80 (br, 4H).

Example 100

4-[2-oxo-2-[5-(7H-pyrrolo[2,3-d]pyrimidin-4-yl)-5,8-diazaspiro[2.6]nonan-8-yl]acetyl]benzonitrile Analytical UPLC-MS method 1: retention time (min.)= 1.98; Observed mass (m/z)=401.172;

Example 101

2-[5-(7H-pyrrolo[2,3-d]pyrimidin-4-yl)-5,8-diazaspiro[2.6]nonane-8-carbonyl]-1H-indole-5-sulfonamide Analytical UPLC-MS method 1: retention time (min.)= 1.76; Observed mass (m/z)=466.163;

Example 102

N-[4-[5-(7H-pyrrolo[2,3-d]pyrimidin-4-yl)-5,8-diazaspiro[2.6]nonane-8-carbonyl]phenyl]methanesulfonamide Analytical UPLC-MS method 1: retention time (min.)= 1.76; Observed mass (m/z)=441.168;

Example 103

N-(2-cyanoethyl)-N-methyl-5-(7H-pyrrolo[2,3-d]pyrimidin-4-yl)-5,8-diazaspiro[2.6]nonane-8-sulfonamide

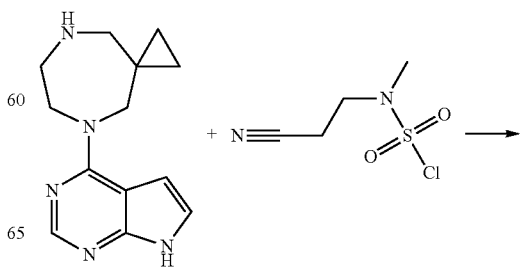

-continued

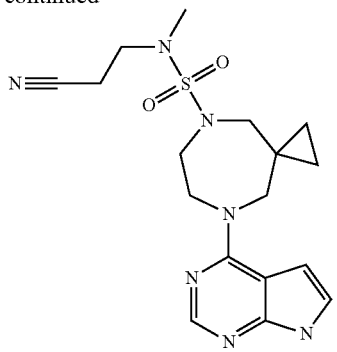

Intermediate 4 (0.05 mmol) was dissolved in THF (1.0 mL). Triethylamine (0.12 mmol) and 2-cyanoethyl(methyl) sulfamoyl chloride (0.06 mmol) was added. The reaction mixture was left at rt for 16 hours. The pure compounds were obtained by standard preparative HPLC purification of the reaction mixture.

Analytical UPLC-MS method 1: retention time (min.)= 1.83; Observed mass (m/z)=390.174;

Examples 104 and 105 were prepared analogously using the relevant starting materials in each case.

Example 104

N,N-diethyl-5-(7H-pyrrolo[2,3-d]pyrimidin-4-yl)-5,8-diazaspiro[2.6]nonane-8-sulfonamide Analytical UPLC-MS method 1: retention time (min.)= 2.01; Observed mass (m/z)=379.193;

Example 105

N-cyclohexyl-N-methyl-5-(7H-pyrrolo[2,3-d]pyrimidin-4-yl)-5,8-diazaspiro[2.6]nonane-8-sulfonamide Analytical UPLC-MS method 1: retention time (min.)= 2.24; Observed mass (m/z)=419.22;

Example 106

4-[2-oxo-2-[5-(7H-pyrrolo[2,3-d]pyrimidin-4-yl)-5,8-diazaspiro[2.6]nonan-8-yl]ethoxy]benzonitrile $^1$H NMR (300 MHz, DMSO) δ 11.71 (1H), 8.12 (1H), 7.70-7.63 (2H), 7.23-6.51 (4H), 4.93 (2H), 4.22-3.80 (7H), 1.23-0.51 (5H).
Analytical UPLC-MS method 1: retention time (min.)= 1.89; Observed mass (m/z)=403.19;

Example 107

4-(5-benzyl-5,8-diazaspiro[2.6]nonan-8-yl)-7H-pyrrolo[2,3-d]pyrimidine

See Intermediate 3.

Example 108

(5-methylisoxazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.75; Observed mass (m/z)=353.165;

Example 109 o-tolyl-[5-(7H-pyrrolo[2,3-d]pyrimidin-4-yl)-5,8-diazaspiro[2.6]nonan-8-yl]methanone Analytical UPLC-MS method 1: retention time (min.)= 1.94; Observed mass (m/z)=362.194;

Example 110 o-tolyl-[5-(7H-pyrrolo[2,3-d]pyrimidin-4-yl)-5,9-diazaspiro[2.6]nonan-9-yl]methanone Analytical UPLC-MS method 1: retention time (min.)= 1.90; Observed mass (m/z)=362.198;

Example 111

(2-fluorophenyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.90; Observed mass (m/z)=366.176;

Example 112

(2-fluorophenyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.85; Observed mass (m/z)=366.17;

Example 113

(4-fluorophenyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.91; Observed mass (m/z)=366.173;

Example 114

(4-fluorophenyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.87; Observed mass (m/z)=366.16;

Example 115

4-[3-oxo-3-[5-(7H-pyrrolo[2,3-d]pyrimidin-4-yl)-5,8-diazaspiro[2.6]nonan-8-yl]propyl]benzonitrile $^1$H NMR (300 MHz, DMSO) δ 11.68 (1H), 8.09 (1H), 7.71-7.59 (2H), 7.46-7.38 (2H), 7.16 (1H), 6.53 (1H), 4.12-3.96 (2H), 3.84 (4H), 3.45-3.38 (2H), 2.95-2.78 (2H), 2.71-2.62 (2H), 0.75-0.44 (4H).
Analytical UPLC-MS method 1: retention time (min.)= 1.91; Observed mass (m/z)=401.211;

Example 116

3-[3-oxo-3-[5-(7H-pyrrolo[2,3-d]pyrimidin-4-yl)-5,8-diazaspiro[2.6]nonan-8-yl]propyl]benzonitrile Analytical UPLC-MS method 1: retention time (min.)=1.92; Observed mass (m/z)=401.208;

Example 117

4-[(E)-3-oxo-3-[5-(7H-pyrrolo[2,3-d]pyrimidin-4-yl)-5,8-diazaspiro[2.6]nonan-8-yl]prop-1-enyl]benzonitrile Analytical UPLC-MS method 1: retention time (min.)=1.99; Observed mass (m/z)=399.166;

Example 118

3-[2-oxo-2-[5-(7H-pyrrolo[2,3-d]pyrimidin-4-yl)-5,8-diazaspiro[2.6]nonan-8-yl]ethoxy]benzonitrile Analytical UPLC-MS method 1: retention time (min.)=1.93; Observed mass (m/z)=403.184;

Example 119

5-[5-(7H-pyrrolo[2,3-d]pyrimidin-4-yl)-5,9-diazaspiro[2.6]nonane-9-carbonyl]thiophene-3-carbonitrile $^1$H NMR (300 MHz, DMSO) δ 11.62 (1H), 8.71 (1H), 8.09 (1H), 7.97-9.88 (1H), 7.15 (1H), 6.55 (1H), 4.52-3.68 (6H), 2.11-1.94 (2H), 1.16-0.94 (4H).
Analytical UPLC-MS method 1: retention time (min.)=1.84; Observed mass (m/z)=379.134;

Example 120

5-[5-(7H-pyrrolo[2,3-d]pyrimidin-4-yl)-5,9-diazaspiro[2.6]nonane-9-carbonyl]thiophene-2-carbonitrile $^1$H NMR (300 MHz, DMSO) δ 11.68 (1H), 8.10 (1H), 8.04-7.41 (2H), 7.18 (1H), 6.52 (1H), 4.44-3.58 (6H), 2.16-1.88 (2H), 1.27-0.94 (4H).
Analytical UPLC-MS method 1: retention time (min.)=1.88; Observed mass (m/z)=379.133;

Example 121

1,2,5-oxadiazol-3-yl-[5-(7H-pyrrolo[2,3-d]pyrimidin-4-yl)-5,9-diazaspiro[2.6]nonan-9-yl]methanone Analytical UPLC-MS method 1: retention time (min.)=1.74; Observed mass (m/z)=340.153;

Example 122

(3-methylisoxazol-5-yl)-[5-(7H-pyrrolo[2,3-d]pyrimidin-4-yl)-5,9-diazaspiro[2.6]nonan-9-yl]methanone $^1$H NMR (300 MHz, DMSO) δ 11.68 (1H), 8.11 (1H), 7.19 (1H), 6.75 (1H), 6.55 (1H), 4.45-3.51 (6H), 2.31-2.22 (3H), 2.20-1.91 (2H), 1.09-0.79 (4H).
Analytical UPLC-MS method 1: retention time (min.)=1.75; Observed mass (m/z)=353.166;

Example 123

(3-ethyl-4,5-dihydroisoxazol-5-yl)-[5-(7H-pyrrolo[2,3-d]pyrimidin-4-yl)-5,9-diazaspiro[2.6]nonan-9-yl]methanone

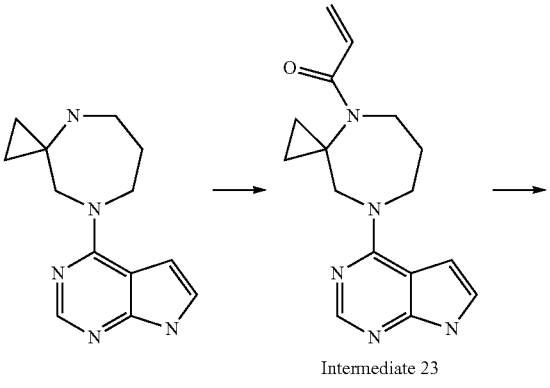

Intermediate 23

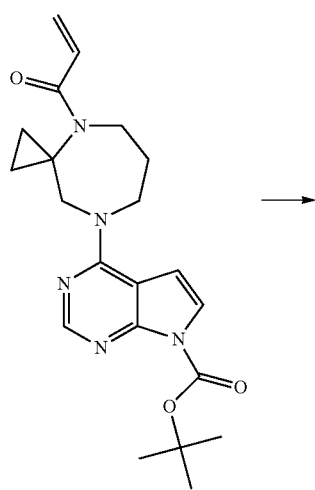

Intermediate 24

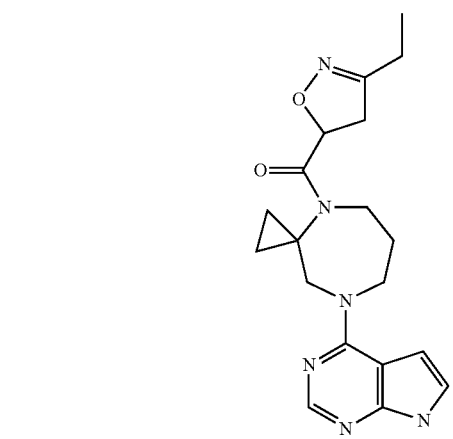

Example 123

Intermediate 23

1-[5-(7H-pyrrolo[2,3-d]pyrimidin-4-yl)-5,9-diazaspiro[2.6]nonan-9-yl]prop-2-en-1-one 4-(5,9-diazaspiro[2.6]nonan-5-yl)-7H-pyrrolo[2,3-d]pyrimidine (Intermediate 16) (2.6 g, 10 mmol) was dissolved in 50 mL DMSO and added 20 mL N,N-diisopropylethylamine. Acrylic acid (0.7 mL, 10 mmol) was added followed by portion wise addition of bromo-tris-pyrrolidinophosphoniumhexafluorophosphate (PyBroP) (4.8 g, 10 mmol). The reaction mixture was stirred overnight at room temperature, then 500 mL brine was added and the reaction was extracted ×3 with ethyl acetate. The combined organic extracts were washed with brine, dried on $MgSO_4$, filtered and evaporated. The product was obtained by trituration from acetonitrile. The obtained product was used without further purification.

Intermediate 27 tert-Butyl 4-(9-prop-2-enoyl-5,9-diazaspiro[2.6]nonan-5-yl)pyrrolo[2,3-d]pyrimidine-7-carboxylate 1-[5-(7H-pyrrolo[2,3-d]pyrimidin-4-yl)-5,9-diazaspiro[2.6]nonan-9-yl]prop-2-en-1-one (Intermediate 23) (100 mg, 0.34 mmol) was suspended in 15 mL acetonitrile, and tert-butoxycarbonyltert-butyl carbonate (130 mg, 0.6 mmol) was added together with N,N-dimethylpyridin-4-amine (62 mg, 0.05 mmol). The reaction mixture was stirred overnight at room temperature. The solvent was evaporated and the crude reaction mixture was purified by chromatography on silica using a gradient from heptane to ethyl acetate.

Pure fractions were combined and evaporated.
Yield=76 mg (56%).

Example 123

(rac)-2-(3-ethyl-2,5-dihydroisoxazol-5-yl)-1-[5-(7H-pyrrolo[2,3-d]pyrimidin-4-yl)-5,8-diazaspiro[2.5]nonan-8-yl]ethanone tert-Butyl 4-(9-prop-2-enoyl-5,9-diazaspiro[2.6]nonan-5-yl)pyrrolo[2,3-d]pyrimidine-7-carboxylate (Intermediate 27) (76 mg, 0.19 mmol), nitropropane (43 uL, 0.48 mmol), $Cu(OAc)_2$ (2 mg, 0.01 mmol), and N-methyl piperidine (10 mg, 0.1 mmol) were combined in 0.7 mL chloroform and the reaction mixture was heated at 60° C. overnight. The solvent was evaporated and the crude reaction mixture was purified by chromatography on silica, starting with pure heptane and ending with pure ethyl acetate. Pure fractions were combined and evaporated to yield the title compound.

Yield=15 mg (21%)
$^1$H NMR (300 MHz, DMSO) δ=11.66 (1H), 8.09 (1H), 7.14-7.18 (1H), 6.49-6.55 (1H), 5.56-5.61 (1H), 4.59-5.19 (1H), 3.50-4.25 (6H), 3.20-3.30 (m, 1H), 2.25-2.40 (m, 2H), 1.85-2.02 (m, 2H), 0.80-1.10 (br, 7H).

Example 124

(3-propyl-4,5-dihydroisoxazol-5-yl)-[5-(7H-pyrrolo[2,3-d]pyrimidin-4-yl)-5,9-diazaspiro[2.6]nonan-9-yl]methanone Prepared from Intermediate 27 as described for Example 123.

Analytical UPLC-MS method 1: retention time (min.)=1.83; Observed mass (m/z)=383.221;

Example 125

2-(4-chlorophenyl)-1-[5-(7H-pyrrolo[2,3-d]pyrimidin-4-yl)-5,8-diazaspiro[2.6]nonan-8-yl]ethanone $^1$H NMR (300 MHz, DMSO) δ 11.65 (1H), 8.08 (1H), 7.36-7.08 (5H), 6.52 (1H), 4.11-4.00 (2H), 3.91-3.80 4H), 3.73-3.65 (2H), 3.50-3.42 (2H), 0.77-0.47 (4H).

Analytical UPLC-MS method 1: retention time (min.)=1.98; Observed mass (m/z)=396.161;

Example 126

2-(4-chlorophenyl)-1-[5-(7H-pyrrolo[2,3-d]pyrimidin-4-yl)-5,9-diazaspiro[2.6]nonan-9-yl]ethanone Analytical UPLC-MS method 1: retention time (min.)=1.92; Observed mass (m/z)=396.158;

Example 127

3-pyridyl-[5-(7H-pyrrolo[2,3-d]pyrimidin-4-yl)-5,8-diazaspiro[2.6]nonan-8-yl]methanone Analytical UPLC-MS method 1: retention time (min.)=1.64; Observed mass (m/z)=349.172;

Example 128

3-pyridyl-[5-(7H-pyrrolo[2,3-d]pyrimidin-4-yl)-5,9-diazaspiro[2.6]nonan-9-yl]methanone Analytical UPLC-MS method 1: retention time (min.)=1.60; Observed mass (m/z)=349.178;

Example 129

4-pyridyl-[5-(7H-pyrrolo[2,3-d]pyrimidin-4-yl)-5,8-diazaspiro[2.6]nonan-8-yl]methanone Analytical UPLC-MS method 1: retention time (min.)=1.63; Observed mass (m/z)=349.178;

Example 130

4-pyridyl-[5-(7H-pyrrolo[2,3-d]pyrimidin-4-yl)-5,9-diazaspiro[2.6]nonan-9-yl]methanone Analytical UPLC-MS method 1: retention time (min.)=1.60; Observed mass (m/z)=349.178;

Example 131

(6-hydroxy-3-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)=1.57; Observed mass (m/z)=365.173;

Example 132

(6-hydroxy-3-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.54; Observed mass (m/z)=365.172;

Example 133

1H-imidazol-4-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.53; Observed mass (m/z)=338.172;

Example 134

1H-imidazol-4-yl-[5-(7H-pyrrolo[2,3-d]pyrimidin-4-yl)-5,9-diazaspiro[2.6]nonan-9-yl]methanone Analytical UPLC-MS method 1: retention time (min.)= 1.49; Observed mass (m/z)=338.176;

Example 135

(2-methyl-3-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.66; Observed mass (m/z)=363.193;

Example 136

(2-methyl-3-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.61; Observed mass (m/z)=363.187;

Example 137

(3-methyl-4-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.68; Observed mass (m/z)=363.196;

Example 138

(3-methyl-4-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.62; Observed mass (m/z)=363.191;

Example 139 pyridazin-4-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.61; Observed mass (m/z)=350.172;

Example 140

2-(2,4-dimethylthiazol-5-yl)-1-[5-(7H-pyrrolo[2,3-d]pyrimidin-4-yl)-5,9-diazaspiro[2.6]nonan-9-yl]ethanone Analytical UPLC-MS method 1: retention time (min.)= 1.68; Observed mass (m/z)=397.182;

Example 141

(5-methylisoxazol-3-yl-[5-(7H-pyrrolo[2,3-d]pyrimidin-4-yl)-5,9-diazaspiro[2.6]nonan-9-yl]methanone $^1$H NMR (600 MHz, DMSO) δ 11.67 (1H), 8.09 (1H), 7.21-7.14 (1H), 6.54-6.48 (1H), 6.41-6.31 (1H), 4.43-3.46 (6H), 3.38 (3H), 3.08-2.85 (1H), 2.15-1.85 (2H), 1.22-0.72 (4H).

Analytical UPLC-MS method 1: retention time (min.)= 1.79; Observed mass (m/z)=353.151;

Example 142

[5-(7H-pyrrolo[2,3-d]pyrimidin-4-yl)-5,9-diazaspiro[2.6]nonan-9-yl]-(thiadiazol-4-yl)methanone $^1$H NMR (600 MHz, DMSO) δ 11.75-11.61 (1H), 9.55-9.46 (1H), 8.15-8.06 (1H), 7.21-7.11 (1H), 6.62-6.48 (1H), 3.55-4.58 (6H), 2.23-1.84 (2H), 1.25-0.44 (4H).

Analytical UPLC-MS method 1: retention time (min.)= 1.70; Observed mass (m/z)=356.122;

Example 143

(2,5-dimethylpyrazol-3-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.75; Observed mass (m/z)=366.201;

Example 144

(3-methylimidazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.56; Observed mass (m/z)=352.186;

Example 145

(3-methylimidazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.50; Observed mass (m/z)=352.167;

Example 146

(4-methylthiadiazol-5-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.81; Observed mass (m/z)=370.144;

Example 147

(4-methylthiadiazol-5-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.74; Observed mass (m/z)=370.144;

Example 148

(5-methyl-1H-pyrazol-3-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.67; Observed mass (m/z)=352.188;

Example 149

(5-methyl-1H-pyrazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.65; Observed mass (m/z)=352.193;

Example 150

(4-methyl-3-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.67; Observed mass (m/z)=363.196;

Example 151

(4-methyl-3-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.63; Observed mass (m/z)=363.196;

Example 152 isoxazol-3-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.77; Observed mass (m/z)=339.153;

Example 153 isoxazol-3-yl-[5-(7H-pyrrolo[2,3-d]pyrimidin-4-yl)-5,9-diazaspiro[2.6]nonan-9-yl]methanone $^1$H NMR (600 MHz, DMSO) δ 11.77-11.62 (1H), 9.09-8.99 (1H), 8.12 (1H), 7.22-7.12 (1H), 6.81-6.71 (1H), 6.55-6.49 (1H), 4.44-3.47 (6H), 2.16-1.85 (2H), 1.18-0.71 (4H).
Analytical UPLC-MS method 1: retention time (min.)= 1.72; Observed mass (m/z)=339.156;

Example 154

(5-methyl-1,3,4-oxadiazol-2-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.66; Observed mass (m/z)=354.169;

Example 155 oxazol-5-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.66; Observed mass (m/z)=339.155;

Example 156 oxazol-5-yl-[5-(7H-pyrrolo[2,3-d]pyrimidin-4-yl)-5,9-diazaspiro[2.6]nonan-9-yl]methanone Analytical UPLC-MS method 1: retention time (min.)= 1.61; Observed mass (m/z)=339.158;

Example 157

1H-pyrazol-4-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.59; Observed mass (m/z)=338.168;

Example 158

2-(4-fluorophenyl)-1-[5-(7H-pyrrolo[2,3-d]pyrimidin-4-yl)-5,8-diazaspiro[2.6]nonan-8-yl]ethanone $^1$H NMR (600 MHz, DMSO) δ: 11.66 (1H), 8.09 (1H), 7.24-7.21 (1H), 7.18-7.14 (2H), 7.09-7.05 (1H), 7.03-6.99 (1H), 6.54-6.51 (1H), 4.06-4.01 (2H), 3.89-3.83 (4H), 3.70-3.66 (2H), 3.50-3.43 (2H), 2.50 (2H), 0.74-0.49 (4H).
Analytical UPLC-MS method 1: retention time (min.)= 1.91; Observed mass (m/z)=380.19;

Example 159

2-(4-fluorophenyl)-1-[5-(7H-pyrrolo[2,3-d]pyrimidin-4-yl)-5,9-diazaspiro[2.6]nonan-9-yl]ethanone Analytical UPLC-MS method 1: retention time (min.)= 1.86; Observed mass (m/z)=380.184;

Example 160 pyrimidin-5-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.61; Observed mass (m/z)=350.172;

Example 161 pyrimidin-5-yl-[5-(7H-pyrrolo[2,3-d]pyrimidin-4-yl)-5,9-diazaspiro[2.6]nonan-9-yl]methanone Analytical UPLC-MS method 1: retention time (min.)= 1.60; Observed mass (m/z)=350.175;

Example 162

2-[5-(7H-pyrrolo[2,3-d]pyrimidin-4-yl)-5,9-diazaspiro[2.6]nonane-9-carbonyl]benzonitrile Analytical UPLC-MS method 1: retention time (min.)= 1.82; Observed mass (m/z)=373.18;

Example 163

(6-hydroxy-2-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.60; Observed mass (m/z)=365.17;

Example 164

(6-hydroxy-2-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.56; Observed mass (m/z)=365.173;

Example 165 pyrimidin-4-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.64; Observed mass (m/z)=350.172;

Example 166 pyrimidin-4-yl-[5-(7H-pyrrolo[2,3-d]pyrimidin-4-yl)-5,9-diazaspiro[2.6]nonan-9-yl]methanone $^1$H NMR (600 MHz, DMSO) δ: 11.75-11.61 (1H), 9.25-9.15 (1H), 9.00-8.89 (1H), 8.12 (1H), 7.67-8.49 (1H), 7.20-7.14 (1H), 6.57-6.48 (1H), 4.58-3.64 (6H), 2.17-1.80 (2H), 1.16-0.49 (4H).
Analytical UPLC-MS method 1: retention time (min.)= 1.60; Observed mass (m/z)=350.169;

Example 167

2-(2-pyridyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.60; Observed mass (m/z)=363.175;

Example 168

(3-methylpyrazin-2-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.68; Observed mass (m/z)=364.183;

Example 169

(6-methylpyrazin-2-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.72; Observed mass (m/z)=364.188;

Example 170

(3,5-dimethylisoxazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.77; Observed mass (m/z)=367.189;

Example 171

(2-methyl-4-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)= 1.64; Observed mass (m/z)=363.175;

Example 172

(2-methyl-4-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)= 1.60; Observed mass (m/z)=363.191;

Example 173

2-(2-chlorophenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 2.00; Observed mass (m/z)=396.139;

Example 174

2-(2-chlorophenyl)-1-[5-(7H-pyrrolo[2,3-d]pyrimidin-4-yl)-5,9-diazaspiro[2.6]nonan-9-yl]ethanone Analytical UPLC-MS method 1: retention time (min.)= 1.95; Observed mass (m/z)=396.16;

Example 175

(5-methylisoxazol-3-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.84; Observed mass (m/z)=353.152;

Example 176

(4-chlorophenyl)-[5-(7H-pyrrolo[2,3-d]pyrimidin-4-yl)-5,8-diazaspiro[2.6]nonan-8-yl]methanone Analytical UPLC-MS method 1: retention time (min.)= 2.02; Observed mass (m/z)=382.116;

Example 177 isoxazol-5-yl-[5-(7H-pyrrolo[2,3-d]pyrimidin-4-yl)-5,8-diazaspiro[2.6]nonan-8-yl]methanone Analytical UPLC-MS method 1: retention time (min.)=1.75; Observed mass (m/z)=339.157;

Example 178

(2-chlorophenyl)-[5-(7H-pyrrolo[2,3-d]pyrimidin-4-yl)-5,9-diazaspiro[2.6]nonan-9-yl]methanone Analytical UPLC-MS method 1: retention time (min.)=1.89; Observed mass (m/z)=382.122;

Example 179

(3-chlorophenyl)-[5-(7H-pyrrolo[2,3-d]pyrimidin-4-yl)-5,9-diazaspiro[2.6]nonan-9-yl]methanone Analytical UPLC-MS method 1: retention time (min.)=1.96; Observed mass (m/z)=382.144;

Example 180

(4-chlorophenyl)-[5-(7H-pyrrolo[2,3-d]pyrimidin-4-yl)-5,9-diazaspiro[2.6]nonan-9-yl]methanone $^1$H NMR (600 MHz, DMSO) δ 11.79-11.57 (1H), 8.13 (1H), 7.50-7.09 (5H), 6.51 (1H), 4.52-3.29 (6H), 2.08 (1H), 1.75 (1H), 1.20-0.52 (4H).
Analytical UPLC-MS method 1: retention time (min.)=1.97; Observed mass (m/z)=382.139;

Example 181 isoxazol-5-yl-[5-(7H-pyrrolo[2,3-d]pyrimidin-4-yl)-5,9-diazaspiro[2.6]nonan-9-yl]methanone $^1$H NMR (600 MHz, DMSO) δ 11.69 (1H), 8.78-8.68 (1H), 8.11 (1H), 7.23-7.14 (1H), 6.95-6.83 (1H), 6.58-6.51 (1H), 4.39-3.52 (6H), 2.18-1.86 (2H), 1.16-0.71 (4H).
Analytical UPLC-MS method 1: retention time (min.)=1.70; Observed mass (m/z)=339.158;

Example 182

1H-pyrazol-3-yl-[5-(7H-pyrrolo[2,3-d]pyrimidin-4-yl)-5,8-diazaspiro[2.6]nonan-8-yl]methanone Analytical UPLC-MS method 1: retention time (min.)=1.62; Observed mass (m/z)=338.174;

Example 183

1H-pyrazol-3-yl-[5-(7H-pyrrolo[2,3-d]pyrimidin-4-yl)-5,9-diazaspiro[2.6]nonan-9-yl]methanone Analytical UPLC-MS method 1: retention time (min.)=1.59; Observed mass (m/z)=338.172;

Example 184

2-(3-methylisoxazol-5-yl)-1-[5-(7H-pyrrolo[2,3-d]pyrimidin-4-yl)-5,8-diazaspiro[2.6]nonan-8-yl]ethanone $^1$H NMR (600 MHz, DMSO) δ 11.67 (1H), 8.10 (1H), 7.18 (1H), 6.55 (1H), 6.16-6.05 (1H), 4.13-4.03 (2H), 3.94 (1H), 3.91-3.90 (1H), 3.89-3.95 (4H), 3.50-3.45 (2H), 2.18-2.12 (2H), 0.79-0.53 (4H).
Analytical UPLC-MS method 1: retention time (min.)=1.73; Observed mass (m/z)=367.184;

Example 185

(2-chlorophenyl)-[5-(7H-pyrrolo[2,3-d]pyrimidin-4-yl)-5,8-diazaspiro[2.6]nonan-8-yl]methanone Analytical UPLC-MS method 1: retention time (min.)=1.93; Observed mass (m/z)=382.143;

Example 186

(3-chlorophenyl)-[5-(7H-pyrrolo[2,3-d]pyrimidin-4-yl)-5,8-diazaspiro[2.6]nonan-8-yl]methanone Analytical UPLC-MS method 1: retention time (min.)=2.01; Observed mass (m/z)=382.118;

Example 187

(5-methylisoxazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.71; Observed mass (m/z)=353.17;

Example 188

2-pyridyl-[5-(7H-pyrrolo[2,3-d]pyrimidin-4-yl)-5,8-diazaspiro[2.6]nonan-8-yl]methanone Analytical UPLC-MS method 1: retention time (min.)=1.69; Observed mass (m/z)=349.175;

Example 189

2-pyridyl-[5-(7H-pyrrolo[2,3-d]pyrimidin-4-yl)-5,9-diazaspiro[2.6]nonan-9-yl]methanone Analytical UPLC-MS method 1: retention time (min.)=1.67; Observed mass (m/z)=349.176;

Example 190

(2-hydroxy-4-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)=1.57; Observed mass (m/z)=365.17;

Example 191

(4-methyloxazol-5-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.70; Observed mass (m/z)=353.174;

Example 192

(4-methyloxazol-5-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.67; Observed mass (m/z)=353.167;

Example 193

(2,5-dimethylpyrazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.71; Observed mass (m/z)=366.2;

Example 194

(5-methyl-1,3,4-oxadiazol-2-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.72; Observed mass (m/z)=354.166;

Example 195

[5-(7H-pyrrolo[2,3-d]pyrimidin-4-yl)-5,8-diazaspiro[2.6]nonan-8-yl]-(1H-1,2,4-triazol-3-yl)methanone Analytical UPLC-MS method 1: retention time (min.)= 1.56; Observed mass (m/z)=339.168;

Example 196

(5-methylpyrazin-2-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.71; Observed mass (m/z)=364.189;

Example 197

(5-methylpyrazin-2-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.67; Observed mass (m/z)=364.183;

Example 198

(6-methylpyrazin-2-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.67; Observed mass (m/z)=364.191;

Example 199

(3,5-dimethylisoxazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.72; Observed mass (m/z)=367.188;

Example 200 isothiazol-3-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.78; Observed mass (m/z)=355.121;

Example 201 isothiazol-3-yl-[5-(7H-pyrrolo[2,3-d]pyrimidin-4-yl)-5,9-diazaspiro[2.6]nonan-9-yl]methanone $^1$H NMR (600 MHz, DMSO) δ 11.66 (1H), 9.21-9.04 (1H), 8.06 (1H), 7.55-7.49 (1H), 7.24-7.10 (1H), 6.60-6.46 (1H), 4.72-3.56 (5H), 2.96 (1H), 2.24-1.80 (2H), 1.30-0.41 (m, 4H).

Analytical UPLC-MS method 1: retention time (min.)= 1.74; Observed mass (m/z)=355.137,

Example 202

[5-(7H-pyrrolo[2,3-d]pyrimidin-4-yl)-5,8-diazaspiro[2.6]nonan-8-yl]-(1,2,5-thiadiazol-3-yl)methanone Analytical UPLC-MS method 1: retention time (min.)= 1.83; Observed mass (m/z)=356.132;

Example 203

[5-(7H-pyrrolo[2,3-d]pyrimidin-4-yl)-5,9-diazaspiro[2.6]nonan-9-yl]-(1,2,5-thiadiazol-3-yl)methanone $^1$H NMR (600 MHz, DMSO) δ 11.67 (1H), 9.11-8.96 (1H), 8.10 (1H), 7.24-7.14 (1H), 6.59-6.50 (1H), 4.64-3.54 (5H), 3.03 (1H), 2.18-1.89 (2H), 1.19-0.47 (4H).

Analytical UPLC-MS method 1: retention time (min.)= 1.76; Observed mass (m/z)=356.132;

Example 204

[5-(7H-pyrrolo[2,3-d]pyrimidin-4-yl)-5,8-diazaspiro[2.6]nonan-8-yl]-(1H-triazol-4-yl)methanone Analytical UPLC-MS method 1: retention time (min.)= 1.61; Observed mass (m/z)=339.17;

Example 205

[5-(7H-pyrrolo[2,3-d]pyrimidin-4-yl)-5,9-diazaspiro[2.6]nonan-9-yl]-(1H-triazol-4-yl)methanone Analytical UPLC-MS method 1: retention time (min.)= 1.58; Observed mass (m/z)=339.165;

Example 206

(5-methyl-1H-pyrazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)=1.61; Observed mass (m/z)=352.15;

Example 207

(5-methyl-1H-pyrazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.59; Observed mass (m/z)=352.19;

Example 208

5-[5-(7H-pyrrolo[2,3-d]pyrimidin-4-yl)-5,8-diazaspiro[2.6]nonane-8-carbonyl]-1H-pyrrole-3-carbonitrile $^1$H NMR (600 MHz, DMSO) δ: 12.31 (1H), 11.67 (1H), 8.10 (1H), 7.68 (1H), 7.16 (1H), 7.04-6.84 (1H), 6.58 (1H), 4.31-3.53 (8H), 0.72-0.66 (4H).
Analytical UPLC-MS method 1: retention time (min.)=1.79; Observed mass (m/z)=362.172;

Example 209

5-[5-(7H-pyrrolo[2,3-d]pyrimidin-4-yl)-5,9-diazaspiro[2.6]nonane-9-carbonyl]-1H-pyrrole-3-carbonitrile Analytical UPLC-MS method 1: retention time (min.)=2.53; Observed mass (m/z)=362.171;

Example 210 isothiazol-4-yl-[5-(7H-pyrrolo[2,3-d]pyrimidin-4-yl)-5,8-diazaspiro[2.6]nonan-8-yl]methanone Analytical UPLC-MS method 1: retention time (min.)=1.71; Observed mass (m/z)=355.126;

Example 211 isothiazol-4-yl-[5-(7H-pyrrolo[2,3-d]pyrimidin-4-yl)-5,9-diazaspiro[2.6]nonan-9-yl]methanone Analytical UPLC-MS method 1: retention time (min.)=1.67; Observed mass (m/z)=355.131;

Example 212

(5-hydroxy-1H-pyrazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.56; Observed mass (m/z)=354.166;

Example 213

(5-fluoro-3-pyridyl)-[5-(7H-pyrrolo[2,3-d]pyrimidin-4-yl)-5,8-diazaspiro[2.6]nonan-8-yl]methanone Analytical UPLC-MS method 1: retention time (min.)=1.74; Observed mass (m/z)=367.128;

Example 214

(5-fluoro-3-pyridyl)-[5-(7H-pyrrolo[2,3-d]pyrimidin-4-yl)-5,9-diazaspiro[2.6]nonan-9-yl]methanone Analytical UPLC-MS method 1: retention time (min.)=1.69; Observed mass (m/z)=367.167;

Example 215

1-[5-(7H-pyrrolo[2,3-d]pyrimidin-4-yl)-5,8-diazaspiro[2.6]nonan-8-yl]-2-(1H-tetrazol-5-yl)ethanone $^1$H NMR (600 MHz, DMSO) δ 11.66 (1H), 8.14-8.03 (1H), 7.21-7.10 (1H), 6.57 (1H), 4.07-3.98 (2H), 3.94-3.86 (4H), 3.85-3.81 (2H), 2.69 (1H), 1.22-0.55 (5H).
Analytical UPLC-MS method 1: retention time (min.)=1.55; Observed mass (m/z)=354.179;

Example 216

[5-(7H-pyrrolo[2,3-d]pyrimidin-4-yl)-5,8-diazaspiro[2.6]nonan-8-yl]-thiazol-4-yl-methanone Analytical UPLC-MS method 1: retention time (min.)=1.69; Observed mass (m/z)=355.131;

Example 217

2-(3-methylisoxazol-5-yl)-1-[5-(7H-pyrrolo[2,3-d]pyrimidin-4-yl)-5,9-diazaspiro[2.6]nonan-9-yl]ethanone Analytical UPLC-MS method 1: retention time (min.)=1.69; Observed mass (m/z)=367.186;

Example 224

N-(2-cyanoethyl)-N-ethyl-5-(7H-pyrrolo[2,3-d]pyrimidin-4-yl)-5,8-diazaspiro[2.6]nonane-8-carboxamide 100 uL of a 0.35 M stock solution of 3-(ethylamino)propanenitrile in chloroform and 200 uL of a 0.15 M stock solution of bis(trichloromethyl) carbonate (triphosgene) in chloroform were combined and added 20 uL N,N-diisopropylethylamine and 20 uL pyridine. The reaction mixture was gently shaken for 3 h at room temperature, then 150 uL of a 0.35 M stock solution of Intermediate 5 in DMSO was added together with 50 uL N,N-diisopropylethylamine. The reaction mixture was gently shaken for 72 h at room temperature. The solvent was removed by evaporation and the residue redissolved in DMSO prior to purification by standard preparative LC/MS Analytical UPLC-MS method 1: retention time (min.)=1.77; Observed mass (m/z)=368.216;

Examples 218-223 and 225 were prepared analogously using the relevant starting materials in each case.

Example 218

N-(cyanomethyl)-N-methyl-5-(7H-pyrrolo[2,3-d]pyrimidin-4-yl)-5,8-diazaspiro[2.6]nonane-8-carboxamide Analytical UPLC-MS method 1: retention time (min.)=1.70; Observed mass (m/z)=340.164;

Example 219

N,N-bis(cyanomethyl)-5-(7H-pyrrolo[2,3-d]pyrimidin-4-yl)-5,8-diazaspiro[2.6]nonane-8-carboxamide Analytical UPLC-MS method 1: retention time (min.)=1.73; Observed mass (m/z)=365.184;

Example 220

N-(2-cyanoethyl)-N-methyl-5-(7H-pyrrolo[2,3-d]pyrimidin-4-yl)-5,8-diazaspiro[2.6]nonane-8-carboxamide Analytical UPLC-MS method 1: retention time (min.)=1.69; Observed mass (m/z)=354.205;

Example 221

(2R)-1-[5-(7H-pyrrolo[2,3-d]pyrimidin-4-yl)-5,8-diazaspiro[2.6]nonane-8-carbonyl]pyrrolidine-2-carbonitrile Analytical UPLC-MS method 1: retention time (min.)=1.77; Observed mass (m/z)=366.208;

Example 222

(2S)-1-[5-(7H-pyrrolo[2,3-d]pyrimidin-4-yl)-5,8-diazaspiro[2.6]nonane-8-carbonyl]pyrrolidine-2-carbonitrile Analytical UPLC-MS method 1: retention time (min.)=1.78; Observed mass (m/z)=366.208;

Example 223

N-isopropyl-N-methyl-5-(7H-pyrrolo[2,3-d]pyrimidin-4-yl)-5,8-diazaspiro[2.6]nonane-8-carboxamide Analytical UPLC-MS method 1: retention time (min.)=1.86; Observed mass (m/z)=343.226;

Example 225

N,N-bis(2-cyanoethyl)-5-(7H-pyrrolo[2,3-d]pyrimidin-4-yl)-5,8-diazaspiro[2.6]nonane-8-carboxamide Analytical UPLC-MS method 1: retention time (min.)=1.69; Observed mass (m/z)=393.219;

Example 226

1-[5-(7H-pyrrolo[2,3-d]pyrimidin-4-yl)-5,9-diazaspiro[2.6]nonan-9-yl]-2-(1H-tetrazol-5-yl)ethanone Analytical UPLC-MS method 1: retention time (min.)=1.52; Observed mass (m/z)=354.179;

Example 227

[5-(7H-pyrrolo[2,3-d]pyrimidin-4-yl)-5,9-diazaspiro[2.6]nonan-9-yl]-thiazol-4-yl-methanone Analytical UPLC-MS method 1: retention time (min.)=1.66; Observed mass (m/z)=355.135;

Example 228

[5-(7H-pyrrolo[2,3-d]pyrimidin-4-yl)-5,9-diazaspiro[2.6]nonan-9-yl]-(1H-1,2,4-triazol-3-yl)methanone Analytical UPLC-MS method 1: retention time (min.)=1.53; Observed mass (m/z)=339.167;

Example 229

(5-methylisothiazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)=1.82; Observed mass (m/z)=369.153;

Example 230

(5-methylisothiazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.78; Observed mass (m/z)=369.153;

Example 231

(5-chloro-1H-1,2,4-triazol-3-yl)-[5-(7H-pyrrolo[2,3-d]pyrimidin-4-yl)-5,8-diazaspiro[2.6]nonan-8-yl]methanone Analytical UPLC-MS method 1: retention time (min.)=1.81; Observed mass (m/z)=373.13;

Example 232

(5-chloro-1H-1,2,4-triazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.75; Observed mass (m/z)=373.132;

Example 233

(3-methylisothiazol-5-yl)-[5-(7H-pyrrolo[2,3-d]pyrimidin-4-yl)-5,8-diazaspiro[2.6]nonan-8-yl]methanone Analytical UPLC-MS method 1: retention time (min.)=1.76; Observed mass (m/z)=369.15;

Example 234

(3-methylisothiazol-5-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.71; Observed mass (m/z)=369.155;

Example 235 isothiazol-5-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.78; Observed mass (m/z)=355.137;

Example 236 isothiazol-5-yl-[5-(7H-pyrrolo[2,3-d]pyrimidin-4-yl)-5,9-diazaspiro[2.6]nonan-9-yl]methanone $^1$H NMR (600 MHz, DMSO) δ 11.74-11.62 (1H), 9.19-9.04 (1H), 8.11 (1H), 7.56-7.41 (1H), 7.19-7.13 (1H), 6.57-6.49 (1H), 4.67-3.48 (6H), 2.16-1.84 (2H), 1.16-0.40 (4H).
Analytical UPLC-MS method 1: retention time (min.)= 1.74; Observed mass (m/z)=355.132;

Example 237

(3-methyl-1H-pyrazol-5-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.67; Observed mass (m/z)=352.19;

Example 238

(3-methyl-1H-pyrazol-5-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.65; Observed mass (m/z)=352.19;

Example 239

[5-(7H-pyrrolo[2,3-d]pyrimidin-4-yl)-5,8-diazaspiro[2.6]nonan-8-yl]-thiazol-5-yl-methanone Analytical UPLC-MS method 1: retention time (min.)= 1.69; Observed mass (m/z)=355.131;

Example 240

[5-(7H-pyrrolo[2,3-d]pyrimidin-4-yl)-5,9-diazaspiro[2.6]nonan-9-yl]-thiazol-5-yl-methanone Analytical UPLC-MS method 1: retention time (min.)= 1.65; Observed mass (m/z)=355.134;

Example 241

(5-methylthiazol-2-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.96; Observed mass (m/z)=369.155;

Example 242

1H-imidazol-5-yl-[5-(7H-pyrrolo[2,3-d]pyrimidin-4-yl)-5,8-diazaspiro[2.6]nonan-8-yl]methanone Analytical UPLC-MS method 1: retention time (min.)= 1.53; Observed mass (m/z)=338.181;

Example 243

1H-imidazol-5-yl-[5-(7H-pyrrolo[2,3-d]pyrimidin-4-yl)-5,9-diazaspiro[2.6]nonan-9-yl]methanone Analytical UPLC-MS method 1: retention time (min.)= 1.49; Observed mass (m/z)=338.174;

Example 244

(3-methylisoxazol-4-yl)-[5-(7H-pyrrolo[2,3-d]pyrimidin-4-yl)-5,8-diazaspiro[2.6]nonan-8-yl]methanone Analytical UPLC-MS method 1: retention time (min.)= 1.74; Observed mass (m/z)=353.173;

Example 245

(3-methylisoxazol-4-yl)-[5-(7H-pyrrolo[2,3-d]pyrimidin-4-yl)-5,9-diazaspiro[2.6]nonan-9-yl]methanone Analytical UPLC-MS method 1: retention time (min.)= 1.70; Observed mass (m/z)=353.171;

Example 246

2-(4-methylthiazol-5-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.71; Observed mass (m/z)=383.166;

Example 247

2-(2-methylthiazol-5-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.71; Observed mass (m/z)=383.161;

Example 248

2-(5-methyl-1H-pyrazol-3-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.66; Observed mass (m/z)=366.205;

Example 249

2-(3,5-dimethylisoxazol-4-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.76; Observed mass (m/z)=381.204;

Example 250

2-(3-methyl-1H-1,2,4-triazol-5-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.54; Observed mass (m/z)=367.2;

Example 251

2-(4-methyl-1,2,5-oxadiazol-3-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.83; Observed mass (m/z)=368.183;

Example 252

1-[5-(7H-pyrrolo[2,3-d]pyrimidin-4-yl)-5,8-diazaspiro[2.6]nonan-8-yl]-2-thiazol-5-yl-ethanone Analytical UPLC-MS method 1: retention time (min.)=1.67; Observed mass (m/z)=369.149;

Example 253

2-(1-methylpyrazol-4-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.64; Observed mass (m/z)=366.205;

Example 254

2-(2-methylthiazol-4-yl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.72; Observed mass (m/z)=383.163;

Example 255

[5-(7H-pyrrolo[2,3-d]pyrimidin-4-yl)-5,9-diazaspiro[2.6]nonan-9-yl]-(1H-pyrrol-2-yl)methanone Analytical UPLC-MS method 1: retention time (min.)=1.77; Observed mass (m/z)=337.177;

Example 256

(4-amino-1,2,5-oxadiazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.80; Observed mass (m/z)=355.164;

Example 257

(5-methyl-4H-1,2,4-triazol-3-yl)-[5-(7H-pyrrolo[2,3-d]pyrimidin-4-yl)-5,9-diazaspiro[2.6]nonan-9-yl]methanone Analytical UPLC-MS method 1: retention time (min.)=1.55; Observed mass (m/z)=353.185;

Example 258

5-[5-(7H-pyrrolo[2,3-d]pyrimidin-4-yl)-5,9-diazaspiro[2.6]nonane-9-carbonyl]furan-2-carbonitrile Analytical UPLC-MS method 1: retention time (min.)=1.85; Observed mass (m/z)=363.155;

Example 259

2-phenyl-1-[5-(7H-pyrrolo[2,3-d]pyrimidin-4-yl)-5,8-diazaspiro[2.6]nonan-8-yl]ethanone Analytical UPLC-MS method 1: retention time (min.)=1.90; Observed mass (m/z)=362.2;

Example 260

(1-phenylcyclopropyl)-[5-(7H-pyrrolo[2,3-d]pyrimidin-4-yl)-5,8-diazaspiro[2.6]nonan-8-yl]methanone Analytical UPLC-MS method 1: retention time (min.)=1.97; Observed mass (m/z)=388.214;

Example 261

2-(4-methoxyphenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.89; Observed mass (m/z)=392.207;

Example 262

2-(m-tolyl)-1-[5-(7H-pyrrolo[2,3-d]pyrimidin-4-yl)-5,8-diazaspiro[2.6]nonan-8-yl]ethanone Analytical UPLC-MS method 1: retention time (min.)=1.97; Observed mass (m/z)=376.215;

Example 263

2-(p-tolyl)-1-[5-(7H-pyrrolo[2,3-d]pyrimidin-4-yl-5, 8-diazaspiro[2.6]nonan-8-yl]ethanone ¹H NMR (600 MHz, DMSO) δ 11.64 (1H), 8.07 (1H), 7.15 (1H), 7.10-6.98 (4H), 6.54-6.49 (1H), 4.06-3.95 (2H), 3.91-3.78 (4H), 3.65-3.61 (2H), 3.46-3.44 (2H), 2.25-2.22 (3H), 0.72-0.45 (4H).
Analytical UPLC-MS method 1: retention time (min.)= 1.97; Observed mass (m/z)=376.215;

Example 264

2-(4-bromophenyl)-1-[5-(7H-pyrrolo[2,3-d]pyrimidin-4-yl)-5,8-diazaspiro[2.6]nonan-8-yl]ethanone ¹H NMR (600 MHz, DMSO) δ 11.67 (1H), 8.09 (1H), 7.45-7.36 (2H), 7.19-7.10 (3H), 6.50 (1H), 4.08-4.01 (2H), 3.92-3.81 (4H), 3.72-3.68 (2H), 3.50-3.42 (2H), 0.78-0.50 (4H).
Analytical UPLC-MS method 1: retention time (min.)= 2.03; Observed mass (m/z)=440.107;

Example 265

2-(2-naphthyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 2.00; Observed mass (m/z)=412.217;

Example 266

2-[4-[2-oxo-2-[5-(7H-pyrrolo[2,3-d]pyrimidin-4-yl)-5,8-diazaspiro[2.6]nonan-8-yl]ethyl]phenyl]acetonitrile ¹H NMR (600 MHz, DMSO) δ 11.68 (1H), 8.07 (1H), 7.26-7.14 (5H), 6.55-6.48 (1H), 4.06-4.01 (2H), 3.99-3.95 (2H), 3.91-3.80 (4H), 3.69 (2H), 3.49-3.46 (2H), 0.73-0.51 (4H).
Analytical UPLC-MS method 1: retention time (min.)= 1.86; Observed mass (m/z)=401.207;

Example 267

2-(4-tert-butylphenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 2.29; Observed mass (m/z)=418.264;

Example 268

2-(4-dimethylaminophenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 1.78; Observed mass (m/z)=405.238;

Example 269

2-(4-chlorophenyl)-2-methyl-1-[5-(7H-pyrrolo[2,3-d]pyrimidin-4-yl)-5,8-diazaspiro[2.6]nonan-8-yl]propan-1-one Analytical UPLC-MS method 1: retention time (min.)= 2.18; Observed mass (m/z)=424.189;

Example 270

2-(2,4-dichlorophenyl)-1-[5-(7H-pyrrolo[2,3-d]pyrimidin-4-yl)-5,8-diazaspiro[2.6]nonan-8-yl]ethanone Analytical UPLC-MS method 1: retention time (min.)= 2.16; Observed mass (m/z)=430.12;

Example 272

2-[2-oxo-2-[5-(7H-pyrrolo[2,3-d]pyrimidin-4-yl)-5,8-diazaspiro[2.6]nonan-8-yl]ethyl]benzonitrile Analytical UPLC-MS method 1: retention time (min.)= 1.90; Observed mass (m/z)=387.193;

Example 273

2-fluoro-5-[2-oxo-2-[5-(7H-pyrrolo[2,3-d]pyrimidin-4-yl)-5,8-diazaspiro[2.6]nonan-8-yl]ethyl]benzonitrile Analytical UPLC-MS method 1: retention time (min.)= 1.92; Observed mass (m/z)=405.182;

Example 274

1-[5-(7H-pyrrolo[2,3-d]pyrimidin-4-yl)-5,8-diazaspiro[2.6]nonan-8-yl]-2-[4-(trifluoromethoxy)phenyl]ethanone ¹H NMR (600 MHz, DMSO) δ: 11.67 (1H), 8.08 (1H), 7.32-7.29 (1H), 7.28-7.22 (2H), 7.21-7.19 (1H), 7.17-7.14 (1H), 6.53 (1H), 4.10-4.02 (2H), 3.90-3.83 (4H), 3.77-3.72 (2H), 3.51-3.46 (2H), 2.51 (2H), 0.75-0.50 (4H).
Analytical UPLC-MS method 1: retention time (min.)= 2.16; Observed mass (m/z)=446.181;

Example 275

2-phenyl-1-[5-(7H-pyrrolo[2,3-d]pyrimidin-4-yl)-5,8-diazaspiro[2.6]nonan-8-yl]propan-1-one Analytical UPLC-MS method 1: retention time (min.)= 1.98; Observed mass (m/z)=376.211;

Example 276

N-[4-[(2-oxo-2-[5-(7H-pyrrolo[2,3-d]pyrimidin-4-yl)-5,8-diazaspiro[2.6]nonan-8-yl]ethyl]phenyl]acetamide Analytical UPLC-MS method 1: retention time (min.)= 1.72; Observed mass (m/z)=419.219;

Example 277

(4-methyl-1H-pyrrol-2-yl)-[5-(7H-pyrrolo[2,3-d]pyrimidin-4-yl)-5,9-diazaspiro[2.6]nonan-9-yl]methanone $^1$H NMR (300 MHz, DMSO) δ 11.63 (1H), 10.98 (1H), 8.06 (1H), 7.18-7.11 (1H), 6.63 (1H), 6.52 (2H), 4.22-3.80 (4H), 2.69 (1H), 2.10-1.91 (5H), 1.27-0.89 (5H).
Analytical UPLC-MS method 1: retention time (min.)= 2.03; Observed mass (m/z)=351.196;

Example 278

2-methyl-5-[5-(7H-pyrrolo[2,3-d]pyrimidin-4-yl)-5,9-diazaspiro[2.6]nonane-9-carbonyl]-1H-pyrrole-3-carbonitrile $^1$H NMR (300 MHz, DMSO) δ 12.10 (1H), 11.64 (1H), 8.08 (1H), 7.19-7.01 (2H), 6.52 (1H), 4.39-3.58 (6H), 2.30 (3H), 2.16-1.87 (2H), 1.52-0.72 (4H).
Analytical UPLC-MS method 1: retention time (min.)= 2.00; Observed mass (m/z)=376.189;

Example 279

4-(5-butyl-5,8-diazaspiro[2.6]nonan-8-yl)-7H-pyrrolo[2,3-d]pyrimidine

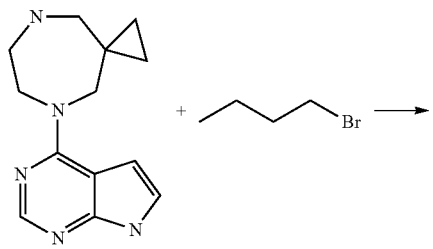

To a solution of intermediate 4 (0.1 mmol) in DMF (1 mL) is added K2CO3 (0.2 mmol) and the suspension is stirred 5 minutes followed by addition of butylbromide (0.1 mmol). The reaction mixture is stirred at 50° C. for 2 hours. The title compound was obtained by standard preparative HPLC purification of the reaction mixture.

$^1$H NMR (300 MHz, DMSO) δ 11.52 (1H), 8.05 (1H), 7.15 (1H), 6.50 (1H), 4.05 (m, 2H), 3.75 (2H), 2.75 (2H), 2.34 (m, 4H), 1.30 (m, 4H), 0.85 (m, 3H), 0.57 (br, 4H)
Example 281 was prepared analogously using the relevant starting materials.

Example 280

4-(9-benzyl-5,9-diazaspiro[2.6]nonan-5-yl)-7H-pyrrolo[2,3-d]pyrimidine

See Intermediate 15.

Example 281

4-(9-butyl-5,9-diazaspiro[2.6]nonan-5-yl)-7H-pyrrolo[2,3-d]pyrimidine $^1$H NMR (300 MHz, DMSO) δ 11.52 (1H), 8.09 (1H), 7.15 (1H), 6.50 (1H), 3.98 (m, 2H), 3.85 (2H), 2.85 (2H), 2.55 (m, 2H), 1.82 (br, 2H), 1.35 (m, 2H), 1.20 (br, 2H), 0.85 (m, 3H), 0.67 (br, 4H)

Example 282

N-[4-(5-benzyl-5,8-diazaspiro[2.6]nonan-8-yl)-7H-pyrrolo[2,3-d]pyrimidin-2-yl]pentanamide See Intermediate 25

Example 283

N-[4-(9-benzyl-5,9-diazaspiro[2.6]nonan-5-yl)-7H-pyrrolo[2,3-d]pyrimidin-2-yl]pentanamide See Intermediate 23

Example 284

[7-methyl-5-(7H-pyrrolo[2,3-d]pyrimidin-4-yl)-5,8-diazaspiro[2.6]nonan-8-yl]-phenyl-methanone $^1$H NMR (300 MHz, DMSO) δ 11.70 (1H), 8.15 (1H), 7.25 (br, 5H), 6.70 (br, 1H), 6.35 (br, 1H), 3.90-4.43 (br, 3H), 3.50-3.70 (br, 4H), 1.03 (m, 3H), 0.80 (br, 2H), 0.55 (br, 2H).

Example 285

2-cyclopentyl-1-[7-methyl-5-(7H-pyrrolo[2,3-d]pyrimidin-4-yl)-5,8-diazaspiro[2.6]nonan-8-yl]ethanone $^1$H NMR (300 MHz, DMSO) δ 11.65 (1H), 8.08 (1H), 7.18 (1H), 6.55 (1H), 4.55 (m, 2H), 4.08 (br, 1H), 3.35-3.55 (br, 4H), 2.25 (m, 1H), 1.68 (br, 3H), 1.05-1.33 (br, 8H), 0.40-0.85 (br, 6H).

Example 286

4-[2-[7-methyl-5-(7H-pyrrolo[2,3-d]pyrimidin-4-yl)-5,8-diazaspiro[2.6]nonan-8-yl]-2-oxo-ethyl]benzonitrile $^1$H NMR (300 MHz, DMSO) δ 11.70 (1H), 8.00-8.10 (1H), 7.70 (0.5H), 7.30 (2H), 7.00-7.15 (2.5H), 6.30-6.50 (1H), 4.35-4.55 (br, 2H), 3.50-4.10 (br, 7H), 1.05-1.22 (3H), 0.45-0.84 (4H).

Example 287

N-[4-[9-(2-phenylacetyl)-5,9-diazaspiro[2.6]nonan-5-yl]-7H-pyrrolo[2,3-d]pyrimidin-2-yl]pentanamide $^1$H NMR (300 MHz, DMSO) δ 11.40 (1H), 9.55 (br, 1H), 7.15 (br, 6H), 6.40 (br, 1H), 4.75 (m, 1H), 4.20 (m, 1H), 3.85 (br, 4H), 2.80 (br, 3H), 1.92 (br, 2H), 1.53 (m, 2H), 0.55-1.35 (10H).

Example 288

N-[4-[9-(5-cyanothiophene-2-carbonyl)-5,9-diazaspiro[2.6]nonan-5-yl]-7H-pyrrolo[2,3-d]pyrimidin-2-yl]pentanamide $^1$H NMR (300 MHz, DMSO) δ 11.47 (1H), 9.60 (1H), 7.94 (1H), 7.82 (br, 1H), 7.02 (1H), 6.47 (1H), 3.80-4.55 (6H), 3.45 (br, 2H), 2.05 (br, 2H), 1.52 (m, 2H), 1.33 (m, 2H), 0.82-125 (br, 7H)

Example 289

N-[4-[8-(5-cyanothiophene-2-carbonyl)-5,8-diazaspiro[2.6]nonan-5-yl]-7H-pyrrolo[2,3-d]pyrimidin-2-yl]pentanamide $^1$H NMR (300 MHz, DMSO) δ 11.45 (1H), 9.55 (1H), 7.91 (1H), 7.48 (1H), 7.03 (1H), 6.47 (1H), 3.80-4.20 (br, 6H), 3.61 (br, 2H), 2.44 (br, 2H), 1.52 (m, 2H), 1.33 (m, 2H), 0.88 (m, 3H), 0.71 (br, 4H)

Example 290

Identical to Intermediate 4

Example 291

Identical to Intermediate 10

Example 292

Identical to Intermediate 16

Example 293

Identical to Intermediate 20

Example 294

Identical to Intermediate 24

Example 295

Identical to Intermediate 26

JAK1, JAK2, JAK3 and TYK2 Kinase Assays:

Human baculovirus-expressed JAK1, 2, 3 and TYK2 were purchased from Carna Biosciences, Inc. All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag. Inhibition of phosphorylation of a synthetic peptide was measured in an HTRF-based assay using the TK substrate-Biotin from the CisbioHTRFKinEASE TK kit. First, 2 μl of TK solution (TK substrate-biotin in kinase buffer [1× enzymatic buffer from HTRFKinEASE TK kit, 1 mM DTT]) is added to a plate containing 1 μl prediluted compound (final assay concentration DMSO: 0.75%). Then, 5 μl kinase-ATP mix (prepared in kinase buffer) is added to the wells and the plates are incubated at RT for 20-30 min. For all four kinases a concentration of ATP that corresponded to the Km for ATP was used. The final concentrations of buffers, substrate, kinase and ATP were: JAK1: 50 mMHepes buffer pH 7.0, 0.01% BSA, 10 mM MgCl$_2$, 1 mM DTT, 7 μM ATP, 50 nMSEB, 1 μM TK Substrate-Biotin and 5 ng JAK1; JAK2: 50 mM Hepes buffer pH 7.0, 0.01% BSA, 5 mM MgCl$_2$, 1 mM DTT, 4 μM ATP, 1 μM TK Substrate-Biotin and 0.1 ng JAK2; JAK3: 50 mMHepes buffer pH 7.0, 0.01% BSA, 5 mM MgCl$_2$, 1 mM DTT, 2 μM ATP, 1 μM TK Substrate-Biotin and 0.3 ng JAK3; TYK2: 50 mMHepes buffer pH 7.0, 0.01% BSA, 5 mM MgCl$_2$, 1 mM DTT, 13 μM ATP, 50 nMSEB, 1 μM TK Substrate-Biotin and 0.8 ng TYK2. Thereafter, the kinase reaction is stopped by adding 4 μl detection mix (final concentrations: 50 mM Hepes buffer pH 7.0, 0.01% BSA, 0.8 M KF, 20 mM EDTA, 42 nM Streptavidin-XL665 and 1:400 STKAbCryptate) and the plates are incubated overnight in the dark. The HTRF signal is read using an Envision plate reader.

In Table 1 selected JAK kinase inhibitory activities are listed with the following indicators: I: $EC_{50}$<100 nM, II: 100 nM≤$EC_{50}$≤1000 nM and III: $EC_{50}$>1000 nM

TABLE 1

| Example number | Structure | JAK1 | JAK2 | JAK3 | TYK2 |
|---|---|---|---|---|---|
| 1 | 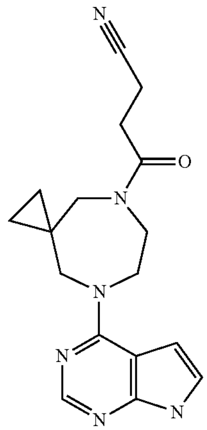 [SMILES: N#CCCC(=O)N1CCN(c2ncnc3[nH]ccc23)CC2(CC2)C1] | I | I | II | II |
| 2 | 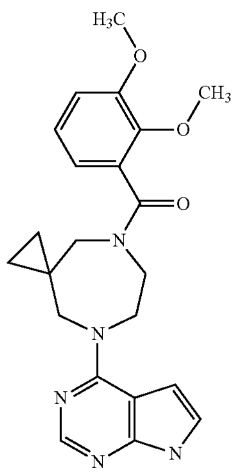 [SMILES: COc1cccc(C(=O)N2CCN(c3ncnc4[nH]ccc34)CC3(CC3)C2)c1OC] | III | III | III | III |
| 3 | 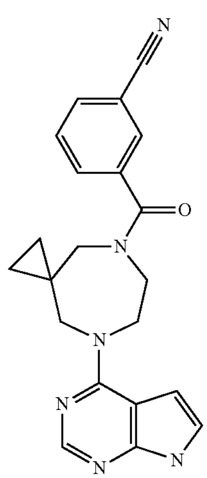 [SMILES: N#Cc1cccc(C(=O)N2CCN(c3ncnc4[nH]ccc34)CC3(CC3)C2)c1] | II | II | III | III |

TABLE 1-continued
| Example number | Structure | JAK1 | JAK2 | JAK3 | TYK2 |
|---|---|---|---|---|---|
| 4 | 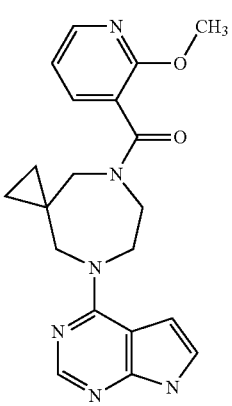 [SMILES: COc1ncccc1C(=O)N1CCN(c2ncnc3[nH]ccc23)CC2(CC2)C1] | III | III | III | III |
| 5 | 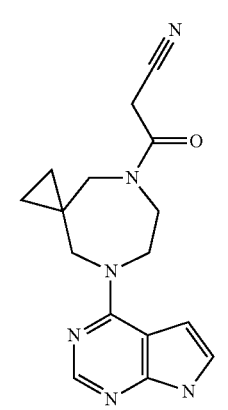 [SMILES: N#CCC(=O)N1CCN(c2ncnc3[nH]ccc23)CC2(CC2)C1] | I | I | I | II |
| 6 | 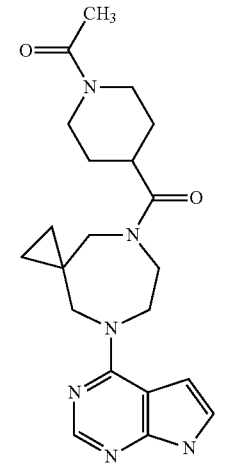 [SMILES: CC(=O)N1CCC(C(=O)N2CCN(c3ncnc4[nH]ccc34)CC3(CC3)C2)CC1] | II | II | III | III |

TABLE 1-continued
| Example number | Structure | JAK1 | JAK2 | JAK3 | TYK2 |
|---|---|---|---|---|---|
| 7 | 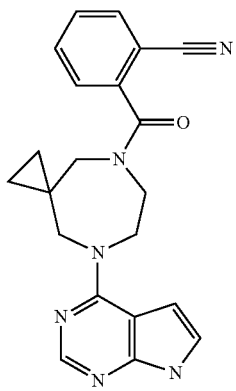 [SMILES: N#Cc1ccccc1C(=O)N1CCN(c2ncnc3[nH]ccc23)CC2(CC2)C1] | III | II | III | III |
| 8 | 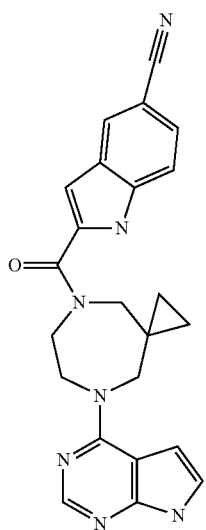 [SMILES: N#Cc1ccc2[nH]c(C(=O)N3CCN(c4ncnc5[nH]ccc45)CC4(CC4)C3)cc2c1] | I | II | II | III |
| 9 | 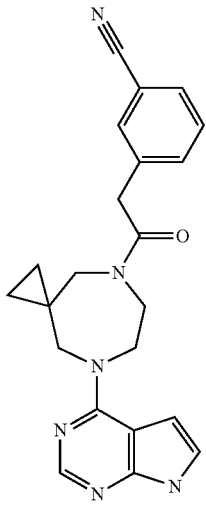 [SMILES: N#Cc1cccc(CC(=O)N2CCN(c3ncnc4[nH]ccc34)CC3(CC3)C2)c1] | II | I | II | III |

TABLE 1-continued
| Example number | Structure | JAK1 | JAK2 | JAK3 | TYK2 |
|---|---|---|---|---|---|
| 10 | 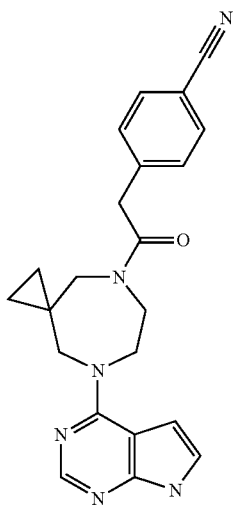 [SMILES: N#Cc1ccc(CC(=O)N2CCN(c3ncnc4[nH]ccc34)CC3(CC3)C2)cc1] | I | I | I | II |
| 11 | 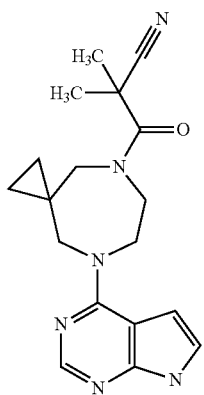 [SMILES: CC(C)(C#N)C(=O)N1CCN(c2ncnc3[nH]ccc23)CC2(CC2)C1] | III | II | II | III |
| 12 | 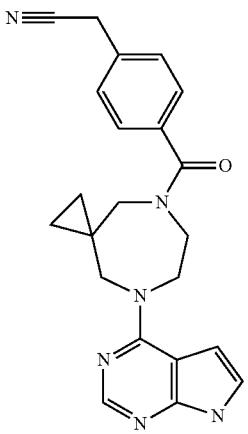 [SMILES: N#CCc1ccc(C(=O)N2CCN(c3ncnc4[nH]ccc34)CC3(CC3)C2)cc1] | II | II | III | III |

TABLE 1-continued

| Example number | Structure | JAK1 | JAK2 | JAK3 | TYK2 |
|---|---|---|---|---|---|
| 13 | 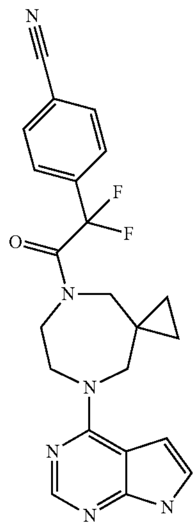 [SMILES: N#Cc1ccc(C(F)(F)C(=O)N2CCN(c3ncnc4[nH]ccc34)CC3(CC3)C2)cc1] | II | I | III | III |
| 14 | 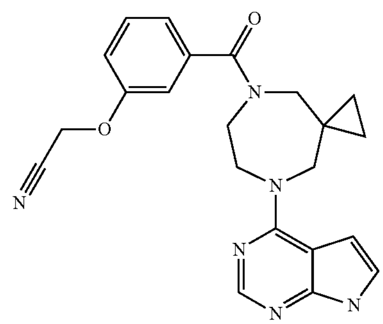 [SMILES: N#CCOc1cccc(C(=O)N2CCN(c3ncnc4[nH]ccc34)CC3(CC3)C2)c1] | II | II | III | III |
| 15 | 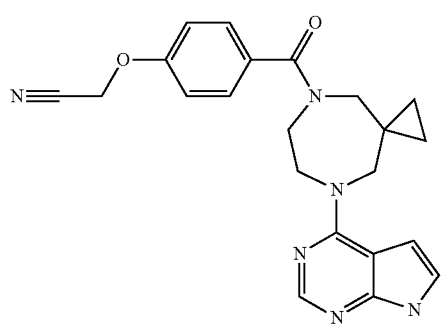 [SMILES: N#CCOc1ccc(C(=O)N2CCN(c3ncnc4[nH]ccc34)CC3(CC3)C2)cc1] | II | II | II | III |
| 16 | 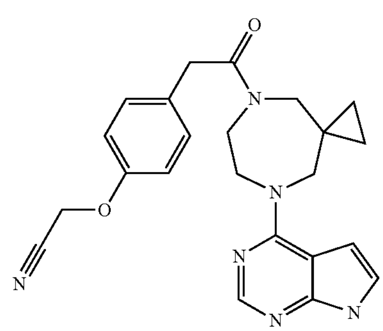 [SMILES: N#CCOc1ccc(CC(=O)N2CCN(c3ncnc4[nH]ccc34)CC3(CC3)C2)cc1] | I | I | II | III |

TABLE 1-continued
| Example number | Structure | JAK1 | JAK2 | JAK3 | TYK2 |
|---|---|---|---|---|---|
| 17 | 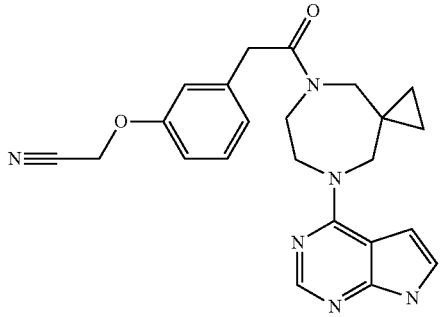 [SMILES: N#CCOc1cccc(CC(=O)N2CCN(c3ncnc4[nH]ccc34)CC3(CC3)C2)c1] | II | II | II | III |
| 18 | 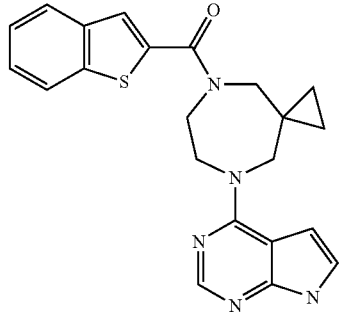 [SMILES: O=C(c1cc2ccccc2s1)N1CCN(c2ncnc3[nH]ccc23)CC2(CC2)C1] | I | II | II | III |
| 19 | 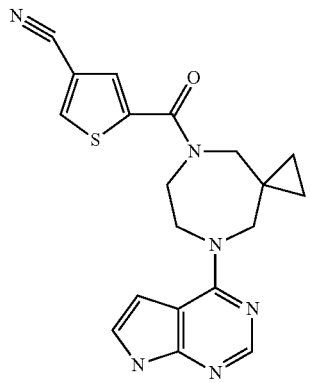 [SMILES: N#Cc1csc(C(=O)N2CCN(c3ncnc4[nH]ccc34)CC3(CC3)C2)c1] | II | I | II | III |
| 20 | 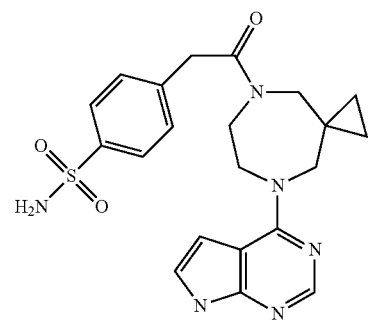 [SMILES: NS(=O)(=O)c1ccc(CC(=O)N2CCN(c3ncnc4[nH]ccc34)CC3(CC3)C2)cc1] | I | I | I | II |

TABLE 1-continued

| Example number | Structure | JAK1 | JAK2 | JAK3 | TYK2 |
|---|---|---|---|---|---|
| 21 | 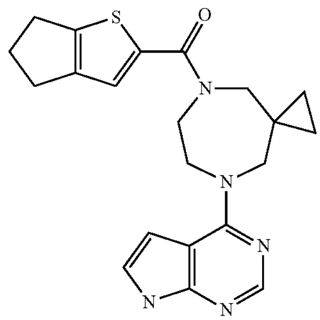 [SMILES: O=C(c1cc2c(s1)CCC2)N1CCN(c2ncnc3[nH]ccc23)CC2(CC2)C1] | II | II | II | III |
| 22 | 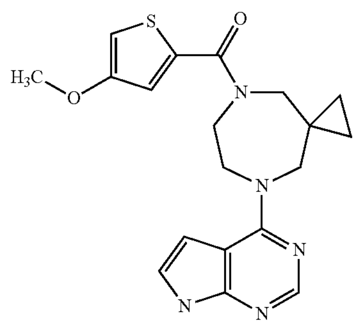 [SMILES: COc1csc(C(=O)N2CCN(c3ncnc4[nH]ccc34)CC3(CC3)C2)c1] | I | II | II | III |
| 23 | 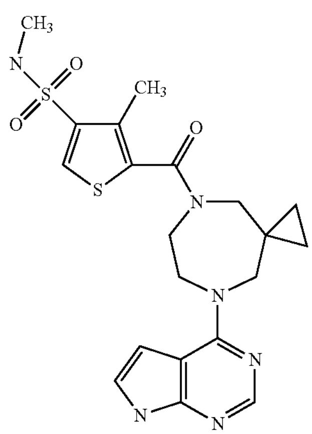 [SMILES: CNS(=O)(=O)c1csc(C(=O)N2CCN(c3ncnc4[nH]ccc34)CC3(CC3)C2)c1C] | II | I | II | III |
| 24 | 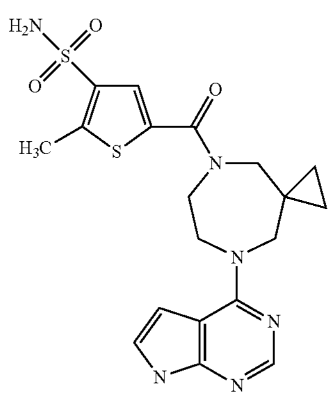 [SMILES: Cc1sc(C(=O)N2CCN(c3ncnc4[nH]ccc34)CC3(CC3)C2)cc1S(N)(=O)=O] | I | I | I | II |

TABLE 1-continued
| Example number | Structure | JAK1 | JAK2 | JAK3 | TYK2 |
|---|---|---|---|---|---|
| 25 | 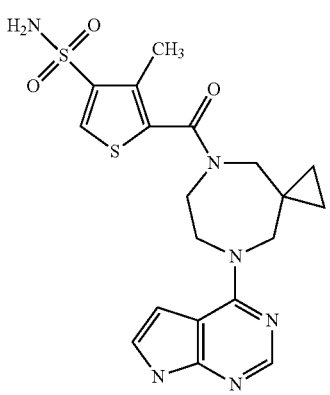 [SMILES: Cc1c(S(N)(=O)=O)csc1C(=O)N1CCN(c2ncnc3[nH]ccc23)CC2(CC2)C1] | II | I | II | III |
| 26 | 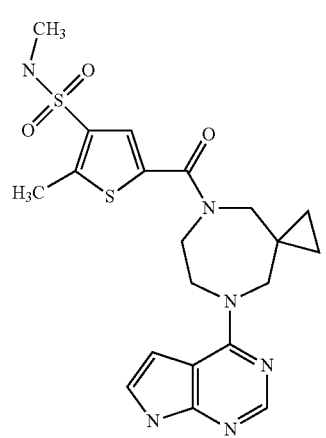 [SMILES: CNS(=O)(=O)c1cc(C(=O)N2CCN(c3ncnc4[nH]ccc34)CC3(CC3)C2)sc1C] | II | I | II | III |
| 27 | 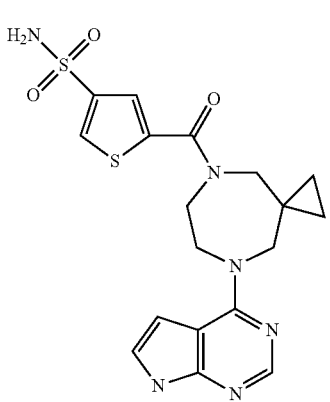 [SMILES: NS(=O)(=O)c1csc(C(=O)N2CCN(c3ncnc4[nH]ccc34)CC3(CC3)C2)c1] | II | I | I | III |

TABLE 1-continued

| Example number | Structure | JAK1 | JAK2 | JAK3 | TYK2 |
|---|---|---|---|---|---|
| 28 | 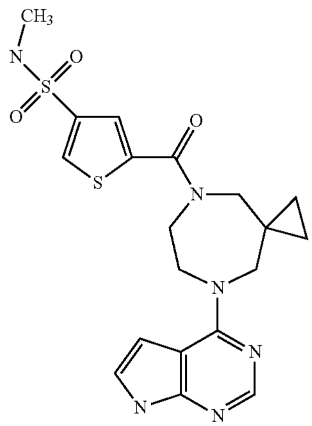 [SMILES: CNS(=O)(=O)c1csc(C(=O)N2CCN(c3ncnc4[nH]ccc34)CC3(CC3)C2)c1] | II | I | II | III |
| 29 | 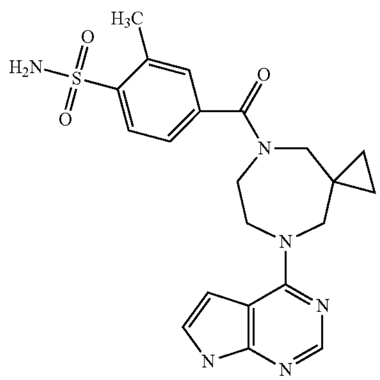 [SMILES: Cc1cc(C(=O)N2CCN(c3ncnc4[nH]ccc34)CC3(CC3)C2)ccc1S(N)(=O)=O] | II | II | II | III |
| 30 | 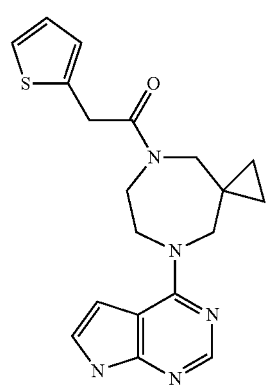 [SMILES: O=C(Cc1cccs1)N1CCN(c2ncnc3[nH]ccc23)CC2(CC2)C1] | I | I | II | II |
| 31 | 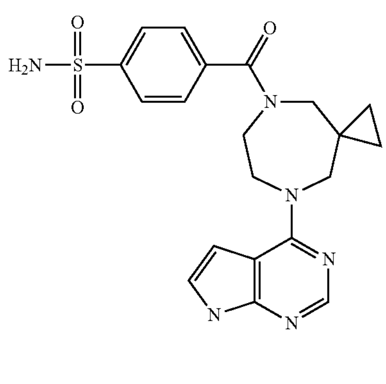 [SMILES: NS(=O)(=O)c1ccc(C(=O)N2CCN(c3ncnc4[nH]ccc34)CC3(CC3)C2)cc1] | I | I | I | II |

TABLE 1-continued
| Example number | Structure | JAK1 | JAK2 | JAK3 | TYK2 |
|---|---|---|---|---|---|
| 32 | 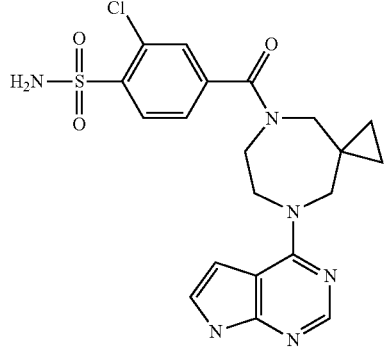 [SMILES: NS(=O)(=O)c1ccc(C(=O)N2CCN(c3ncnc4[nH]ccc34)CC3(CC3)C2)cc1Cl] | I | II | II | III |
| 33 | 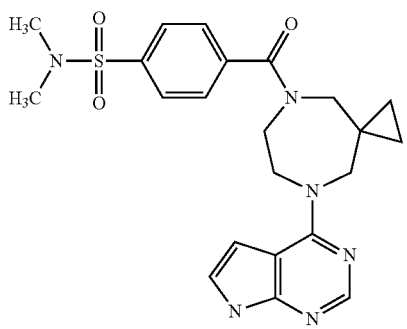 [SMILES: CN(C)S(=O)(=O)c1ccc(C(=O)N2CCN(c3ncnc4[nH]ccc34)CC3(CC3)C2)cc1] | II | II | II | III |
| 34 | 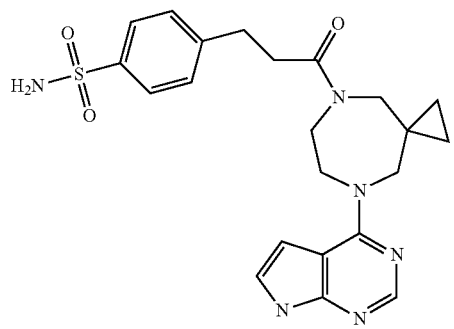 [SMILES: NS(=O)(=O)c1ccc(CCC(=O)N2CCN(c3ncnc4[nH]ccc34)CC3(CC3)C2)cc1] | I | I | I | II |
| 35 | 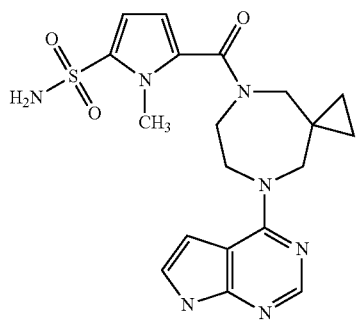 [SMILES: Cn1c(C(=O)N2CCN(c3ncnc4[nH]ccc34)CC3(CC3)C2)ccc1S(N)(=O)=O] | II | II | II | III |

TABLE 1-continued

| Example number | Structure | JAK1 | JAK2 | JAK3 | TYK2 |
|---|---|---|---|---|---|
| 36 | 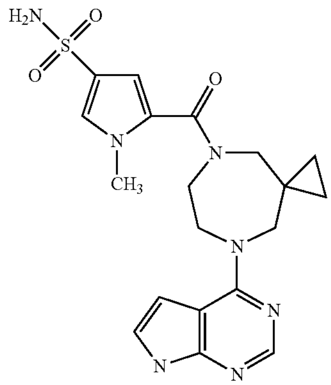 [SMILES: Cn1cc(S(N)(=O)=O)cc1C(=O)N1CCN(c2ncnc3[nH]ccc23)CC2(CC2)C1] | II | II | II | III |
| 37 | 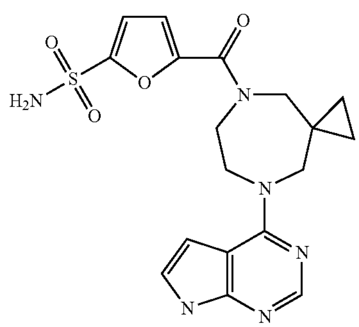 [SMILES: NS(=O)(=O)c1ccc(C(=O)N2CCN(c3ncnc4[nH]ccc34)CC3(CC3)C2)o1] | II | I | II | III |
| 38 | 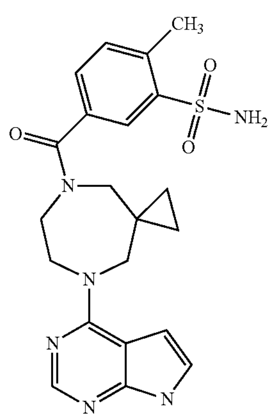 [SMILES: Cc1ccc(C(=O)N2CCN(c3ncnc4[nH]ccc34)CC3(CC3)C2)cc1S(N)(=O)=O] | I | I | II | II |
| 39 | 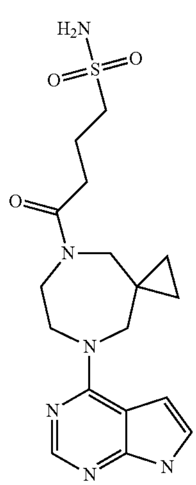 [SMILES: NS(=O)(=O)CCCC(=O)N1CCN(c2ncnc3[nH]ccc23)CC2(CC2)C1] | I | I | I | III |

TABLE 1-continued
| Example number | Structure | JAK1 | JAK2 | JAK3 | TYK2 |
|---|---|---|---|---|---|
| 40 | 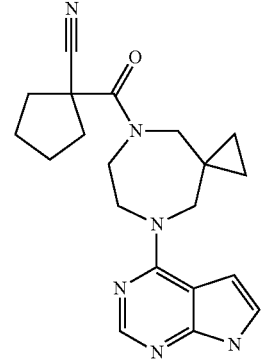 [SMILES: N#CC1(C(=O)N2CCN(c3ncnc4[nH]ccc34)CC3(CC3)C2)CCCC1] | III | II | II | III |
| 41 | 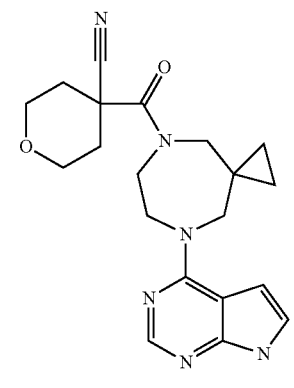 [SMILES: N#CC1(C(=O)N2CCN(c3ncnc4[nH]ccc34)CC3(CC3)C2)CCOCC1] | III | II | II | III |
| 42 | 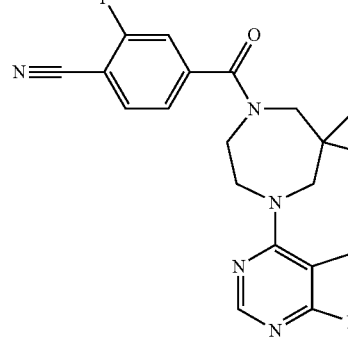 | II | II | II | III |
| 43 | 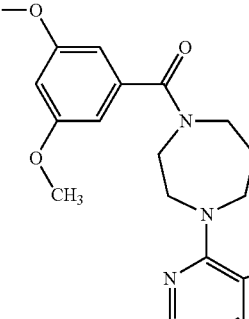 | III | III | III | III |

TABLE 1-continued
| Example number | Structure | JAK1 | JAK2 | JAK3 | TYK2 |
|---|---|---|---|---|---|
| 44 | 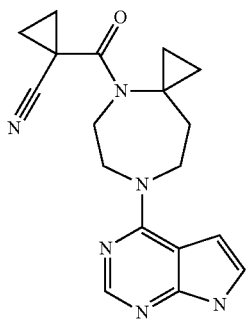 [SMILES: N#CC1(C(=O)N2CCN(c3ncnc4[nH]ccc34)CCC23CC3)CC1] | II | II | III | III |
| 45 | 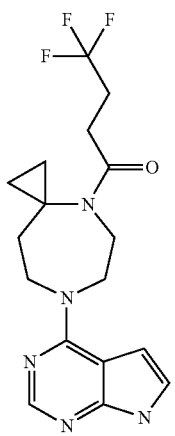 [SMILES: O=C(CCC(F)(F)F)N1CCN(c2ncnc3[nH]ccc23)CCC12CC2] | II | II | II | III |
| 46 | 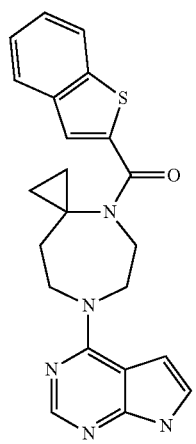 [SMILES: O=C(c1cc2ccccc2s1)N1CCN(c2ncnc3[nH]ccc23)CCC12CC2] | II | II | III | III |

TABLE 1-continued
| Example number | Structure | JAK1 | JAK2 | JAK3 | TYK2 |
|---|---|---|---|---|---|
| 47 | 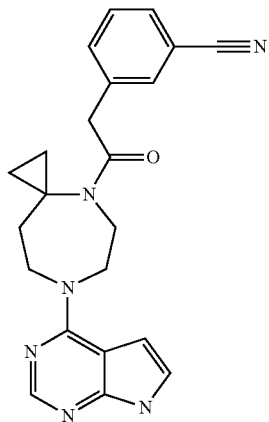 [SMILES: N#Cc1cccc(CC(=O)N2CCN(c3ncnc4[nH]ccc34)CCC23CC3)c1] | III | III | III | III |
| 48 | 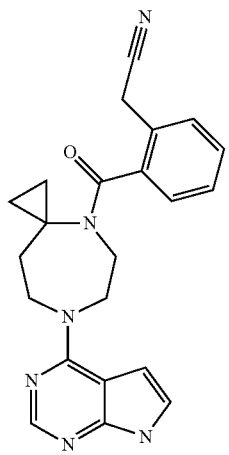 [SMILES: N#CCc1ccccc1C(=O)N1CCN(c2ncnc3[nH]ccc23)CCC12CC2] | III | III | III | III |
| 49 | 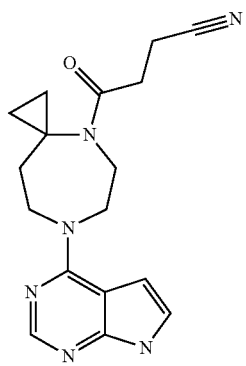 [SMILES: N#CCCC(=O)N1CCN(c2ncnc3[nH]ccc23)CCC12CC2] | II | II | II | III |

TABLE 1-continued

| Example number | Structure | JAK1 | JAK2 | JAK3 | TYK2 |
|---|---|---|---|---|---|
| 50 | 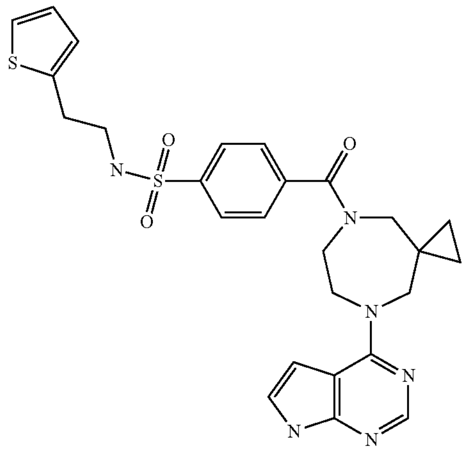 [SMILES: O=C(c1ccc(S(=O)(=O)NCCc2cccs2)cc1)N1CCN(c2ncnc3[nH]ccc23)CC2(CC2)C1] | II | II | II | III |
| 51 | 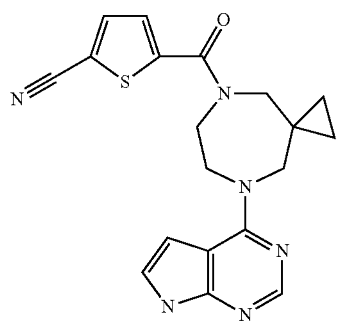 [SMILES: N#Cc1ccc(C(=O)N2CCN(c3ncnc4[nH]ccc34)CC3(CC3)C2)s1] | I | I | I | II |
| 52 | 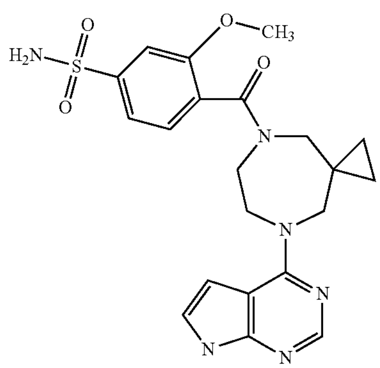 [SMILES: COc1cc(S(N)(=O)=O)ccc1C(=O)N1CCN(c2ncnc3[nH]ccc23)CC2(CC2)C1] | II | I | II | III |
| 53 | 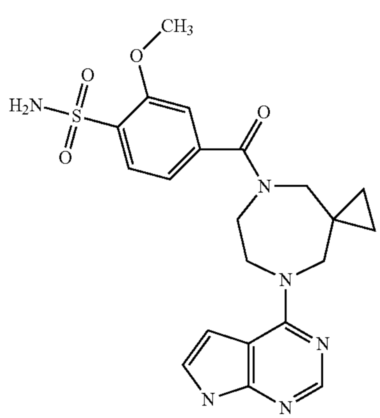 [SMILES: COc1cc(C(=O)N2CCN(c3ncnc4[nH]ccc34)CC3(CC3)C2)ccc1S(N)(=O)=O] | II | II | III | III |

TABLE 1-continued
| Example number | Structure | JAK1 | JAK2 | JAK3 | TYK2 |
|---|---|---|---|---|---|
| 54 | 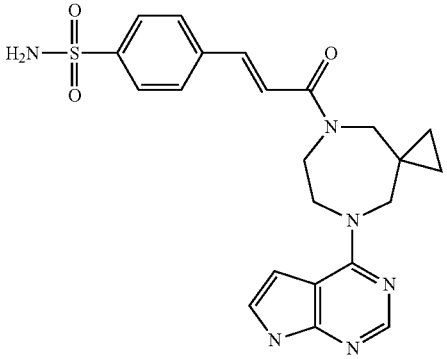 [SMILES: NS(=O)(=O)c1ccc(/C=C/C(=O)N2CCN(c3ncnc4[nH]ccc34)CC3(CC3)C2)cc1] | I | I | II | II |
| 55 | 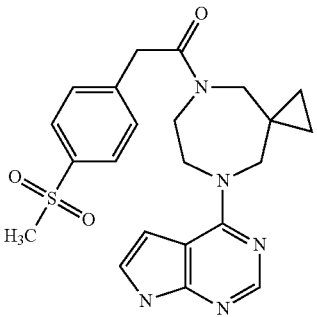 [SMILES: CS(=O)(=O)c1ccc(CC(=O)N2CCN(c3ncnc4[nH]ccc34)CC3(CC3)C2)cc1] | I | I | II | III |
| 56 | 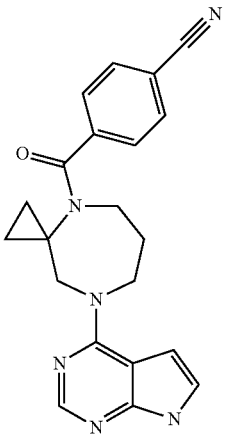 [SMILES: N#Cc1ccc(C(=O)N2CCCN(c3ncnc4[nH]ccc34)CC23CC3)cc1] | I | I | II | III |
| 57 | 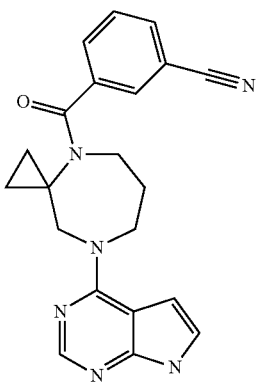 [SMILES: N#Cc1cccc(C(=O)N2CCCN(c3ncnc4[nH]ccc34)CC23CC3)c1] | II | I | II | II |

TABLE 1-continued
| Example number | Structure | JAK1 | JAK2 | JAK3 | TYK2 |
|---|---|---|---|---|---|
| 58 | 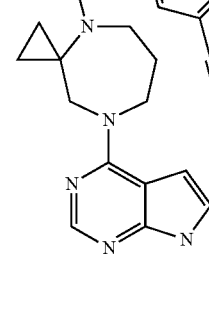 | III | III | III | III |
| 59 | 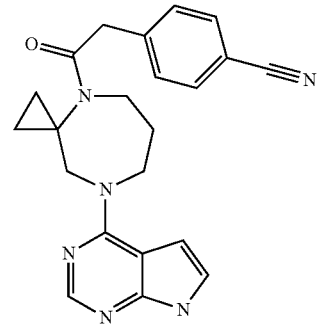 [SMILES: N#Cc1ccc(CC(=O)N2CCCN(c3ncnc4[nH]ccc34)CC23CC3)cc1] | II | II | III | III |
| 60 | 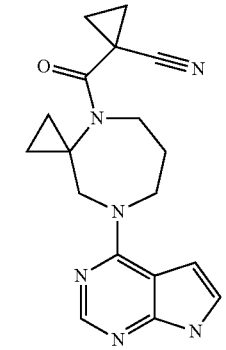 [SMILES: N#CC1(C(=O)N2CCCN(c3ncnc4[nH]ccc34)CC23CC3)CC1] | II | I | II | III |
| 61 | 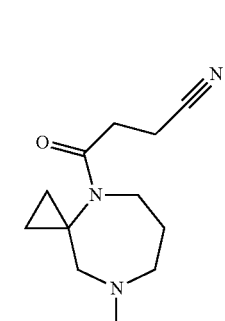 | II | II | II | III |

TABLE 1-continued
| Example number | Structure | JAK1 | JAK2 | JAK3 | TYK2 |
|---|---|---|---|---|---|
| 62 | 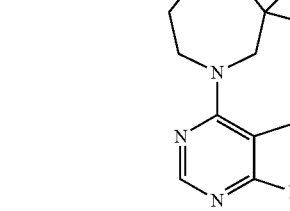 | II | II | II | III |
| 63 | 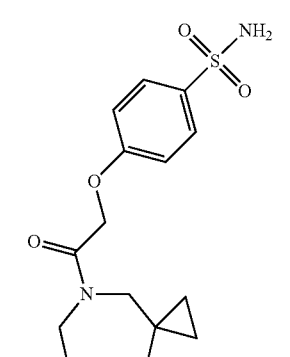 | I | I | I | I |
| 64 | 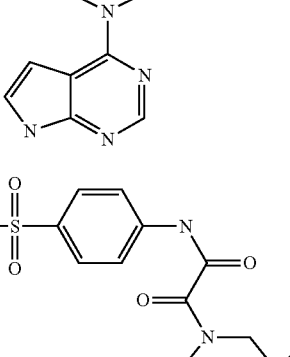 | I | I | I | II |
| 65 | 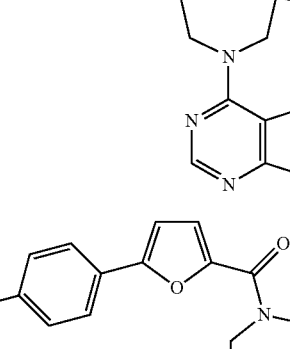 | I | I | II | II |

TABLE 1-continued
| Example number | Structure | JAK1 | JAK2 | JAK3 | TYK2 |
|---|---|---|---|---|---|
| 66 | 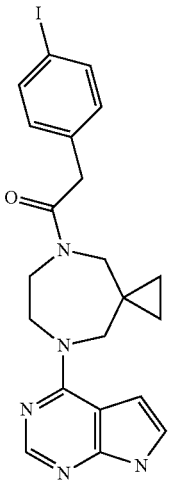 [SMILES: O=C(Cc1ccc(I)cc1)N1CCN(c2ncnc3[nH]ccc23)CC2(CC2)C1] | I | I | II | II |
| 67 | 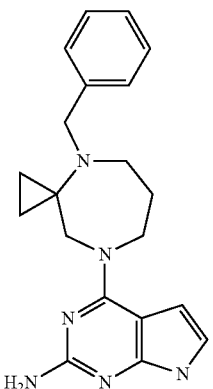 | III | III | III | III |
| 68 | 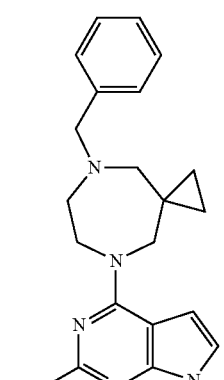 | III | III | III | III |

TABLE 1-continued

| Example number | Structure | JAK1 | JAK2 | JAK3 | TYK2 |
|---|---|---|---|---|---|
| 69 | 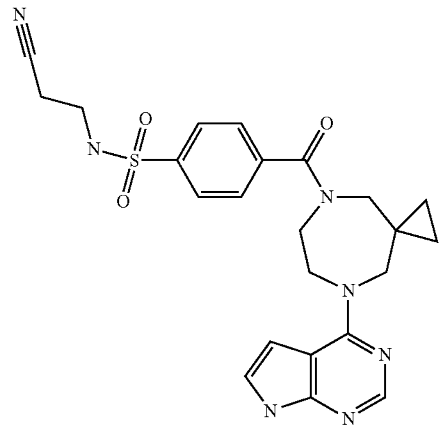 [SMILES: N#CCCNS(=O)(=O)c1ccc(C(=O)N2CCN(c3ncnc4[nH]ccc34)CC3(CC3)C2)cc1] | II | II | II | III |
| 70 | 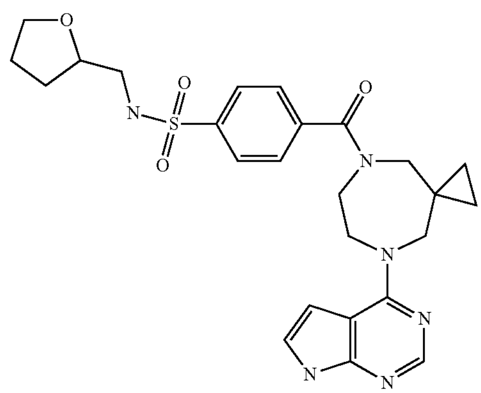 [SMILES: O=C(c1ccc(S(=O)(=O)NCC2CCCO2)cc1)N1CCN(c2ncnc3[nH]ccc23)CC2(CC2)C1] | II | II | II | III |
| 71 | 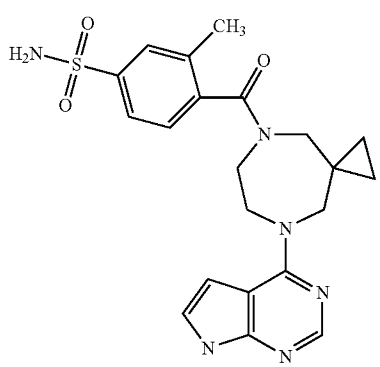 [SMILES: Cc1cc(S(N)(=O)=O)ccc1C(=O)N1CCN(c2ncnc3[nH]ccc23)CC2(CC2)C1] | II | II | II | III |
| 72 | 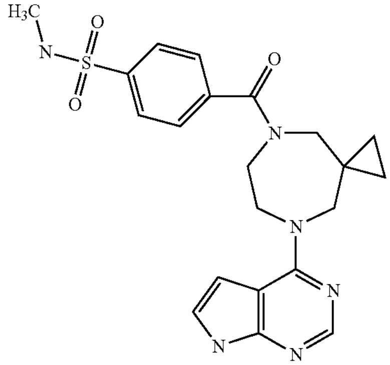 [SMILES: CNS(=O)(=O)c1ccc(C(=O)N2CCN(c3ncnc4[nH]ccc34)CC3(CC3)C2)cc1] | II | I | II | III |

TABLE 1-continued

| Example number | Structure | JAK1 | JAK2 | JAK3 | TYK2 |
|---|---|---|---|---|---|
| 73 | 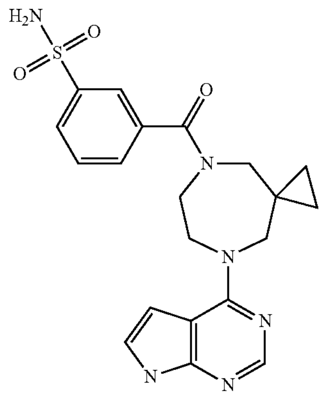 [SMILES: NS(=O)(=O)c1cccc(C(=O)N2CCN(c3ncnc4[nH]ccc34)CC3(CC3)C2)c1] | II | II | II | III |
| 74 | 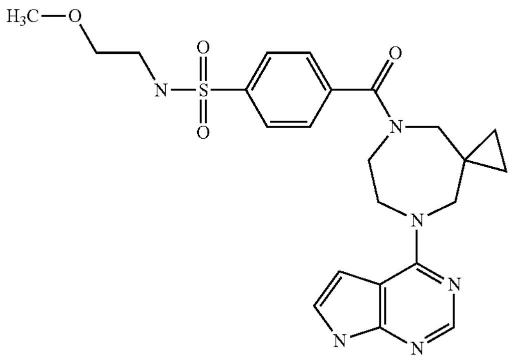 [SMILES: COCCNS(=O)(=O)c1ccc(C(=O)N2CCN(c3ncnc4[nH]ccc34)CC3(CC3)C2)cc1] | II | II | II | III |
| 75 | 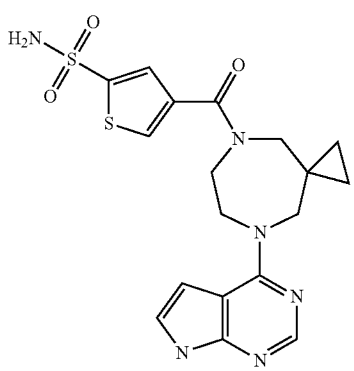 [SMILES: NS(=O)(=O)c1cc(C(=O)N2CCN(c3ncnc4[nH]ccc34)CC3(CC3)C2)cs1] | I | I | II | II |
| 76 | 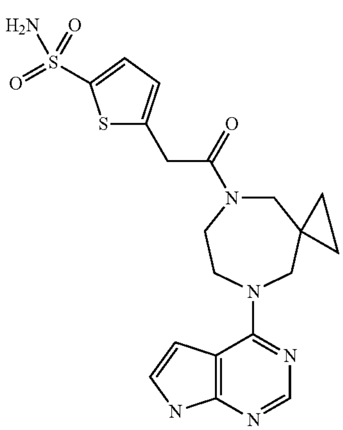 [SMILES: NS(=O)(=O)c1ccc(CC(=O)N2CCN(c3ncnc4[nH]ccc34)CC3(CC3)C2)s1] | I | I | I | II |

TABLE 1-continued

| Example number | Structure | JAK1 | JAK2 | JAK3 | TYK2 |
|---|---|---|---|---|---|
| 77 | 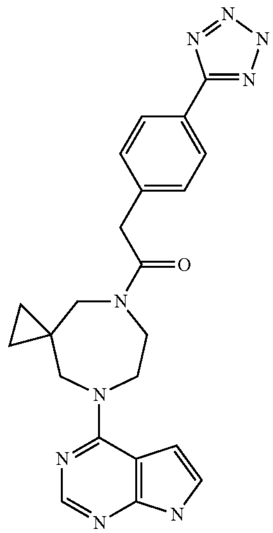 [SMILES: O=C(Cc1ccc(-c2nn[nH]n2)cc1)N1CCN(c2ncnc3[nH]ccc23)CC2(CC2)C1] | I | I | II | II |
| 78 | 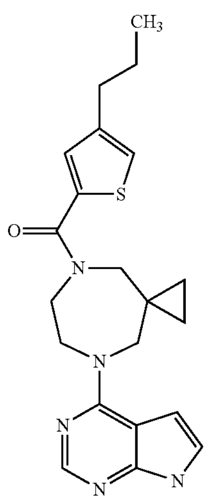 [SMILES: CCCc1csc(C(=O)N2CCN(c3ncnc4[nH]ccc34)CC3(CC3)C2)c1] | II | II | II | III |
| 79 | 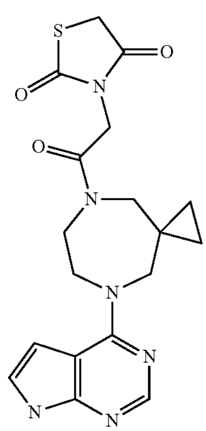 [SMILES: O=C(CN1C(=O)CSC1=O)N1CCN(c2ncnc3[nH]ccc23)CC2(CC2)C1] | I | I | I | |

TABLE 1-continued
| Example number | Structure | JAK1 | JAK2 | JAK3 | TYK2 |
|---|---|---|---|---|---|
| 80 | 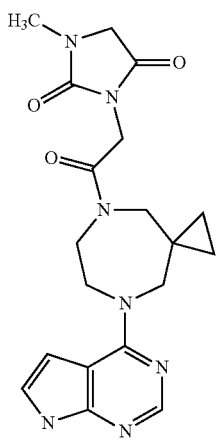 [SMILES: CN1CC(=O)N(CC(=O)N2CCN(c3ncnc4[nH]ccc34)CC3(CC3)C2)C1=O] | II | I | II | |
| 81 | 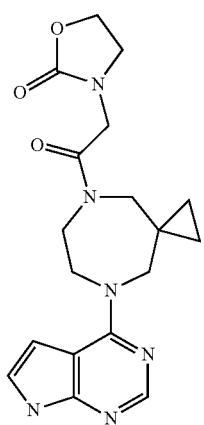 [SMILES: O=C(CN1CCOC1=O)N1CCN(c2ncnc3[nH]ccc23)CC2(CC2)C1] | II | II | II | |
| 82 | 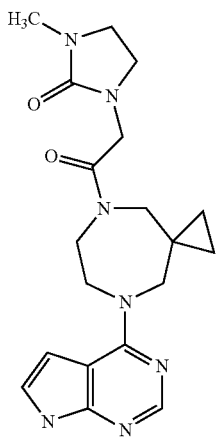 [SMILES: CN1CCN(CC(=O)N2CCN(c3ncnc4[nH]ccc34)CC3(CC3)C2)C1=O] | II | II | II | |

TABLE 1-continued
| Example number | Structure | JAK1 | JAK2 | JAK3 | TYK2 |
|---|---|---|---|---|---|
| 83 | 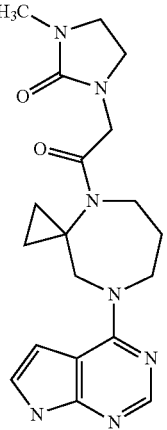 | II | II | II | |
| 84 | 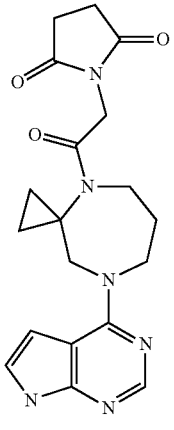 [SMILES: O=C1CCC(=O)N1CC(=O)N1CCCN(c2ncnc3[nH]ccc23)CC12CC2] | II | II | II | |
| 85 | 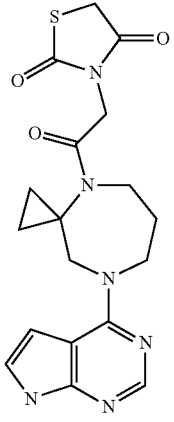 [SMILES: O=C1CSC(=O)N1CC(=O)N1CCCN(c2ncnc3[nH]ccc23)CC12CC2] | II | II | II | |

TABLE 1-continued
| Example number | Structure | JAK1 | JAK2 | JAK3 | TYK2 |
|---|---|---|---|---|---|
| 86 | 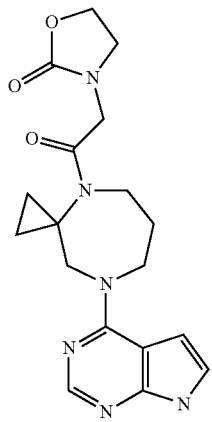 [SMILES: O=C1OCCN1CC(=O)N1CCCN(c2ncnc3[nH]ccc23)CC12CC2] | III | II | III | |
| 87 | 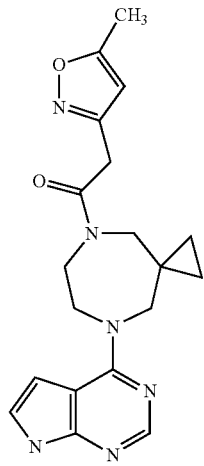 [SMILES: Cc1cc(CC(=O)N2CCN(c3ncnc4[nH]ccc34)CC3(CC3)C2)no1] | I | I | II | II |
| 88 | 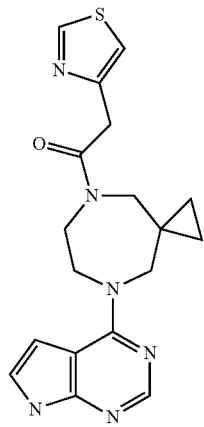 [SMILES: O=C(Cc1cscn1)N1CCN(c2ncnc3[nH]ccc23)CC2(CC2)C1] | II | II | II | |

TABLE 1-continued
| Example number | Structure | JAK1 | JAK2 | JAK3 | TYK2 |
|---|---|---|---|---|---|
| 89 | 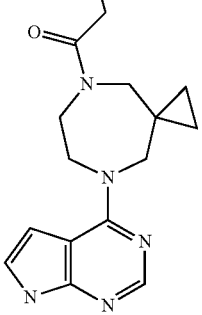 | | II | II | II |
| 90 | 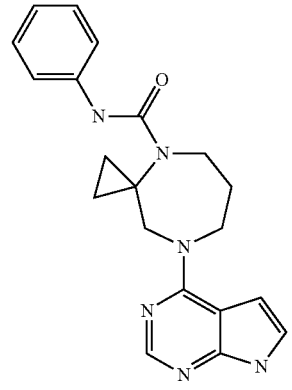 [SMILES: O=C(Nc1ccccc1)N1CCCN(c2ncnc3[nH]ccc23)CC12CC2] | I | II | II | III |
| 91 | 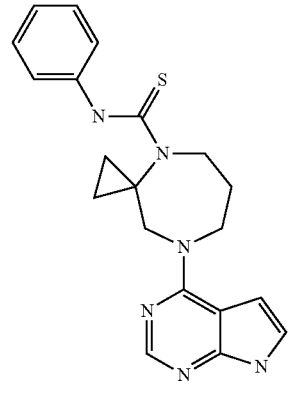 [SMILES: S=C(Nc1ccccc1)N1CCCN(c2ncnc3[nH]ccc23)CC12CC2] | I | I | II | III |
| 92 | 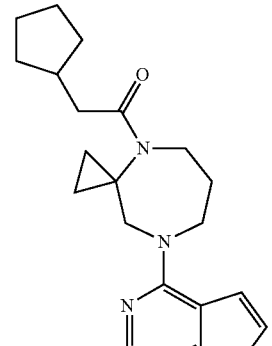 | I | II | II | III |

TABLE 1-continued

| Example number | Structure | JAK1 | JAK2 | JAK3 | TYK2 |
|---|---|---|---|---|---|
| 93 | 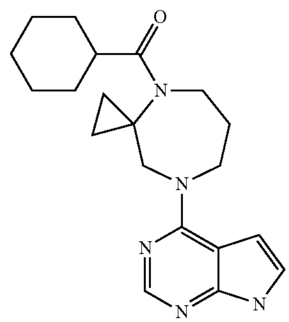 [SMILES: O=C(C1CCCCC1)N1CCCN(c2ncnc3[nH]ccc23)CC12CC2] | I | I | II | II |
| 94 | 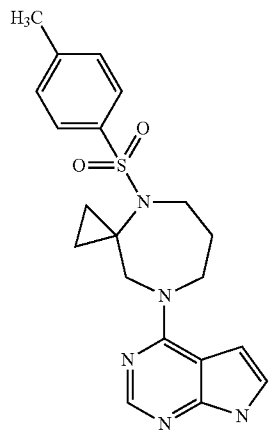 [SMILES: Cc1ccc(S(=O)(=O)N2CCCN(c3ncnc4[nH]ccc34)CC23CC3)cc1] | III | III | III | III |
| 95 | 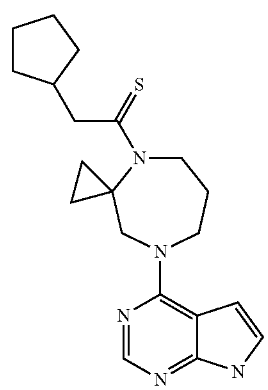 [SMILES: S=C(CC1CCCC1)N1CCCN(c2ncnc3[nH]ccc23)CC12CC2] | I | II | II | III |
| 96 | 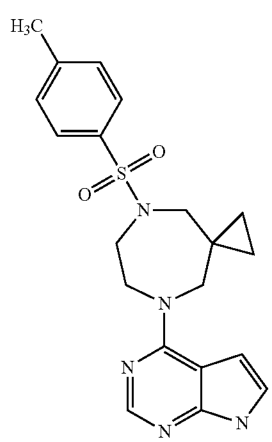 [SMILES: Cc1ccc(S(=O)(=O)N2CCN(c3ncnc4[nH]ccc34)CC3(CC3)C2)cc1] | II | II | III | |

TABLE 1-continued
| Example number | Structure | JAK1 | JAK2 | JAK3 | TYK2 |
|---|---|---|---|---|---|
| 97 | 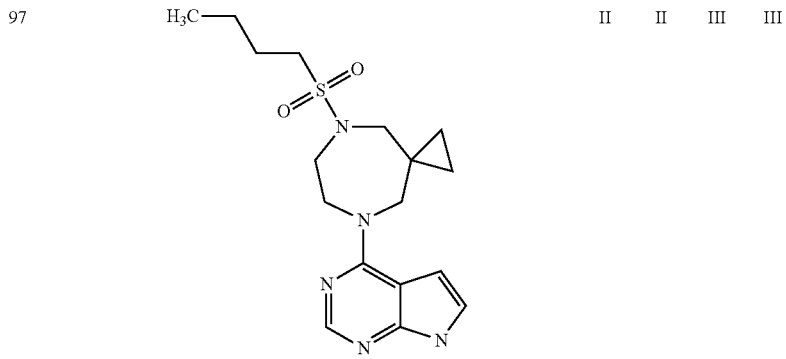 | II | II | III | III |
| 98 | 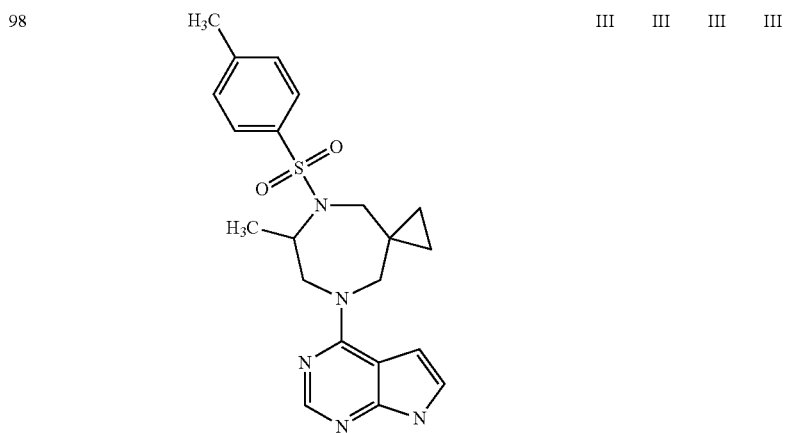 | III | III | III | III |
| 99 | 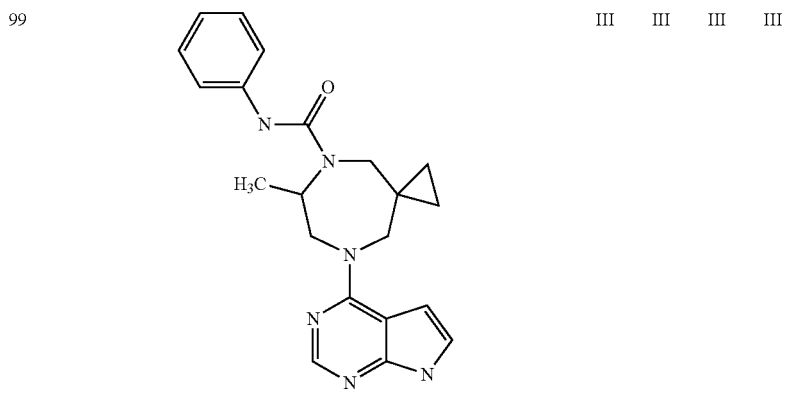 | III | III | III | III |

TABLE 1-continued
| Example number | Structure | JAK1 | JAK2 | JAK3 | TYK2 |
|---|---|---|---|---|---|
| 100 | 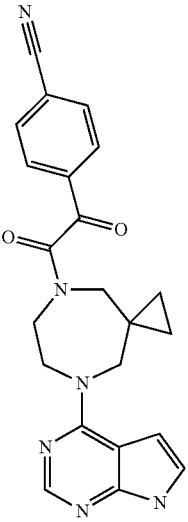 [SMILES: N#Cc1ccc(C(=O)C(=O)N2CCN(c3ncnc4[nH]ccc34)CC3(CC3)C2)cc1] | I | I | III | III |
| 101 | 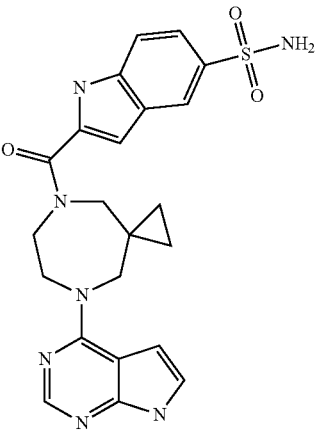 [SMILES: NS(=O)(=O)c1ccc2[nH]c(C(=O)N3CCN(c4ncnc5[nH]ccc45)CC4(CC4)C3)cc2c1] | I | I | II | II |
| 102 | 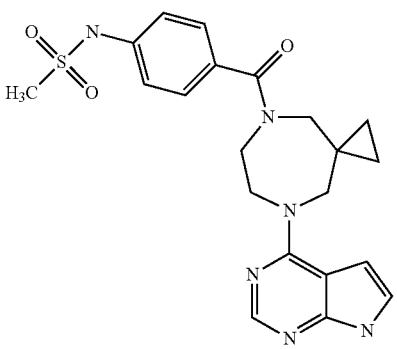 [SMILES: CS(=O)(=O)Nc1ccc(C(=O)N2CCN(c3ncnc4[nH]ccc34)CC3(CC3)C2)cc1] | II | II | II | III |

TABLE 1-continued

| Example number | Structure | JAK1 | JAK2 | JAK3 | TYK2 |
|---|---|---|---|---|---|
| 103 | (structure) | II | II | III | III |
| 104 | (structure) | III | II | III | III |
| 105 | (structure) | II | II | III | III |

TABLE 1-continued

| Example number | Structure | JAK1 | JAK2 | JAK3 | TYK2 |
|---|---|---|---|---|---|
| 106 | 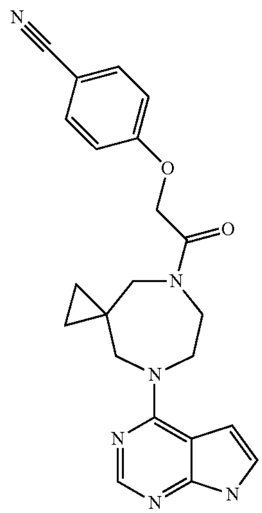 [SMILES: N#Cc1ccc(OCC(=O)N2CCN(c3ncnc4[nH]ccc34)CC3(CC3)C2)cc1] | I | I | II | II |
| 107 | 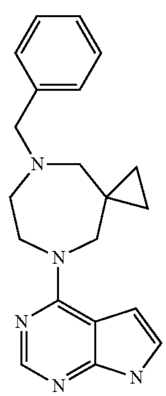 [SMILES: c1ccc(CN2CCN(c3ncnc4[nH]ccc34)CC3(CC3)C2)cc1] | III | III | III | III |
| 108 | 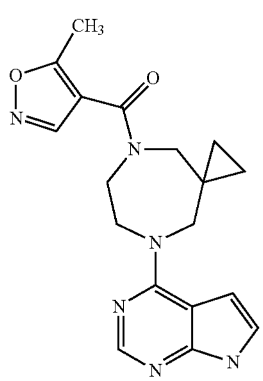 | II | II | II | |

TABLE 1-continued

| Example number | Structure | JAK1 | JAK2 | JAK3 | TYK2 |
|---|---|---|---|---|---|
| 109 | 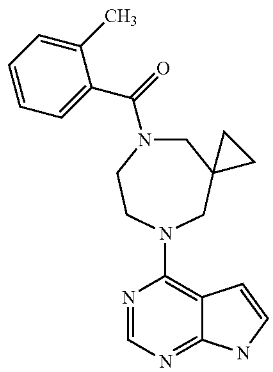 [SMILES: Cc1ccccc1C(=O)N1CCN(c2ncnc3[nH]ccc23)CC2(CC2)C1] | III | II | III | |
| 110 | 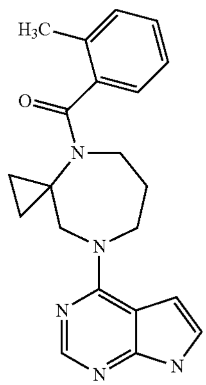 [SMILES: Cc1ccccc1C(=O)N1CCCN(c2ncnc3[nH]ccc23)CC12CC2] | II | II | III | |
| 111 | 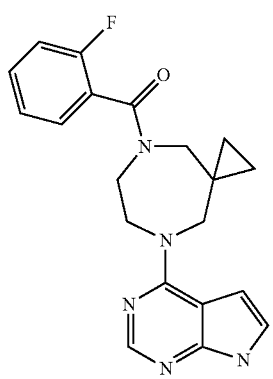 [SMILES: O=C(c1ccccc1F)N1CCN(c2ncnc3[nH]ccc23)CC2(CC2)C1] | II | I | III | |
| 112 | 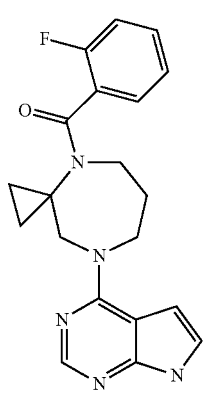 [SMILES: O=C(c1ccccc1F)N1CCCN(c2ncnc3[nH]ccc23)CC12CC2] | II | I | II | |

TABLE 1-continued
| Example number | Structure | JAK1 | JAK2 | JAK3 | TYK2 |
|---|---|---|---|---|---|
| 113 | 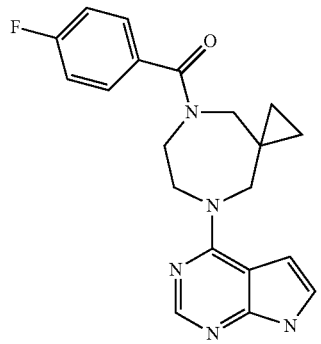 [SMILES: O=C(c1ccc(F)cc1)N1CCN(c2ncnc3[nH]ccc23)CC2(CC2)C1] | II | II | II | |
| 114 | 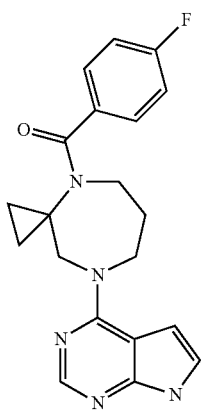 [SMILES: O=C(c1ccc(F)cc1)N1CCCN(c2ncnc3[nH]ccc23)CC12CC2] | II | I | II | |
| 115 | 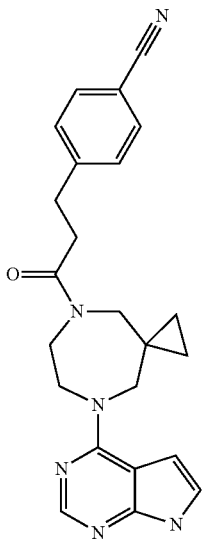 [SMILES: N#Cc1ccc(CCC(=O)N2CCN(c3ncnc4[nH]ccc34)CC3(CC3)C2)cc1] | I | I | I | II |

TABLE 1-continued

| Example number | Structure | JAK1 | JAK2 | JAK3 | TYK2 |
|---|---|---|---|---|---|
| 116 | 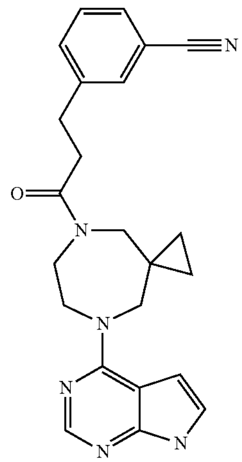 [SMILES: N#Cc1cccc(CCC(=O)N2CCN(c3ncnc4[nH]ccc34)CC3(CC3)C2)c1] | II | I | II | III |
| 117 | 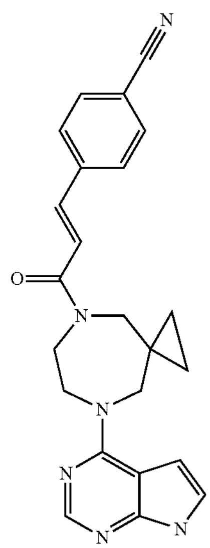 [SMILES: N#Cc1ccc(/C=C/C(=O)N2CCN(c3ncnc4[nH]ccc34)CC3(CC3)C2)cc1] | II | II | | |
| 118 | 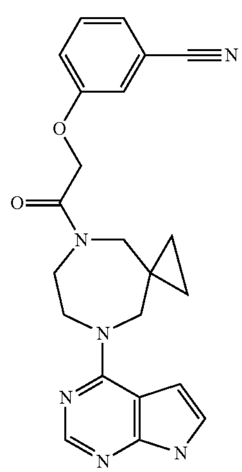 [SMILES: N#Cc1cccc(OCC(=O)N2CCN(c3ncnc4[nH]ccc34)CC3(CC3)C2)c1] | II | I | II | |

TABLE 1-continued

| Example number | Structure | JAK1 | JAK2 | JAK3 | TYK2 |
|---|---|---|---|---|---|
| 119 | 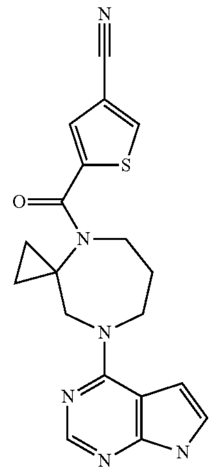 [SMILES: N#Cc1csc(C(=O)N2CCCN(c3ncnc4[nH]ccc34)CC23CC3)c1] | I | I | II | II |
| 120 | 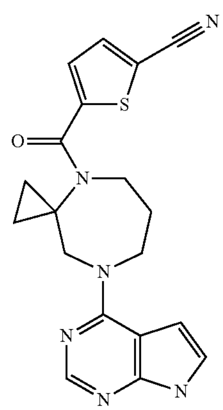 [SMILES: N#Cc1ccc(C(=O)N2CCCN(c3ncnc4[nH]ccc34)CC23CC3)s1] | I | I | I | II |
| 121 | 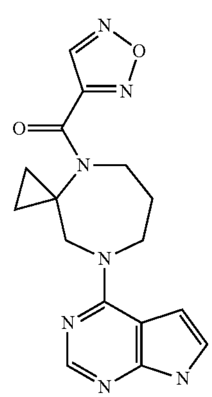 [SMILES: O=C(c1cnon1)N1CCCN(c2ncnc3[nH]ccc23)CC12CC2] | II | II | I | |

TABLE 1-continued
| Example number | Structure | JAK1 | JAK2 | JAK3 | TYK2 |
|---|---|---|---|---|---|
| 122 | 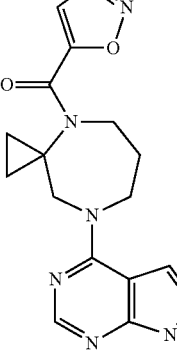 | I | I | II | |
| 123 | 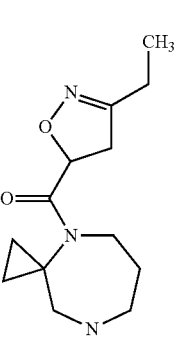 | II | II | II | III |
| 124 | 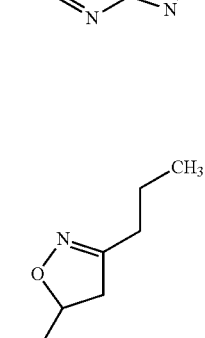 | II | II | II | |

TABLE 1-continued
| Example number | Structure | JAK1 | JAK2 | JAK3 | TYK2 |
|---|---|---|---|---|---|
| 125 | 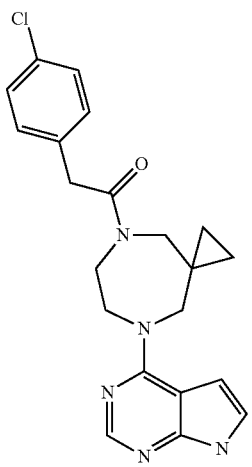 [SMILES: O=C(Cc1ccc(Cl)cc1)N1CCN(c2ncnc3[nH]ccc23)CC2(CC2)C1] | I | I | II | II |
| 126 | 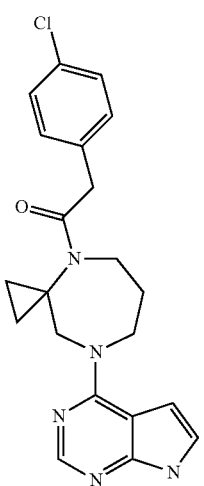 [SMILES: O=C(Cc1ccc(Cl)cc1)N1CCCN(c2ncnc3[nH]ccc23)CC12CC2] | II | I | II | |
| 127 | 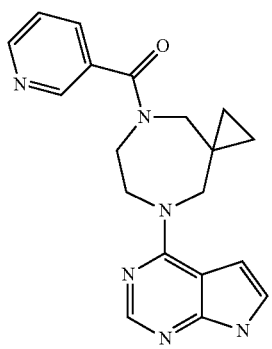 [SMILES: O=C(c1cccnc1)N1CCN(c2ncnc3[nH]ccc23)CC2(CC2)C1] | II | II | III | |

TABLE 1-continued
| Example number | Structure | JAK1 | JAK2 | JAK3 | TYK2 |
|---|---|---|---|---|---|
| 128 | 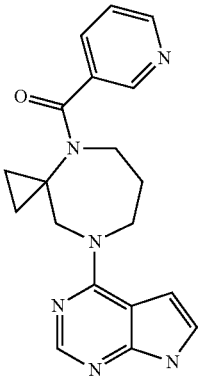 [SMILES: O=C(c1cccnc1)N1CCCN(c2ncnc3[nH]ccc23)CC12CC2] | II | II | III | |
| 129 | 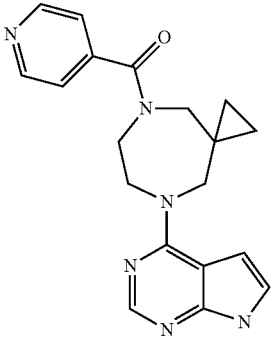 [SMILES: O=C(c1ccncc1)N1CCN(c2ncnc3[nH]ccc23)CC2(CC2)C1] | II | II | III | |
| 130 | 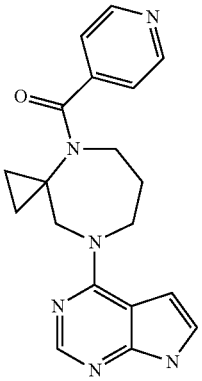 [SMILES: O=C(c1ccncc1)N1CCCN(c2ncnc3[nH]ccc23)CC12CC2] | II | II | III | |
| 131 | 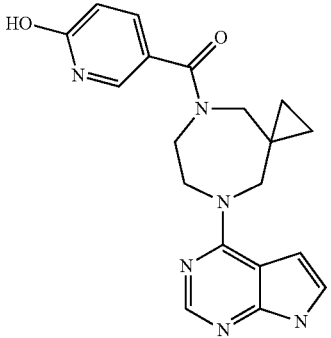 [SMILES: O=C(c1ccc(O)nc1)N1CCN(c2ncnc3[nH]ccc23)CC2(CC2)C1] | II | II | II | |

TABLE 1-continued
| Example number | Structure | JAK1 | JAK2 | JAK3 | TYK2 |
|---|---|---|---|---|---|
| 132 | 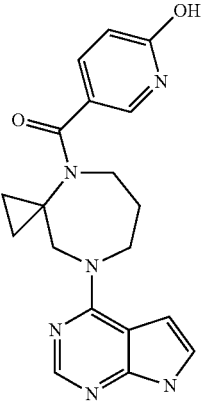 [SMILES: O=C(c1ccc(O)nc1)N1CCCN(c2ncnc3[nH]ccc23)CC12CC2] | II | II | II | |
| 133 | 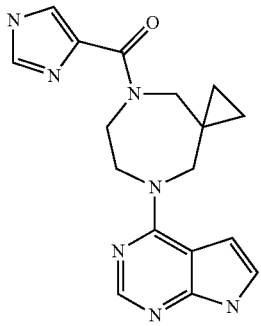 [SMILES: O=C(c1c[nH]cn1)N1CCN(c2ncnc3[nH]ccc23)CC2(CC2)C1] | II | II | II | |
| 134 | 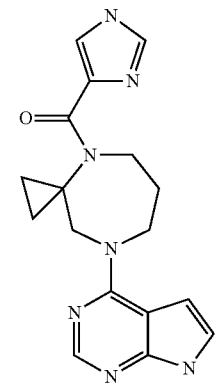 [SMILES: O=C(c1c[nH]cn1)N1CCCN(c2ncnc3[nH]ccc23)CC12CC2] | II | II | II | |
| 135 | 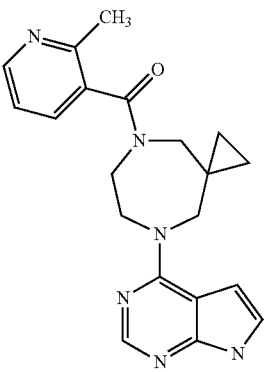 | III | III | III | |

TABLE 1-continued

| Example number | Structure | JAK1 | JAK2 | JAK3 | TYK2 |
|---|---|---|---|---|---|
| 136 | 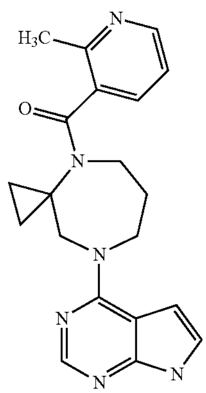 [SMILES: Cc1ncccc1C(=O)N1CCCN(c2ncnc3[nH]ccc23)CC12CC2] | III | II | III | |
| 137 | 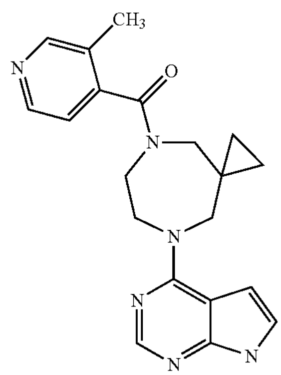 [SMILES: Cc1cnccc1C(=O)N1CCN(c2ncnc3[nH]ccc23)CC2(CC2)C1] | III | II | III | |
| 138 | 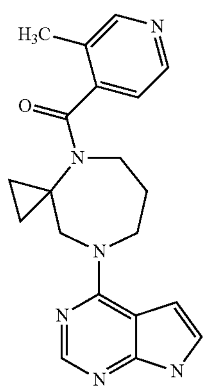 [SMILES: Cc1cnccc1C(=O)N1CCCN(c2ncnc3[nH]ccc23)CC12CC2] | III | II | III | |
| 139 | 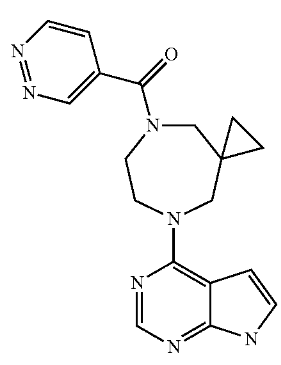 [SMILES: O=C(c1ccnnc1)N1CCN(c2ncnc3[nH]ccc23)CC2(CC2)C1] | II | II | III | |

TABLE 1-continued

| Example number | Structure | JAK1 | JAK2 | JAK3 | TYK2 |
|---|---|---|---|---|---|
| 140 | 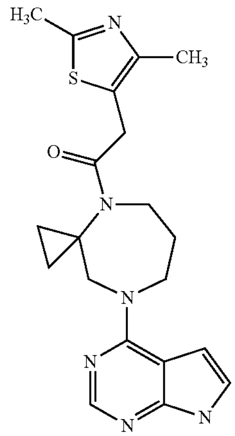 [SMILES: Cc1nc(C)c(CC(=O)N2CCCN(c3ncnc4[nH]ccc34)CC23CC3)s1] | III | III | III | |
| 141 | 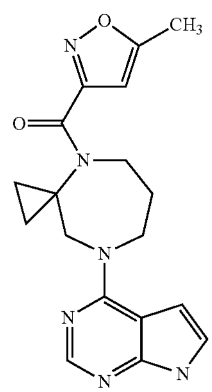 [SMILES: Cc1cc(C(=O)N2CCCN(c3ncnc4[nH]ccc34)CC23CC3)no1] | I | I | II | II |
| 142 | 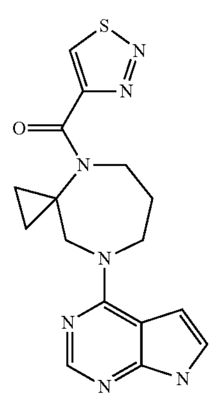 [SMILES: O=C(c1csnn1)N1CCCN(c2ncnc3[nH]ccc23)CC12CC2] | I | I | II | II |
| 143 | 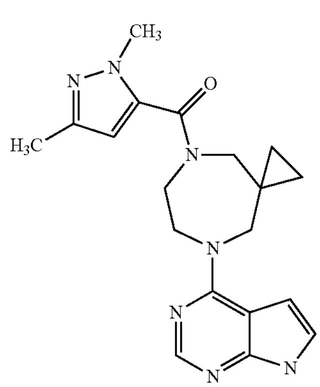 [SMILES: Cc1cc(C(=O)N2CCN(c3ncnc4[nH]ccc34)CC3(CC3)C2)n(C)n1] | III | III | III | |

TABLE 1-continued
| Example number | Structure | JAK1 | JAK2 | JAK3 | TYK2 |
|---|---|---|---|---|---|
| 144 | 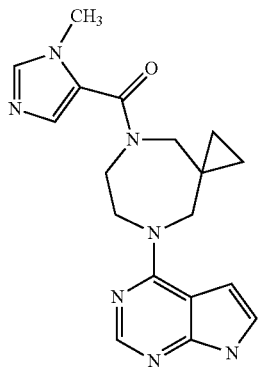 [SMILES: Cn1cncc1C(=O)N1CCN(c2ncnc3[nH]ccc23)CC2(CC2)C1] | | II | II | III |
| 145 | 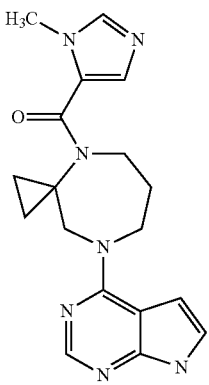 [SMILES: Cn1cncc1C(=O)N1CCCN(c2ncnc3[nH]ccc23)CC12CC2] | | II | II | III |
| 146 | 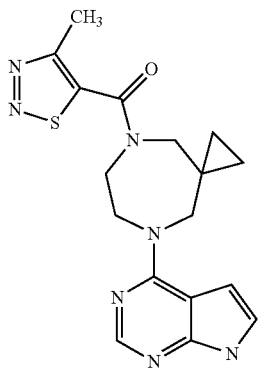 [SMILES: Cc1nnsc1C(=O)N1CCN(c2ncnc3[nH]ccc23)CC2(CC2)C1] | | II | II | III |
| 147 | 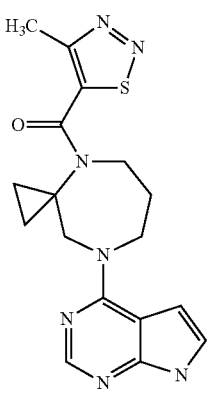 | | II | II | III |

TABLE 1-continued

| Example number | Structure | JAK1 | JAK2 | JAK3 | TYK2 |
|---|---|---|---|---|---|
| 148 | 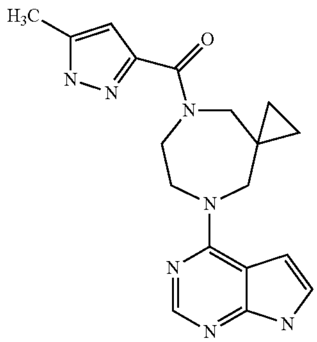 [SMILES: Cc1cc(C(=O)N2CCN(c3ncnc4[nH]ccc34)CC3(CC3)C2)n[nH]1] | II | II | III | |
| 149 | 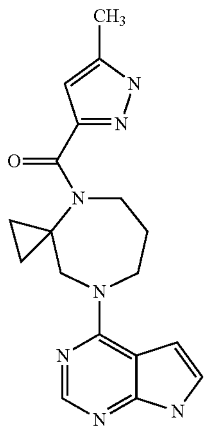 [SMILES: Cc1cc(C(=O)N2CCCN(c3ncnc4[nH]ccc34)CC23CC3)n[nH]1] | II | II | III | |
| 150 | 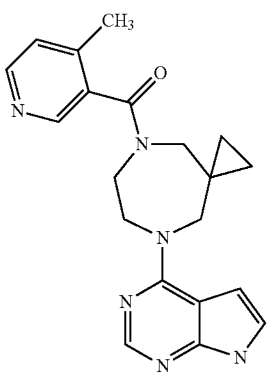 [SMILES: Cc1ccncc1C(=O)N1CCN(c2ncnc3[nH]ccc23)CC2(CC2)C1] | II | III | III | |
| 151 | 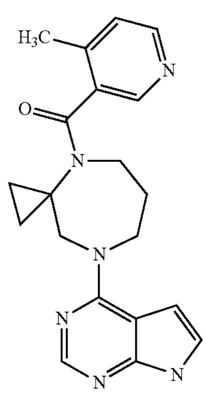 [SMILES: Cc1ccncc1C(=O)N1CCCN(c2ncnc3[nH]ccc23)CC12CC2] | II | II | III | |

TABLE 1-continued

| Example number | Structure | JAK1 | JAK2 | JAK3 | TYK2 |
|---|---|---|---|---|---|
| 152 | 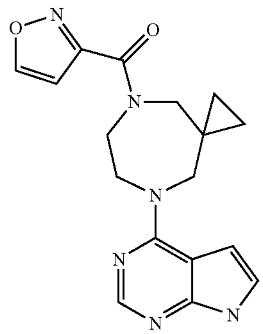 [SMILES: O=C(c1ccon1)N1CCN(c2ncnc3[nH]ccc23)CC2(CC2)C1] | II | II | II | |
| 153 | 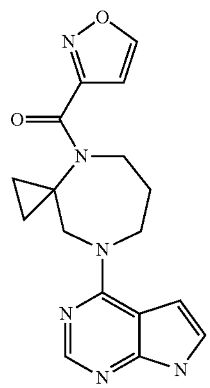 [SMILES: O=C(c1ccon1)N1CCCN(c2ncnc3[nH]ccc23)CC12CC2] | I | I | II | II |
| 154 | 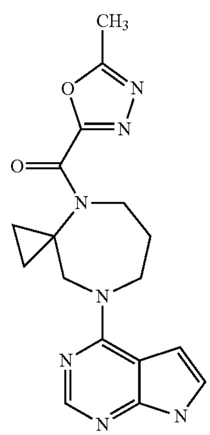 [SMILES: Cc1nnc(C(=O)N2CCCN(c3ncnc4[nH]ccc34)CC23CC3)o1] | II | I | II | |
| 155 | 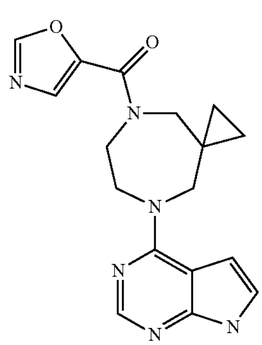 [SMILES: O=C(c1cnco1)N1CCN(c2ncnc3[nH]ccc23)CC2(CC2)C1] | II | II | II | |

TABLE 1-continued
| Example number | Structure | JAK1 | JAK2 | JAK3 | TYK2 |
|---|---|---|---|---|---|
| 156 | 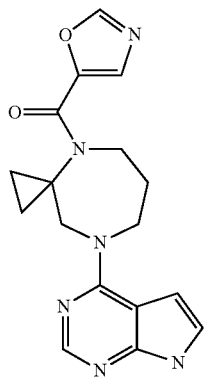 [SMILES: O=C(c1cnco1)N1CCCN(c2ncnc3[nH]ccc23)CC12CC2] | II | II | II | |
| 157 | 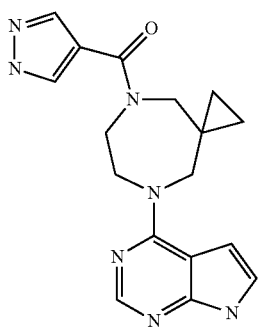 [SMILES: O=C(c1cn[nH]c1)N1CCN(c2ncnc3[nH]ccc23)CC2(CC2)C1] | II | II | II | |
| 158 | 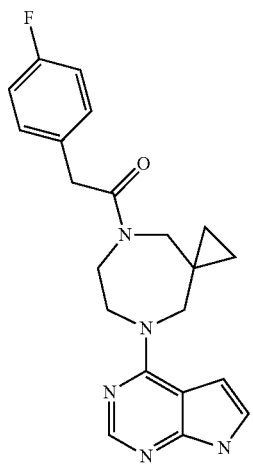 [SMILES: O=C(Cc1ccc(F)cc1)N1CCN(c2ncnc3[nH]ccc23)CC2(CC2)C1] | I | I | II | II |

TABLE 1-continued
| Example number | Structure | JAK1 | JAK2 | JAK3 | TYK2 |
|---|---|---|---|---|---|
| 159 | 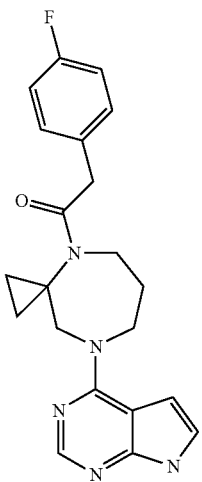 [SMILES: O=C(Cc1ccc(F)cc1)N1CCCN(c2ncnc3[nH]ccc23)CC12CC2] | II | I | III | |
| 160 | 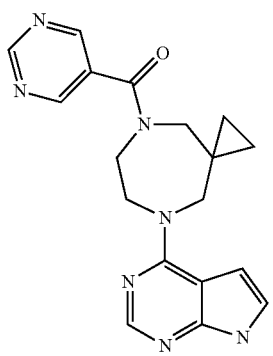 [SMILES: O=C(c1cncnc1)N1CCN(c2ncnc3[nH]ccc23)CC2(CC2)C1] | III | II | III | |
| 161 | 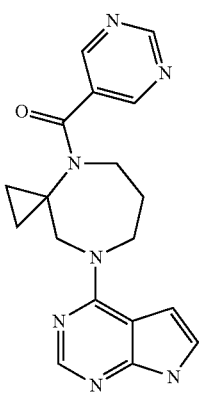 [SMILES: O=C(c1cncnc1)N1CCCN(c2ncnc3[nH]ccc23)CC12CC2] | II | II | III | |

TABLE 1-continued
| Example number | Structure | JAK1 | JAK2 | JAK3 | TYK2 |
|---|---|---|---|---|---|
| 162 | 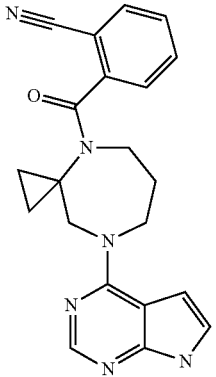 [SMILES: N#Cc1ccccc1C(=O)N1CCCN(c2ncnc3[nH]ccc23)CC12CC2] | III | II | III | |
| 163 | 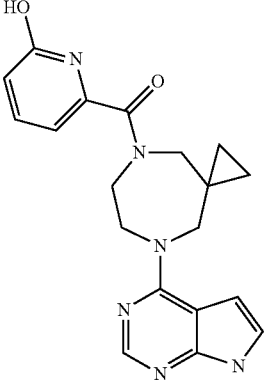 [SMILES: O=C(c1cccc(O)n1)N1CCN(c2ncnc3[nH]ccc23)CC2(CC2)C1] | II | II | III | |
| 164 | 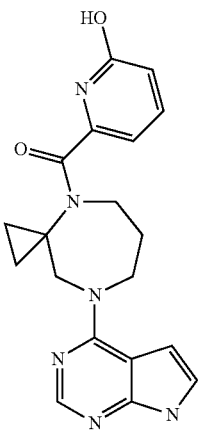 [SMILES: O=C(c1cccc(O)n1)N1CCCN(c2ncnc3[nH]ccc23)CC12CC2] | II | II | III | |
| 165 | 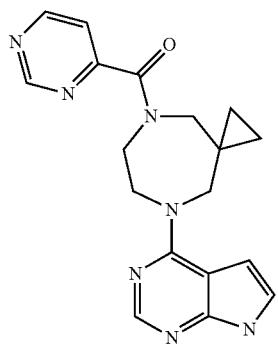 [SMILES: O=C(c1ccncn1)N1CCN(c2ncnc3[nH]ccc23)CC2(CC2)C1] | III | II | III | |

TABLE 1-continued
| Example number | Structure | JAK1 | JAK2 | JAK3 | TYK2 |
|---|---|---|---|---|---|
| 166 | 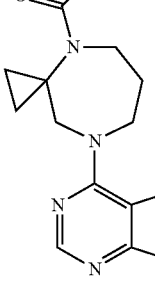 | I | I | II | |
| 167 | 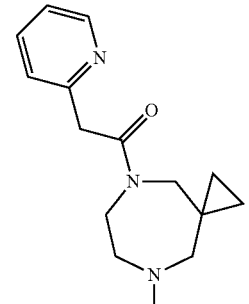 | II | II | III | |
| 168 | 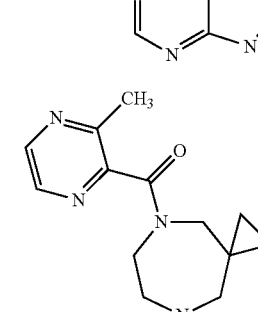 | III | III | III | |
| 169 | 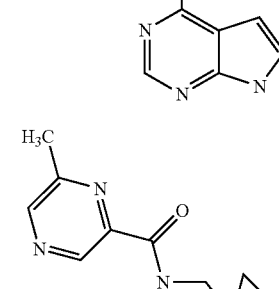 | III | II | III | |

TABLE 1-continued
| Example number | Structure | JAK1 | JAK2 | JAK3 | TYK2 |
|---|---|---|---|---|---|
| 170 | 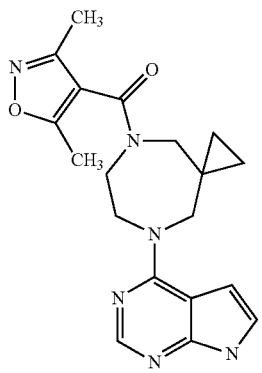 [SMILES: Cc1noc(C)c1C(=O)N1CCN(c2ncnc3[nH]ccc23)CC2(CC2)C1] | III | III | III | |
| 171 | 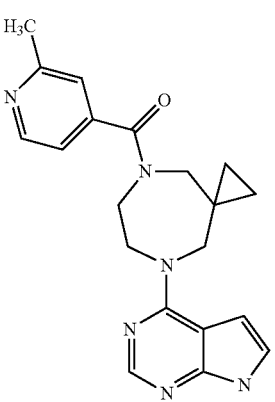 [SMILES: Cc1cc(C(=O)N2CCN(c3ncnc4[nH]ccc34)CC3(CC3)C2)ccn1] | II | III | III | |
| 172 | 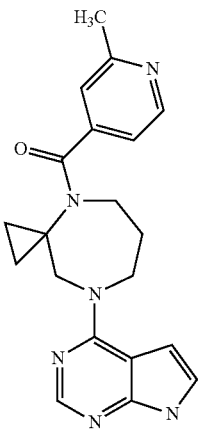 [SMILES: Cc1cc(C(=O)N2CCCN(c3ncnc4[nH]ccc34)CC23CC3)ccn1] | II | II | III | |

TABLE 1-continued

| Example number | Structure | JAK1 | JAK2 | JAK3 | TYK2 |
|---|---|---|---|---|---|
| 173 | 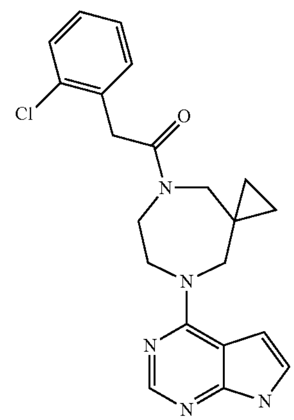 [SMILES: O=C(Cc1ccccc1Cl)N1CCN(c2ncnc3[nH]ccc23)CC2(CC2)C1] | II | I | II | |
| 174 | 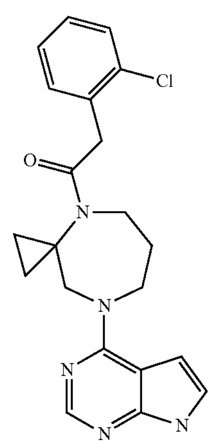 [SMILES: O=C(Cc1ccccc1Cl)N1CCCN(c2ncnc3[nH]ccc23)CC12CC2] | II | II | III | |
| 175 | 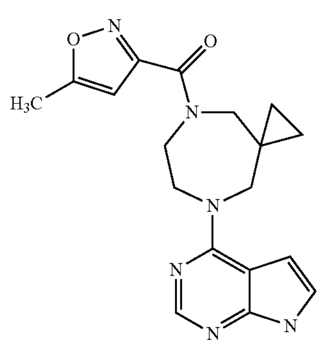 [SMILES: Cc1cc(C(=O)N2CCN(c3ncnc4[nH]ccc34)CC3(CC3)C2)no1] | II | II | II | |
| 176 | 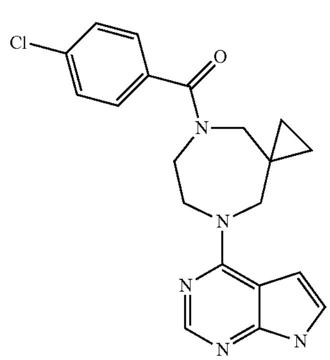 [SMILES: O=C(c1ccc(Cl)cc1)N1CCN(c2ncnc3[nH]ccc23)CC2(CC2)C1] | II | I | II | |

TABLE 1-continued

| Example number | Structure | JAK1 | JAK2 | JAK3 | TYK2 |
|---|---|---|---|---|---|
| 177 | 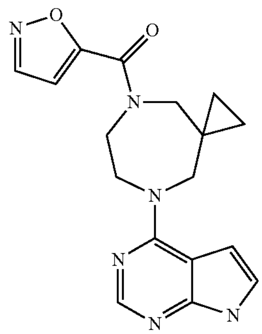 | II | II | II | |
| 178 | 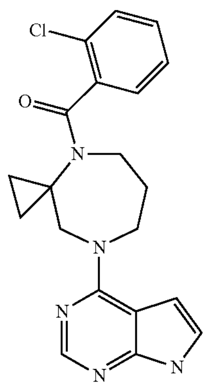 [SMILES: O=C(c1ccccc1Cl)N1CCCN(c2ncnc3[nH]ccc23)CC12CC2] | II | II | III | |
| 179 | 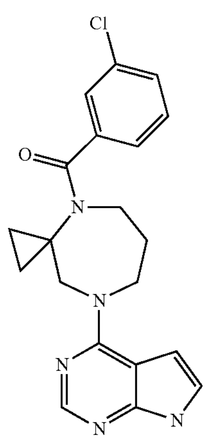 [SMILES: O=C(c1cccc(Cl)c1)N1CCCN(c2ncnc3[nH]ccc23)CC12CC2] | II | I | II | |
| 180 | 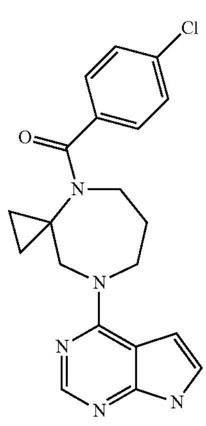 [SMILES: O=C(c1ccc(Cl)cc1)N1CCCN(c2ncnc3[nH]ccc23)CC12CC2] | I | I | II | |

TABLE 1-continued
| Example number | Structure | JAK1 | JAK2 | JAK3 | TYK2 |
|---|---|---|---|---|---|
| 181 | 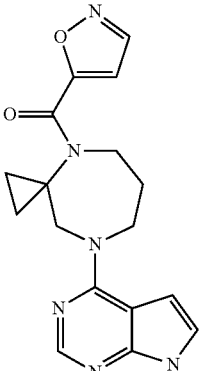 | I | I | II | |
| 182 | 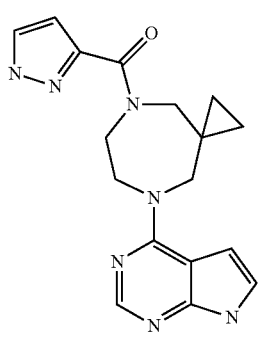 | II | II | II | |
| 183 | 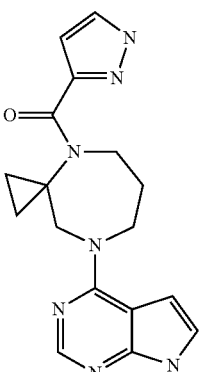 | II | II | II | |
| 184 | 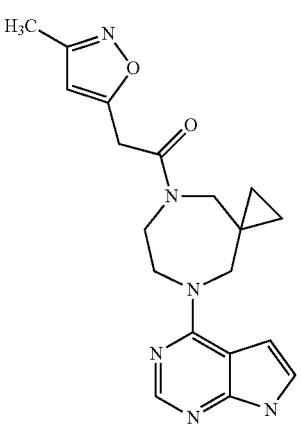 [SMILES: Cc1cc(CC(=O)N2CCN(c3ncnc4[nH]ccc34)CC3(CC3)C2)on1] | I | I | II | |

TABLE 1-continued

| Example number | Structure | JAK1 | JAK2 | JAK3 | TYK2 |
|---|---|---|---|---|---|
| 185 | 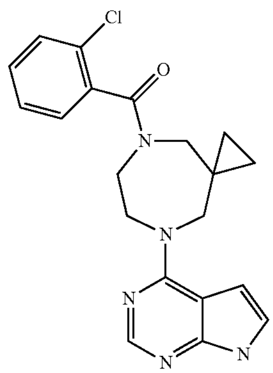 [SMILES: O=C(c1ccccc1Cl)N1CCN(c2ncnc3[nH]ccc23)CC2(CC2)C1] | | II | II | III |
| 186 | 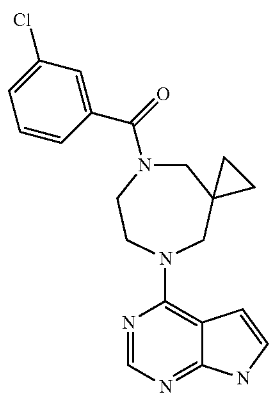 [SMILES: O=C(c1cccc(Cl)c1)N1CCN(c2ncnc3[nH]ccc23)CC2(CC2)C1] | | II | II | III |
| 187 | 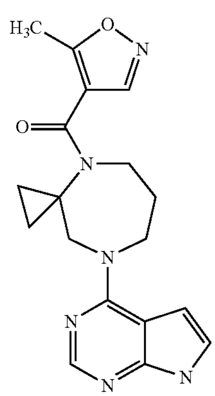 [SMILES: Cc1oncc1C(=O)N1CCCN(c2ncnc3[nH]ccc23)CC12CC2] | | II | II | II |
| 188 | 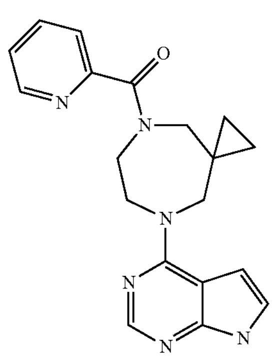 [SMILES: O=C(c1ccccn1)N1CCN(c2ncnc3[nH]ccc23)CC2(CC2)C1] | III | II | III | |

TABLE 1-continued
| Example number | Structure | JAK1 | JAK2 | JAK3 | TYK2 |
|---|---|---|---|---|---|
| 189 | 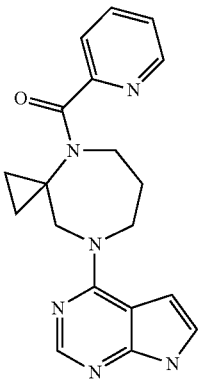 [SMILES: O=C(c1ccccn1)N1CCCN(c2ncnc3[nH]ccc23)CC12CC2] | II | I | III | |
| 190 | 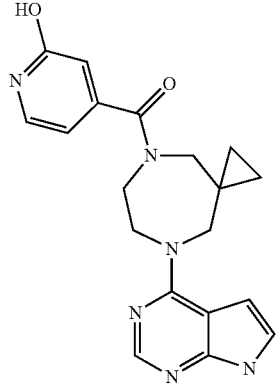 [SMILES: O=C(c1ccnc(O)c1)N1CCN(c2ncnc3[nH]ccc23)CC2(CC2)C1] | II | II | III | |
| 191 | 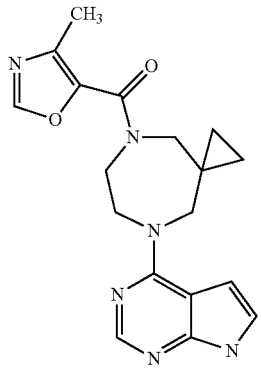 [SMILES: Cc1ncoc1C(=O)N1CCN(c2ncnc3[nH]ccc23)CC2(CC2)C1] | II | II | III | |
| 192 | 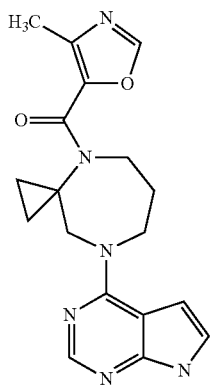 [SMILES: Cc1ncoc1C(=O)N1CCCN(c2ncnc3[nH]ccc23)CC12CC2] | II | II | II | |

TABLE 1-continued
| Example number | Structure | JAK1 | JAK2 | JAK3 | TYK2 |
|---|---|---|---|---|---|
| 193 | 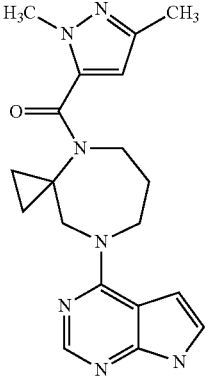 [SMILES: Cc1cc(C(=O)N2CCCN(c3ncnc4[nH]ccc34)CC23CC3)n(C)n1] | | II | I | III |
| 194 | 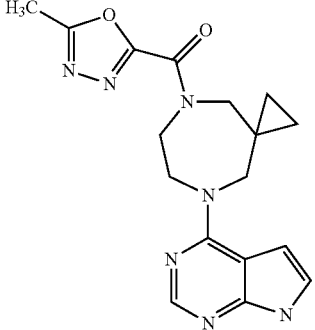 [SMILES: Cc1nnc(C(=O)N2CCN(c3ncnc4[nH]ccc34)CC3(CC3)C2)o1] | | II | II | III |
| 195 | 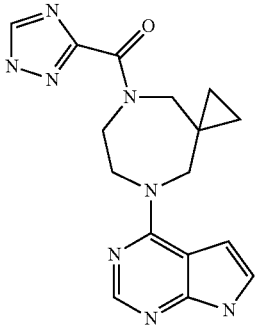 | | II | II | III |
| 196 | 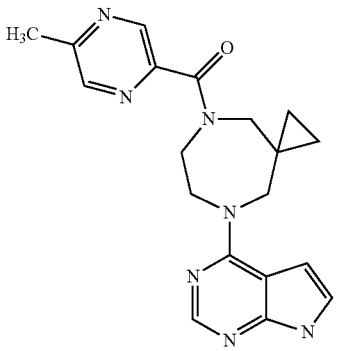 [SMILES: Cc1cnc(C(=O)N2CCN(c3ncnc4[nH]ccc34)CC3(CC3)C2)cn1] | | III | III | III |

TABLE 1-continued
| Example number | Structure | JAK1 | JAK2 | JAK3 | TYK2 |
|---|---|---|---|---|---|
| 197 | 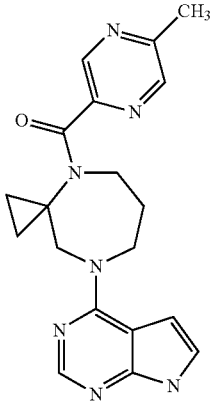 [SMILES: Cc1cnc(C(=O)N2CCCN(c3ncnc4[nH]ccc34)CC23CC3)cn1] | II | II | III | |
| 198 | 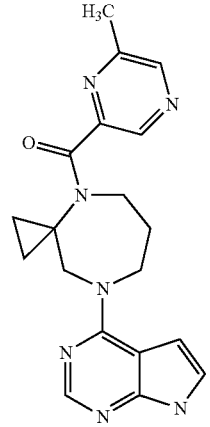 [SMILES: Cc1cncc(C(=O)N2CCCN(c3ncnc4[nH]ccc34)CC23CC3)n1] | II | II | III | |
| 199 | 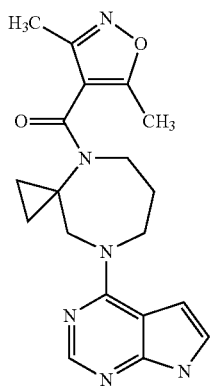 [SMILES: Cc1noc(C)c1C(=O)N1CCCN(c2ncnc3[nH]ccc23)CC12CC2] | III | III | III | |
| 200 | 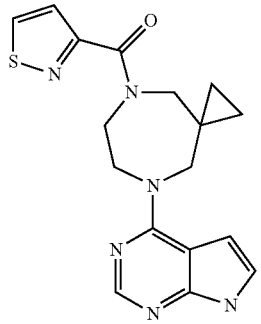 [SMILES: O=C(c1ccsn1)N1CCN(c2ncnc3[nH]ccc23)CC2(CC2)C1] | II | II | II | |

TABLE 1-continued

| Example number | Structure | JAK1 | JAK2 | JAK3 | TYK2 |
|---|---|---|---|---|---|
| 201 | 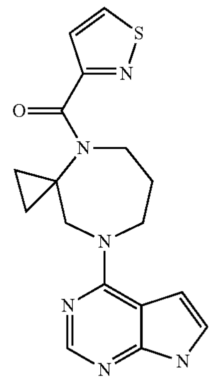 | I | I | II | II |
| 202 | 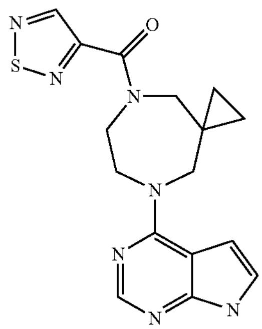 [SMILES: O=C(c1cnsn1)N1CCN(c2ncnc3[nH]ccc23)CC2(CC2)C1] | II | II | II | |
| 203 | 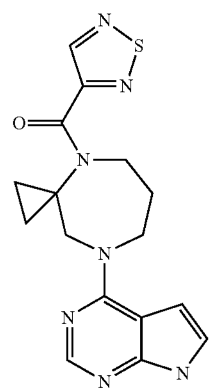 [SMILES: O=C(c1cnsn1)N1CCCN(c2ncnc3[nH]ccc23)CC12CC2] | I | I | II | II |
| 204 | 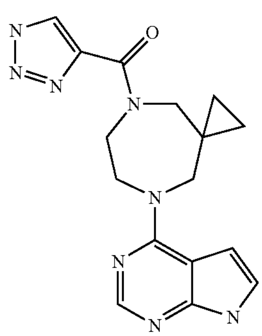 [SMILES: O=C(c1c[nH]nn1)N1CCN(c2ncnc3[nH]ccc23)CC2(CC2)C1] | II | II | II | |

TABLE 1-continued
| Example number | Structure | JAK1 | JAK2 | JAK3 | TYK2 |
|---|---|---|---|---|---|
| 205 | 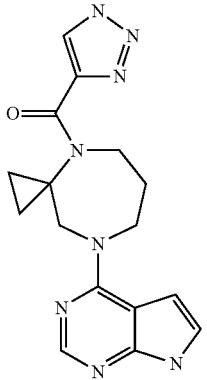 [SMILES: O=C(c1c[nH]nn1)N1CCCN(c2ncnc3[nH]ccc23)CC12CC2] | II | II | II | |
| 206 | 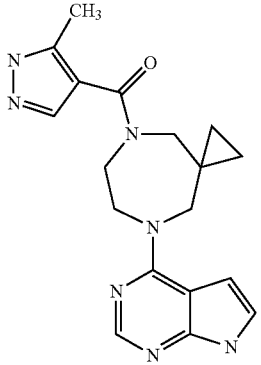 [SMILES: Cc1[nH]ncc1C(=O)N1CCN(c2ncnc3[nH]ccc23)CC2(CC2)C1] | II | II | II | |
| 207 | 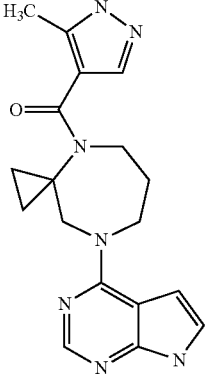 | III | II | III | |
| 208 | 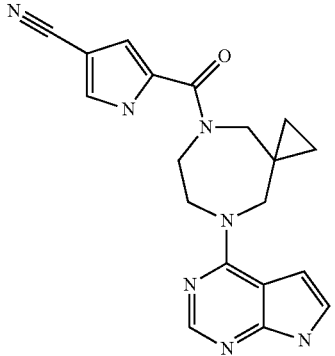 [SMILES: N#Cc1c[nH]c(C(=O)N2CCN(c3ncnc4[nH]ccc34)CC3(CC3)C2)c1] | I | I | II | |

TABLE 1-continued
| Example number | Structure | JAK1 | JAK2 | JAK3 | TYK2 |
|---|---|---|---|---|---|
| 209 | 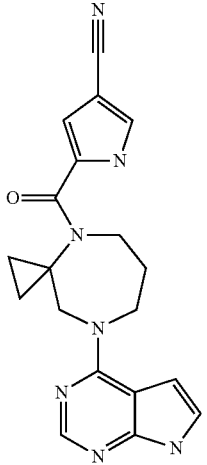 [SMILES: N#Cc1c[nH]c(C(=O)N2CCCN(c3ncnc4[nH]ccc34)CC23CC3)c1] | I | I | I | I |
| 210 | 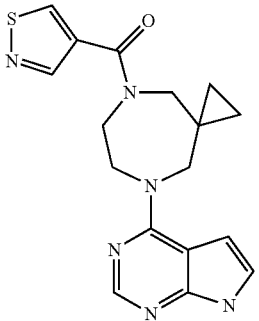 [SMILES: O=C(c1cnsc1)N1CCN(c2ncnc3[nH]ccc23)CC2(CC2)C1] | II | II | II | |
| 211 | 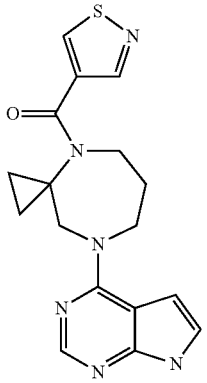 [SMILES: O=C(c1cnsc1)N1CCCN(c2ncnc3[nH]ccc23)CC12CC2] | II | II | II | |
| 212 | 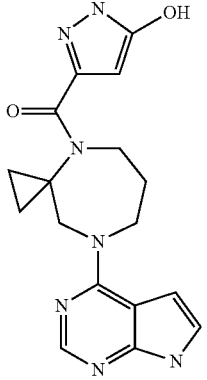 [SMILES: O=C(c1cc(O)[nH]n1)N1CCCN(c2ncnc3[nH]ccc23)CC12CC2] | II | II | II | |

TABLE 1-continued

| Example number | Structure | JAK1 | JAK2 | JAK3 | TYK2 |
|---|---|---|---|---|---|
| 213 | 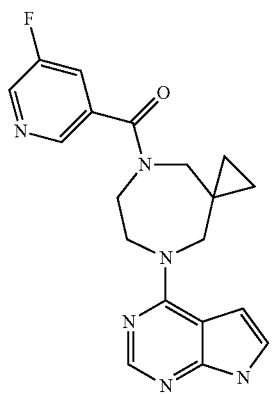 [SMILES: O=C(c1cncc(F)c1)N1CCN(c2ncnc3[nH]ccc23)CC2(CC2)C1] | II | II | III | |
| 214 | 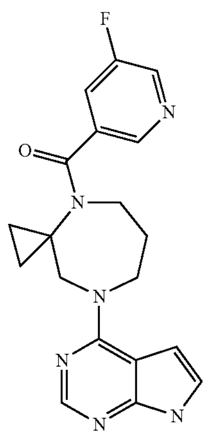 [SMILES: O=C(c1cncc(F)c1)N1CCCN(c2ncnc3[nH]ccc23)CC12CC2] | II | II | II | |
| 215 | 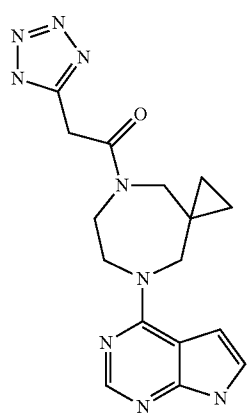 [SMILES: O=C(Cc1nnn[nH]1)N1CCN(c2ncnc3[nH]ccc23)CC2(CC2)C1] | I | I | II | |
| 216 | 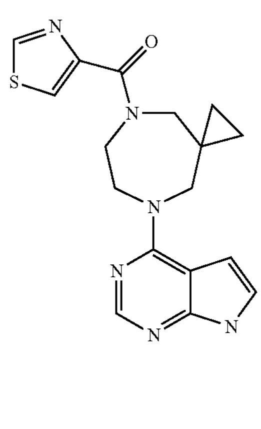 [SMILES: O=C(c1cscn1)N1CCN(c2ncnc3[nH]ccc23)CC2(CC2)C1] | II | II | II | |

TABLE 1-continued
| Example number | Structure | JAK1 | JAK2 | JAK3 | TYK2 |
|---|---|---|---|---|---|
| 217 | 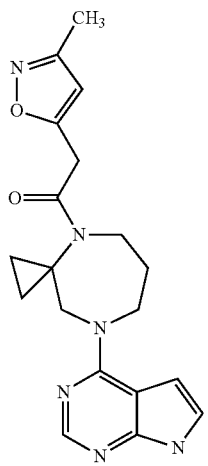 [SMILES: Cc1cc(CC(=O)N2CCCN(c3ncnc4[nH]ccc34)CC23CC3)on1] | | II | II | III |
| 218 | 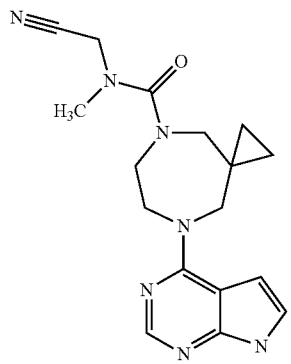 [SMILES: CN(CC#N)C(=O)N1CCN(c2ncnc3[nH]ccc23)CC2(CC2)C1] | | II | I | II |
| 219 | 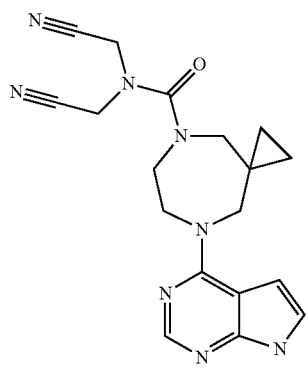 [SMILES: N#CCN(CC#N)C(=O)N1CCN(c2ncnc3[nH]ccc23)CC2(CC2)C1] | | II | I | II |

TABLE 1-continued
| Example number | Structure | JAK1 | JAK2 | JAK3 | TYK2 |
|---|---|---|---|---|---|
| 220 | 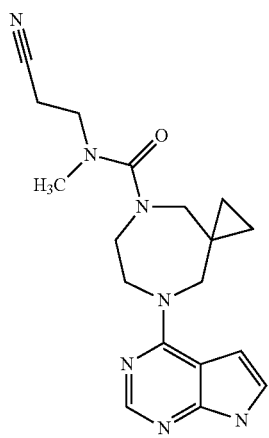 [SMILES: CN(CCC#N)C(=O)N1CCN(c2ncnc3[nH]ccc23)CC2(CC2)C1] | II | II | II | |
| 221 | 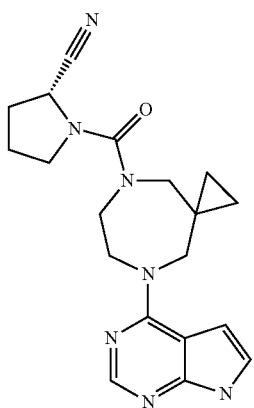 [SMILES: N#C[C@H]1CCCN1C(=O)N1CCN(c2ncnc3[nH]ccc23)CC2(CC2)C1] | II | I | II | |
| 222 | 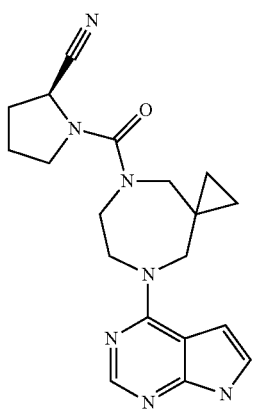 [SMILES: N#C[C@@H]1CCCN1C(=O)N1CCN(c2ncnc3[nH]ccc23)CC2(CC2)C1] | II | I | II | |

TABLE 1-continued
| Example number | Structure | JAK1 | JAK2 | JAK3 | TYK2 |
|---|---|---|---|---|---|
| 223 | 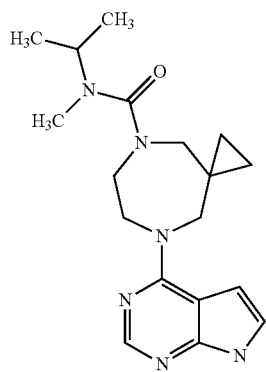 [SMILES: CC(C)N(C)C(=O)N1CCN(c2ncnc3[nH]ccc23)CC2(CC2)C1] | II | II | II | |
| 224 | 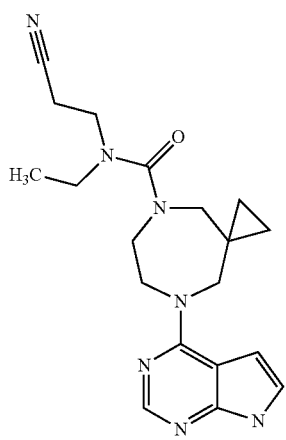 [SMILES: CCN(CCC#N)C(=O)N1CCN(c2ncnc3[nH]ccc23)CC2(CC2)C1] | III | II | II | |
| 225 | 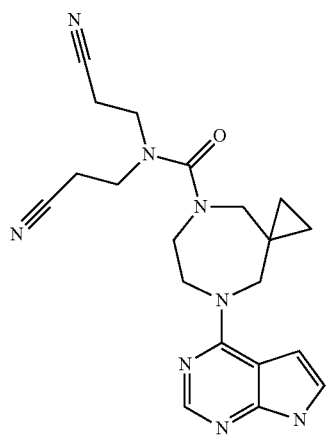 [SMILES: N#CCCN(CCC#N)C(=O)N1CCN(c2ncnc3[nH]ccc23)CC2(CC2)C1] | III | II | II | |

TABLE 1-continued

| Example number | Structure | JAK1 | JAK2 | JAK3 | TYK2 |
|---|---|---|---|---|---|
| 226 | 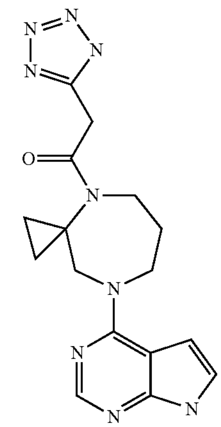 [SMILES: O=C(Cc1nnn[nH]1)N1CCCN(c2ncnc3[nH]ccc23)CC12CC2] | III | | II | III |
| 227 | 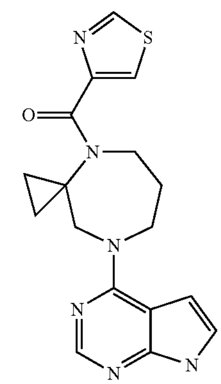 [SMILES: O=C(c1cscn1)N1CCCN(c2ncnc3[nH]ccc23)CC12CC2] | II | | I | II |
| 228 | 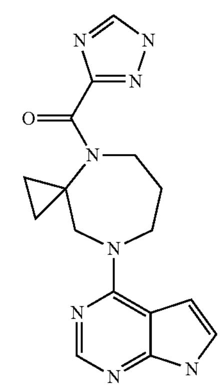 [SMILES: O=C(c1nc[nH]n1)N1CCCN(c2ncnc3[nH]ccc23)CC12CC2] | II | | II | III |
| 229 | 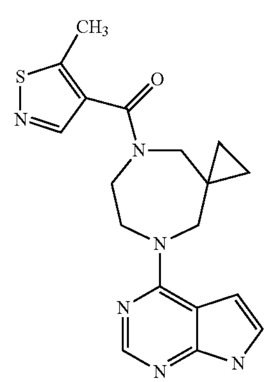 [SMILES: Cc1sncc1C(=O)N1CCN(c2ncnc3[nH]ccc23)CC2(CC2)C1] | II | | II | III |

TABLE 1-continued

| Example number | Structure | JAK1 | JAK2 | JAK3 | TYK2 |
|---|---|---|---|---|---|
| 230 | 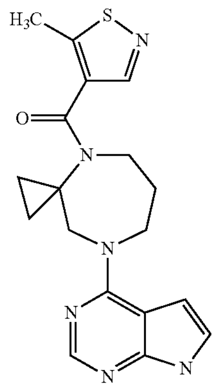 [SMILES: Cc1sncc1C(=O)N1CCCN(c2ncnc3[nH]ccc23)CC12CC2] | II | I | II | |
| 231 | 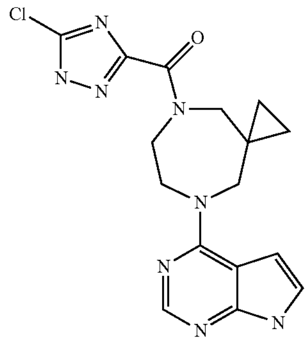 [SMILES: O=C(c1n[nH]c(Cl)n1)N1CCN(c2ncnc3[nH]ccc23)CC2(CC2)C1] | II | II | II | |
| 232 | 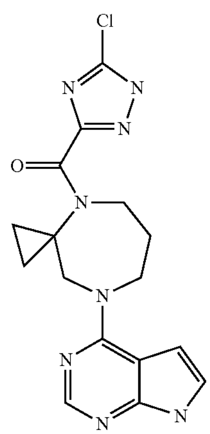 [SMILES: O=C(c1n[nH]c(Cl)n1)N1CCCN(c2ncnc3[nH]ccc23)CC12CC2] | II | I | II | |
| 233 | 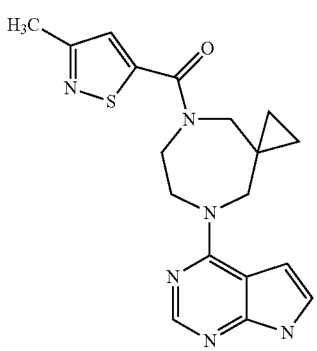 [SMILES: Cc1cc(C(=O)N2CCN(c3ncnc4[nH]ccc34)CC3(CC3)C2)sn1] | II | II | III | |

TABLE 1-continued
| Example number | Structure | JAK1 | JAK2 | JAK3 | TYK2 |
|---|---|---|---|---|---|
| 234 | 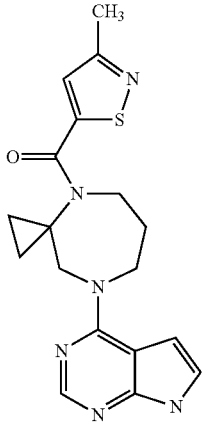 [SMILES: Cc1cc(C(=O)N2CCCN(c3ncnc4[nH]ccc34)CC23CC3)sn1] | III | II | III | |
| 235 | 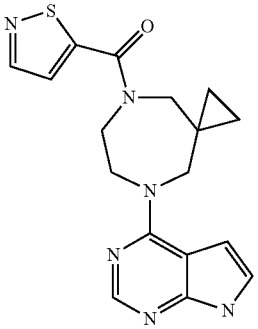 [SMILES: O=C(c1ccns1)N1CCN(c2ncnc3[nH]ccc23)CC2(CC2)C1] | II | II | II | |
| 236 | 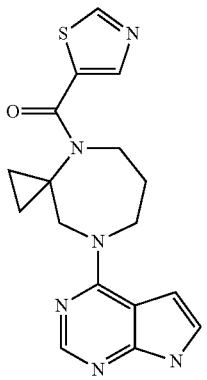 [SMILES: O=C(c1cncs1)N1CCCN(c2ncnc3[nH]ccc23)CC12CC2] | I | I | II | II |
| 237 | 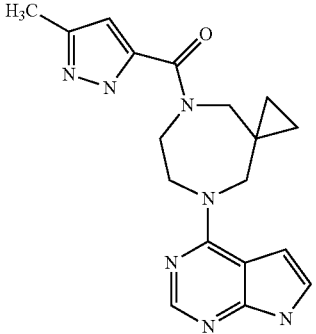 [SMILES: Cc1cc(C(=O)N2CCN(c3ncnc4[nH]ccc34)CC3(CC3)C2)[nH]n1] | II | II | III | |

TABLE 1-continued

| Example number | Structure | JAK1 | JAK2 | JAK3 | TYK2 |
|---|---|---|---|---|---|
| 238 | 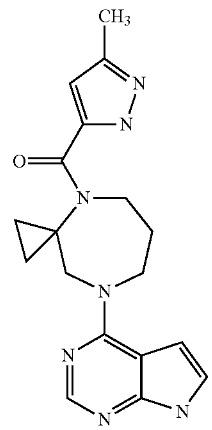 [SMILES: Cc1cc(C(=O)N2CCCN(c3ncnc4[nH]ccc34)CC23CC3)[nH]n1] | II | II | III | |
| 239 | 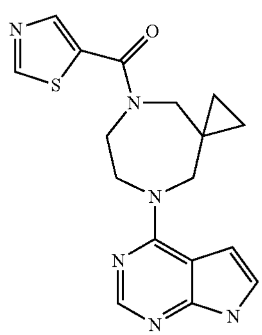 | II | II | II | |
| 240 | 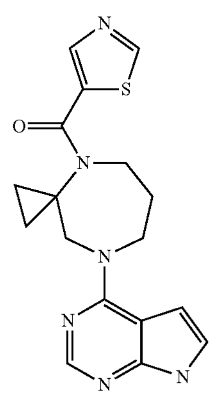 [SMILES: O=C(c1cncs1)N1CCCN(c2ncnc3[nH]ccc23)CC12CC2] | II | II | II | |
| 241 | 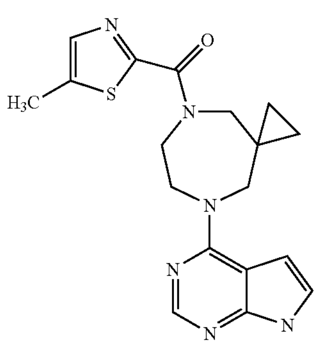 [SMILES: Cc1cnc(C(=O)N2CCN(c3ncnc4[nH]ccc34)CC3(CC3)C2)s1] | II | II | II | |

TABLE 1-continued

| Example number | Structure | JAK1 | JAK2 | JAK3 | TYK2 |
|---|---|---|---|---|---|
| 242 | 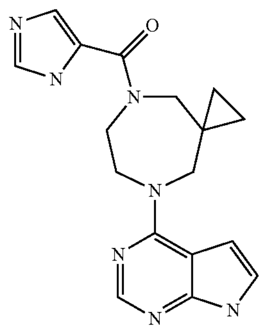 [SMILES: O=C(c1cnc[nH]1)N1CCN(c2ncnc3[nH]ccc23)CC2(CC2)C1] | II | II | II | |
| 243 | 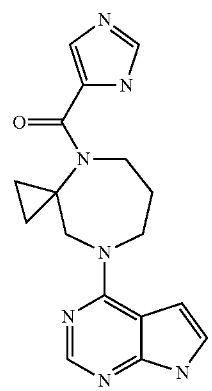 [SMILES: O=C(c1cnc[nH]1)N1CCCN(c2ncnc3[nH]ccc23)CC12CC2] | II | II | | |
| 244 | 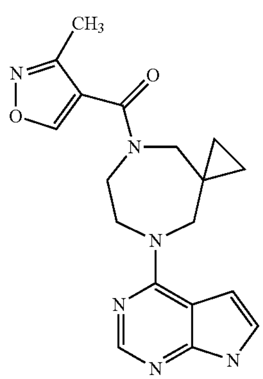 [SMILES: Cc1nocc1C(=O)N1CCN(c2ncnc3[nH]ccc23)CC2(CC2)C1] | II | II | II | |
| 245 | 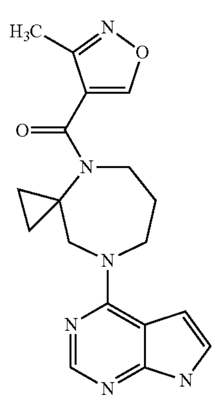 [SMILES: Cc1nocc1C(=O)N1CCCN(c2ncnc3[nH]ccc23)CC12CC2] | III | II | III | |

TABLE 1-continued
| Example number | Structure | JAK1 | JAK2 | JAK3 | TYK2 |
|---|---|---|---|---|---|
| 246 | 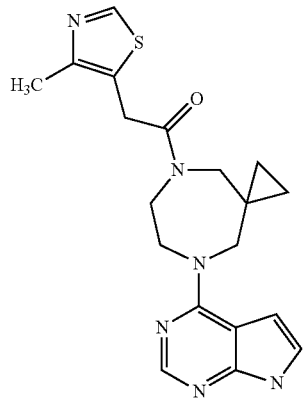 [SMILES: Cc1ncsc1CC(=O)N1CCN(c2ncnc3[nH]ccc23)CC2(CC2)C1] | II | II | III | |
| 247 | 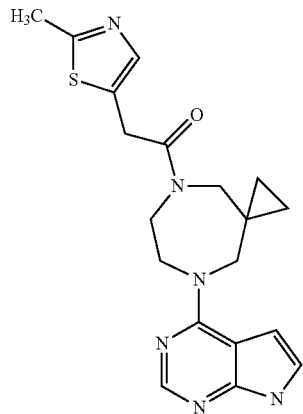 [SMILES: Cc1ncc(CC(=O)N2CCN(c3ncnc4[nH]ccc34)CC3(CC3)C2)s1] | II | I | III | |
| 248 | 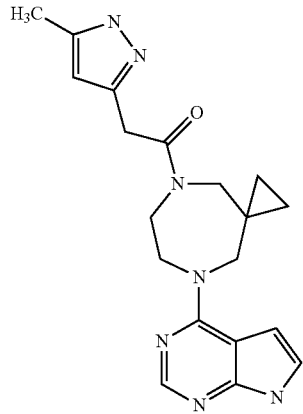 [SMILES: Cc1cc(CC(=O)N2CCN(c3ncnc4[nH]ccc34)CC3(CC3)C2)n[nH]1] | II | I | III | |

TABLE 1-continued
| Example number | Structure | JAK1 | JAK2 | JAK3 | TYK2 |
|---|---|---|---|---|---|
| 249 | 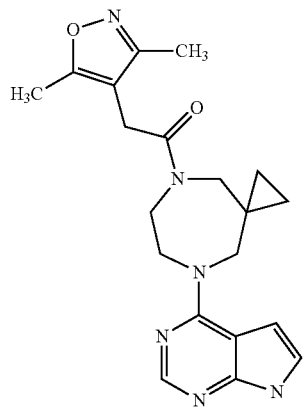 [SMILES: Cc1noc(C)c1CC(=O)N1CCN(c2ncnc3[nH]ccc23)CC2(CC2)C1] | II | II | III | |
| 250 | 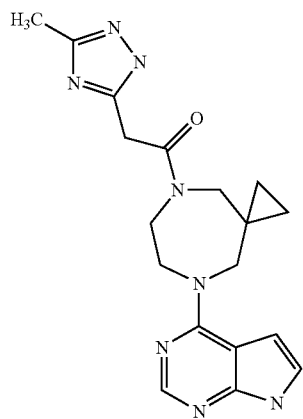 [SMILES: Cc1n[nH]c(CC(=O)N2CCN(c3ncnc4[nH]ccc34)CC3(CC3)C2)n1] | II | II | II | |
| 251 | 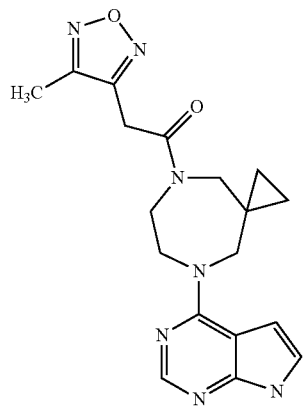 [SMILES: Cc1nonc1CC(=O)N1CCN(c2ncnc3[nH]ccc23)CC2(CC2)C1] | I | I | II | |

TABLE 1-continued
| Example number | Structure | JAK1 | JAK2 | JAK3 | TYK2 |
|---|---|---|---|---|---|
| 252 | 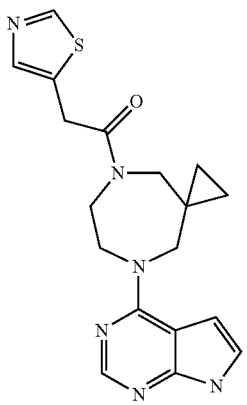 [SMILES: O=C(Cc1cncs1)N1CCN(c2ncnc3[nH]ccc23)CC2(CC2)C1] | II | I | II | |
| 253 | 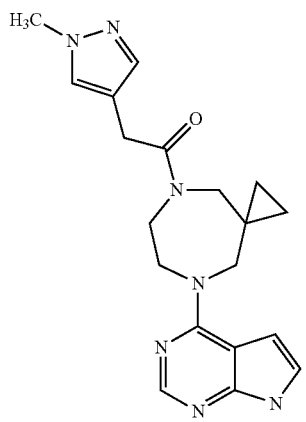 [SMILES: Cn1cc(CC(=O)N2CCN(c3ncnc4[nH]ccc34)CC3(CC3)C2)cn1] | II | II | III | |
| 254 | 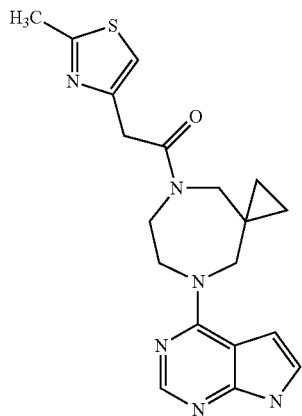 [SMILES: Cc1nc(CC(=O)N2CCN(c3ncnc4[nH]ccc34)CC3(CC3)C2)cs1] | II | II | III | |

TABLE 1-continued
| Example number | Structure | JAK1 | JAK2 | JAK3 | TYK2 |
|---|---|---|---|---|---|
| 255 | 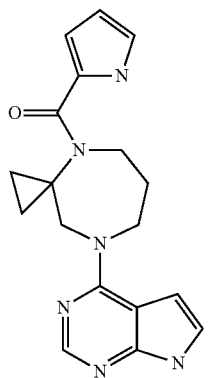 [SMILES: O=C(c1ccc[nH]1)N1CCCN(c2ncnc3[nH]ccc23)CC12CC2] | I | I | II | II |
| 256 | 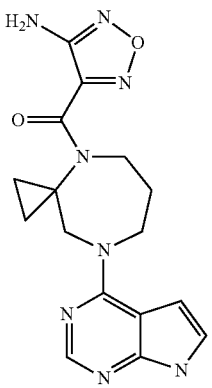 | I | I | I | II |
| 257 | 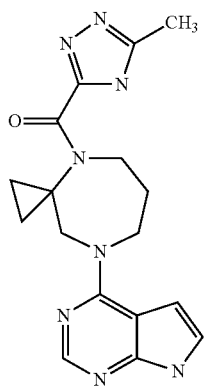 [SMILES: Cc1nnc(C(=O)N2CCCN(c3ncnc4[nH]ccc34)CC23CC3)[nH]1] | II | II | III | |

TABLE 1-continued
| Example number | Structure | JAK1 | JAK2 | JAK3 | TYK2 |
|---|---|---|---|---|---|
| 258 | 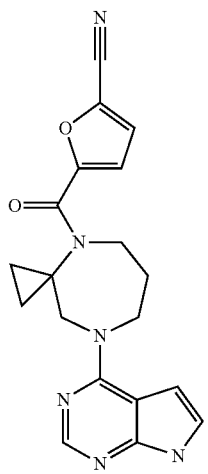 [SMILES: N#Cc1ccc(C(=O)N2CCCN(c3ncnc4[nH]ccc34)CC23CC3)o1] | I | I | II | II |
| 259 | 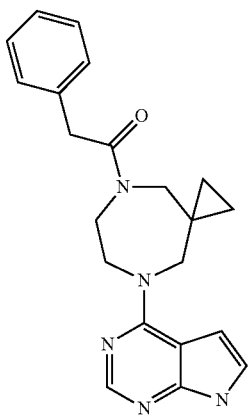 [SMILES: O=C(Cc1ccccc1)N1CCN(c2ncnc3[nH]ccc23)CC2(CC2)C1] | II | I | II | |
| 260 | 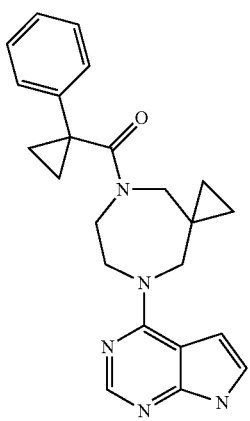 [SMILES: O=C(N1CCN(c2ncnc3[nH]ccc23)CC2(CC2)C1)C1(c2ccccc2)CC1] | III | II | III | |

TABLE 1-continued
| Example number | Structure | JAK1 | JAK2 | JAK3 | TYK2 |
|---|---|---|---|---|---|
| 261 | 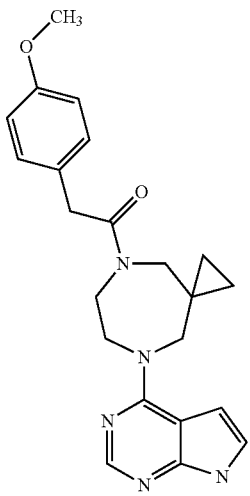 [SMILES: COc1ccc(CC(=O)N2CCN(c3ncnc4[nH]ccc34)CC3(CC3)C2)cc1] | II | I | II | |
| 262 | 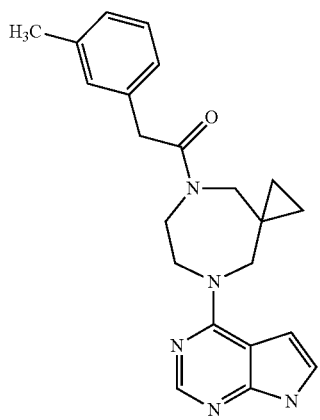 [SMILES: Cc1cccc(CC(=O)N2CCN(c3ncnc4[nH]ccc34)CC3(CC3)C2)c1] | II | I | III | |
| 263 | 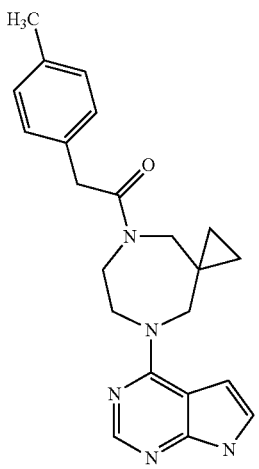 [SMILES: Cc1ccc(CC(=O)N2CCN(c3ncnc4[nH]ccc34)CC3(CC3)C2)cc1] | I | I | II | II |

TABLE 1-continued
| Example number | Structure | JAK1 | JAK2 | JAK3 | TYK2 |
|---|---|---|---|---|---|
| 264 | 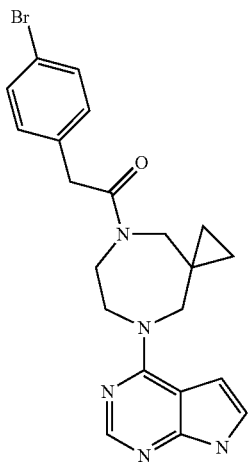 [SMILES: O=C(Cc1ccc(Br)cc1)N1CCN(c2ncnc3[nH]ccc23)CC2(CC2)C1] | I | I | I | II |
| 265 | 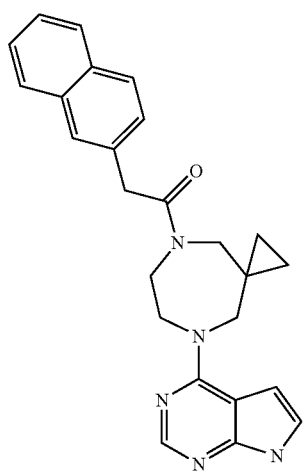 [SMILES: O=C(Cc1ccc2ccccc2c1)N1CCN(c2ncnc3[nH]ccc23)CC2(CC2)C1] | II | I | II | |
| 266 | 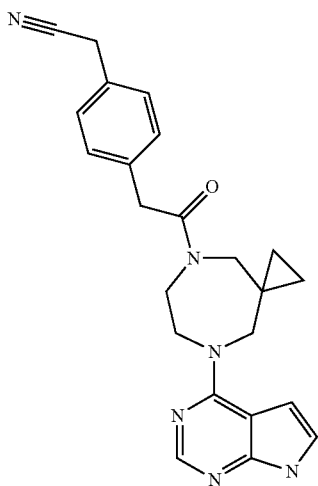 [SMILES: N#CCc1ccc(CC(=O)N2CCN(c3ncnc4[nH]ccc34)CC3(CC3)C2)cc1] | I | I | II | |

TABLE 1-continued
| Example number | Structure | JAK1 | JAK2 | JAK3 | TYK2 |
|---|---|---|---|---|---|
| 267 | 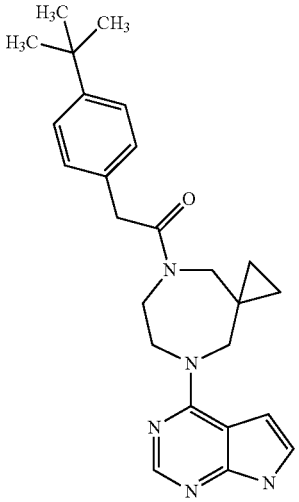 [SMILES: CC(C)(C)c1ccc(CC(=O)N2CCN(c3ncnc4[nH]ccc34)CC3(CC3)C2)cc1] | II | II | II | |
| 268 | 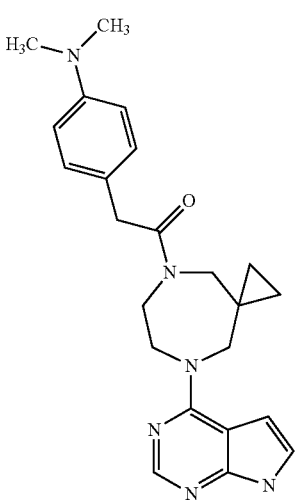 [SMILES: CN(C)c1ccc(CC(=O)N2CCN(c3ncnc4[nH]ccc34)CC3(CC3)C2)cc1] | II | I | II | |
| 269 | 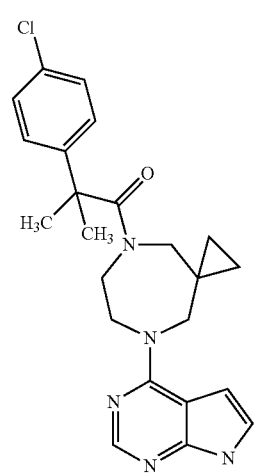 [SMILES: CC(C)(C(=O)N1CCN(c2ncnc3[nH]ccc23)CC2(CC2)C1)c1ccc(Cl)cc1] | II | II | II | |

TABLE 1-continued
| Example number | Structure | JAK1 | JAK2 | JAK3 | TYK2 |
|---|---|---|---|---|---|
| 270 | 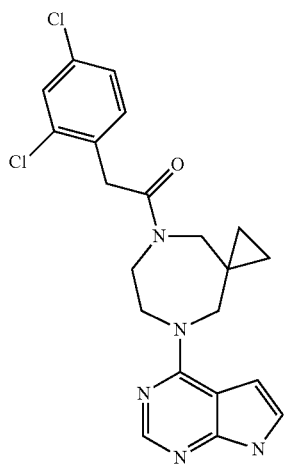 [SMILES: O=C(Cc1ccc(Cl)cc1Cl)N1CCN(c2ncnc3[nH]ccc23)CC2(CC2)C1] | II | I | II | |
| 271 | 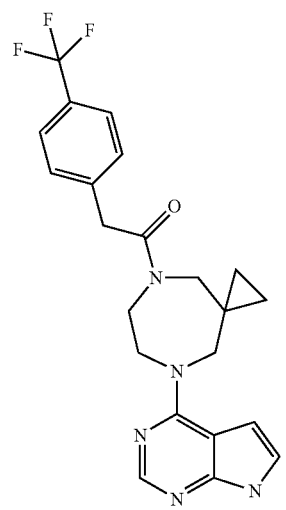 [SMILES: O=C(Cc1ccc(C(F)(F)F)cc1)N1CCN(c2ncnc3[nH]ccc23)CC2(CC2)C1] | I | I | II | II |
| 272 | 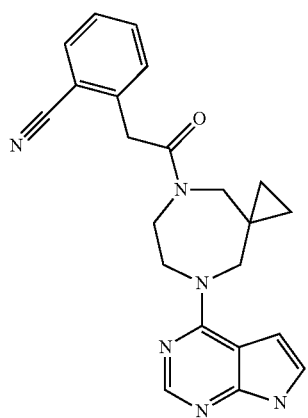 [SMILES: N#Cc1ccccc1CC(=O)N1CCN(c2ncnc3[nH]ccc23)CC2(CC2)C1] | II | I | II | |

TABLE 1-continued
| Example number | Structure | JAK1 | JAK2 | JAK3 | TYK2 |
|---|---|---|---|---|---|
| 273 | 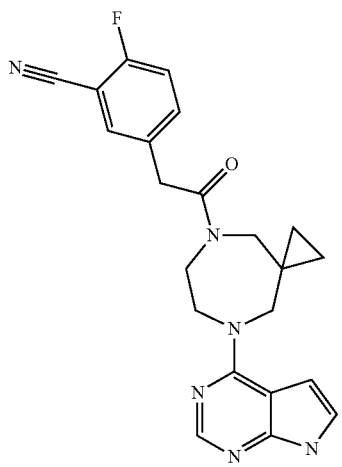 [SMILES: N#Cc1cc(CC(=O)N2CCN(c3ncnc4[nH]ccc34)CC3(CC3)C2)ccc1F] | II | I | II | |
| 274 | 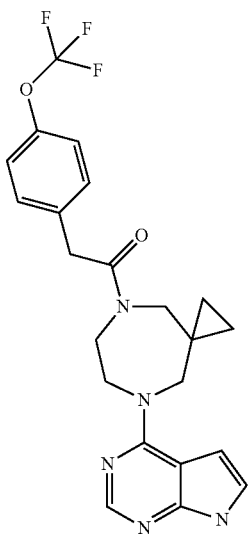 [SMILES: O=C(Cc1ccc(OC(F)(F)F)cc1)N1CCN(c2ncnc3[nH]ccc23)CC2(CC2)C1] | I | I | II | III |
| 275 | 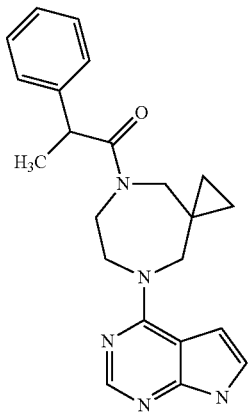 [SMILES: CC(C(=O)N1CCN(c2ncnc3[nH]ccc23)CC2(CC2)C1)c1ccccc1] | II | I | II | |

TABLE 1-continued
| Example number | Structure | JAK1 | JAK2 | JAK3 | TYK2 |
|---|---|---|---|---|---|
| 276 | 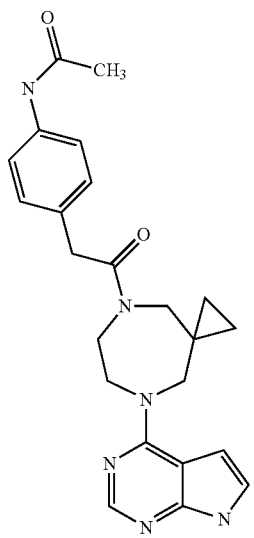 [SMILES: CC(=O)Nc1ccc(CC(=O)N2CCN(c3ncnc4[nH]ccc34)CC3(CC3)C2)cc1] | II | II | III | |
| 277 | 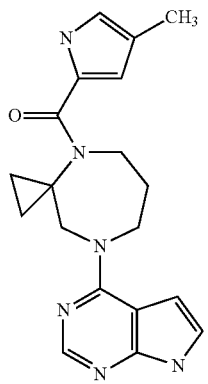 [SMILES: Cc1c[nH]c(C(=O)N2CCCN(c3ncnc4[nH]ccc34)CC23CC3)c1] | I | I | II | II |
| 278 | 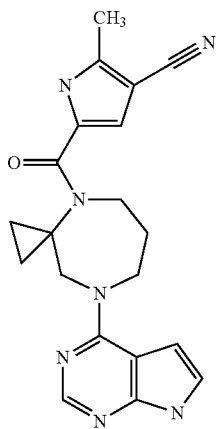 [SMILES: Cc1[nH]c(C(=O)N2CCCN(c3ncnc4[nH]ccc34)CC23CC3)cc1C#N] | I | I | II | II |

TABLE 1-continued
| Example number | Structure | JAK1 | JAK2 | JAK3 | TYK2 |
|---|---|---|---|---|---|
| 279 | 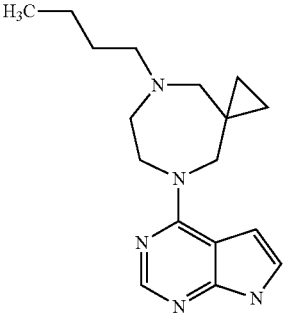 [SMILES: CCCCN1CCN(c2ncnc3[nH]ccc23)CC2(CC2)C1] | III | III | III | III |
| 280 | 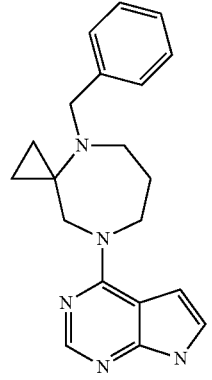 [SMILES: c1ccc(CN2CCCN(c3ncnc4[nH]ccc34)CC23CC3)cc1] | III | II | III | |
| 281 | 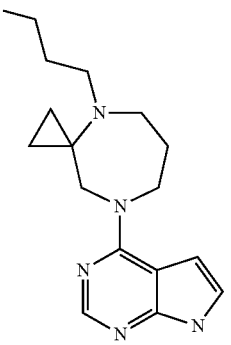 | II | II | II | III |
| 282 | 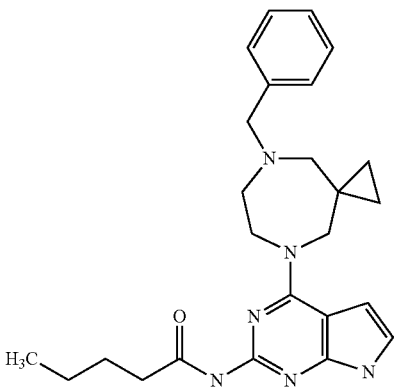 [SMILES: CCCCC(=O)Nc1nc(N2CCN(Cc3ccccc3)CC3(CC3)C2)c2cc[nH]c2n1] | III | III | III | III |

TABLE 1-continued
| Example number | Structure | JAK1 | JAK2 | JAK3 | TYK2 |
|---|---|---|---|---|---|
| 283 | 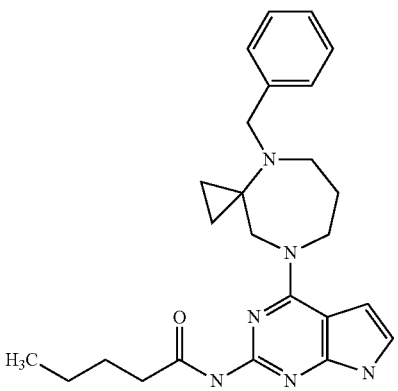 [SMILES: CCCCC(=O)Nc1nc(N2CCCN(Cc3ccccc3)C3(CC3)C2)c2cc[nH]c2n1] | III | III | III | III |
| 284 | 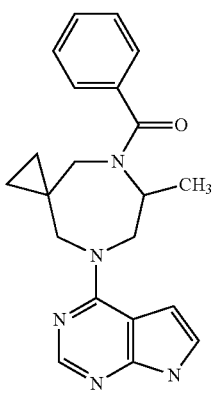 [SMILES: CC1CN(c2ncnc3[nH]ccc23)CC2(CC2)CN1C(=O)c1ccccc1] | III | III | III | III |
| 285 | 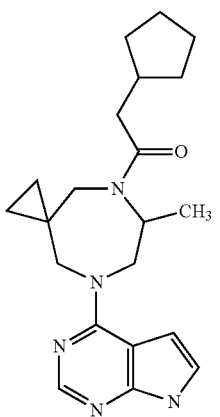 [SMILES: CC1CN(c2ncnc3[nH]ccc23)CC2(CC2)CN1C(=O)CC1CCCC1] | II | II | III | III |

TABLE 1-continued

| Example number | Structure | JAK1 | JAK2 | JAK3 | TYK2 |
|---|---|---|---|---|---|
| 286 | 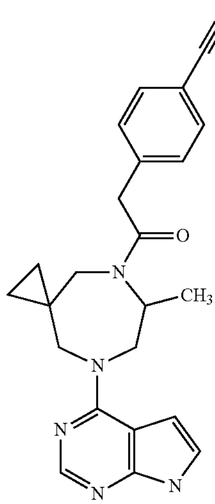 | III | III | III | III |
| 287 | 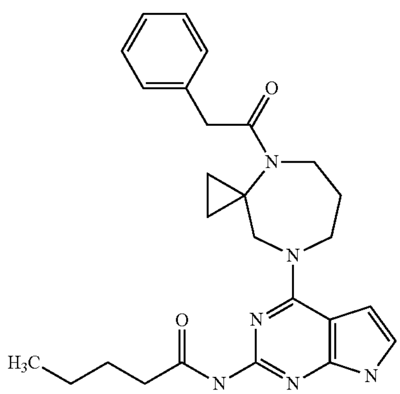 [SMILES: CCCCC(=O)Nc1nc(N2CCCN(C(=O)Cc3ccccc3)C3(CC3)C2)c2cc[nH]c2n1] | | | | |
| 288 | 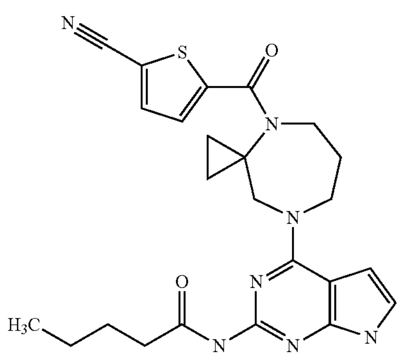 [SMILES: CCCCC(=O)Nc1nc(N2CCCN(C(=O)c3ccc(C#N)s3)C3(CC3)C2)c2cc[nH]c2n1] | | | | |
| 289 | 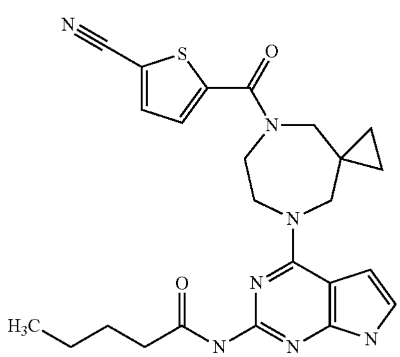 [SMILES: CCCCC(=O)Nc1nc(N2CCN(C(=O)c3ccc(C#N)s3)CC3(CC3)C2)c2cc[nH]c2n1] | | | | |

TABLE 1-continued
| Example number | Structure | JAK1 | JAK2 | JAK3 | TYK2 |
|---|---|---|---|---|---|
| 290 | 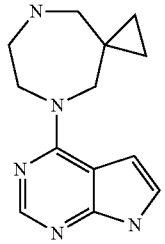 [SMILES: c1nc(N2CCNCC3(CC3)C2)c2cc[nH]c2n1] | III | III | III | III |
| 291 | 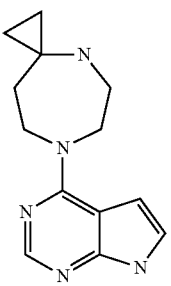 [SMILES: c1nc(N2CCNC3(CC2)CC3)c2cc[nH]c2n1] | III | III | III | III |
| 292 | 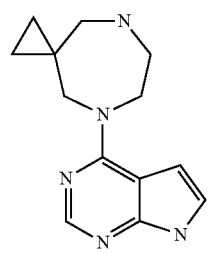 [SMILES: c1nc(N2CCNCC3(CC3)C2)c2cc[nH]c2n1] | III | III | III | III |
| 293 | 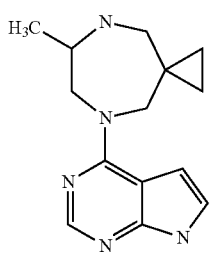 [SMILES: CC1CN(c2ncnc3[nH]ccc23)CC2(CC2)CN1] | III | III | III | III |
| 294 | 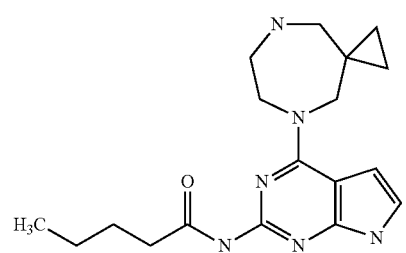 [SMILES: CCCCC(=O)Nc1nc(N2CCNCC3(CC3)C2)c2cc[nH]c2n1] | III | III | III | III |
| 295 | 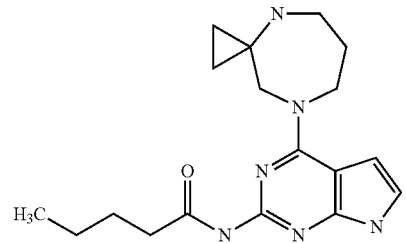 [SMILES: CCCCC(=O)Nc1nc(N2CCCNC3(CC3)C2)c2cc[nH]c2n1] | III | III | III | III |

The invention claimed is:
1. A compound of general formula I

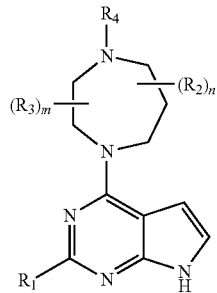

wherein
m is 0;
R₁ is hydrogen;
(R₂)ₙ selected so as to form a spirocyclic homopiperazine compound selected from

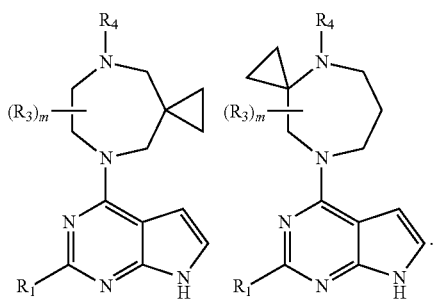

R₄ is selected from the group consisting of hydrogen,

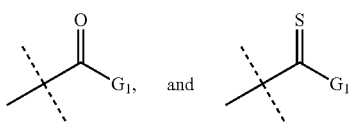

wherein
G₁ is selected from the group consisting of alkyl-, alkenyl-, cycloalkyl-, heterocyclyl-, $R_{G1a}$—C(=O)-L-, $(R_{G1a})_2$N—C(=O)-L-, aryl-, arylalkyl-, aryloxyalkyl-, heteroaryl-, heteroarylalkyl-, cycloalkylalkyl-, heterocyclylalkyl-, $(R_{G1a})_2$N-L-, any of which may be optionally substituted with one or more $R_{G1c}$;
$R_{G1a}$ is selected from the group consisting of hydrogen, alkyl-, heteroalkyl-, alkenyl-, alkynyl-, cycloalkyl-, heterocyclyl-, aryl- and heteroaryl- any of which may be optionally substituted with one or more $R_{G1c}$; or in the case where two $R_{G1a}$s are attached to the same N, they may together with the N atom to which they are attached form a heterocycle which may be optionally substituted with one or more $R_{G1c}$;
$R_{G1c}$ is selected from the group consisting of alkyl, heteroaryl, halogen, oxo, cyano, hydroxy, —SO₂NH₂, —NH₂, $R_{G1d}$O-L-, $(R_{G1d})_2$N—S(=O)₂-L-, $R_{G1d}$—S(=O)₂-L-, and $(R_{G1d})_2$N—S(=O)₂-L-;
$R_{G1d}$ is selected from the group consisting of hydrogen or of alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, heteroarylalkyl- and alkoxyalkyl- any of which may be optionally substituted with one or more substituents selected from the group consisting of halogen, cyano, hydroxy, trifluoromethyl, oxo, —NH₂, —SO₂NH₂, —SONH₂, —CONH₂; or in the case where two $R_{G1d}$s are attached to the same N, they may together with the N atom to which they are attached form a heterocycle which may be optionally substituted with one or more substituents selected from the group consisting of halogen, cyano, hydroxy, trifluoromethyl, oxo, —NH₂, —SO₂NH₂, —SONH₂, —CONH₂;
L is a covalent bond or L is independently at each occurrence selected from the group consisting of alkyl-, heteroalkyl-, cycloalkyl-, heterocyclyl-, alkylcycloalkyl-, cycloalkylalkyl-, aryl and heteroaryl;
and pharmaceutically acceptable salts, hydrates, or solvates thereof.

2. The compound according to claim 1 of general formula Ia

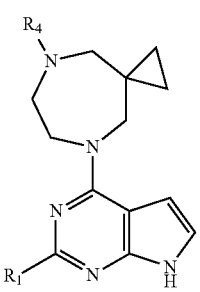

wherein R₁ and R₄ are as defined in claim 1.
3. The compound according to claim 1 wherein R₄ is

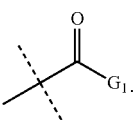

4. The compound according to claim 1 wherein G₁ is selected from the group consisting of methyl, ethyl, propyl, isopropyl phenyl, pyridyl, indolyl, tetrazolyl, furyl, thiazolyl, imidazolyl, pyrazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, benzothiophenyl, 5,6-dihydro-4H-cyclopenta[b]thiophenyl, pyrrolyl, oxadiazolyl, 1,2,5-oxadiazolyl, 1,3,4-oxadiazolyl, thiadiazolyl, pyridazinyl or 1,2,5-thiadiazolyl piperidinyl, thiazolidinyl, imidazolidinyl, oxazolidinyl, 4,5-dihydroisoxazolyl, cyclopropyl, cyclobutyl, cyclopentyl, cyclohexyl, benzyl, thienylmethyl, phenylethyl, tetrahydropyranyl, thienylethyl, phenyloxymethyl thiazolidinylmethyl, imidazolidinylmethyl, oxazolidinylmethyl, pyrrolidinylmethyl, isoxazolylmethyl, thiazolylmethyl, imidazolylmethyl, cyclopentylmethyl, pyridylmethyl, tetrazolylmethyl, oxadiazolylmethyl and pyrazolylmethyl, (alkyl)₂-N—, phenyl-NH— either of which may be optionally substituted with one or more $R_{G1c}$.
5. The compound according to claim 1 wherein each $R_{G1c}$ is independently Selected from the group consisting of cyano, methyl-O—, methyl, ethyl, propyl, isopropyl, butyl, oxo, —SO₂NH₂, —NH₂, methyl-NH—S(═O)₂—, (methyl)₂-N—S(═O)₂—, fluoro, chloro, bromo, iodo, methyl-S(═O)₂—, tetrazolyl, hydroxyl.

6. The compound according to claim 1 wherein each $R_{G1c}$ is independently selected from the group consisting of cyano, methyl-O—, methyl, oxo, —SO₂NH₂, methyl-NH—S(═O)₂—, fluoro, chloro, methyl-S(═O)₂—.

7. The compound according to claim 1 wherein each $R_{G1d}$ is independently selected from the group consisting of hydrogen, alkyl-, cyclolalkylalkyl-, heterocyclylalkyl-, wherein said alkyl-, cyclolalkylalkyl-, heterocyclylalkyl- may be optionally substituted with one or more substituents selected from the group consisting of halogen, cyano and —SO₂NH₂.

8. The compound according to claim 1 which is selected from:

4-Oxo-4-[8-(7H-pyrrolo[2,3-d]pyrimidin-4-yl)-5,8-diazaspiro[2.6]non-5-yl]butyronitrile;

(2,3-Dimethoxyphenyl)-[8-(7H-pyrrolo[2,3-d]pyrimidin-4-yl)5,8-diazaspiro[2.6]non-5-yl]methanone;

3-[8-(7H-pyrrolo[2,3-d]pyrimidin-4-yl)-5,8-diazaspiro[2.6]nonane-5-carbonyl]benzonitrile;

(2-Methoxypyridin-3-yl)-[8-(7H-pyrrolo[2,3-d]pyrimidin-4-yl)-5,8-diazaspiro[2.6]non-5-yl]methanone;

3-Oxo-3-[8-(7H-pyrrolo[2,3-d]pyrimidin-4-yl)-5,8-diazaspiro[2.6]non-5-yl]propionitrile;

1-{4-[8-(7H-pyrrolo[2,3-d]pyrimidin-4-yl)-5,8-diazaspiro[2.6]nonane-5-carbonyl]piperidin-1-yl}ethanone;

2-[8-(7H-pyrrolo[2,3-d]pyrimidin-4-yl)-5,8-diazaspiro[2.6]nonane-5-carbonyl]benzonitrile;

2-[8-(7H-pyrrolo[2,3-d]pyrimidin-4-yl)-5,8-diazaspiro[2.6]nonane-5-carbonyl]-1H-indole-5-carbonitrile;

3-{2-Oxo-2-[8-(7H-pyrrolo[2,3-d]pyrimidin-4-yl)-5,8-diazaspiro[2.6]non-5-yl]ethyl}benzonitrile;

4-{2-Oxo-2-[8-(7H-pyrrolo[2,3-d]pyrimidin-4-yl-5,8-diazaspiro[2.6]non-5-yl]ethyl}benzonitrile;

2,2-Dimethyl-3-oxo-3-[8-(7H-pyrrolo[2,3-d]pyrimidin-4-yl)-5,8-diazaspiro[2.6]non-5-yl]propionitrile;

{4-[8-(7H-pyrrolo[2,3-d]pyrimidin-4-yl)-5,8-diazaspiro[2.6]nonane-5-carbonyl]phenyl}acetonitrile;

4-[1,1-difluoro-2-oxo-2-[5-(7H-pyrrolo[2,3-d]pyrimidin-4-yl)-5,8-diazaspiro[2.6]nonan-8-yl]ethyl]benzonitrile;

2-[3-[5-(7H-pyrrolo[2,3-d]pyrimidin-4-yl)-5,8-diazaspiro[2.6]nonane-8-carbonyl]phenoxy]acetonitrile;

2-[4-[5-(7H-pyrrolo[2,3-d]pyrimidin-4-yl)-5,8-diazaspiro[2.6]nonane-8-carbonyl]phenoxy]acetonitrile;

2-[4-[2-oxo-2-[5-(7H-pyrrolo[2,3-d]pyrimidin-4-yl)-5,8-diazaspiro[2.6]nonan-8-yl]ethyl]phenoxy]acetonitrile;

2-[3-[2-oxo-2-[5-(7H-pyrrolo[2,3-d]pyrimidin-4-yl)-5,8-diazaspiro[2.6]nonan-8-yl]ethyl]phenoxy]acetonitrile;

benzothiophen-2-yl-[5-(7H-pyrrolo[2,3-d]pyrimidin-4-yl)-5,8-diazaspiro[2.6]nonan-8-yl]methanone;

5-[5-(7H-pyrrolo[2,3-d]pyrimidin-4-yl)-5,8-diazaspiro[2.6]nonane-8-carbonyl]thiophene-3-carbonitrile;

4-[2-oxo-2-[5-(7H-pyrrolo[2,3-d]pyrimidin-4-yl)-5,8-diazaspiro[2.6]nonan-8-yl]ethyl]benzenesulfonamide;

5,6-dihydro-4H-cyclopenta[b]thiophen-2-yl-[5-(7H-pyrrolo[2,3-d]pyrimidin-4-yl)-5,8-diazaspiro[2.6]nonan-8-yl]methanone;

(4-methoxy-2-thienyl)-[5-(7H-pyrrolo[2,3-d]pyrimidin-4-yl)-5,8-diazaspiro[2.6]nonan-8-yl]methanone;

N,4-dimethyl-5-[5-(7H-pyrrolo[2,3-d]pyrimidin-4-yl)-5,8-diazaspiro[2.6]nonane-8-carbonyl]thiophene-3-sulfonamide;

2-methyl-5-[5-(7H-pyrrolo[2,3-d]pyrimidin-4-yl)-5,8-diazaspiro[2.6]nonane-8-carbonyl]thiophene-3-sulfonamide;

4-methyl-5-[5-(7H-pyrrolo[2,3-d]pyrimidin-4-yl)-5,8-diazaspiro[2.6]nonane-8-carbonyl]thiophene-3-sulfonamide;

N,2-dimethyl-5-[5-(7H-pyrrolo[2,3-d]pyrimidin-4-yl)-5,8-diazaspiro[2.6]nonane-8-carbonyl]thiophene-3-sulfonamide;

5-[5-(7H-pyrrolo[2,3-d]pyrimidin-4-yl)-5,8-diazaspiro[2.6]nonane-8-carbonyl]thiophene-3-sulfonamide;

N-methyl-5-[5-(7H-pyrrolo[2,3-d]pyrimidin-4-yl)-5,8-diazaspiro[2.6]nonane-8-carbonyl]thiophene-3-sulfonamide;

2-methyl-4-[5-(7H-pyrrolo[2,3-d]pyrimidin-4-yl)-5,8-diazaspiro[2.6]nonane-8-carbonyl]benzenesulfonamide;

1-[5-(7H-pyrrolo[2,3-d]pyrimidin-4-yl)-5,8-diazaspiro[2.6]nonan-8-yl]-2-(2-thienyl)ethanone;

4-[5-(7H-pyrrolo[2,3-d]pyrimidin-4-yl)-5,8-diazaspiro[2.6]nonane-8-carbonyl]benzenesulfonamide;

2-chloro-4-[5-(7H-pyrrolo[2,3-d]pyrimidin-4-yl)-5,8-diazaspiro[2.6]nonane-8-carbonyl]benzenesulfonamide;

N,N-dimethyl-4-[5-(7H-pyrrolo[2,3-d]pyrimidin-4-yl)-5,8-diazaspiro[2.6]nonane-8-carbonyl]benzenesulfonamide;

4-[3-oxo-3-[5-(7H-pyrrolo[2,3-d]pyrimidin-4-yl)-5,8-diazaspiro[2.6]nonan-8-yl]propyl]benzenesulfonamide;

1-methyl-5-[5-(7H-pyrrolo[2,3-d]pyrimidin-4-yl)-5,8-diazaspiro[2.6]nonane-8-carbonyl]pyrrole-2-sulfonamide;

1-methyl-5-[5-(7H-pyrrolo[2,3-d]pyrimidin-4-yl)-5,8-diazaspiro[2.6]nonane-8-carbonyl]pyrrole-3-sulfonamide 5-[5-(7H-pyrrolo[2,3-d]pyrimidin-4-yl)-5,8-diazaspiro[2.6]nonane-8-carbonyl]furan-2-sulfonamide;

2-methyl-5-[5-(7H-pyrrolo[2,3-d]pyrimidin-4-yl)-5,8-diazaspiro[2.6]nonane-8-carbonyl]benzenesulfonamide;

4-oxo-4-[5-(7H-pyrrolo[2,3-d]pyrimidin-4-yl)-5,8-diazaspiro[2.6]nonan-8-yl]butane-1-sulfonamide;

1-[5-(7H-pyrrolo[2,3-d]pyrimidin-4-yl)-5,8-diazaspiro[2.6]nonane-8-carbonyl]cyclopentanecarbonitrile;

4-[5-(7H-pyrrolo[2,3-d]pyrimidin-4-yl)-5,8-diazaspiro[2.6]nonane-8-carbonyl]tetrahydropyran-4-carbonitrile;

2-fluoro-4-[5-(7H-pyrrolo[2,3-d]pyrimidin-4-yl)-5,8-diazaspiro[2.6]nonane-8-carbonyl]benzonitrile;

(3,5-dimethoxyphenyl)-[5-(7H-pyrrolo[2,3-d]pyrimidin-4-yl)-5,8-diazaspiro[2.6]nonan-8-yl]methanone;

1-[6-(7H-pyrrolo[2,3-d]pyrimidin-4-yl)-6,9-diazaspiro[2.6]nonane-9-carbonyl]cyclopropanecarbonitrile;

4,4,4-trifluoro-1-[6-(7H-pyrrolo[2,3-d]pyrimidin-4-yl)-6,9-diazaspiro[2.6]nonan-9-yl]butan-1-one;

benzothiophen-2-yl-[6-(7H-pyrrolo[2,3-d]pyrimidin-4-yl)-6,9-diazaspiro[2.6]nonan-9-yl]methanone;

3-[2-oxo-2-[6-(7H-pyrrolo[2,3-d]pyrimidin-4-yl)-6,9-diazaspiro[2.6]nonan-9-yl]ethyl]benzonitrile;

2-[2-[6-(7H-pyrrolo[2,3-d]pyrimidin-4-yl)-6,9-diazaspiro[2.6]nonane-9-carbonyl]phenyl]acetonitrile;

4-oxo-4-[6-(7H-pyrrolo[2,3-d]pyrimidin-4-yl)-6,9-diazaspiro[2.6]nonan-9-yl]butanenitrile;

4-[5-(7H-pyrrolo[2,3-d]pyrimidin-4-yl)-5,8-diazaspiro[2.6]nonane-8-carbonyl]-N-[2-(2-thienyl)ethyl]benzenesulfonamide;

5-[5-(7H-pyrrolo[2,3-d]pyrimidin-4-yl)-5,8-diazaspiro[2.6]nonane-8-carbonyl]thiophene-2-carbonitrile;

3-methoxy-4-[5-(7H-pyrrolo[2,3-d]pyrimidin-4-yl)-5,8-diazaspiro[2.6]nonane-8-carbonyl]benzenesulfonamide;
2-methoxy-4-[5-(7H-pyrrolo[2,3-d]pyrimidin-4-yl)-5,8-diazaspiro[2.6]nonane-8-carbonyl]benzenesulfonamide;
4-[(E)-3-oxo-3-[5-(7H-pyrrolo[2,3-d]pyrimidin-4-yl)-5,8-diazaspiro[2.6]nonan-8-yl]prop-1-enyl]benzenesulfonamide;
2-(4-methylsulfonylphenyl)-1-[5-(7H-pyrrolo[2,3-d]pyrimidin-4-yl)-5,8-diazaspiro[2.6]nonan-8-yl]ethanone;
4-[5-(7H-pyrrolo[2,3-d]pyrimidin-4-yl)-5,9-diazaspiro[2.6]nonane-9-carbonyl]benzonitrile;
3-[5-(7H-pyrrolo[2,3-d]pyrimidin-4-yl)-5,9-diazaspiro[2.6]nonane-9-carbonyl]benzonitrile;
3-[2-oxo-2-[5-(7H-pyrrolo[2,3-d]pyrimidin-4-yl)-5,9-diazaspiro[2.6]nonan-9-yl]ethyl]benzonitrile;
4-[2-oxo-2-[5-(7H-pyrrolo[2,3-d]pyrimidin-4-yl)-5,9-diazaspiro[2.6]nonan-9-yl]ethyl]benzonitrile;
1-[5-(7H-pyrrolo[2,3-d]pyrimidin-4-yl)-5,9-diazaspiro[2.6]nonane-9-carbonyl]cyclopropanecarbonitrile;
4-oxo-4-[5-(7H-pyrrolo[2,3-d]pyrimidin-4-yl)-5,9-diazaspiro[2.6]nonan-9-yl]butanenitrile;
4-[5-(7H-pyrrolo[2,3-d]pyrimidin-4-yl)-5,8-diazaspiro[2.6]nonane-8-carbonyl]benzonitrile;
4-[2-oxo-2-[5-(7H-pyrrolo[2,3-d]pyrimidin-4-yl)-5,8-diazaspiro[2.6]nonan-8-yl]ethoxy]benzenesulfonamide;
2-oxo-2-[5-(7H-pyrrolo[2,3-d]pyrimidin-4-yl)-5,8-diazaspiro[2.6]nonan-8-yl]-N-(4-sulfamoylphenyl)acetamide;
4-[5-[5-(7H-pyrrolo[2,3-d]pyrimidin-4-yl)-5,8-diazaspiro[2.6]nonane-8-carbonyl]-2-furyl]benzenesulfonamide;
2-(4-iodophenyl)-1-[5-(7H-pyrrolo[2,3-d]pyrimidin-4-yl)-5,8-diazaspiro[2.6]nonan-8-yl]ethanone;
4-(9-benzyl-5,9-diazaspiro[2.6]nonan-5-yl)-7H-pyrrolo[2,3-d]pyrimidin-2-amine;
4-(5-benzyl-5,8-diazaspiro[2.6]nonan-8-yl)-7H-pyrrolo[2,3-d]pyrimidin-2-amine;
N-(2-cyanoethyl)-4-[5-(7H-pyrrolo[2,3-d]pyrimidin-4-yl)-5,8-diazaspiro[2.6]nonane-8-carbonyl]benzenesulfonamide;
4-[5-(7H-pyrrolo[2,3-d]pyrimidin-4-yl)-5,8-diazaspiro[2.6]nonane-8-carbonyl]-N-(tetrahydrofuran-2-ylmethyl)benzenesulfonamide;
3-methyl-4-[5-(7H-pyrrolo[2,3-d]pyrimidin-4-yl)-5,8-diazaspiro[2.6]nonane-8-carbonyl]benzenesulfonamide;
N-methyl-4-[5-(7H-pyrrolo[2,3-d]pyrimidin-4-yl)-5,8-diazaspiro[2.6]nonane-8-carbonyl]benzenesulfonamide;
3-[5-(7H-pyrrolo[2,3-d]pyrimidin-4-yl)-5,8-diazaspiro[2.6]nonane-8-carbonyl]benzenesulfonamide;
N-(2-methoxyethyl)-4-[5-(7H-pyrrolo[2,3-d]pyrimidin-4-yl)-5,8-diazaspiro[2.6]nonane-8-carbonyl]benzenesulfonamide;
4-[5-(7H-pyrrolo[2,3-d]pyrimidin-4-yl)-5,8-diazaspiro[2.6]nonane-8-carbonyl]thiophene-2-sulfonamide;
5-[2-oxo-2-[5-(7H-pyrrolo[2,3-d]pyrimidin-4-yl)-5,8-diazaspiro[2.6]nonan-8-yl]ethyl]thiophene-2-sulfonamide;
1-[5-(7H-pyrrolo[2,3-d]pyrimidin-4-yl)-5,8-diazaspiro[2.6]nonan-8-yl]-2-[4-(2H-tetrazol-5-yl)phenyl]ethanone;
(4-propyl-2-thienyl)-[5-(7H-pyrrolo[2,3-d]pyrimidin-4-yl)-5,8-diazaspiro[2.6]nonan-8-yl]methanone;
3-[2-oxo-2-[5-(7H-pyrrolo[2,3-d]pyrimidin-4-yl)-5,8-diazaspiro[2.6]nonan-8-yl]ethyl]thiazolidine-2,4-dione;
1-methyl-3-[2-oxo-2-[5-(7H-pyrrolo[2,3-d]pyrimidin-4-yl)-5,8-diazaspiro[2.6]nonan-8-yl]ethyl]imidazolidine-2,4-dione;
3-[2-oxo-2-[5-(7H-pyrrolo[2,3-d]pyrimidin-4-yl)-5,8-diazaspiro[2.6]nonan-8-yl]ethyl]oxazolidin-2-one;
1-methyl-3-[2-oxo-2-[5-(7H-pyrrolo[2,3-d]pyrimidin-4-yl)-5,8-diazaspiro[2.6]nonan-8-yl]ethyl]imidazolidin-2-one;
1-methyl-3-[2-oxo-2-[5-(7H-pyrrolo[2,3-d]pyrimidin-4-yl)-5,9-diazaspiro[2.6]nonan-9-yl]ethyl]imidazolidin-2-one;
1-[2-oxo-2-[5-(7H-pyrrolo[2,3-d]pyrimidin-4-yl)-5,9-diazaspiro[2.6]nonan-9-yl]ethyl]pyrrolidine-2,5-dione;
3-[2-oxo-2-[5-(7H-pyrrolo[2,3-d]pyrimidin-4-yl)-5,9-diazaspiro[2.6]nonan-9-yl]ethyl]thiazolidine-2,4-dione;
3-[2-oxo-2-[5-(7H-pyrrolo[2,3-d]pyrimidin-4-yl)-5,9-diazaspiro[2.6]nonan-9-yl]ethyl]oxazolidin-2-one;
2-(5-methylisoxazol-3-yl)-1-[5-(7H-pyrrolo[2,3-d]pyrimidin-4-yl)-5,8-diazaspiro[2.6]nonan-8-yl]ethanone;
1-[5-(7H-pyrrolo[2,3-d]pyrimidin-4-yl)-5,8-diazaspiro[2.6]nonan-8-yl]-2-thiazol-4-yl-ethanone;
2-(1H-imidazol-5-yl)-1-[5-(7H-pyrrolo[2,3-d]pyrimidin-4-yl)-5,8-diazaspiro[2.6]nonan-8-yl]ethanone;
N-phenyl-5-(7H-pyrrolo[2,3-d]pyrimidin-4-yl)-5,9-diazaspiro[2.6]nonane-9-carboxamide;
N-phenyl-5-(7H-pyrrolo[2,3-d]pyrimidin-4-yl)-5,9-diazaspiro[2.6]nonane-9-carbothioamide;
2-cyclopentyl-1-[5-(7H-pyrrolo[2,3-d]pyrimidin-4-yl)-5,9-diazaspiro[2.6]nonan-9-yl]ethanone; cyclohexyl-[5-(7H-pyrrolo[2,3-d]pyrimidin-4-yl)-5,9-diazaspiro[2.6]nonan-9-yl]methanone;
4-[9-(p-tolylsulfonyl)-5,9-diazaspiro[2.6]nonan-5-yl]-7H-pyrrolo[2,3-d]pyrimidine;
2-cyclopentyl-1-[5-(7H-pyrrolo[2,3-d]pyrimidin-4-yl)-5,9-diazaspiro[2.6]nonan-9-yl]ethanethione;
4-[8-(p-tolylsulfonyl)-5,8-diazaspiro[2.6]nonan-5-yl]-7H-pyrrolo[2,3-d]pyrimidine;
4-(8-butylsulfonyl-5,8-diazaspiro[2.6]nonan-5-yl)-7H-pyrrolo[2,3-d]pyrimidine;
4-[7-methyl-8-(p-tolylsulfonyl)-5,8-diazaspiro[2.6]nonan-5-yl]-7H-pyrrolo[2,3-d]pyrimidine;
7-methyl-N-phenyl-5-(7H-pyrrolo[2,3-d]pyrimidin-4-yl)-5,8-diazaspiro[2.6]nonane-8-carboxamide;
4-[2-oxo-2-[5-(7H-pyrrolo[2,3-d]pyrimidin-4-yl)-5,8-diazaspiro[2.6]nonan-8-yl]acetyl]benzonitrile;
2-[5-(7H-pyrrolo[2,3-d]pyrimidin-4-yl)-5,8-diazaspiro[2.6]nonane-8-carbonyl]-1H-indole-5-sulfonamide;
N-[4-[5-(7H-pyrrolo[2,3-d]pyrimidin-4-yl)-5,8-diazaspiro[2.6]nonane-8-carbonyl]phenyl]methanesulfonamide;
N-(2-cyanoethyl)-N-methyl-5-(7H-pyrrolo[2,3-d]pyrimidin-4-yl)-5,8-diazaspiro[2.6]nonane-8-sulfonamide;
N,N-diethyl-5-(7H-pyrrolo[2,3-d]pyrimidin-4-yl)-5,8-diazaspiro[2.6]nonane-8-sulfonamide;
N-cyclohexyl-N-methyl-5-(7H-pyrrolo[2,3-d]pyrimidin-4-yl)-5,8-diazaspiro[2.6]nonane-8-sulfonamide;
4-[2-oxo-2-[5-(7H-pyrrolo[2,3-d]pyrimidin-4-yl)-5,8-diazaspiro[2.6]nonan-8-yl]ethoxy]benzonitrile;
4-(5-benzyl-5,8-diazaspiro[2.6]nonan-8-yl)-7H-pyrrolo[2,3-d]pyrimidine;
(5-methylisoxazol-4-yl)-[5-(7H-pyrrolo[2,3-d]pyrimidin-4-yl)-5,8-diazaspiro[2.6]nonan-8-yl]methanone;
o-tolyl-[5-(7H-pyrrolo[2,3-d]pyrimidin-4-yl)-5,8-diazaspiro[2.6]nonan-8-yl]methanone;
o-tolyl-[5-(7H-pyrrolo[2,3-d]pyrimidin-4-yl)-5,9-diazaspiro[2.6]nonan-9-yl]methanone;

(2-fluorophenyl)-[5-(7H-pyrrolo[2,3-d]pyrimidin-4-yl)-5,8-diazaspiro[2.6]nonan-8-yl]methanone;
(2-fluorophenyl)-[5-(7H-pyrrolo[2,3-d]pyrimidin-4-yl)-5,9-diazaspiro[2.6]nonan-9-yl]methanone;
(4-fluorophenyl)-[5-(7H-pyrrolo[2,3-d]pyrimidin-4-yl)-5,8-diazaspiro[2.6]nonan-8-yl]methanone;
(4-fluorophenyl)-[5-(7H-pyrrolo[2,3-d]pyrimidin-4-yl)-5,9-diazaspiro[2.6]nonan-9-yl]methanone;
4-[3-oxo-3-[5-(7H-pyrrolo[2,3-d]pyrimidin-4-yl)-5,8-diazaspiro[2.6]nonan-8-yl]propyl]benzonitrile;
3-[3-oxo-3-[5-(7H-pyrrolo[2,3-d]pyrimidin-4-yl)-5,8-diazaspiro[2.6]nonan-8-yl]propyl]benzonitrile;
4-[(E)-3-oxo-3-[5-(7H-pyrrolo[2,3-d]pyrimidin-4-yl)-5,8-diazaspiro[2.6]nonan-8-yl]prop-1-enyl]benzonitrile;
3-[2-oxo-2-[5-(7H-pyrrolo[2,3-d]pyrimidin-4-yl)-5,8-diazaspiro[2.6]nonan-8-yl]ethoxy]benzonitrile;
5-[5-(7H-pyrrolo[2,3-d]pyrimidin-4-yl)-5,9-diazaspiro[2.6]nonane-9-carbonyl]thiophene-3-carbonitrile;
5-[5-(7H-pyrrolo[2,3-d]pyrimidin-4-yl)-5,9-diazaspiro[2.6]nonane-9-carbonyl]thiophene-2-carbonitrile;
1,2,5-oxadiazol-3-yl-[5-(7H-pyrrolo[2,3-d]pyrimidin-4-yl)-5,9-diazaspiro[2.6]nonan-9-yl]methanone;
(3-methylisoxazol-5-yl)-[5-(7H-pyrrolo[2,3-d]pyrimidin-4-yl)-5,9-diazaspiro[2.6]nonan-9-yl]methanone;
(3-ethyl-4,5-dihydroisoxazol-5-yl)-[5-(7H-pyrrolo[2,3-d]pyrimidin-4-yl)-5,9-diazaspiro[2.6]nonan-9-yl]methanone;
1-[5-(7H-pyrrolo[2,3-d]pyrimidin-4-yl)-5,9-diazaspiro[2.6]nonan-9-yl]prop-2-en-1-one;
(rac)-2-(3-ethyl-2,5-dihydroisoxazol-5-yl)-1-[5-(7H-pyrrolo[2,3-d]pyrimidin-4-yl)-5,8-diazaspiro[2.5]nonan-8-yl]ethanone;
(3-propyl-4,5-dihydroisoxazol-5-yl)-[5-(7H-pyrrolo[2,3-d]pyrimidin-4-yl)-5,9-diazaspiro[2.6]nonan-9-yl]methanone;
2-(4-chlorophenyl)-1-[5-(7H-pyrrolo[2,3-d]pyrimidin-4-yl)-5,8-diazaspiro[2.6]nonan-8-yl]ethanone;
2-(4-chlorophenyl)-1-[5-(7H-pyrrolo[2,3-d]pyrimidin-4-yl)-5,9-diazaspiro[2.6]nonan-9-yl]ethanone;
3-pyridyl-[5-(7H-pyrrolo[2,3-d]pyrimidin-4-yl)-5,8-diazaspiro[2.6]nonan-8-yl]methanone
3-pyridyl-[5-(7H-pyrrolo[2,3-d]pyrimidin-4-yl)-5,9-diazaspiro[2.6]nonan-9-yl]methanone;
4-pyridyl-[5-(7H-pyrrolo[2,3-d]pyrimidin-4-yl)-5,8-diazaspiro[2.6]nonan-8-yl]methanone;
4-pyridyl-[5-(7H-pyrrolo[2,3-d]pyrimidin-4-yl)-5,9-diazaspiro[2.6]nonan-9-yl]methanone;
(6-hydroxy-3-pyridyl)-[5-(7H-pyrrolo[2,3-d]pyrimidin-4-yl)-5,8-diazaspiro[2.6]nonan-8-yl]methanone;
(6-hydroxy-3-pyridyl)-[5-(7H-pyrrolo[2,3-d]pyrimidin-4-yl)-5,9-diazaspiro[2.6]nonan-9-yl]methanone;
1H-imidazol-4-yl-[5-(7H-pyrrolo[2,3-d]pyrimidin-4-yl)-5,8-diazaspiro[2.6]nonan-8-yl]methanone;
1H-imidazol-4-yl-[5-(7H-pyrrolo[2,3-d]pyrimidin-4-yl)-5,9-diazaspiro[2.6]nonan-9-yl]methanone;
(2-methyl-3-pyridyl)-[5-(7H-pyrrolo[2,3-d]pyrimidin-4-yl)-5,8-diazaspiro[2.6]nonan-8-yl]methanone;
(2-methyl-3-pyridyl)-[5-(7H-pyrrolo[2,3-d]pyrimidin-4-yl)-5,9-diazaspiro[2.6]nonan-9-yl]methanone;
(3-methyl-4-pyridyl)-[5-(7H-1-pyrrolo[2,3-d]pyrimidin-4-yl)-5,8-diazaspiro[2.6]nonan-8-yl]methanone;
(3-methyl-4-pyridyl)-[5-(7H-pyrrolo[2,3-d]pyrimidin-4-yl)-5,9-diazaspiro[2.6]nonan-9-yl]methanone;
pyridazin-4-yl-[5-(7H-pyrrolo[2,3-d]pyrimidin-4-yl)-5,8-diazaspiro[2.6]nonan-8-yl]methanone;
2-(2,4-dimethylthiazol-5-yl)-1-[5-(7H-pyrrolo[2,3-d]pyrimidin-4-yl)-5,9-diazaspiro[2.6]nonan-9-yl]ethanone
(5-methylisoxazol-3-yl)-[5-(7H-pyrrolo[2,3-d]pyrimidin-4-yl)-5,9-diazaspiro[2.6]nonan-9-yl]methanone;
[5-(7H-pyrrolo[2,3-d]pyrimidin-4-yl)-5,9-diazaspiro[2.6]nonan-9-yl]-(thiadiazol-4-yl)methanone;
(2,5-dimethylpyrazol-3-yl)-[5-(7H-pyrrolo[2,3-d]pyrimidin-4-yl)-5,8-diazaspiro[2.6]nonan-8-yl]methanone;
(3-methylimidazol-4-yl)-[5-(7H-pyrrolo[2,3-d]pyrimidin-4-yl)-5,8-diazaspiro[2.6]nonan-8-yl]methanone;
(3-methylimidazol-4-yl)-[5-(7H-pyrrolo[2,3-d]pyrimidin-4-yl)-5,9-diazaspiro[2.6]nonan-9-yl]methanone;
(4-methylthiadiazol-5-yl)-[5-(7H-pyrrolo[2,3-d]pyrimidin-4-yl)-5,8-diazaspiro[2.6]nonan-8-yl]methanone;
(4-methylthiadiazol-5-yl)-[5-(7H-pyrrolo[2,3-d]pyrimidin-4-yl)-5,9-diazaspiro[2.6]nonan-9-yl]methanone;
(5-methyl-1H-pyrazol-3-yl)-[5-(7H-pyrrolo[2,3-d]pyrimidin-4-yl)-5,8-diazaspiro[2.6]nonan-8-yl]Methanone;
(5-methyl-1H-pyrazol-3-yl)-[5-(7H-pyrrolo[2,3-d]pyrimidin-4-yl)-5,9-diazaspiro[2.6]nonan-9-yl]methanone;
(4-methyl-3-pyridyl)-[5-(7H-pyrrolo[2,3-d]pyrimidin-4-yl)-5,8-diazaspiro[2.6]nonan-8-yl]methanone;
(4-methyl-3-pyridyl)-[5-(7H-pyrrolo[2,3-d]pyrimidin-4-yl)-5,9-diazaspiro[2.6]nonan-9-yl]methanone;
isoxazol-3-yl-[5-(7H-pyrrolo[2,3-d]pyrimidin-4-yl)-5,8-diazaspiro[2.6]nonan-8-yl]methanone;
isoxazol-3-yl-[5-(7H-pyrrolo[2,3-d]pyrimidin-4-yl)-5,9-diazaspiro[2.6]nonan-9-yl]methanone;
(5-methyl-1,3,4-oxadiazol-2-yl)-[5-(7H-pyrrolo[2,3-d]pyrimidin-4-yl)-5,9-diazaspiro[2.6]nonan-9-yl]methanone;
oxazol-5-yl-[5-(7H-pyrrolo[2,3-d]pyrimidin-4-yl)-5,8-diazaspiro[2.6]nonan-8-yl]methanone; oxazol-5-yl-[5-(7H-pyrrolo[2,3-d]pyrimidin-4-yl)-5,9-diazaspiro[2.6]nonan-9-yl]methanone;
1H-pyrazol-4-yl-[5-(7H-pyrrolo[2,3-d]pyrimidin-4-yl)-5,8-diazaspiro[2.6]nonan-8-yl]methanone;
2-(4-fluorophenyl)-1-[5-(7H-pyrrolo[2,3-d]pyrimidin-4-yl)-5,8-diazaspiro[2.6]nonan-8-yl]ethanone;
2-(4-fluorophenyl)-1-[5-(7H-pyrrolo[2,3-d]pyrimidin-4-yl)-5,9-diazaspiro[2.6]nonan-9-yl]ethanone;
pyrimidin-5-yl-[5-(7H-pyrrolo[2,3-d]pyrimidin-4-yl)-5,8-diazaspiro[2.6]nonan-8-yl]methanone pyrimidin-5-yl-[5-(7H-pyrrolo[2,3-d]pyrimidin-4-yl)-5,9-diazaspiro[2.6]nonan-9-yl]methanone
2-[5-(7H-pyrrolo[2,3-d]pyrimidin-4-yl)-5,9-diazaspiro[2.6]nonane-9-carbonyl]benzonitrile;
(6-hydroxy-2-pyridyl-[5-(7H-pyrrolo[2,3-d]pyrimidin-4-yl)-5,8-diazaspiro[2.6]nonan-8-yl]methanone;
(6-hydroxy-2-pyridyl)-[5-(7H-pyrrolo[2,3-d]pyrimidin-4-yl)-5,9-diazaspiro[2.6]nonan-9-yl]methanone;
pyrimidin-4-yl-[5-(7H-pyrrolo[2,3-d]pyrimidin-4-yl)-5,8-diazaspiro[2.6]nonan-8-yl]methanone;
pyrimidin-4-yl-[5-(7H-pyrrolo[2,3-d]pyrimidin-4-yl)-5,9-diazaspiro[2.6]nonan-9-yl]methanone;
2-(2-pyridyl)-1-[5-(7H-pyrrolo[2,3-d]pyrimidin-4-yl)-5,8-diazaspiro[2.6]nonan-8-yl]ethanone;
(3-methylpyrazin-2-yl)-[5-(7H-pyrrolo[2,3-d]pyrimidin-4-yl)-5,8-diazaspiro[2.6]nonan-8-yl]methanone;
(6-methylpyrazin-2-yl)-[5-(7H-pyrrolo[2,3-d]pyrimidin-4-yl)-5,8-diazaspiro[2.6]nonan-8-yl]methanone;
(3,5-dimethylisoxazol-4-yl)-[5-(7H-pyrrolo[2,3-d]pyrimidin-4-yl)-5,8-diazaspiro[2.6]nonan-8-yl]methanone;
(2-methyl-4-pyridyl)-[5-(7H-pyrrolo[2,3-d]pyrimidin-4-yl)-5,8-diazaspiro[2.6]nonan-8-yl]methanone;

(2-methyl-4-pyridyl)-[5-(7H-pyrrolo[2,3-d]pyrimidin-4-yl)-5,9-diazaspiro[2.6]nonan-9-yl]methanone;
2-(2-chlorophenyl)-1-[5-(7H-pyrrolo[2,3-d]pyrimidin-4-yl)-5,8-diazaspiro[2.6]nonan-8-yl]ethanone;
2-(2-chlorophenyl)-1-[5-(7H-pyrrolo[2,3-d]pyrimidin-4-yl)-5,9-diazaspiro[2.6]nonan-9-yl]ethanone;
(5-methylisoxazol-3-yl)-[5-(7H-pyrrolo[2,3-d]pyrimidin-4-yl)-5,8-diazaspiro[2.6]nonan-8-yl]methanone;
(4-chlorophenyl)-[5-(7H-pyrrolo[2,3-d]pyrimidin-4-yl)-5,8-diazaspiro[2.6]nonan-8-yl]methanone;
isoxazol-5-yl-[5-(7H-pyrrolo[2,3-d]pyrimidin-4-yl)-5,8-diazaspiro[2.6]nonan-8-yl]methanone;
(2-chlorophenyl)-[5-(7H-pyrrolo[2,3-d]pyrimidin-4-yl)-5,9-diazaspiro[2.6]nonan-9-yl]methanone;
(3-chlorophenyl)-[5-(7H-pyrrolo[2,3-d]pyrimidin-4-yl)-5,9-diazaspiro[2.6]nonan-9-yl]methanone;
(4-chlorophenyl)-[5-(7H-pyrrolo[2,3-d]pyrimidin-4-yl)-5,9-diazaspiro[2.6]nonan-9-yl]methanone;
isoxazol-5-yl-[5-(7H-pyrrolo[2,3-d]pyrimidin-4-yl)-5,9-diazaspiro[2.6]nonan-9-yl]methanone;
1H-pyrazol-3-yl-[5-(7H-pyrrolo[2,3-d]pyrimidin-4-yl)-5,8-diazaspiro[2.6]nonan-8-yl]methanone;
1H-pyrazol-3-yl-[5-(7H-pyrrolo[2,3-d]pyrimidin-4-yl)-5,9-diazaspiro[2.6]nonan-9-yl]methanone;
2-(3-methylisoxazol-5-yl)-1-[5-(7H-pyrrolo[2,3-d]pyrimidin-4-yl)-5,8-diazaspiro[2.6]nonan-8-yl]ethanone;
(2-chlorophenyl)-[5-(7H-pyrrolo[2,3-d]pyrimidin-4-yl)-5,8-diazaspiro[2.6]nonan-8-yl]methanone;
(3-chlorophenyl)-[5-(7H-pyrrolo[2,3-d]pyrimidin-4-yl)-5,8-diazaspiro[2.6]nonan-8-yl]methanone;
(5-methylisoxazol-4-yl)-[5-(7H-pyrrolo[2,3-d]pyrimidin-4-yl)-5,9-diazaspiro[2.6]nonan-9-yl]methanone;
2-pyridyl-[5-(7H-pyrrolo[2,3-d]pyrimidin-4-yl)-5,8-diazaspiro[2.6]nonan-8-yl]methanone;
2-pyridyl-[5-(7H-pyrrolo[2,3-d]pyrimidin-4-yl)-5,9-diazaspiro[2.6]nonan-9-yl]methanone;
(2-hydroxy-4-pyridyl)-[5-(7H-pyrrolo[2,3-d]pyrimidin-4-yl)-5,8-diazaspiro[2.6]nonan-8-yl]methanone;
(4-methyloxazol-5-yl)-[5-(7H-pyrrolo[2,3-d]pyrimidin-4-yl)-5,8-diazaspiro[2.6]nonan-8-yl]methanone;
(4-methyloxazol-5-yl)-[5-(7H-pyrrolo[2,3-d]pyrimidin-4-yl)-5,9-diazaspiro[2.6]nonan-9-yl]methanone;
(2,5-dimethylpyrazol-3-yl)-[5-(7H-pyrrolo[2,3-d]pyrimidin-4-yl)-5,9-diazaspiro[2.6]nonan-9-yl]methanone;
(5-methyl-1,3,4-oxadiazol-2-yl)-[5-(7H-pyrrolo[2,3-d]pyrimidin-4-yl)-5,8-diazaspiro[2.6]nonan-8-yl]methanone;
[5-(7H-pyrrolo[2,3-d]pyrimidin-4-yl)-5,8-diazaspiro[2.6]nonan-8-yl]-(1H-1,2,4-triazol-3-yl)methanone;
(5-methylpyrazin-2-yl)-[5-(7H-pyrrolo[2,3-d]pyrimidin-4-yl)-5,8-diazaspiro[2.6]nonan-8-yl]methanone;
(5-methylpyrazin-2-yl)-[5-(7H-pyrrolo[2,3-d]pyrimidin-4-yl)-5,9-diazaspiro[2.6]nonan-9-yl]methanone;
(6-methylpyrazin-2-yl)-[5-(7H-pyrrolo[2,3-d]pyrimidin-4-yl)-5,9-diazaspiro[2.6]nonan-9-yl]methanone;
(3,5-dimethylisoxazol-4-yl)-[5-(7H-pyrrolo[2,3-d]pyrimidin-4-yl)-5,9-diazaspiro[2.6]nonan-9-yl]methanone;
isothiazol-3-yl-[5-(7H-pyrrolo[2,3-d]pyrimidin-4-yl)-5,8-diazaspiro[2.6]nonan-8-yl]methanone;
isothiazol-3-yl-[5-(7H-pyrrolo[2,3-d]pyrimidin-4-yl)-5,9-diazaspiro[2.6]nonan-9-yl]methanone;
[5-(7H-pyrrolo[2,3-d]pyrimidin-4-yl)-5,8-diazaspiro[2.6]nonan-8-yl]-(1,2,5-thiadiazol-3-yl)methanone;
[5-(7H-pyrrolo[2,3-d]pyrimidin-4-yl)-5,9-diazaspiro[2.6]nonan-9-yl]-(1,2,5-thiadiazol-3-yl)methanone;
[5-(7H-pyrrolo[2,3-d]pyrimidin-4-yl)-5,8-diazaspiro[2.6]nonan-8-yl]-(1H-triazol-4-yl)methanone;
[5-(7H-pyrrolo[2,3-d]pyrimidin-4-yl)-5,9-diazaspiro[2.6]nonan-9-yl]-(1H-triazol-4-yl)methanone;
(5-methyl-1H-pyrazol-4-yl)-[5-(7H-pyrrolo[2,3-d]pyrimidin-4-yl)-5,8-diazaspiro[2.6]nonan-8-yl]methanone;
(5-methyl-1H-pyrazol-4-yl)-[5-(7H-pyrrolo[2,3-d]pyrimidin-4-yl)-5,9-diazaspiro[2.6]nonan-9-yl]methanone;
5-[5-(7H-pyrrolo[2,3-d]pyrimidin-4-yl)-5,8-diazaspiro[2.6]nonane-8-carbonyl]-1H-pyrrole-3-carbonitrile;
5-[5-(7H-pyrrolo[2,3-d]pyrimidin-4-yl)-5,9-diazaspiro[2.6]nonane-9-carbonyl]-1H-pyrrole-3-carbonitrile;
isothiazol-4-yl-[5-(7H-pyrrolo[2,3-d]pyrimidin-4-yl)-5,8-diazaspiro[2.6]nonan-8-yl]methanone;
isothiazol-4-yl-[5-(7H-pyrrolo[2,3-d]pyrimidin-4-yl)-5,9-diazaspiro[2.6]nonan-9-yl]methanone;
(5-hydroxy-1H-pyrazol-3-yl)-[5-(7H-pyrrolo[2,3-d]pyrimidin-4-yl)-5,9-diazaspiro[2.6]nonan-9-yl]methanone;
(5-fluoro-3-pyridyl)-[5-(7H-pyrrolo[2,3-d]pyrimidin-4-yl)-5,8-diazaspiro[2.6]nonan-8-yl]methanone;
(5-fluoro-3-pyridyl)-[5-(7H-pyrrolo[2,3-d]pyrimidin-4-yl)-5,9-diazaspiro[2.6]nonan-9-yl]methanone;
1-[5-(7H-pyrrolo[2,3-d]pyrimidin-4-yl)-5,8-diazaspiro[2.6]nonan-8-yl]-2-(1H-tetrazol-5-yl)ethanone;
[5-(7H-pyrrolo[2,3-d]pyrimidin-4-yl)-5,8-diazaspiro[2.6]nonan-8-yl]-thiazol-4-yl-methanone;
2-(3-methylisoxazol-5-yl)-1-[5-(7H-pyrrolo[2,3-d]pyrimidin-4-yl)-5,9-diazaspiro[2.6]nonan-9-yl]ethanone;
N-(2-cyanoethyl)-N-ethyl-5-(7H-pyrrolo[2,3-d]pyrimidin-4-yl)-5,8-diazaspiro[2.6]nonane-8-carboxamide;
N-(cyanomethyl)-N-methyl-5-(7H-pyrrolo[2,3-d]pyrimidin-4-yl)-5,8-diazaspiro[2.6]nonane-8-carboxamide;
N,N-bis(cyanomethyl)-5-(7H-pyrrolo[2,3-d]pyrimidin-4-yl)-5,8-diazaspiro[2.6]nonane-8-carboxamide;
N-(2-cyanoethyl)-N-methyl-5-(7H-pyrrolo[2,3-d]pyrimidin-4-yl)-5,8-diazaspiro[2.6]nonane-8-carboxamide;
(2R)-1-[5-(7H-pyrrolo[2,3-d]pyrimidin-4-yl)-5,8-diazaspiro[2.6]nonane-8-carbonyl]pyrrolidine-2-carbonitrile;
(2S)-1-[5-(7H-pyrrolo[2,3-d]pyrimidin-4-yl)-5,8-diazaspiro[2.6]nonane-8-carbonyl]pyrrolidine-2-carbonitrile;
N-isopropyl-N-methyl-5-(7H-pyrrolo[2,3-d]pyrimidin-4-yl)-5,8-diazaspiro[2.6]nonane-8-carboxamide;
N,N-bis(2-cyanoethyl)-5-(7H-pyrrolo[2,3-d]pyrimidin-4-yl)-5,8-diazaspiro[2.6]nonane-8-carboxamide;
1-[5-(7H-pyrrolo[2,3-d]pyrimidin-4-yl)-5,9-diazaspiro[2.6]nonan-9-yl]-2-(1H-tetrazol-5-yl)ethanone;
[5-(7H-pyrrolo[2,3-d]pyrimidin-4-yl)-5,9-diazaspiro[2.6]nonan-9-yl]-thiazol-4-yl-methanone;
[5-(7H-pyrrolo[2,3-d]pyrimidin-4-yl)-5,9-diazaspiro[2.6]nonan-9-yl]-(1H-1,2,4-triazol-3-yl) methanone;
(5-methylisothiazol-4-yl)-[5-(7H-pyrrolo[2,3-d]pyrimidin-4-yl)-5,8-diazaspiro[2.6]nonan-8-yl]methanone;
(5-methylisothiazol-4-yl)-[5-(7H-pyrrolo[2,3-d]pyrimidin-4-yl)-5,9-diazaspiro[2.6]nonan-9-yl]methanone;
(5-chloro-1H-1,2,4-triazol-3-yl)-[5-(7H-pyrrolo[2,3-d]pyrimidin-4-yl)-5,8-diazaspiro[2.6]nonan-8-yl]methanone;
(5-chloro-1H-1,2,4-triazol-3-yl)-[5-(7H-pyrrolo[2,3-d]pyrimidin-4-yl)-5,9-diazaspiro[2.6]nonan-9-yl]methanone;
(3-methylisothiazol-5-yl)-[5-(7H-pyrrolo[2,3-d]pyrimidin-4-yl)-5,8-diazaspiro[2.6]nonan-8-yl]methanone;

(3-methylisothiazol-5-yl)-[5-(7H-pyrrolo[2,3-d]pyrimidin-4-yl)-5,9-diazaspiro[2.6]nonan-9-yl]methanone;
isothiazol-5-yl-[5-(7H-pyrrolo[2,3-d]pyrimidin-4-yl)-5,8-diazaspiro[2.6]nonan-8-yl]methanone;
isothiazol-5-yl-[5-(7H-pyrrolo[2,3-d]pyrimidin-4-yl)-5,9-diazaspiro[2.6]nonan-9-yl]methanone;
(3-methyl-1H-pyrazol-5-yl)-[5-(7H-pyrrolo[2,3-d]pyrimidin-4-yl)-5,8-diazaspiro[2.6]nonan-8-yl]methanone;
(3-methyl-1H-pyrazol-5-yl)-[5-(7H-pyrrolo[2,3-d]pyrimidin-4-yl)-5,9-diazaspiro[2.6]nonan-9-yl]methanone;
[5-(7H-pyrrolo[2,3-d]pyrimidin-4-yl)-5,8-diazaspiro[2.6]nonan-8-yl]-thiazol-5-yl-methanone;
[5-(7H-pyrrolo[2,3-d]pyrimidin-4-yl)-5,9-diazaspiro[2.6]nonan-9-yl]-thiazol-5-yl-methanone;
(5-methylthiazol-2-yl)-[5-(7H-pyrrolo[2,3-d]pyrimidin-4-yl)-5,8-diazaspiro[2.6]nonan-8-yl]methanone;
1H-imidazol-5-yl-[5-(7H-1-pyrrolo[2,3-d]pyrimidin-4-yl)-5,8-diazaspiro[2.6]nonan-8-yl]methanone;
1H-imidazol-5-yl-[5-(7H-pyrrolo[2,3-d]pyrimidin-4-yl)-5,9-diazaspiro[2.6]nonan-9-yl]methanone;
(3-methylisoxazol-4-yl)-[5-(7H-pyrrolo[2,3-d]pyrimidin-4-yl)-5,8-diazaspiro[2.6]nonan-8-yl]methanone;
(3-methylisoxazol-4-yl)-[5-(7H-pyrrolo[2,3-d]pyrimidin-4-yl)-5,9-diazaspiro[2.6]nonan-9-yl]methanone;
2-(4-methylthiazol-5-yl)-1-[5-(7H-pyrrolo[2,3-d]pyrimidin-4-yl)-5,8-diazaspiro[2.6]nonan-8-yl]ethanone;
2-(2-methylthiazol-5-yl)-1-[5-(7H-pyrrolo[2,3-d]pyrimidin-4-yl)-5,8-diazaspiro[2.6]nonan-8-yl]ethanone;
2-(5-methyl-1H-pyrazol-3-yl)-1-[5-(7H-pyrrolo[2,3-d]pyrimidin-4-yl)-5,8-diazaspiro[2.6]nonan-8-yl]ethanone;
2-(3,5-dimethylisoxazol-4-yl)-1-[5-(7H-pyrrolo[2,3-d]pyrimidin-4-yl)-5,8-diazaspiro[2.6]nonan-8-yl]ethanone;
2-(3-methyl-1H-1,2,4-triazol-5-yl)-1-[5-(7H-pyrrolo[2,3-d]pyrimidin-4-yl)-5,8-diazaspiro[2.6]nonan-8-yl]ethanone;
2-(4-methyl-1,2,5-oxadiazol-3-yl)-1-[5-(7H-pyrrolo[2,3-d]pyrimidin-4-yl)-5,8-diazaspiro[2.6]nonan-8-yl]ethanone;
1-[5-(7H-pyrrolo[2,3-d]pyrimidin-4-yl)-5,8-diazaspiro[2.6]nonan-8-yl]-2-thiazol-5-yl-ethanone;
2-(1-methylpyrazol-4-yl)-1-[5-(7H-pyrrolo[2,3-d]pyrimidin-4-yl)-5,8-diazaspiro[2.6]nonan-8-yl]ethanone;
2-(2-methylthiazol-4-yl)-1-[5-(7H-pyrrolo[2,3-d]pyrimidin-4-yl)-5,8-diazaspiro[2.6]nonan-8-yl]ethanone;
[5-(7H-pyrrolo[2,3-d]pyrimidin-4-yl)-5,9-diazaspiro[2.6]nonan-9-yl]-(1H-pyrrol-2-yl)methanone;
(4-amino-1,2,5-oxadiazol-3-yl)-[5-(7H-pyrrolo[2,3-d]pyrimidin-4-yl)-5,9-diazaspiro[2.6]nonan-9-yl]methanone;
(5-methyl-4H-1,2,4-triazol-3-yl)-[5-(7H-pyrrolo[2,3-d]pyrimidin-4-yl)-5,9-diazaspiro[2.6]nonan-9-yl]methanone;
5-[5-(7H-pyrrolo[2,3-d]pyrimidin-4-yl)-5,9-diazaspiro[2.6]nonane-9-carbonyl]furan-2-carbonitrile;
2-phenyl-1-[5-(7H-pyrrolo[2,3-d]pyrimidin-4-yl)-5,8-diazaspiro[2.6]nonan-8-yl]ethanone;
(1-phenylcyclopropyl)-[5-(7H-pyrrolo[2,3-d]pyrimidin-4-yl)-5,8-diazaspiro[2.6]nonan-8-yl]methanone;
2-(4-methoxyphenyl)-1-[5-(7H-pyrrolo[2,3-d]pyrimidin-4-yl)-5,8-diazaspiro[2.6]nonan-8-yl]ethanone;
2-(m-tolyl)-1-[5-(7H-pyrrolo[2,3-d]pyrimidin-4-yl)-5,8-diazaspiro[2.6]nonan-8-yl]ethanone;
2-(p-tolyl)-1-[5-(7H-pyrrolo[2,3-d]pyrimidin-4-yl)-5,8-diazaspiro[2.6]nonan-8-yl]ethanone;
2-(4-bromophenyl)-1-[5-(7H-pyrrolo[2,3-d]pyrimidin-4-yl)-5,8-diazaspiro[2.6]nonan-8-yl]ethanone;
2-(2-naphthyl)-1-[5-(7H-pyrrolo[2,3-d]pyrimidin-4-yl)-5,8-diazaspiro[2.6]nonan-8-yl]ethanone;
2-[4-[2-oxo-2-[5-(7H-pyrrolo[2,3-d]pyrimidin-4-yl)-5,8-diazaspiro[2.6]nonan-8-yl]ethyl]phenyl]acetonitrile;
2-(4-tert-butylphenyl)-1-[5-(7H-pyrrolo[2,3-d]pyrimidin-4-yl)-5,8-diazaspiro[2.6]nonan-8-yl]ethanone;
2-(4-dimethylaminophenyl)-1-[5-(7H-pyrrolo[2,3-d]pyrimidin-4-yl)-5,8-diazaspiro[2.6]nonan-8-yl]ethanone;
2-(4-chlorophenyl)-2-methyl-1-[5-(7H-pyrrolo[2,3-d]pyrimidin-4-yl)-5,8-diazaspiro[2.6]nonan-8-yl]propan-1-one;
2-(2,4-dichlorophenyl)-1-[5-(7H-pyrrolo[2,3-d]pyrimidin-4-yl)-5,8-diazaspiro[2.6]nonan-8-yl]ethanone;
2-[2-oxo-2-[5-(7H-pyrrolo[2,3-d]pyrimidin-4-yl)-5,8-diazaspiro[2.6]nonan-8-yl]ethyl]benzonitrile;
2-fluoro-5-[2-oxo-2-[5-(7H-pyrrolo[2,3-d]pyrimidin-4-yl)-5,8-diazaspiro[2.6]nonan-8-yl]ethyl]benzonitrile;
1-[5-(7H-pyrrolo[2,3-d]pyrimidin-4-yl)-5,8-diazaspiro[2.6]nonan-8-yl]-2-[4-(trifluoromethoxy)phenyl]ethanone;
2-phenyl-1-[5-(7H-pyrrolo[2,3-d]pyrimidin-4-yl)-5,8-diazaspiro[2.6]nonan-8-yl]propan-1-one;
N-[4-[2-oxo-2-[5-(7H-pyrrolo[2,3-d]pyrimidin-4-yl)-5,8-diazaspiro[2.6]nonan-8-yl]ethyl]phenyl]acetamide;
(4-methyl-1H-pyrrol-2-yl)-[5-(7H-pyrrolo[2,3-d]pyrimidin-4-yl)-5,9-diazaspiro[2.6]nonan-9-yl]methanone;
2-methyl-5-[5-(7H-pyrrolo[2,3-d]pyrimidin-4-yl)-5,9-diazaspiro[2.6]nonane-9-carbonyl]-1H-pyrrole-3-carbonitrile;
4-(5-butyl-5,8-diazaspiro[2.6]nonan-8-yl)-7H-pyrrolo[2,3-d]pyrimidine;
4-(9-benzyl-5,9-diazaspiro[2.6]nonan-5-yl)-7H-pyrrolo[2,3-d]pyrimidine;
4-(9-butyl-5,9-diazaspiro[2.6]nonan-5-yl)-7H-pyrrolo[2,3-d]pyrimidine;
N-[4-(5-benzyl-5,8-diazaspiro[2.6]nonan-8-yl)-7H-pyrrolo[2,3-d]pyrimidin-2-yl]pentanamide;
N-[4-(9-benzyl-5,9-diazaspiro[2.6]nonan-5-yl)-7H-pyrrolo[2,3-d]pyrimidin-2-yl]pentanamide;
[7-methyl-5-(7H-pyrrolo[2,3-d]pyrimidin-4-yl)-5,8-diazaspiro[2.6]nonan-8-yl]-phenyl-methanone;
2-cyclopentyl-1-[7-methyl-5-(7H-pyrrolo[2,3-d]pyrimidin-4-yl)-5,8-diazaspiro[2.6]nonan-8-yl]ethanone;
4-[2-[7-methyl-5-(7H-pyrrolo[2,3-d]pyrimidin-4-yl)-5,8-diazaspiro[2.6]nonan-8-yl]-2-oxo-ethyl]Benzonitrile;
N-[4-[9-(2-phenylacetyl)-5,9-diazaspiro[2.6]nonan-5-yl]-7H-pyrrolo[2,3-d]pyrimidin-2-yl]pentanamide;
N-[4-[9-(5-cyanothiophene-2-carbonyl)-5,9-diazaspiro[2.6]nonan-5-yl]-7H-pyrrolo[2,3-d]pyrimidin-2-yl]pentanamide;
N-[4-[8-(5-cyanothiophene-2-carbonyl)-5,8-diazaspiro[2.6]nonan-5-yl]-7H-pyrrolo[2,3-d]pyrimidin-2-yl]pentanamide;
5-(7H-pyrrolo[2,3-d]pyrimidin-4-yl)-5,8-diazaspiro[2.6]nonane;
4-(6,9-diazaspiro[2.6]nonan-6-yl)-7H-pyrrolo[2,3-d]pyrimidine;
4-(5,9-diazaspiro[2.6]nonan-5-yl)-7H-pyrrolo[2,3-d]pyrimidine;
4-(6-methyl-5,8-diazaspiro[2.6]nonan-8-yl)-7H-pyrrolo[2,3-d]pyrimidine;
N-[4-(5,9-diazaspiro[2.6]nonan-5-yl)-7H-pyrrolo[2,3-d]pyrimidin-2-yl]pentanamide;

N-[4-(5,8-diazaspiro[2.6]nonan-8-yl)-7H-pyrrolo[2,3-d]pyrimidin-2-yl]pentanamide; and 1-[5-(7H-pyrrolo[2,3-d]pyrimidin-4-yl)-5,8-diazaspiro[2.6]nonan-8-yl]-2-[4-(trifluoromethyl)phenyl]ethanone.

9. A pharmaceutical composition comprising a compound according to claim 1 or a pharmaceutically acceptable salt, hydrate, or solvate thereof together with a pharmaceutically acceptable vehicle or excipient.

* * * * *